United States Patent
Walensky et al.

(10) Patent No.: US 9,822,165 B2
(45) Date of Patent: Nov. 21, 2017

(54) HYDROCARBON STAPLED STABILIZED ALPHA-HELICES OF THE HIV-1 GP41 MEMBRANE PROXIMAL EXTERNAL REGION

(75) Inventors: Loren D. Walensky, Newton, MA (US); Gregory Bird, Pelham, NH (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 70 days.

(21) Appl. No.: 13/378,929

(22) PCT Filed: Jun. 18, 2010

(86) PCT No.: PCT/US2010/039223
§ 371 (c)(1),
(2), (4) Date: Feb. 23, 2012

(87) PCT Pub. No.: WO2010/148335
PCT Pub. Date: Dec. 23, 2010

(65) Prior Publication Data
US 2012/0141527 A1    Jun. 7, 2012

Related U.S. Application Data

(60) Provisional application No. 61/218,209, filed on Jun. 18, 2009.

(51) Int. Cl.
*C07K 16/10* (2006.01)
*A61K 39/21* (2006.01)
*A61K 39/12* (2006.01)

(52) U.S. Cl.
CPC .......... *C07K 16/1045* (2013.01); *A61K 39/12* (2013.01); *A61K 39/21* (2013.01); *C07K 16/1063* (2013.01); *C07K 2317/34* (2013.01); *C07K 2317/76* (2013.01); *C12N 2740/16034* (2013.01); *C12N 2740/16122* (2013.01); *C12N 2740/16134* (2013.01)

(58) Field of Classification Search
CPC ................ C07K 16/1063; A61K 39/12; C12N 2740/16134; C12N 2740/16122
See application file for complete search history.

(56) References Cited

U.S. PATENT DOCUMENTS 6,271,198 B1    8/2001 Braisted et al.

FOREIGN PATENT DOCUMENTS

| JP | 2001-503064 A | 3/2001 |
| WO | WO-98/20036 A1 | 5/1998 |
| WO | WO-2005044839 | 5/2005 |
| WO | WO 2009/042895 A2 * | 4/2009 |
| WO | 2009108261 A2 | 9/2009 |

OTHER PUBLICATIONS

Gray, E. S., et al., Mar. 2008, 4E10-resistant variants in a human immunodeficiency virus type 1 subtype C-infectred individual with an anti-membrane-proximal external region-neutralizing antibody response, J. Virol. 82(5):2367-2375.*

Ingale, S., et al., 2010, Synthesis and analysis of the membrane proximal external region epitopes of HIV-1, J. Pept. Sci. 16:716-722.*

Kim, M., et al., Nov. 2013, Immunogenicity of membrane-bound HIV-1 gp41 membrane-proximal external region (MPER) segments is dominated by residue accessibility and modulated by stereochemistry, J. Biol. Chem. 288(44):31888-31901.*

Schafmeister, C. E., et al., 2000, An all-hydrocarbon cross-linking system for enhancing the helicity and metabolic stability of peptides, J. Am. Chem. Soc. 122:5891-5892.*

Andrews, M. J., and A. B. Tabot, 1999, Forming stable helical peptides using natural and artificial amino acids, Tetrahedron 55:11711-11743.*

Barouch, D. H., Oct. 2008, Challenges in the development of an HIV-1 vaccine, Nature 455:613-619.*

Johnston, M. I., and A. S. Fauci, 2008, An HIV vaccine-challenges and prospects, The New England Journal of Medicine 359(9):888-890.*

Walker, B. D., and D. R. Burton, May 2008, Toward an AIDS vaccine, Science 320:760-764.*

Lewis, G. K., et al., Nov. 2014, Antibody persistence and T-cell balance: two key factors confronting Hiv vaccine development, Proc. Natl. Acad. Sci. 111(44):15614-15621.*

Wang et al., "Inhibition of HIV-1 Fusion by Hydrogen-Bond-Surrogate-Based a Helics", Angew. Chem. Int. Ed., vol. 47, pp. 1879-1882 (2008).

Cardoso et al., Structural basis of enhanced binding of extended and helically constrained peptide epitopes of the broadly neutralizing HIV-1 antibody 4E10. J Mol Biol. Feb. 2, 2007;365(5):1533-44. Epub Nov. 10, 2006.

Sawyer, Aileron Therapeutics. Chem Biol & Drug Des. Dec. 18, 2008;73(1):3-6.

Joyce et al. Enhancement of alpha—helicity in the HIV-1 inhibitory peptide DP178 leads to an increased affinity for human monoclonal antibody 2F5 but does not elicit neutralizing responses in vitro. Implications for vaccine design. J Biol Chem. Nov. 29, 2002;277(48):45811-20.

(Continued)

*Primary Examiner* — Jeffrey Parkin
(74) *Attorney, Agent, or Firm* — Burns & Levinson, LLP; Daniel W. Clarke

(57) ABSTRACT

The invention provides structurally constrained viral peptides for use as therapeutic and vaccination agents, and for the production of antibodies for use in a number of applications including as therapeutic agents. The invention further provides methods and kits for use of the structurally constrained peptides and antibodies of the instant invention. The invention is based, at least in part, on the result provided herein demonstrating that viral hydrocarbon stapled helical peptides display excellent proteolytic, acid, and thermal stability, restore the native helical structure of the peptide, are highly effective in interfering with the viral fusogenic process, and possess superior pharmacokinetic properties compared to the corresponding unmodified peptides.

18 Claims, 48 Drawing Sheets

(56) References Cited

OTHER PUBLICATIONS

Nelson et al. An affinity-enhanced neutralizing antibody against the membrane-proximal external region of human immunodeficiency virus type 1 gp41 recognizes an epitope between those of 2F5 and 4E10. J Virol. Apr. 2007;81(8):4033-43.

Dwyer John J et al., Design of helical, oligomeric HIV-1 fusion inhibitor peptides with potent activity against enfuvirtide-resistant virus, Proceedings of the National Academy of Sciences, National Academy of Sciences, vol. 104, No. 31, Jul. 2007, pp. 12772-12777.

Eran Noah et al: The Membrane Proximal External Region of the HIV-1 Envelope Glycoprotein gp41 contributes to the Stabilization of the Six-Helix Bundle Formed with a Matching N' Peptide, Biochemistry, vol. 47, No. 26, Jul. 2008, pp. 6782-6792.

Liu et al., HIV gp41 C-terminal heptad repeat contains multifunctional domains, Journal of Biological Chemistry, American Society for Biochemistry and Molecular Biology, vol. 282, No. 13, Mar. 2007, pp. 9612-9620.

Long Y-Q et al., alfa-Helix stabilized Peptides via an all Hydrocarbon-staple Conferring an improved inhibitory activity against 3-Processing of HIV-1 Integrase., Peptide and Science—Present and Future Proceedings of the International Peptide Symposium, vol. 4th, Dec. 31, 2007, pp. 1-2, XP002555225.

Walensky et al. Activation of apoptosis in vivo by a hydrocarbon-stapled BH3 helix, American Association for the Advancement of Science, vol. 305, 2004, pp. 1466-1470.

Walensky et al. "Hydrocarbon-Stapled Peptides: Principles, Practice, and Progress" *Journal of Medicinal Chemistry.* 2014, 57, pp. 6275-6288.

Bird et al. "Stapled HIV-1 Peptides Recapitulate Antigenic Structures and Engage Broadly Neutralizing Antibodies" *Nat Struct Mol Biol.* 2014; 21(12): pp. 1058-1067.

Adam Penn-Nicholson, et al., "Assessment of Antibody Responses Against GP41 in HIV-1-Infected Patients Using Soluble GP41 Fusion Proteins and Peptides Derived from M Group Consensus Envelope", Virology, Mar. 15, 2008, 372(2), pp. 442-456.

\* cited by examiner

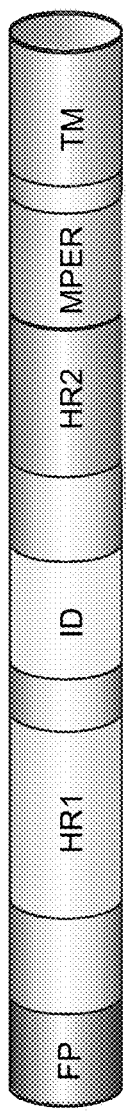
FIG. 1A
MTWMEWDREINNYTSLIHSLIEESQNQQEKNEQELLELDKWASLWNWFNITNWLWYIK
FIG. 1B
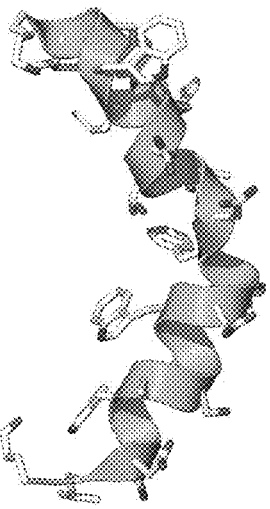
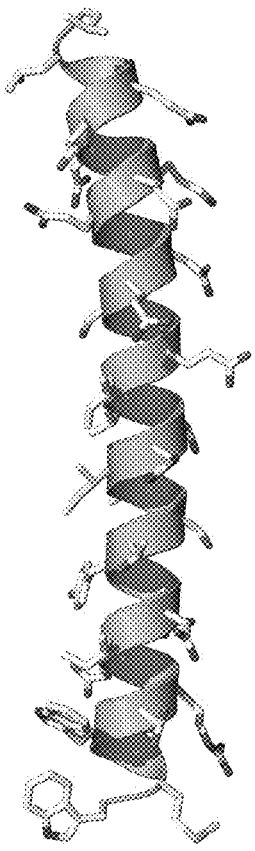
FIG. 1C

FIG. 2A

| | | SEQ ID NO: |
|---|---|---|
| HIV_gp41 | RQLLSGIVQQQNNLLRAIEAQQHLLQLTVWGIKQLQA RILAVERYLQDQQL | 3 |
| Ebolavirus | DGLICGLRQLANETTQALQLFLRATTELRTFSILNRKAIDFLIL | 4 |
| Marburg | NNLVCRLRRLANQTAKSLELLLRVTTEERTFSLINRHAIDFL | 5 |
| leukemia | MSLASGKSLLHEVDKDISQLTQAIVKNHKNLLKIAQYAAQNRRGLDLLFW | 6 |
| parainfl. | ALGVATSAQITAAVALVEAKQARSDIEKLKEAIRDTNKAVQSVQSSIGN LIVAIKSVQDYVNKEI | 7 |
| RSV | SGIAVSKVLHLEGEVNKIKNALLSTNKAVVSLSNGVSVLTSKVLDLKSYINNQLLPI | 8 |
| SARS | NVLYENQKQIANQFNKAISQIQESLITTTSTALGKLQDVVNQNAQALNTL VKQLSSNFGAISSVLNDILSRLDIKVEAE | 9 |

| | | SEQ ID NO: |
|---|---|---|
| gp41 | WNNMTWMEWEKEIDNYTSIIYTLLETSQNQQEKNEQELLELDK | 10 |
| Ebolavirus | DWTKNITDKIDQIIHDFVDKTLPD | 11 |
| Marburg | IEDLSRNISEQIDQIKKDEQ | 12 |
| leukemia | CCFLNITNSHVSILQE-RPPLENRVLTGWGL | 13 |
| parainfl | YTPNDITLNNSVALDPIDISIELNKAKSDLEESKEWIRRSNQKLDSIGNWHQSSTT | 14 |
| RSV | PIINYYDPLVFPSDEFDASISQVNEKINQSLAHRRSDELLFINVNTGKSTTNIM | 15 |
| SARS | TSPDVDFGDISGINASVVNIQKEIDRLNEVAKNLNESLIDLQELGKY | 16 |

FIG. 2C

HR2-MPER (MPER region underlined)

```
                                                                                          SEQ ID NO:
HIV-1       MTWMEWDREINNYTSLIHSLIEESQNQQEKNEQELLELDKWANLWNWFDISKWLWYIK      17
YU2         MTWMKWEREIDNYTHIIYSLIEQSQNQQEKNEQELLALDKWASLWNWFDITKWLWYIK      18
SIV         MTWQEWERQVDFLEANITQLLEEAQIQQEKNMYELQKLNSWDIFGNWFDLTSWIRYIQ      19
HXBc2       TTWMEWDREINNYTSLIHSLIEESQNQQEKNEQELLELDKWASLWNWFNITNWLWYIK      20
ADA         TTWMEWDREINNYTSLIHSLIEESQNQQEKNEQELLELDKWASLWNWFNITNWLWYIK      21
HXBc2P3.2   MTWMQWEKEISNYSYEIYRLIEESQNQQEKNEQELLALDKWTSLMSWFDISNWLWYIK      22
IIIB        MTWMEWDREINNYTSLIHSLIEESQNQQEKNEQELLELDKWASLWNWFNITNWLWYIK      23
```

Example of HIV/SARS MPER region homology:

```
HIV-1_KR5086   662   ELLELDKWANLWNWFDISKWLWYIKIFIMIVGGLVGLRII         701    24
                     +L EL K+        KW WY +++   + GL+  +  ++
SARS-spike    1181   DLQELGK

FIG. 3B

FIG. 4 gp41(626-645)        BTWBEWDREINNYTSLIHSL        SEQ ID NO: 26

SAH-gp41(626-645)(A) BTWXEWDXEINNYTSLIHSL        SEQ ID NO: 27

FIG. 5A heptad repeat domain

--abcdefgabcdefgabcdefgabcdefga--

FIG. 5B

HIV gp41 (626-663)

MTWMEWDREINNYTSLIHSLIEESQNQQEKNEQELLEL        SEQ ID NO: 28

FIG. 5C heptad position a, d

--W--W---I--Y---I--L---S--Q---N--E---L        SEQ ID NO: 29
(residues as per Dwyer et al. *PNAS*, 104: 12772, 2007)

FIG. 5D

-TW---WDR-I--Y---I--LI---Q--QEK-E---L-EL        SEQ ID NO: 30

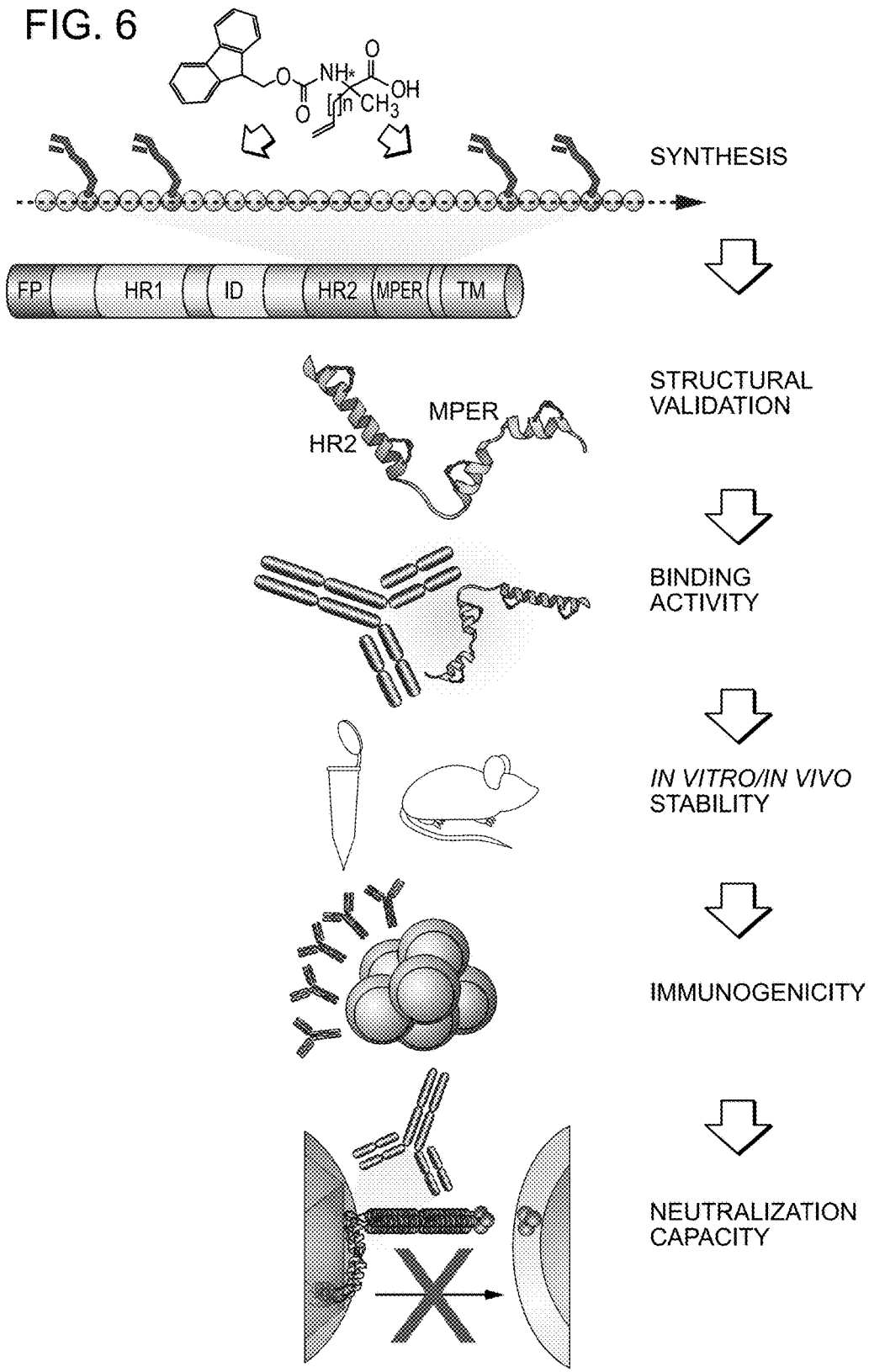

FIG. 8 C
i,i+4 and i,i+4
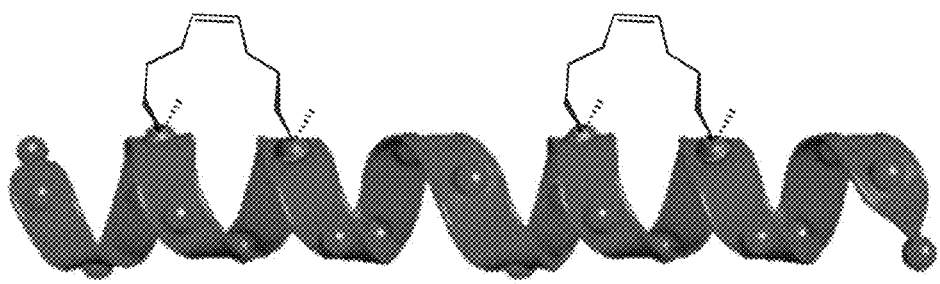
i,i+7 and i,i+7
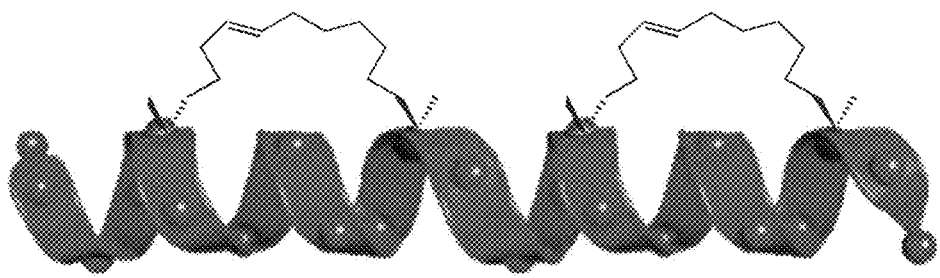
FIG. 8 D
i,i+4 and i,i+7
i,i+4 and i,i+4 and i,i+4
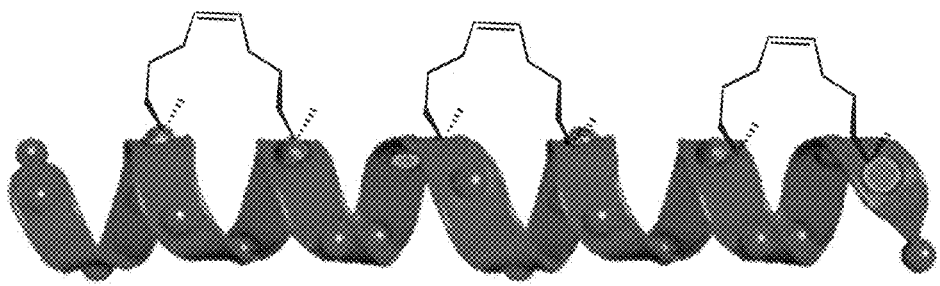

(R)-2-Fmoc-2-methyl-pent-4-enoic acid    (S)-2-Fmoc-2-methyl-oct-7-enoic acid

FIG. 10A

```
         A         C        I         E           J          F         G
       ┌───┐     ┌───┐   ┌────┐    ┌─────┐     ┌─────┐    ┌─────┐   ┌─────┐                           SEQ
                                                                                                     ID NO:
  626 BTWBEWDREINNYTSLIHSLIEESQNQQEKNEQELLELDKWASLWNWF 673                                              44
       └───┘     └───┘        └─┘              └─────┘     └───┘ └───┘
         B         D           K                 F           K    H

BTWBEWDREINNYTSLIHSLIEESQNQQEKNEQELLE                             gp41(626-662)                   45
      BTWBEWDREINNYTSLIHSLIEESQNQXEKNXQELLE                             SAH-gp41(626-662)(F)            46
      BTWXEWDXEINNYTSLIHSLIEESQNQQEKNEQELLE                             SAH-gp41(626-662)(A)            47
      BTWBEWDREINNYTSLIHSLIXESXQQEKNEQELLE                              SAH-gp41(626-662)(E)            48

YTSLIHSLIEESQNQQEKNEQELLELDKWASLWNWF                gp41(638-673)                   49
                    YTXLIHXLIEESQNQXEKNXQELLELDKWASLWNWF                SAH-gp41(638-673)(D)            50
                    YTSLIHSLIEESQNXEKNXQELLELDKWASLWNWF                 SAH-gp41(638-673)(F)            51
                    YTSLIHSLIEESQNQQEKNEQELLELXKWAXLWNWF                SAH-gp41(638-673)(G)            52
                    YTSLIHSLIEESQNQQEKNEQELLELDKXASLXNWF                SAH-gp41(638-673)(H)            53
                    YTSLXHSLXEESQNQQEKNEQELLELDKWASLWNWF                SAH-gp41(638-673)(I)            54
                    YTSLIHSLIXESQXQQEKNEQELLELDKWASLWNWF                SAH-gp41(638-673)(E)            55
                    YTSLIHSLIEESQNQXKNEXELLELDKWASLWNWF                 SAH-gp41(638-673)(J)            56
                    YTSLIHSLIEESQNQQEKNEXELLXLDKWASLWNWF                SAH-gp41(638-673)(K)            57
```

FIG. 10B

```
      A         C        I       E           J          G
      ┌─┐      ┌─┐      ┌─┐     ┌─┐         ┌─┐        ┌─┐
626 BTWBEWDREINNYTSLIHSLIEESQNQQEKNEQELLELDKWASLWNWF 673
      └─┘      └─┘      └─┘     └─┘         └─┘        └─┘
       B        D                F           K          H
```

|                                           |                        | SEQ ID NO: |
|-------------------------------------------|------------------------|------------|
| BTWBEWDREINNYTSLIHSLIEESQNQQEKNEQELLE      | gp41(626-662)          | 44         |
| BTWXEWDX

FIG. 10B (continued)

| Sequence | Name | SEQ ID |
|---|---|---|
| YTSLIHSLIEESQNQQEKNEQELLELDKWASLWNWF | gp41(638-673) | 49 |
| YTXLIHXLIEESQNQQEKNEQELLELDKXASLXNWF | SAH-gp41(638-673)(D, H) | 64 |
| YTXLIHXLIEESQNQQEKNEQELLELXKWAXLWNWF | SAH-gp41(638-673)(D, G) | 65 |
| YTSLIHXLIEESQNQXEKNXQELLELDKXASLXNWF | SAH-gp41(638-673)(F, H) | 66 |
| YTXLIHXLIEESQNQXEKNXQELLELDKWASLWNWF | SAH-gp41(638-673)(D, F) | 67 |
| YTSLIHSLIEESQXQQEKNEQELLELXKWAXLWNWF | SAH-gp41(638-673)(E, G) | 68 |
| YTSLIHSLIXESQXQQEKNEXELLIXLDKWASLWNWF | SAH-gp41(638-673)(E, K) | 69 |
| YTXLIHXLIEESQNQXEKNXQELLELXKWAXLWNWF | SAH-gp41(638-673)(D, F, G) | 70 |
| BTWBXWDRXINNYTSLIHSLIEESQNQEKNEQELLE | SAH-gp41(626-662)(A') | 71 |
| BTWBEWDREINNYTSLIEESQNXQEKNEQELLE | SAH-gp41(626-662)(F') | 72 |
| BTWBXWDRXINNYTSLIHSLIEESQNXQEKNXQELLE | SAH-gp41(626-662)(A',F) | 73 |
| BTWBXWDRXINNYTSLIHSLIEESQNXQEKXEQELLE | SAH-gp41(626-662)(A',F') | 74 |

FIG. 12A

*i, i + 4 SAH-MPERs*

ELDKWXSLWXWFNITNWLWYIK 75

ELDKXASLXNWFNITNWLWYIK 76
ELDXWASXWNWFNITNWLWYIK 77
ELXKWAXLWNWFNITNWLWYIK 78
EXDKWXSLWNWFNITNWLWYIK 79

XLDKXASLWNWFNITNWLWYIK 80

ELDKWASLWNWFXITNXLWY 81

ELDKWASLXNWFXITNWLWY 82

FIG. 12B

*i, i + 3 SAH-MPERs*

ELDKWASLWNWFNITNWLXYIX 83

ELDKWASLWNWFNITNWXWYXK 84

ELDKWASLWNWFNITNXLWXIK 85

ELDKWASLWNWFNITXWLXYIK 86

ELDKWASLWNWFNIXNWXWYIK 87

ELDKWASLWNWFNXTNXLWYIK 88

ELDKWASLWNWFXITXWLWYIK 89

FIG. 12C
*(i, i + 4,) (i, i +3) SAH-MPERs*

XLDKXASLWNWFNITNXLWXIK  90
EXDKWXSLWNWFNITNXLWXIK  91
ELXKWAXLWNWFNITNXLWXIK  92
ELDXWASXWNWFNITNXLWXIK  93
XLDKXASLWNWFNXTNXLWYIK  94
EXDKWXSLWNWFNXTNXLWYIK  95
ELXKWAXLWNWFNXTNXLWYIK  96
ELDXWASXWNWFNXTNXLWYIK  97

FIG. 12D
*SAH-MPERs of differential length and crosslink compositions*

NWFNITN*LWXIKKKK  98
NWFNITN*LW#IKKKK  99
NWFNITNXLWXIKKKK  100
XLDKXASLWNWFNITN*LWXIKKKK  101
EXDKWXSLWNWFNITN*LWXIKKKK  102
ELXKWAXLWNWFNITN*LWXIKKKK  103
ELDXWASXWNWFNITN*LWXIKKKK  104
ELDKXASLXNWFNITN*LWXIKKKK  105

Non-natural amino acid substitutions:

| Sequence | Seq ID No |
|---|---|
| ELDKWASLWNW-LMePhe-NITNWLWYIK | 106 |
| ELDKWASLWNW-DMePhe-NITNWLWYIK | 107 |
| ELDKWASLWNW-LβPhe-NITNWLWYIK | 108 |
| ELDKWASLWNW-DβPhe-NITNWLWYIK | 109 |
| ELDKWASLWNW-LHfe-NITNWLWYIK | 110 |
| ELDKWASLWNW-DHfe-NITNWLWYIK | 111 |
| ELDKWASLWNW-LIdc-NITNWLWYIK | 112 |
| ELDKWASLWNW-LNal-NITNWLWYIK | 113 |
| ELDKWASLWNW-DNal-NITNWLWYIK | 114 |
| ELDKWASLWNW-LPhg-NITNWLWYIK | 115 |
| ELDKWASLWNW-DPhg-NITNWLWYIK | 116 |
| ELDKWASLWNW-LTic-NITNWLWYIK | 117 |
| ELDKWASLWNW-DTic-NITNWLWYIK | 118 |
| ELDKWASLWNW-DTiq-NITNWLWYIK | 119 |
| ELDKWASLWNW-LPhe-NITNWLWYIK | 120 |
| ELDKWASLWNW-DPhe-NITNWLWYIK | 121 |
| ELDKWASLWNW-Atc-NITNWLWYIK | 122 |
| ELDKWASLWNW-Aic-NITNWLWYIK | 123 |
| ELDKWASLWNW-L2Igl-NITNWLWYIK | 124 |
| ELDKWASLWNW-D2Igl-NITNWLWYIK | 125 |
| ELDKWASLWNW-LBip-NITNWLWYIK | 126 |
| ELDKWASLWNW-DBip-NITNWLWYIK | 127 |
| ELDKWASLWNW-Bzg-NITNWLWYIK | 128 |

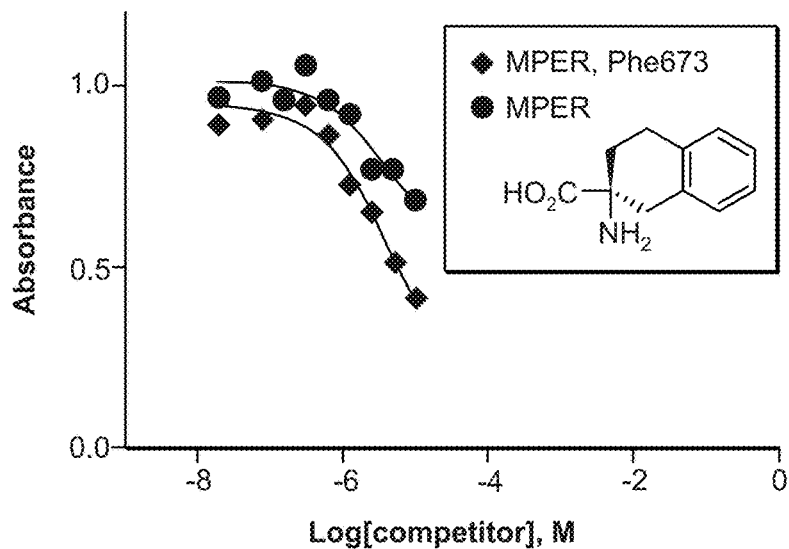

FIG. 15E

| IC50 nM | enfuvirtide$_{(638-673)}$ | SAH-gp41$_{(638-673)}$(D) | SAH-gp41$_{(638-673)}$(G) | SAH-gp41$_{(638-673)}$(D,G) | SAH-gp41$_{(638-673)}$(D,H) |
|---|---|---|---|---|---|
| HXBc2 | 446 +/- 191 | 30 +/- 12 | 802 +/- 66 | 978 +/- 540 | 146 +/- 58 |
| ADA | 762 +/- 492 | 129 +/- 51 | 600 +/- 194 | >3000 nM | 161 +/- 34 |
| HXBc2P 3.2 | 330 +/- 103 | 77 +/- 6 | 662 +/- 38 | 833 +/- 441 | 87 +/- 29 |
| A-MLV | >3000 nM | >3000 nM | >3000 nM | >3000 nM | >3000 nM |

FIG. 17A

```
626 MTWMEWDREINNYTSLIHSLIEESQNQQEKNEQELLELDKWASLWNWF 673
    fgabcdefgabcdefgabcdefgabcdefgabcdefgabcdefgabcd
               YTSLIHSLIEESQNQQEKNEQELLELDKWASLWNWF Enfuvirtide
    MTWMEWDREINNYTSLIHSLIEESQNQQEKNEQELLE            T649v
     SWETWEREIENYTRQIYRILEESQEQQDRN                  Sifuvirtide
    MTWMEWDREINNYTSLIHSLIEESQNQQEK                   T-2410
    TTWEEWDREINEYTSRIESLIRESQEQQEK                   T-2429
    MTWMAWDRAIANYAALIHALIEAAQNQQEK                   T-2638
    TTWEAWDRAIAEYAARIEALIRASQEQQEK                   T-290676
    TTWEAWDRAIAEYAARIEALIRAAQEQQEK                   T-2635
         SWETWEREIENYTRQIYRILEESQE

FIG. 18A

SAS-gp41 Peptide | Carrier Protein

| Week | Day | Procedure |
|---|---|---|
| 0 | 0 | Prebleed |
| 0 | 0 | Inoculate* |
| 2 | 14 | 20 ml serum |
| 4 | 29 | Inoculate^ |
| 4 | 31 | Bleed |
| 6 | 44 | Bleed |
| 8 | 57 | Inoculate^ |
| 10 | 72 | Bleed |
| 12 | 85 | Inoculate^ |
| 14 | 99 | Bleed |

* KLH-Peptide in Complete Freund's; 500 µg/rabbit
^ KLH-Peptide in Incomplete Freund's; 250 µg /rabbit

FIG. 19B

| Group | Animal | SAH-HR2 Titer: 1/dilution | | | | | |
|---|---|---|---|---|---|---|---|
| | | Week | | | | | |
| | | 0 | 2 | 4 | 6 | 10 | 14 |
| 1: SAH-HR2 | 160 | <50 | 96 | 1240 | 15800 | 333000 | 270000 |
| | 161 | <50 | 403 | 195000 | 776000 | 712000 | 514000 |
| | 162 | <50 | 247 | 2010 | 9220 | 516000 | 718000 |

| Group | Animal | HR2(626-662) Titer: 1/dilution | | | | | |
|---|---|---|---|---|---|---|---|
| | | Week | | | | | |
| | | 0 | 2 | 4 | 6 | 10 | 14 |
| 2: HR2 (626-662) | 163 | <50 | <50 | <50 | <50 | 9040 | 108000 |
| | 164 | <50 | 1700 | 8780 | 16000 | 62300 | 89800 |
| | 165 | <50 | <50 | 23900 | 105000 | 353000 | 660000 |

FIG. 19C

| Group | Animal | HR2(626-662) Titer: 1/dilution | | | | | |
|---|---|---|---|---|---|---|---|
| | | Week | | | | | |
| | | 0 | 2 | 4 | 6 | 10 | 14 |
| 1: SAH-HR2 | 160 | <50 | <50 | 248 | 678 | 22400 | 160000 |
| | 161 | <50 | <50 | <50 | 90 | 2570 | 4580 |
| | 162 | <50 | <50 | <50 | 427 | 198000 | 547000 |

| Group | Animal | SAH-HR2 Titer: 1/dilution | | | | | |
|---|---|---|---|---|---|---|---|
| | | Week | | | | | |
| | | 0 | 2 | 4 | 6 | 10 | 14 |
| 2: HR2 (626-662) | 163 | <50 | <50 | <50 | <50 | 196 | 656 |
| | 164 | <50 | 65 | 162 | 487 | 3280 | 6400 |
| | 165 | <50 | <50 | <50 | 263 | 6620 | 14100 |

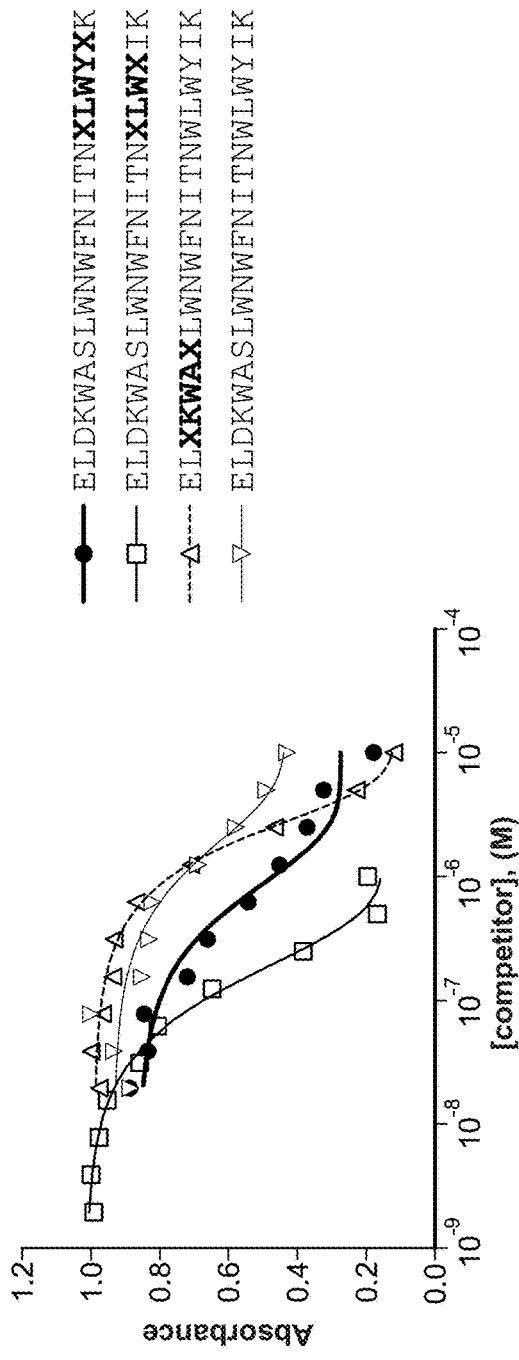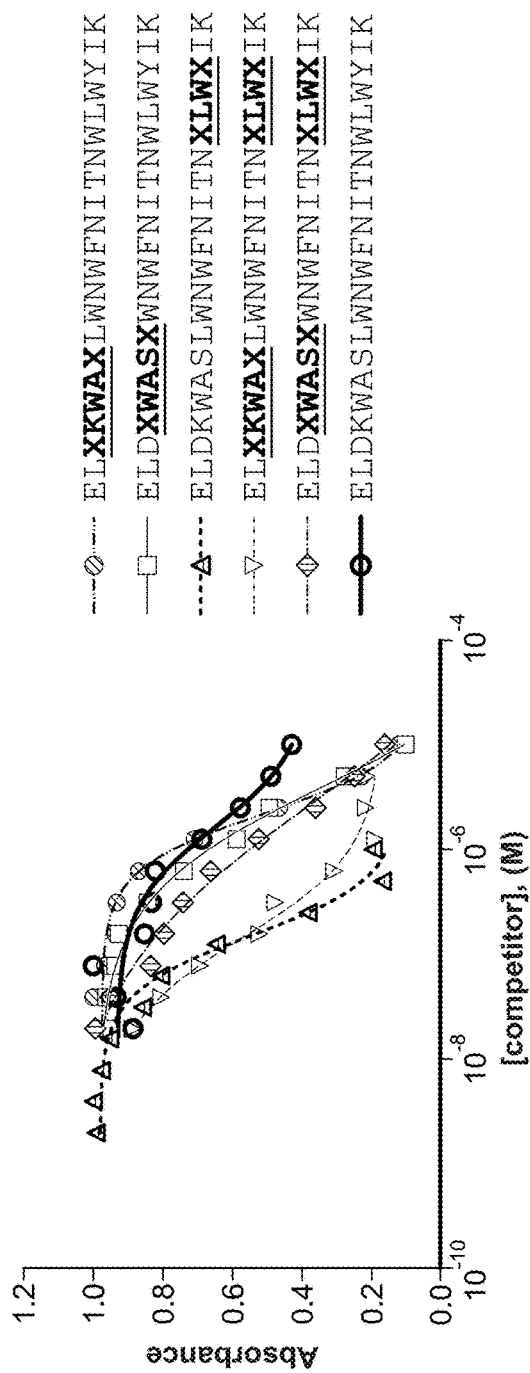
FIG. 21A
FIG. 21B

| SAH-RSV HR2 Sequences | SEQ ID |
|---|---|
| FXASIXQVNEKINQSLAFIRKSDELLHNVNAGKST | 141 |
| FDXSISXVNEKINQSLAFIRKSDELLHNVNAGKST | 142 |
| FDAXISQXNEKINQSLAFIRKSDELLHNVNAGKST | 143 |
| FDASISQVNEKINQSLAFIRKSXELLXNVNAGKST | 144 |
| FDASISQVNEKINQSLAFIRKSDXLLHXVNAGKST | 145 |
| FDASISQVNEKINQSLAFIRKSDEXLHNXNAGKST | 146 |

- ☐ RSV-wild type
- ○ SAH-RSV C-term (ELL)
- ◆ SAH-RSV N-term (ISQ)

FIG. 24

```
SEQ ID NO: 1
MRVKEKYQHL WRWGWRWGTM LLGMLMICSA TEKLWVTVYY GVPVWKEATT TLFCASDAKA
YDTEVHNVWA THACVPTDPN PQEVVLVNVT ENFNMWKNDM VEQMHEDIIS LWDQSLKPCV
KLTPLCVSLK CTDLKNDTNT NSSSGRMIME KGEIKNCSFN ISTSIRGKVQ KEYAFFYKLD
IIPIDNDTTS YKLTSCNTSV ITQACPKVSF EPIPIHYCAP AGFAILKCNN KTFNGTGPCT
NVSTVQCTHG IRPVVSTQLL LNGSLAEEEV VIRSVNFTDN AKTIIVQLNT SVEINCTRPN
NNTRKRIRIQ RGPGRAFVTI GKIGNMRQAH CNISRAKWNN TLKQIASKLR EQFGNNKTII
FKQSSGGDPE IVTHSFNCGG EFFYCNSTQL FNSTWFNSTW STEGSNNTEG SDTITLPCRI
KQIINMWQKV GKAMYAPPIS GQIRCSSNIT GLLLTRDGGN SNNESEIFRP GGGDMRDNWR
SELYKYKVVK IEPLGVAPTK AKRRVVQREK RAVGIGALFL GFLGAAGSTM GAASMLTVQ
ARQLLSGIVQ QQNNLLRAIE AQQHLLQLTV WGIKQLQARI LAVERYLKDQ QLLGIWGCSG
KLICTTAVPW NASWSNKSLE QIWNHTTWME WDREINNYTS LIHSLIEESQ NQQEKNEQEL
LELDKWASLW NWFNITNWLW YIKLFIMIVG GLVGLRIVFA VLSIVNRVRQ GYSPLSFQTH
LPTPRGPDRP EGIEEEGGER DRDRSIRLVN GSLALIWDDL RSLCLFSYHR LRDLLLIVTR
IVELLGRRGW EALKYWWNLL QYWSQELKNS AVSLLNATAI AVAEGTDRVI EVVQGACRAI
RHIPRRIRQG LERILL

SEQ ID NO: 2 YU2 mutant
MRATEIRKNY QHLWKGGTLL LGMLMICSAA EQLWVTVYYG VPVWKEATTT LFCASDAKAY
DTEVHNVWAT HACVPTDPNP QEVKLENVTE NFNMWKNNMV EQMHEDIISL WDQSLKPCVK
LTPLCVTLNC TDLRNATNTT SSSWETMEKG EIKNCSFNIT TSIRDKVQKE YALFYNLDVV
PIDNASYRLI SCNTSVITQA CPKVSFEPIP IHYCAPAGFA ILKCNDKKEN GTGPCTNVST
VQCTHGIRPV VSTQLLLNGS LAEEEIVIRS ENFTNNAKTI IVQLNESVVI NCTRPNNNTR
KSINIGPGRA LYTTGEIIGD IRQAHCNLSK TQWENTLEQI AIKLKEQFGN NKTIIFNPSS
GGDPEIVTHS FNCGGEFFYC NSTQLFTWND TRKLNNTGRN ITLPCRIKQI INMWQEVGKA
MYAPPIRGQI RCSSNITGLL LTRDGGKDTN GTEIFRPGGG DMRDNWRSEL YKYKVKIEP
LGVAPTKAKR RVVQREKRAV GLGALFLGFL GAAGSTMGAA SITLTVQARQ LLSGIVQQQN
NLLRAIEAQQ HLLQLTVWGI KQLQARVLAV ERYLRDQQLL GIWGCSGKLI CTTTVPWNTS
WSNKSLNEIW DNMTWMKWER EIDNYTHIIY SLIEQSONQQ EKNEQELLAL DKWASLWNWF
DITKWLWYIK IFIMIVGGLI GLRIVFVVLS IVNRVRQGYS PLSFQTHLPA QRGPDRPDGI
EEEGGERDRD RSGPIVDGFL AIIWVDLRSL CLFSYHRLRD LLIVTRIVE LLGRRGWGVL
KYWWNLLQYW IQELKNSAVS LLNATAIAVA EGTDRVIEIL QRAFRAVLHI PVRIRQGLER
ALL
```

HYDROCARBON STAPLED STABILIZED ALPHA-HELICES OF THE HIV-1 GP41 MEMBRANE PROXIMAL EXTERNAL REGION

REFERENCE TO RELATED APPLICATIONS

This application is a 35 U.S.C. §371 U.S. national entry of International Application PCT/US2010/039223 (WO 2010/148335) having an International filing date of Jun. 18, 2010 which is related to PCT patent application PCT/US2009/000438, International Filing Date Jan. 23, 2009 entitled "Compositions and Methods for the Treatment of Viral Infections", both of which are incorporated herein by reference in its their entirety. This application claims priority to U.S. Provisional Patent Application Ser. No. 61/218,209 filed on Jun. 18, 2009, which is incorporated herein by reference in its entirety.

STATEMENT OF RIGHTS TO INVENTIONS MADE UNDER FEDERALLY SPONSORED RESEARCH

This invention was made with government support under grant number R01AI084102 awarded by The National Institutes of Health. The government has certain rights in the invention.

BACKGROUND

The molecular process of viral fusion, in which viral coat proteins recognize and bind to surface receptors of the host cell, is a critical target in the prevention and treatment of viral infections. Upon recognition of the viral glycoprotein by host cellular receptors, viral fusion proteins undergo conformational changes that are essential to viral fusion and infection. A series of hydrophobic amino acids, located at the N- and C-termini organize to form a complex that pierces the host cell membrane. Adjacent viral glycoproteins containing two amphipathic heptad repeat domains fold back on each other to form a trimer of hairpins, consisting of a bundle of six α-helices which is referred to as a spike. Each of the glycoproteins of the trimer is tethered to the viral surface by a membrane-proximal ectodomain region (MPER). This six-helix bundle motif is highly conserved among many viral families, including Filovirus (ebola), (Malashkevich, V. N., et al., PNAS, 1999. 96: 2662-2667; Weissenhorn, W., et al., Molecular Cell, 1998. 2(5): p. 605-616), Orthomyxovirus (influenza) (Wilson, I. A., J. J. Skehel, and D. C. Wiley, Nature, 1981. 289: 366-37; Bullough, P. A., et al., Nature, 1994. 371(6492): p. 37-43), Coronavirus (SARS) (Xu, Y. H., et al. Journal of Biological Chemistry, 2004. 279: 49414-49419), Paramyxovirus (HRSV) (Zhao, X., et al., PNAS, 2000. 97: 14172-14177) and Retrovirus (HIV) (Chan, D. C., et al., Cell, 1997. 89: 263-27; Weissenhorn, W., et al., Nature, 1997. 387: 426-430).

Vaccines can provide an effective method to prevent viral infection. However, selection and/or generation of an appropriate viral antigen is not a trivial undertaking. The challenge of vaccine development is especially difficult for the prevention of infection by viruses with greater structural diversity and/or that undergo rapid mutation. Substantial challenges to vaccine development arise from many aspects of HIV-1 biology including viral sequence diversity of HIV proteins of which the virion surface gp160 spike protein is an example (Korber, B., et al. 2001. Evolutionary and immunological implications of contemporary HIV-1 variation. Br. Med. Bull. 58, 19-42). As in the general viral fusion steps described above, gp160 is synthesized as a precursor, cleaved by furin-like enzymes in the trans golgi into gp120 and gp41 subunits that noncovalently associate, and assembled into heterotrimers. gp120 binds to cell-surface CD4, then undergoes conformational change revealing a coreceptor attachment site (Feng et al., 1996. HIV-1 entry co-factor: functional cDNA cloning of a seven-transmembrane, G protein coupled receptor. Science 272, 872-877) whose ligation in turn induces structural rearrangements within the transmembrane gp41 subunit to fuse viral and host cell membranes (Chan et al., 1997. Core structure of gp41 from the HIV envelope glycoprotein. Cell 89, 263-273.). gp160 is extensively glycosylated, displays prominent variable loop segments, exists in several conformational states, and is proteolytically labile. As a result antibody responses to HIV tend to be strain specific, and vaccines to such epitopes are not substantially useful in the prevention of HIV infection.

Naturally occurring viral cross-species neutralizing antibodies are rarely elicited against conserved structural elements that are typically shielded, difficult to access, or transient, in HIV infection as well as other viral infections. Not surprisingly, only a handful of human broadly neutralizing antibodies (BNAbs) have been identified to date against HIV (reviewed in Douek et al., 2006. The rational design of an AIDS vaccine. Cell 124, 677-681). Those BNAbs with the greatest viral clade and strain breadth, including the monoclonal antibodies 2F5 and 4E10 (derived from immortalized B cells of HIV-1-infected individuals) and Z13e1 (selected from an affinity-matured phage display library using bone marrow RNA derived from a clade B-infected individual), each targets the membrane-proximal ectodomain region (MPER) of gp41 (Nelson et al., An affinity enhanced neutralizing antibody against the MPER of human immunodeficiency virus type 1 (HIV-1) gp41 recognizes an epitope between those of 2F5 and 4E10. J. Virol. 81, 4033-4043). The MPER, although accessible to antibody, rarely, if ever, elicits BNAbs during natural infection.

SUMMARY OF THE INVENTION

The invention provides structurally constrained viral peptides, particularly HIV based peptides, and methods of use of those peptides as therapeutic and prophylactic agents.

In an embodiment, the invention provides structurally constrained peptides having 3 to 22 amino acids of an MPER domain. In certain embodiments, the 3 to 22 amino acids of the MPER domain can be contiguous amino acids in the primary sequence of the peptide. In certain embodiments, the amino acids are adjacent to each other e.g., be present on the same face of the helix, in at least one native state of the peptide sequence in the context of the full length protein. For example, the adjacent amino acids can be present in a single stacked column of amino acids in a helix, or in adjacent stacks of amino acids in a single face of the structured helix. In an embodiment, the structurally constrained peptide includes at least one modification from the group consisting of: hydrocarbon staple, amino acid mutation, and non-natural amino acid incorporation. In certain embodiments, the structurally constrained peptide includes 2, 3, 4, 5 or more modifications. In certain embodiments, the constrained peptide comprises various hydrocarbon staples including, but not limited to, pairing selected from the group consisting of an R3-S6 pairing, an R6-S3 pairing, an R3-S5 pairing, and an R5-S3 pairing.

In an embodiment, 3 to 22 amino acids of MPER domain comprises at least 3 contiguous amino acids, or at least two amino acids on a single face of a helix, or at least two interacting face amino acids; or a conservative substitution thereof. A single face of a helix comprises one, two, three, or four adjacent stacked columns of amino acids wherein the stacked columns of amino acids are defined by positions a, d, and g; positions b and e; or positions c and f; in an alpha helix having 7 amino acids per two turns wherein the amino acids are consecutively and serially assigned positions a-g (see, e.g., FIG. 3); and positions a and d; positions b and e; or positions c and f in a $3^{10}$ helix having 2 amino acids per two turns wherein the amino acids are consecutively and serially assigned positions a-f; or homologues thereof.

The invention provides MPER amino acid sequences for use in the invention. The structurally constrained MPER peptides of the invention include at least amino acids 10-22 of SEQ ID NO: 137 (ELDKWASLWNWFNITNWLWYIK) (e.g., with 1, 2, 3, 4, 5, 6, 7, 8, or 9 additional amino acids of the sequence) comprising a hydrocarbon staple between positions 17 and 20 and optionally a hydrocarbon staple between positions 3 and 7 (e.g., SEQ ID NO: 85, 92, 98-100, and 103); at least 3 contiguous amino acids, or at least two amino acids on a single face of a helix, or at least two interacting face amino acids of an amino acid sequence selected from the group consisting of amino acids 37-57 of SEQ ID NO: 17-23; amino acids 19-36 of SEQ ID NO: 50-57 and 64-70; SEQ ID NO: 24-25, SEQ ID NO: 41-43, SEQ ID NO: 75-128, and SEQ ID NO: 135-140; or homologues thereof. The structurally constrained peptides of the invention can include an MPER sequence only, or an MPER sequence flanked on the C-terminus, or the N-terminus, or both with other amino acid sequences. The peptides provided by the invention can further include non-amino acid modifications in addition to modifications to structurally constrain the peptides. For example, peptides can include functional groups for targeting of the peptides in vivo, or to alter the pharmacokinetic and/or pharmacodynamic properties of the peptide. Such modifications are known in the art.

Amino acid positions that constitute a stacked column of amino acids is defined by positions corresponding to positions on a sequence provided by SEQ ID NO: 1, HIV gp-160. The sequence of the structurally constrained peptide can be aligned with the sequence of SEQ ID NO: 1, particularly for HIV MPER domains. Methods for performing sequence alignments are well known to those of skill in the art. Further, corresponding amino acids in helixes can be determined using any of a number of publicly available coil detection programs. In reference to the sequence provided in SEQ ID NO: 1, the stacked columns of amino acids include, for example, the following groups of amino acids Glu-662, Lys-665, Trp-666, Leu-669, and Trp-672; Leu-663, Trp-666, Ala-667, and Trp-670; Asp-664, Ala-667, Ser-668, and Asn-671; Lys-665, Ser-668, Leu-669, and Trp-672; Trp-666, Leu-669, and Trp-670; Ala-667, Trp-670, and Asn-671; Ser-668, Asn-671, and Trp-672; Ile-675, Trp-678, and Tyr-681; Asn-676, Leu-679, and Ile-682; Thr-677, Trp-680, and Lys-683; Ile-675, Trp-678, Trp-679, and Ile-682; Thr-676, Leu-679, Trp-680, and Lys-683; Asn-677, Trp-680, Tyr-681; Trp-678, Tyr-681, Ile-682; Leu-679, Ile-682, and Lys-683; or homologues thereof.

The invention also provides peptides having at least 3 interacting face amino acids or a conservative substitution of an interacting face amino acid, from the peptide sequence of SEQ ID NO: 1, or homologues thereof. The interacting face of the peptide is a single face of the peptide wherein the interacting face amino acids are selected from positions corresponding to amino acids Trp-672, Phe-673, Asn-674, Ile-675, Thr-676, Leu-679, and W-680 of SEQ ID NO: 1. These amino acid positions are known to include variations in other HIV sequences. Other possible amino acids for the indicated positions include Asn/Asp/Ser-674, and Thr/Ser-676.

The structurally constrained peptides provided by the invention can include additional amino acid sequences, either other sequences from gp160 (e.g., SEQ ID NO: 1) that naturally occur adjacent to the MPER domain, or sequences from other portions of SEQ ID NO: 1, other proteins, or synthetic sequences. The additional amino acid sequences may or may not be structurally constrained. In certain embodiments, the invention provides a structurally constrained MPER sequence operably linked to an HR2 sequence. In certain embodiments of the invention, the HR-2 peptides can be used alone without being linked to an MPER sequence. For example, the n-terminus of the MPER sequence can be operably linked to the C-terminus of the HR-2 sequence, for example as shown in FIGS. 2C, 7B, and 9. The invention provides for the use of HR-2 sequences in conjunction with MPER sequences, having at least 3 contiguous amino acids of an HR-2 peptide, or at least two amino acids on a single face of a helix of an HR-2 peptide, or at least two interacting face amino acids of an HR-2 peptide; or a conservative substitution thereof. A single face of a helix of the HR-2 peptide includes one, two, three, or four adjacent stacked columns of amino acids wherein the stacked column of amino acids is defined by positions a, d, and g; positions b and e; or positions c and f; in an alpha helix, wherein position a is an amino acid in the helix, and the amino acids are consecutively and serially assigned letters a through g in an alpha helix; or homologues thereof. For example, an alpha-helix and a stacked column of amino acids of a peptide is defined as positions 1, 4, 5, 8, 11, 12, 15, 18, 19, 22, 25, 26, 29, 32, and 33; or positions 2, 5, 6, 9, 12, 13, 16, 19, 20, 23, 26, 27, 30, 33, and 34; or positions 3, 6, 7, 10, 13, 14, 17, 20, 21, 24, 27, 28, 31, and 34; or positions 4, 7, 8, 11, 14, 15, 18, 21, 22, 25, 28, 29, 32, and 35; or positions 5, 8, 9, 12, 15, 16, 19, 22, 23, 26, 29, 30, and 33; or positions 6, 9, 10, 13, 16, 17, 20, 23, 24, 27, 30, 31, and 34; or 7, 10, 11, 14, 17, 18, 21, 24, 25, 28, 31, 32, and 35 SEQ ID NO: 10-23, SEQ ID NO: 26-40, SEQ ID NO: 45-48, SEQ ID NO: 58-63, SEQ ID NO: 71-74, and amino acids 1-25 of SEQ ID NO: 49-57, amino acids 1-25 of SEQ ID NO: 64-70; and the sequence of SEQ ID NO: 76-128 and 135-140; or homologues thereof. As provided herein, a single face of a peptide having an alpha-helical structure can include one, two, three, or four adjacent stacked columns of amino acids.

The invention further provides peptides having the interacting face amino acids of the HR-2 peptide. The interacting face is an example of one face on the helical peptides provided by the instant invention. Amino acids in interacting faces include amino acids corresponding to positions Thr-627, Trp-628, Trp-631, Asp-632, Arg-633, Ile-635, Tyr-638, Ile-642, Leu-645, Ile-646, Ser-649, Gln-650, Gln-652, Gln-653, Glu-654, Lys-655, Asn-656, Glu-657, Glu-659, Leu-660, Glu-662, and Leu-663 on SEQ ID NO: 1, or may be further limited to amino acids corresponding to positions Trp-628, Trp-631, Ile-635, Tyr-638, Ile-642, Leu-645, Ser-649, Gln-652, Asn-656, Glu-659, and Leu-663 on SEQ ID NO: 1.

The invention provides examples of HR-2 peptides, for use with or without MPER peptide sequences. In the structurally constrained peptides of the invention, the HR-2 peptide sequences that can be used in the invention include amino acid sequences that have at least 3 contiguous amino acids, or at least two amino acids on a single face of a helix, or at least two interacting face amino acids of an amino acid sequence such as those provided by amino acids 37-57 of SEQ ID NO: 17-23; amino acids 19-36 of SEQ ID NO: 50-57 and 64-70; SEQ ID NO: 24-25, SEQ ID NO: 41-43, SEQ ID NO: 75-128, and SEQ ID NO: 135-140 operably linked either directly or indirectly to the carboxy-terminus to a peptide that comprises at least 3 contiguous amino acids, or at least two amino acids on a single face of a helix, or at least two interacting face amino acids of an amino acid sequence selected from the group consisting of SEQ ID NO: 10-23, SEQ ID NO: 26-40, SEQ ID NO: 45-48, SEQ ID NO: 58-63, SEQ ID NO: 71-74, and amino acids 1-25 of SEQ ID NO: 49-57, and amino acids 1-25 of SEQ ID NO: 64-70.

The invention provides any of the structurally constrained peptides of the invention in a pharmaceutically acceptable carrier. The invention further provides a peptide of the invention in a pharmaceutical carrier in a unit dosage form. In certain embodiments of the invention, the pharmaceutically acceptable carrier includes a vaccine adjuvant.

The invention provides structurally constrained peptides of the invention functionally linked to a carrier protein. In certain embodiments, the carrier protein includes a protein to alter the pharmacokinetic and/or pharmacokinetic properties of the structurally constrained peptide. In certain embodiments, the carrier protein can have adjuvant properties. In certain embodiments, the structurally constrained peptide of the composition is functionally linked to a carrier protein in a specified orientation as established by a site-directed linkage.

The invention further provides antibodies that specifically bind any of the structurally constrained peptides of the invention. In certain embodiments, the antibody is a neutralizing antibody, for example a broadly neutralizing antibody. Antibodies can include any naturally or non-naturally occurring antibody format including, but not limited to, polyclonal antibody, monoclonal antibody, single chain antibody, Fab molecules, Fab proteins, univalent antibodies, bi-specific antibodies, and humanized antibodies. In certain embodiments, the antibodies of the invention do not include antibodies having the paired CDRs of known broadly neutralizing antibodies such as 2F5, Z13e1, and 4E10 monoclonal antibodies. However, it is understood that the antibodies of the invention can include one or more CDRs from known broadly neutralizing antibodies so long as all of the CDRs are not identical.

The invention further provides methods for making and/or selecting antibodies that specifically bind to a structurally constrained peptide of the invention. Methods for making antibodies to specific antigens are well known in the art. For example, the invention provides the method for making an antibody including administering a structurally constrained peptide of the invention, with or without an adjuvant, to a subject to promote an immune response. It is understood that the antibodies that are raised in the subject are polyclonal antibodies. However, methods for preparation of monoclonal antibodies from an immunized subject are well known in the art. Upon preparation of a monoclonal antibody, sequences of the CDRs can be determined. This allows for manipulation of the epitope binding portion of the antibody into various formats. It is further understood that antibodies can be obtained by library screening methods rather than by immunization of a subject. Such methods are well known in the art. Again, CDRs can be isolated from antibodies selected from libraries for manipulation and insertion into the desired antibody format. Antibodies generated by the methods of the invention can include, but are not limited to, polyclonal antibody, monoclonal antibody, single chain antibody, Fab molecules, Fab proteins, univalent antibodies, bi-specific antibodies, and humanized antibodies. Methods for isolation and purification of antibodies from a subject are well known in the art. The antibody can be isolated as a protein, or as a B-cell expressing an antibody.

The invention provides pharmaceutically acceptable compositions including an antibody of the instant invention. The pharmaceutically acceptable composition of the invention can be packaged in a unit dosage form.

The invention provides methods for the prevention, amelioration, or treatment of a viral infection, for example in a subject, by administration of a structurally constrained peptide of the invention or an antibody of the invention to the subject in a therapeutically effective amount. The method can further include one or more of identifying a subject as being in need of prevention, amelioration, or treatment of a viral infection, or monitoring the subject for the prevention, amelioration, or treatment of a viral infection. In certain embodiments, the viral infection includes HIV infection. In certain embodiments, the invention provides methods of prevention, amelioration, and treatment of viral infection where in the method includes at least one of inhibition or suppression of viral fusion or viral infectivity.

The invention provides for the preparation of a medicament including a structurally constrained peptide of the invention or an antibody that binds specifically thereto in a pharmaceutically acceptable carrier. The medicaments can be for the prevention and/or treatment of viral infection, particularly for HIV infection.

In certain embodiments, the invention provides kits including at least one of a structurally constrained peptide of the invention or an antibody of the invention and instructions for use.

Other embodiments of the invention will be understood base on the disclosure provided infra.

BRIEF DESCRIPTION OF THE DRAWINGS

FIGS. 1A-F show (A) a schematic of the domains of the gp41 glycoprotein with the amino acid sequence of the HR2 and MPER (amino acid 626 to 683 of SEQ ID NO: 1) domains below. The MPER domain sequence is underlined; and ribbon diagrams of the (B) HR2 (amino acids 626 to 661 of SEQ ID NO: 1) and (C) MPER domains (amino acids 662 to 683 of SEQ ID NO: 1) with the R groups of the amino acids indicated. (D) To infect the host cell, the indicated gp41 subunits adopt a continuum of structural configurations that are fleeting and partially masked. (E) Hydrocarbon stapling was applied to reinforce neutralization-competent structures and prevent their degradation in an effort to maximize immunogen exposure and neutralizing immune response, as illustrated for 4E10 and 2F5 antibody recognition of the natural MPER structure, and to (F) provide a peptide or antibody derived thereof that inhibits fusion by interfering with the interaction of the HR1 and HR2 domains.

FIG. 2 shows an amino acid sequences for (A) HIV-1 gp41 HR-1 (SEQ ID NO: 3-9), (B) HIV-1 gp41 HR-2 (SEQ ID NO: 10-16), and (C) HIV-1 gp41 HR2-MPER (SEQ ID NO: 17-23) domains from different HIV strains and an example of a homologous region in the HIV-1KR5086 virus (SEQ ID NO: 24) the SARS virus (SEQ ID NO: 25). Dashes indicate spaces inserted for proper alignment and do not indicate amino acids.

FIGS. 3A-B show the (A) HIV six-helix bundle and key interhelix interactions of the helices N36 and C34. One of the N36 and two C34 helices are faded for clarity. The helical wheel further illustrates key contacts among the helices based upon the a, b, c, d, e, f, g, nomenclature. (B) The fusogenic bundle formed by HR-analog domains from RSV, influenza, SARS and Ebola. The six-helix fusogenic bundle is highly conserved across many species.

FIG. 4 shows an exemplary synthetic design of a truncated SAH-gp41 compound (SEQ ID NO: 26), and SAH-gp41$_{(626-645)}$(A) (SEQ ID NO: 27). X=S5 amino acid, B=norleucine.

FIG. 5 illustrates the heptad repeat domain motif as applied to HIV gp41 (amino acids 626-662 of SEQ ID NO: 28) and associated preferred amino acid residues. Examples of sequence template from within the HIV-1 HR2 domain depicting the specific amino acid residues necessary to preserve the HR1 interaction are provided in (C, SEQ ID NO: 29) and (D, SEQ ID NO: 30). Thus, the positions indicated with a dash may be amenable to substitution/mutation without disruption of activity.

FIG. 6 shows the workflow that translates an embodiment of the invention into practice.

FIGS. 8A-D show exemplary combinations of helix-stabilizing crosslinks for the stabilization of alpha-helices formed at positions (A) i, and i+4 across one turn in the helix using two S5 amino acids; (B) i, and i+7, across two turns of the helix using one S8 and one R5 amino acid or one R8 and one S5 amino acid; (C) a double crosslink employing two i, i+4, two i, i+7, or one i, i+4 and one i, i+7 crosslink; and D) a triple crosslink employing any combination of i, i+4, i, i+7, or other crosslinks (e.g. i, i+3).

FIGS. 10A-B show various stapled HIV HR domains including (A) sequences of SAH-gp41 (SEQ ID NO: 44-45, 49) singly stapled peptides (e.g., N-term: Ac, FITC-βAla, Biotin-βAla; C-term: CONH$_2$, COOH) (SEQ ID NO: 46-48 and 50-57), (B) sequences of doubly and triply stapled SAH gp41 peptides, (e.g., N-term: Ac, FITC-βAla, Biotin-βAla; C-term: CONH$_2$, COOH). X=S5 amino acid, B=norleucine (SEQ ID NO: 58-74).

FIG. 12 shows exemplary staple positions for the alpha- and 3$_{10}$-helices of the MPER domain of gp41 inserting the stapling "S5" amino acid at (A, SEQ ID NO: 75-82) (i, i+4) positions, (B, SEQ ID NO: 83-89) (i, i+3) positions, and (C) both (i, i+4) and (i, i+3) positions (SEQ ID NO: 90-97). FIG. 12D shows exemplary staple positions in SAH-MPERs of differential length and staple compositions, including the use of (i, i+3) crosslinks that contain R3 and S6 crosslinking non-natural amino acids (SEQ ID NO: 98-105).

FIGS. 13A-C show (A) exemplary commercially available structurally constrained phenylalanine analogs; (B) shows the bound conformation of the MPER kink region and simulated constrained structures of the kink region using one of the Phe analogs; (C) shows the synthesized peptides comprised of amino acids 662-683 of SEQ ID NO: 1 in which F673 is replaced by a series of phenylalanine analogs (SEQ ID NOs: 106-128); (C) also shows the results from a 4E10 antibody competition binding ELISA assay, which indicates that the MPER construct containing an installed non-natural amino acid-based kink retains high affinity 4E10 binding, comparable to the native peptide.

FIGS. 15A-E show the activity of enfuvirtide and the structurally constrained peptides of the instant invention in an infectivity assay using HIV viral strains (A) HXBc2; unstapled peptide enfuvirtide (SEQ ID NO: 49) and stapled peptides, in order, SEQ ID NO: 51, 52, 65, and 66. (B) ADA; unstapled peptide enfuvirtide (SEQ ID NO: 49) and stapled peptides, in order, SEQ ID NO: 50, 52, 65, and 64. (C) HXBc2P 3.2; unstapled peptide enfuvirtide (SEQ ID NO: 49) and stapled peptides, in order, SEQ ID NO: 50, 52, 65, and 64. (D) control A-MLV viral strain; unstapled peptide enfuvirtide (SEQ ID NO: 49) and stapled peptides, in order, SEQ ID NO: 50, 52, 65, and 64; with the results summarized in the (E) table.

FIGS. 16H-I document that the structurally constrained peptides of the instant invention are specific to blocking HIV-1 infectivity as the control virus A-MLV is completely unaffected by treatment with the corresponding stapled peptides.

FIG. 18 shows (A) exemplary alternate conjugation sites for structurally constrained gp41 peptides to provide different antigen presentation orientations upon immunization relative to a carrier, such as a carrier protein and (B-D) three exemplary approaches to introduce a lipid recognition motif into SAH-MPER peptides to maximize immunologic response (S. M. Alam et al., *Proc Natl Acad Sci USA* 106, 20234 (2009); J. P. Julien et al., *J Virol* 84, 4136 (2010); E. M. Scherer, et al, *Proc Natl Acad Sci USA* 107, 1529 (2010)), including (B) incorporation of a myristoylated lysine and other lipopeptide conjugates (D. S. Watson, F. C. Szoka, *Vaccine* 27, 4672 (2009); H. Y. Xu et al., *J Virol* 84, 1076 (2010)) at the C-terminus of the MPER peptide, (C) expanding the hydrocarbon staple itself as a hydrophobic and lipidic moiety [e.g. install and derivatize an 11-carbon chain (i, i+7) staple using (S)-2-(4'-pentenyl) alanine and (R)-2-(4'-octenyl)alanine] and (D) generating MPER-coated liposomes[15] by incorporating a hexa-histidine motif at the C-terminus of SAH-MPER constructs for conjugation to lipid-NTA-Ni-containing liposomes (K. J. Oh et al., *J Biol Chem* 281, 36999 (2006); L. D. Walensky et al., *Mol Cell* 24, 199 (2006)).

FIG. 19 shows the results of an immunogenicity study in which SAH-HR2(A,F) and its corresponding unmodified peptide were upscaled for conjugation to KLH and then deployed in a rabbit immunization protocol using timed boosts according to the schedule depicted in (A), followed by ELISA analysis of the derived antisera against the corresponding antigen (B) and cross-antigen analysis (C). The results demonstrate that structured antigens that lock the peptidic motif into its native three dimensional shape not only generate more robust antibody responses, but without this structural stabilization, the resultant antisera are essentially unable to recognize the helical gp41 domain.

FIGS. 21A-21B show the results from 4E10 antibody competition binding ELISA assays using "S5"-crosslinked SAH-MPER peptides with (i, i+3), (i, i+4), and double (i, i+3), (i, i+4) staples. Specifically, FIG. 21A-B show the capacity of "S5"-substituted, singly stapled (i, i+4) or (i, i+3) peptides (SEQ ID NOs: 135, 136, 78, and 137), and doubly-stapled (i, i+4), (i, i+3), (SEQ ID NOs: 78, 77, 85, 92, 93, and 137) to effectively compete with the wild-type FITC-MPER peptide for 4E10 antibody binding, surpassing the activity of wild-type Ac-MPER peptide.

FIG. 23A-B show (A) exemplary hydrocarbon-stapled RSV HR2 domain peptides containing i, i+4 crosslinks (SEQ ID NO: 141-146) and (B) the results from fluorescence polarization binding analysis using FITC-SAH-RSV peptides and recombinant RSV 5-helix bundle.

FIG. 24 shows SEQ ID NO: 1 and SEQ ID NO: 2.

DETAILED DESCRIPTION

Figures 1D, 1E:
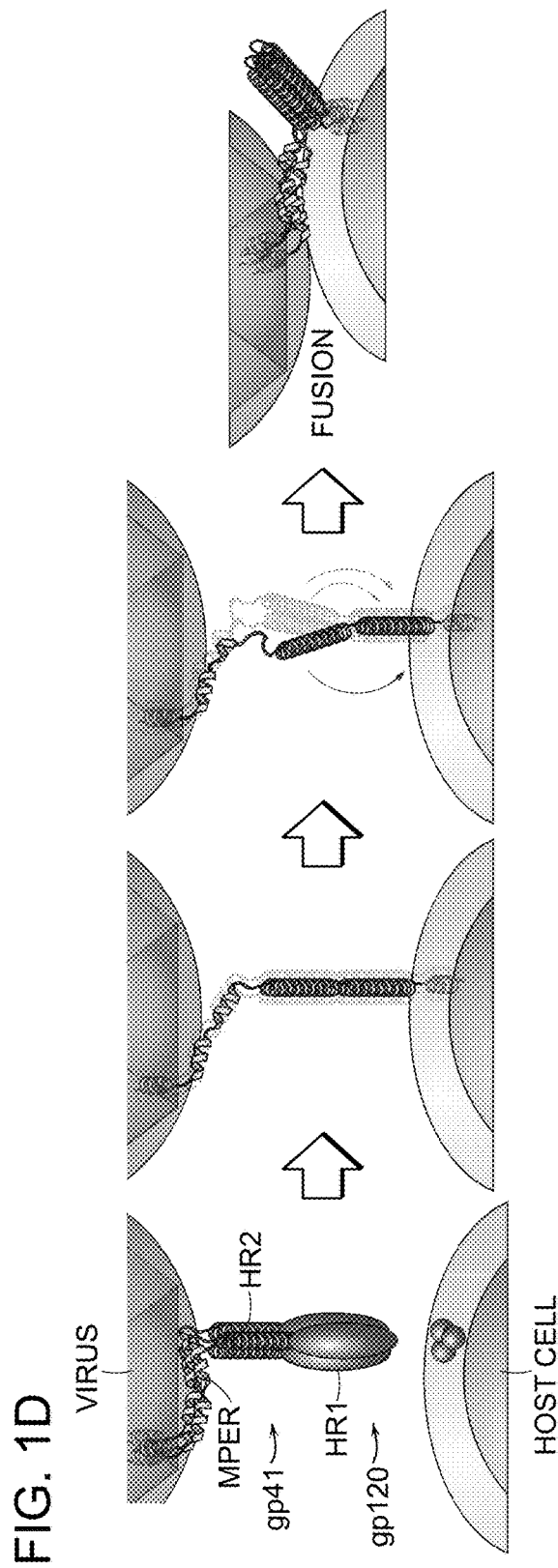

The present invention is directed to compositions, kits and methods utilizing structurally constrained viral peptides. The compositions are useful for treating and/or preventing viral infections. The compositions are useful as vaccines for the stimulation of an immune response in a subject. The compostions can also be used to generate antibodies against the structurally constrained peptides that are isolated and used as preventive and/or therapeutic agents. The antibodies can be isolated directly from the subject or laboratory animals for use in any of a number of applications including as a therapeutic agent. Alternatively, B cells can be collected from the subject or laboratory animals and fused to an immortalized cell, such as a myeloma cell, for the preparation of monoclonal antibodies.

The invention is based, at least in part, on the results provided herein demonstrating that hydrocarbon-stapled, alpha-helical viral peptides have excellent structural, proteolytic, acid, and thermal stability, and are highly effective in interfering with virus/cell fusion, strongly suggesting that an antibody that binds to the peptide will provide a broadly neutralizing antibody for the prevention or treatment of viral infection, particularly HIV infection and AIDS. Further, the peptides have superior pharmacologic properties in vivo compared to their unmodified counterparts, reducing the frequency and quantity of structurally constrained peptide that needs to be administered as compared to a native peptide sequence, and ensuring that antigenic exposure is sustained. In addition, by properly orienting the critical immunogenic motif to the immune system through directional synthetic conjugation, the peptides have superior capacity to elicit high titers of the relevant antibodies for neutralization.

The structurally constrained viral peptides provided herein include at least one heptad repeat domain-2 (HR-2) or at least one MPER domain. In certain embodiments, the peptides include both an HR domain and an MPER domain, or portions thereof.

In the compounds provided herein, the alpha helix HR-2 domain is stabilized with at least one molecular tether, e.g., hydrocarbon staple, but may include two, three or more hydrocarbon staples. The inclusion of multiple hydrocarbon staples is particularly suited for alpha helical peptides that are 20 or more amino acids in length. The inclusion of more than one (e.g., 2, 3, 4, 5, depending on the length of the peptide) hydrocarbon staples provides for exceptional structural, acid and thermal stability of the modified polypeptides, yielding bioactive peptides with strikingly enhanced pharmacologic properties in vivo.

In the compounds provided herein, the MPER domain is structurally constrained by one or more modifications of the native sequence. The alpha-helix and/or the $3_{10}$ helix of the MPER domain can be stabilized similarly to the HR-2 domain, using a molecular tether such as a hydrocarbon staple. The kink region between the two helices in the MPER domain can be stabilized by any of a number of chemical modifications including, but not limited to, a hydrocarbon staple or other molecular tether to promote or maintain the desired angle between the two helices or orient the helices relative to each other. Alternatively, or in addition, amino acid substitutions can be made in or adjacent to the kink region to include natural or non-natural amino acids to promote the desired structure of the kink, to promote or maintain the desired angle between the two helices or to orient the helices relative to each other. In an embodiment, at least one of the helices of the MPER domain includes a molecular tether such as a hydrocarbon staple to promote or maintain the helical nature of the domain. In another embodiment, both of the helices of the MPER domain include a molecular tether such as a hydrocarbon staple to promote or maintain the helical nature of the domain. In a embodiment, both of the helices of the MPER domain include a molecular tether such as a hydrocarbon staple, as well as a constrained phenylalanine analog, to promote or maintain the helical nature of the domain and reinforce the kink between the helices.

gp41 HR-2-derived peptides, T20 and T649V, based upon the sequences of residues 638-673 and residues 626-662, respectively, were prepared and the circular dichroism (CD) spectra determined at physiologic pH. The native peptides lack the characteristic minima at 222 nm and 208 nm that reflect α-helical structure in solution, indicating instead that they predominantly exist as random coils. Indeed, the calculated α-helical content (Forood, B., E. J. Feliciano, and K. P. Nambiar, *PNAS,* 1993. 90(3): p. 838-84; J. Martin Scholtz, *Biopolymers,* 1991. 31(13): p. 1463-1470; Lawless, M. K., et al., *Biochemistry,* 1996. 35(42): p. 13697-13708) was only ~25% for T20 and 14% for T649v. Thus, synthetic gp41-derived HR-2 peptides are predominantly disordered in solution, reflecting a significant loss of bioactive structure.

The MPER region, which is adjacent to the HR-2 region in HIV has been demonstrated to be the epitope for binding of at least three of the known broadly neutralizing antibodies effective to prevent and/or suppress HIV infection, 2F5, Z13e1, and 4E10 antibodies. (See FIG. 7 for epitope binding sites.) However, multiple attempts to use peptides from this region for immunization of subjects to generate neutralizing antibodies have not been successful (see, e.g., Penn-Nicholson et al., 2008. Assessment of antibody responses against gp41 in HIV-1-infected patients using soluble gp41 fusion proteins and peptides derived from M group consensus envelope. *Virology.* 2008 Mar. 15; 372: 442-456; Zwick et al., 2005. Anti-Human Immunodeficiency Virus Type 1 (HIV-1) Antibodies 2F5 and 4E10 Require Surprisingly Few Crucial Residues in the Membrane-Proximal External Region of Glycoprotein gp41 To Neutralize HIV-1. *J. Virol.,* 79:1252-1261, and references cited therein, all of which are incorporated by reference). Attempts to use the full length gp41 and/or gp120 proteins for the generation of BNAbs have been equally unsuccessful. Although antibodies that bind to the antigen used have been identified, the antibodies do not have a broad neutralizing function.

As demonstrated herein, and in the related PCT application PCT/US2009/000438 by the same inventor, which is hereby incorporated by reference, structurally constrained peptides based on the sequence of the HR-2 domain and a sequence traversing the HR-2 and MPER domains demonstrate substantially higher alpha-helicity, five helix bundle binding, antiviral activity, proteolytic and thermal stability, and more desirable pharmacokinetic and biodistribution properties than a comparable non-structurally constrained peptide, enfuvirtide, an approved last resort drug for the treatment of AIDS (SEQ ID NO: 1 aa 638-673). Enfuvirtide is a treatment of last resort for many reasons including the development of resistance, cost of goods, poor in vivo stability requiring frequent and high level subcutaneous dosing, lack of oral bioavailability, and the prominence of other classes of orally available drugs. Importantly, however, enfuvirtide offers the unique advantage of preventing infection, whereas the other classes of anti-HIV drugs are post-infection virus suppressors. As demonstrated herein, and in the related application, structurally constrained peptides are more effective in inhibiting infection in an in vitro assay than the unstructured enfuvirtide. Moreover, structured peptides were able to overcome resistance to enfuvirtide in an infectivity assay using enfuvirtide resistant HIV strains, were at least 10-fold more stable than enfuvirtide in vivo, and exhibited oral bioavailability.

These data demonstrate that the structured peptides of the instant invention more effectively mimic the structure of the viral spike than unstructured peptides. Therefore, the structurally constrained peptides provided herein should be effective at eliciting an immune response, preferably a broad neutralizing antibody immune response, against the viral antigen.

Definitions

As used herein, "adjuvant" for use with a structurally constrained peptide of the instant invention in a vaccine composition is understood as a substance that when mixed with an antigen or immunogen, or carrier-conjugated antigen or immunogen, helps deposit or sequester the injected material to increase antibody response. Adjuvants include Freund's complete and incomplete adjuvants, CpG-ODN, Imject Alum, Ribi adjuvant, and others known in the art.

An "agent" is understood herein to include a therapeutically active compound or a potentially therapeutic active compound. An agent can be a previously known or unknown compound. As used herein, an agent is typically a non-cell based compound, however, an agent can include a biological therapeutic agent, e.g., peptide or nucleic acid therapeutic, cytokine, antibody, etc.

As used herein, "AIDS" or "Acquired Immune Deficiency Syndrome" is understood as a disease characterized by HIV infection in conjunction with at least one AIDS related disorder including, but not limited to, opportunistic infections (e.g., cryptosporidiosis, microsporidiosis, *Mycobacterium avium* complex (MAC) and viruses, astrovirus, adenovirus, rotavirus and cytomegalovirus), *Pneumocystis* pneumonia, Kaposi's sarcoma, high grade B cell lymphomas such as Burkitt's lymphoma; or any other clinically acceptable indicators of AIDS or AIDS progression. Opportunistic infections associated with AIDS typically occur when the T-cell CD4 count drops below 200/mL. Methods of diagnosis of AIDS, such as HIV antibody, antigen, and PCR tests, and CD4 counts, are well known to those of skill in the art.

As used herein "amelioration" or "treatment" is understood as meaning to lessen or decrease at least one sign, symptom, indication, or effect of a specific disease or condition. For example, amelioration or treatment of HIV infection can be to reduce viral load, to increase CD4+ cell count, to delay or eliminate the onset of one or more AIDS related diseases including opportunistic infections (e.g., cryptosporidiosis, microsporidiosis, *Mycobacterium avium* complex (MAC) and viruses, astrovirus, adenovirus, rotavirus and cytomegalovirus), *Pneumocystis* pneumonia, Kaposi's sarcoma, high grade B cell lymphomas such as Burkitt's lymphoma; or any other clinically acceptable indicators of disease state or progression. Amelioration and treatment can require the administration of more than one dose of an agent, either alone or in conjunction with other therapeutic agents and interventions. Amelioration or treatment do not require that the disease or condition be cured.

Figure 11:
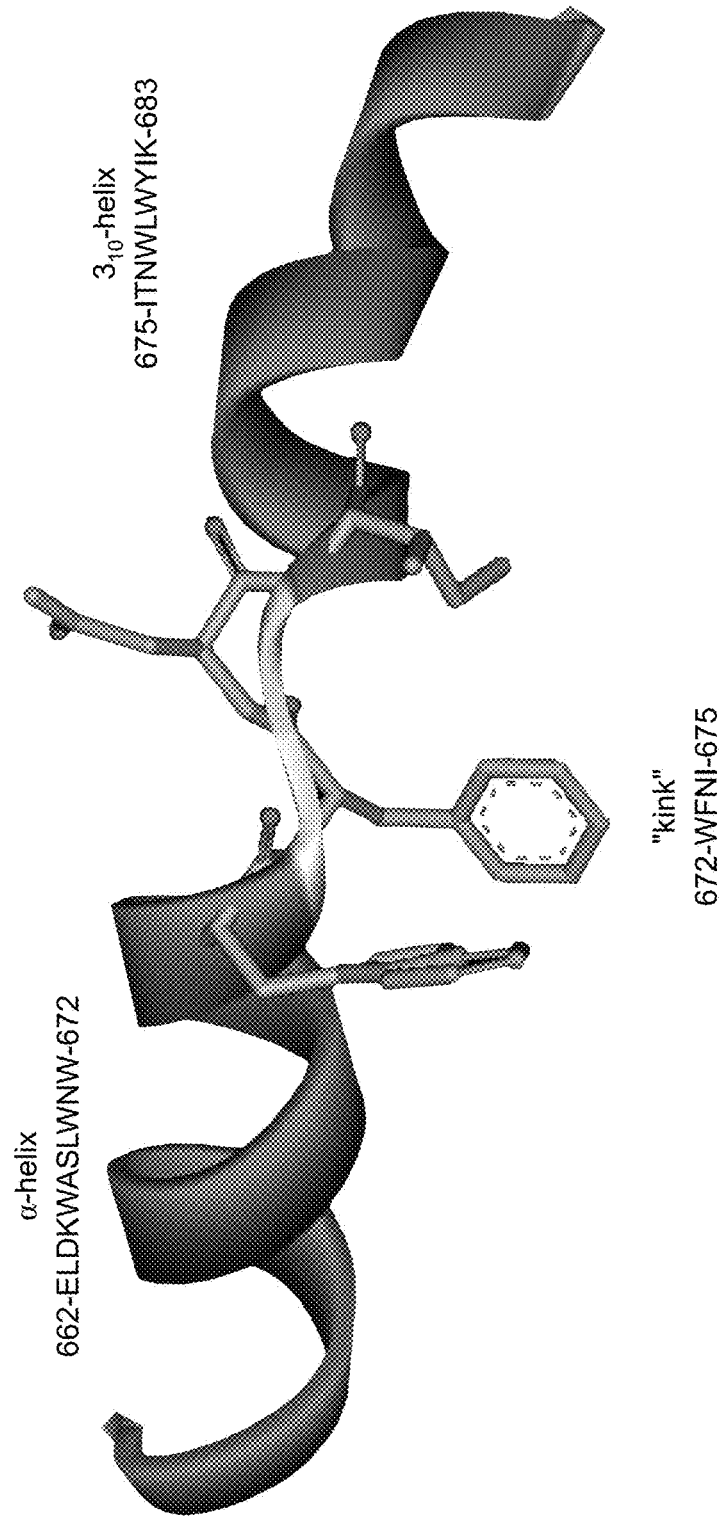
FIG. 11 shows a schematic of the three structural elements of the MPER region of gp41 (amino acids 662 to 683 of SEQ ID NO: 1), the alpha-helix from amino acid 662 to 672, the "kink" from amino acid 672 to 675 showing the R groups of the amino acids, and the 3$_{10}$-helix from amino acid 675 to 683. A 3$_{10}$ helix is a form of an alpha-helix where there are 3.0 residues per turn, forming a H-bonded loop containing 10 atoms. For example, a "standard" alpha helix can also be referred to as a 3.6$_{13}$ helix using this nomenclature.

The term "amino acid" refers to a molecule containing both an amino group and a carboxyl group. Suitable amino acids include, without limitation, both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)) as well as the naturally occurring and non-naturally occurring amino acids including beta-amino acids, prepared by organic synthesis or other metabolic routes and that can be applied for specialized uses such as increasing chemical diversity, functionality, binding capacity, structural mimesis, and stability (e.g. FIG. 11A).

The term "amino acid side chain" or "amino acid R group" refers to a moiety attached to the α-carbon in an amino acid. For example, the amino acid side chain or R group for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an alpha di-substituted amino acid, a beta-amino acid).

As used herein, an "antibody" includes any reactive fragment or fragments of naturally occurring and non-naturally occurring antibodies such as Fab molecules, Fab proteins, single chain polypeptides, or the multi-functional antibodies having binding affinity for the antigen. The term includes antibodies of all formats including IgG, IgA, IgM, and IgE. The term includes chimeric antibodies, altered antibodies, univalent antibodies, bi-specific antibodies, monoclonal antibodies, polyclonal antibodies, human antibodies, and humanized antibodies. Methods for preparing antibodies are well known in the art.

As used herein, "broadly neutralizing antibody" or "BNAb" is understood as an antibody obtained by any method that when delivered at an effective dose can be used as a therapeutic agent for the prevention or treatment of HIV infection or AIDS against more than 7 strains of HIV, preferably more than 8, 9, 10, 11, 12, 13, 14, 15, 16, 17, 18, 19, 20, or more strains of HIV. The invention further provides "neutralizing antibodies" when delivered at an effective dose can be used as a therapeutic agent for the prevention or treatment of HIV infection or AIDS. Neutralizing antibodies are effective prophylactic or therapeutic agents against at least one, preferably 2, 3, 4, 5, 6, 7, 8, 9, or 10 strains of HIV. The term "neutralizing antibodies" includes the subclass of BNAbs. Previously identified BNAbs against HIV include, but are not limited to, 2F5, Z13e1, and 4E10 (NIH AIDS Research and Reference Reagent Program Catalogue: HIV-1 gp41 Monoclonal Antibody (4E10) Catalog Number 10091 HIV-1 gp41 MAb (IgG1 Z13e1) Catalog Number 11557 HIV-1 gp41 Monoclonal Antibody (2F5) Catalog Number 1475). In an embodiment, a BNAb is generated or selected using a structurally constrained peptide of the instant invention. In a preferred embodiment, a BNAb is generated or selected using a structurally constrained peptide of the instant invention and the antibody does not include a paired heavy and light chain of any of the 2F5, Z13e1, and 4E10 antibodies. In an embodiment, a BNAb is generated or selected using a structurally constrained peptide of the instant invention and the antibody does not include the complementarity determining regions (CDR) from a paired heavy and light chain of any of the 2F5, Z13e1, and 4E10 antibodies.

As used herein, "carrier protein" for use with a structurally constrained peptide of the instant invention in a vaccine composition is understood as a protein or other substance that when conjugated to the constrained peptide elicit a strong and/or enhanced immunogenic response from T and B cells. Examples of carrier proteins include, Blue Carrier Immunogenic Protein Bovine Serum Albumin (BSA), Keyhole Limpet Hemocyanin (KLH), Ovalbumin (OVA), Cationized Bovine Serum Albumin (cBSA), or other carrier conjugates known in the art.

As used herein, "changed as compared to a control" sample or subject is understood as having a level of the analyte or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody) or a substance produced by a reporter construct (e.g, β-galactosidase or luciferase). Depending on the method used for detection the amount and measurement of the change can vary. Changed as compared to a control reference sample can also include decreased binding of a ligand, e.g., a viral spike, a receptor, e.g., viral cell surface receptor, in the presence of an antibody, antagonist, or other inhibitor. Determination of statistical significance is within the ability of those skilled in the art.

As used herein, the term "chimera" or "chimeric", with reference to the polypeptides of the invention refers to a polypeptide having at least two different HR domains or having a single HR domain region or having an MPER domain that is combined in a manner not found in nature. Exemplary HR and MPER domains are shown in FIGS. 2, 7, 9, and 10. FIG. 2c contains MPERs from various strains of HIV (and SIV), illustrating the conserved nature of this domain. For example, the chimera polypeptide may have a first portion of an HIV-1 gp41 HR-2 domain and a second portion from a SIV gp41 HR-2 domain. These chimeric polypeptides are encoded by nucleotide sequences which can be been fused or ligated together resulting in a coding sequence which does not occur naturally. The chimera includes any functional derivative, fragments, variants, analogues, or chemical derivatives which may be substantially similar to the wild-type HR polypeptides (HIV-1 gp41 HR-2) and which possess similar activity (i.e., most preferably, 90%, more preferably, 70%, preferably 40%, or at least 10% of the wild-type HR activity, e g, inhibiting fusion, viral infectivity).

"Co-administration" as used herein is understood as administration of one or more agents to a subject such that the agents are present and active in the subject at the same time. Co-administration does not require a preparation of an admixture of the agents or simultaneous administration of the agents.

A "conservative amino acid substitution" is one in which the amino acid residue is replaced with an amino acid residue having a similar side chain. For example, families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Other conserved amino acid substitutions can also occur across amino acid side chain families, such as when substituting an asparagine for aspartic acid in order to modify the charge of a peptide. Thus, a predicted nonessential amino acid residue in a HR domain polypeptide, for example, is preferably replaced with another amino acid residue from the same side chain family or homologues across families (e.g. asparagine for aspartic acid, glutamine for glutamic acid). Conservative changes can further include substitution of chemically homologous non-natural amino acids (i.e. a synthetic non-natural hydrophobic amino acid in place of leucine, a synthetic non-natural aromatic amino acid in place of tryptophan).

"Contacting a cell" is understood herein as providing an agent to a test cell e.g., a cell to be treated in culture or in an animal, such that the agent or isolated cell can interact with the test cell or cell to be treated, potentially be taken up by the test cell or cell to be treated, and have an effect on the test cell or cell to be treated. The agent or isolated cell can be delivered to the cell directly (e.g., by addition of the agent to culture medium or by injection into the cell or tissue of interest), or by delivery to the organism by an enteral or parenteral route of administration for delivery to the cell by circulation, lymphatic, or other means.

As used herein, "detecting", "detection" and the like are understood that an assay performed for identification of a specific analyte in a sample, a product from a reporter construct in a sample, or an activity of an agent in a sample (e.g., binding inhibition, inhibition of syncytia formation, infectivity inhibition). Detection can include the determination of the viral load, the presence of an antibody, the binding specificity of the antibody. The amount of analyte or activity detected in the sample can be none or below the level of detection of the assay or method.

By "diagnosing" as used herein refers to a clinical or other assessment of the condition of a subject based on observation, testing, or circumstances for identifying a subject having a disease, disorder, or condition based on the presence of at least one sign or symptom of the disease, disorder, or condition. Typically, diagnosing using the method of the invention includes the observation of the subject for other signs or symptoms of the disease, disorder, or condition.

The terms "effective amount," or "effective dose" refers to that amount of an agent to produce the intended pharmacological, therapeutic or preventive result. The pharmacologically effective amount results in the amelioration of one or more signs or symptoms of a viral disorder, or prevents infection by a virus or the advancement of a viral disease, or causes the regression of the disease or decreases viral transmission. For example, a therapeutically effective amount preferably refers to the amount of a therapeutic agent that decreases the rate of viral transmission, decreases viral load, or decreases the number of virus infected cells, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more as compared to an untreated control subject. A therapeutically effective amount, with reference to HIV, also refers to the amount of a therapeutic agent that increases CD4+ cell counts, increases time to progression to AIDS, or increases survival time by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more as compared to an untreated control subject. More than one dose of an agent may be required to provide an effective dose.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease signs or symptoms, extension of life, improvement in quality of life, or other effect generally recognized as positive by medical doctors familiar with treating the particular type of disease or condition.

As used herein, an "epitope" is understood as a region of an antigen, e.g., a peptide including a structured peptide, to which an antibody specifically binds. Epitopes include both contiguous, linear amino acid sequences and non-contiguous amino acids that are in close proximity to each other in a folded peptide such that the amino acids are recognized in their three-dimensional confirmation in the folded peptide, e.g., a series of amino acids on a single face of a helix.

Figure 3A:
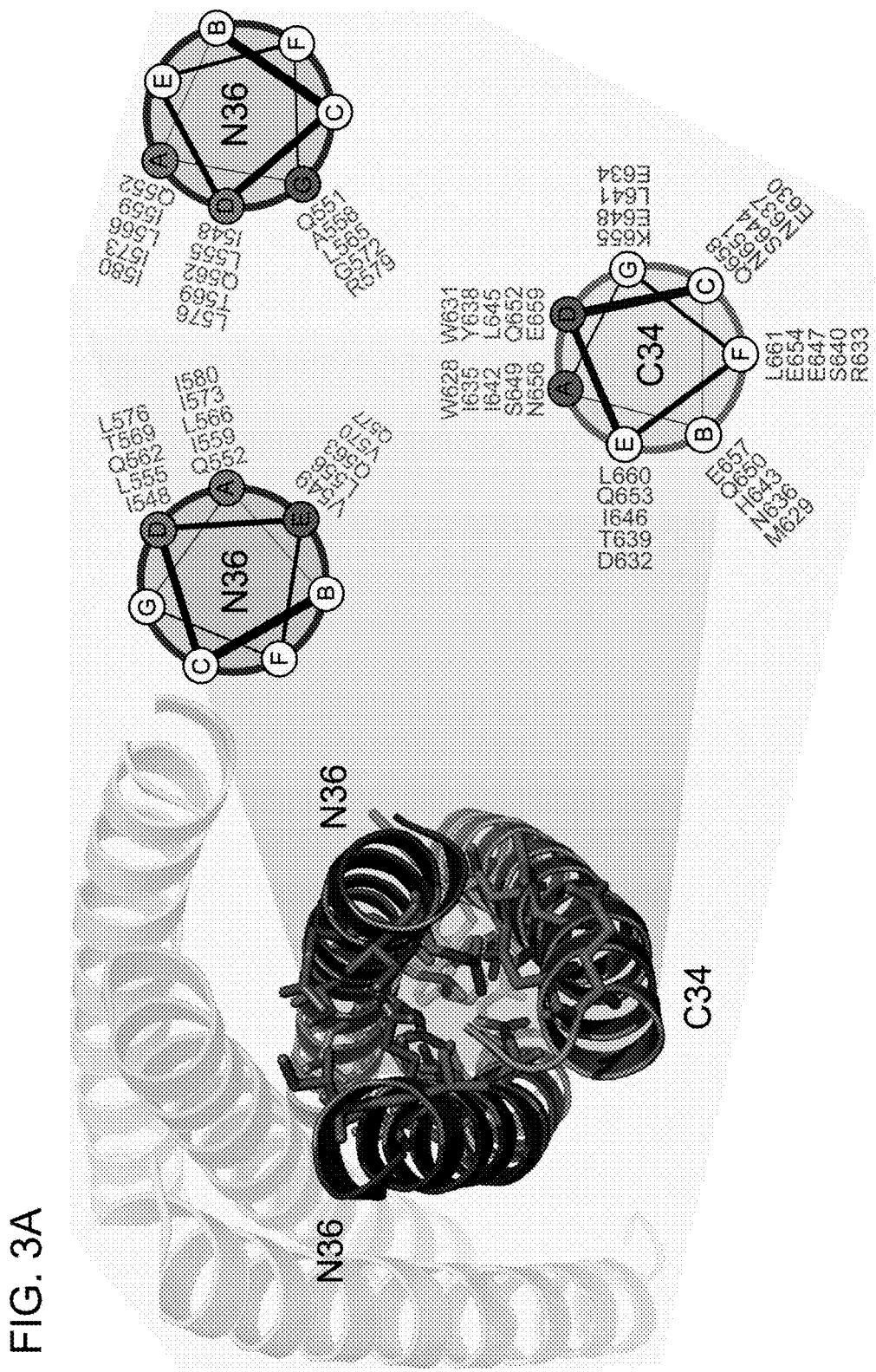
Figure 3B:
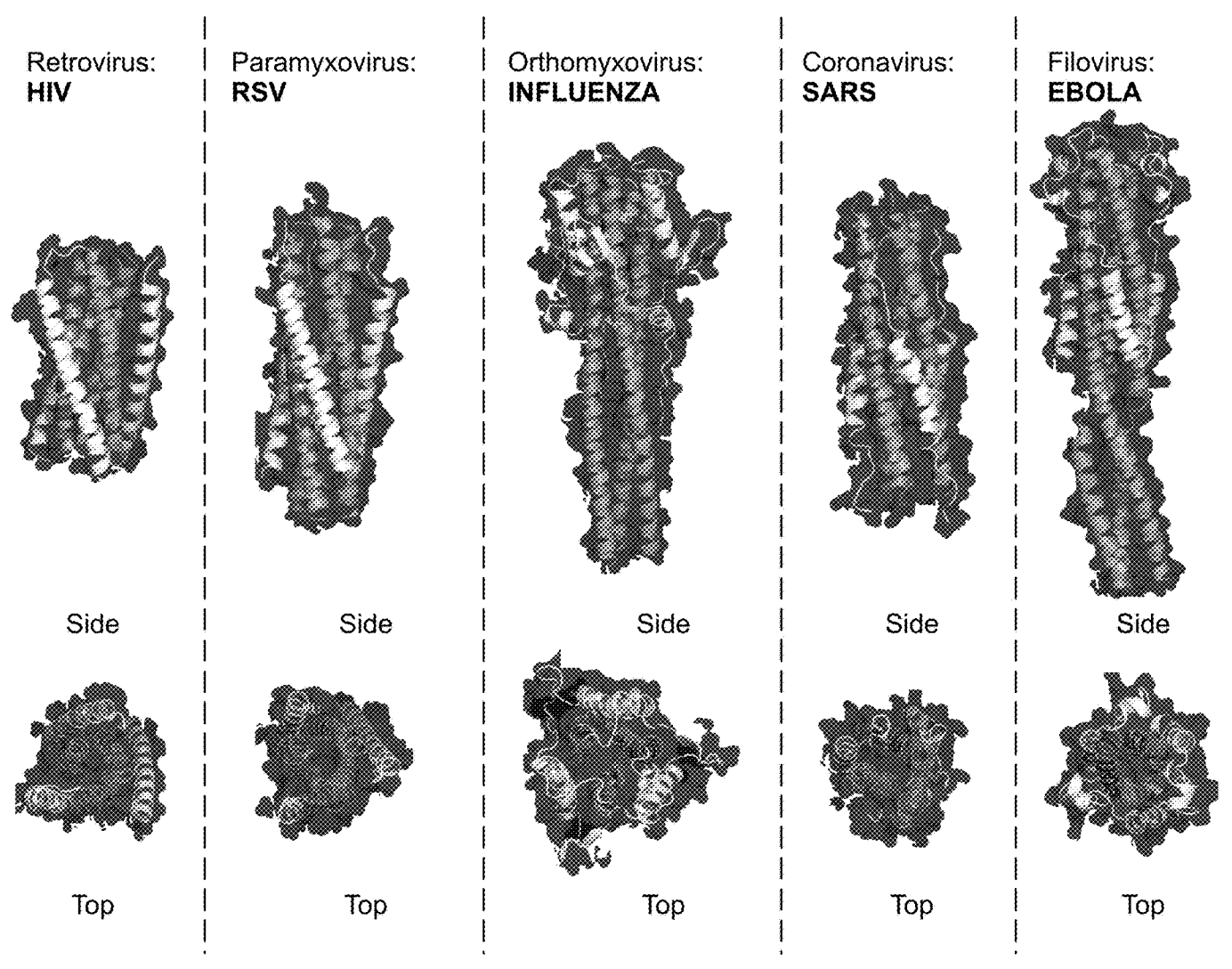

As use herein, the "face" of a helix, for example, an alpha-helix or a $3_{10}$ helix, is understood as the amino acids that are "stacked" in a helix of a protein so that when the helix is positioned vertically, the amino acids in a single face are depicted as being one on top of the other (see, e.g., FIG. 3). For example, an alpha-helix has about 3.6 amino acids per turn. Therefore, when a peptide having a sequence abcdefga'b'c'd'e'f'g' forms an alpha helix, the fourth and fifth amino acids (i+3 and i+4), i.e., amino acids d and e, will "stack" over the first amino acid (position 1+~3. 6 amino acids), and the eighth amino acid, amino acid a' (i+7), will stack over amino acid a to form a face of the helix and starting a new turn with amino acid a' (see, e.g., FIG. 3). In an alpha-helix, amino acid b, the second amino acid, will "stack" with the fifth and sixth amino acids, i.e., amino acids e and f at the +3 and +4 positions, and with amino acid b' at the +7 position to form a face of the helix. Faces on helices starting with amino acid c, d, e, f, and g can be readily determined based on the above disclosure. Furthermore, a face of a helix can include two adjacent, three adjacent, or four adjacent columns of "stacked" residues. For example, again referring to FIG. 3A, lists of "stacked" residues (e.g., next to D on one helix L576, T569, Q652, L555, I548) are provided adjacent to each of the helix positions DAE on one helix, GDA on a second helix, and all helixes ADGCFBE on the third helix. Any two adjacent helices to form a face as depicted in FIG. 3A can be selected from the helix pairs AD, DG, GC, CF, FB, BE, and EA. Any three adjacent helices to form a face as depicted in FIG. 3A can be selected from the helix groups ADG, DGC, GCF, CFB, FBE, BEA, and EAD. Any four adjacent helices to form a face as depicted in FIG. 3A can be selected from the helix groups ADGC, DGCF, GCFB, CFBE, FBEA, BEAD, and EADG.

An example of a "face" of a helix includes the "interacting face" of the helix. An "interacting face" amino acid residue is a residue that makes contact with one or more helices in the helix bundle, see e.g., FIG. 3, when altered from the wild-type sequence of the polypeptide, results in abolishing or substantially abolishing the polypeptide functional activity. Substantially abolishing is understood as reducing the functional activity of an MPER or HR domain to less than about 50%, less than about 40%, less than about 30% of the wild-type peptide in an appropriate assay (e.g., 4E10 binding assay, syncytia formation assay, infectivity inhibition assay, etc). The interacting face amino acid residues of the HR and HR-like domains can readily be determined by methods well known in the art and are described herein. In one embodiment, an essential amino acid residue is in the "a" or "d" position of a heptad repeat domain, while non-essential amino acids may occur in a "b", "c", "e", "f" or "g" position (FIG. 3). The term "interacting face" amino acid residue as used herein, includes conservative substitutions of the interacting face amino acids that do not disrupt function of the sequence. Generally, the "interacting face" amino acid residues are found at the interacting face of the alpha helix. For example, in the HIV gp41 HR-2 domain the interacting face includes the "a" and "d" position amino acids. (See FIG. 3). In another embodiment, a modified polypeptide comprises a gp41 HR-1 domain having a Leu-556, Leu-565, Val-570, Gly-572, and Arg-579 (Lu, M., et al., J. Vir, 2001. 75(22); p. 11146-11156). Essential amino acids for an MPER include for example Trp-672, Phe-673, and Thr-676 (Dawson et al, J Vir, 2006, 80(4), p 1680-7). It is understood that the interacting face of a helix formed by a peptide is not required for the activity of the peptide as an immunogen.

As used herein a "heptad repeat domain" and "HR domain" refers to a polypeptide that forms an alpha-helix when properly folded and participates in the mechanism of viral fusion. The terms, "heptad repeat domain" and "HR domain" include "HR-like" and "HR-analog" polypeptides. Numerous viral proteins involved in cell attachment and fusion contain HR, HR-like and HR-analog domains including, HIV, parainfluenza, coronavirus, and others (see FIG. 2). Generally, HR domains are derived from gp41 of HIV, while HR-analog domains are derived from the envelope glycoproteins of non-HIV viruses. Many HR and HR-analog domain polypeptides are known in the art and described herein. In one embodiment, the HR domain has an amino acid sequence which is 40%, 50%, 60%, 70%, 80%, 90% or 100% identical to a sequence shown in either FIG. 2A or 2B (SEQ ID NOs: 3-16, 26-40, 45-48, 58-63, 71-74; or the HR2 portion of SEQ ID NO: 17-25, 49-57, 64-70, or 75-89); wherein the peptide forms an alpha helix. In one embodiment, a heptad repeat domain is a peptide having an amino acid sequence identical to at least 3, 4, 5, 6, 7, 8, 9, 10, 11, 12, 13, 14, 15, 16, 17, 18, 19, 20, 21, 22, 23, 24, 25, 26, 27, 28, 29, or 30 contiguous amino acids of any of SEQ ID NO: SEQ ID NOs: 3-16, 26-40, 45-48, 58-63, 71-74; or the HR2 portion of SEQ ID NO: 17-25, 49-57, 64-70, or 75-89. In an embodiment, the heptad repeat domain is a peptide having an amino acid sequence having at least 2, 3, 4, 5, 6, 7, 8, 9, 10, or more amino acids on a single face of a helix of an HR or HR-like domain. It should be noted that HR and HR-like domains may have low homology but share a common alpha helical structure, with more conservation on the interaction surfaces than non-interacting surfaces (see especially FIGS. 2 and 3).

In one embodiment, the HR modified polypeptide includes a heptad repeat domain having the formula: a b c d e f g, wherein a and d are hydrophobic amino acid residues and b, c, e, f and g are any amino acid. Preferably, the formula is repeated in tandem two or more times, wherein each position a-g is independently selected in each repeat.

For example, in an embodiment the heptad repeat domain of the modified polypeptide has the formula (capital letter indicates amino acid, lower case letter indicates position): W(a), b, c, W(d), e, f, g, I(a), b, c, Y(d), e, f, g, I(a), b, c, L(d), e, f, g, S(a), b, c, Q(d), e, f, g, N(a), b, c, E(d), e, f, g, L(a), or conservative amino acid substitutions thereof and wherein the b, c, e, f and g can be any amino acid (see FIG. 5C, SEQ ID NO.: 29).

In a further, embodiment the heptad repeat domain of the modified polypeptide has the formula: T(g), W(a), b, c, W(d), D(e), R(f), g, I(a), b, c, Y(d), e, f, g, I(a), b, c, L(d), I(e), f, g, a, Q(b), c, d, Q(e), E(f), K(g), a, E(b), c, d, L(e), f, E(g), L(a), or conservative amino acid substitutions thereof and wherein non-designated amino acids can be any amino acid (see FIG. 5D, SEQ ID NO.: 30).

The HR regions are known to comprise a plurality of 7 amino acid residue stretches or "heptads" (the 7 amino acids in each heptad designated "a" through "g"), wherein the amino acids in the "a" position and "d" position are generally hydrophobic. Generally the HR region will include one or more leucine zipper-like motifs (also referred to as "leucine zipper-like repeats") comprising an 8 amino acid sequence initiating with, and ending with, an isoleucine or leucine. Heptads and leucine zipper like-motifs contribute to formation of a coiled coil structure of gp41, and of a coiled coil structure of peptides derived from the HR regions. Generally, coiled coils are known to be comprised of two or more helices that wrap around each other in forming oligomers, with the hallmark of coiled coils being a heptad repeat of amino acids with a predominance of hydrophobic residues at the first ("a") and fourth ("d") positions, charged residues frequently at the fifth ("e") and seventh ("g") positions, and with the amino acids in the "a" position and "d" position being primary determinants that influence the oligomeric state and strand orientation (see, e.g., Akey et al., 2001, Biochemistry, 40:6352-60).

The effect on stability and oligomerization state of a model coiled coil, by substituting various amino acids at various positions including the "a" and "d" positions, have been reported previously, wherein formation of a trimeric structure was particularly dependent on the substitution at the "d" position (see, e.g., Tripet et al., J. Mol. Biol. 300:377-402 (2000); Wagschal et al., J. Mol. Biol. 285:785-803 (2000); and Dwyer et al., PNAS USA. 104; 12772-12777 (2007).

It will be apparent to one skilled in the art that any peptide derived from the native sequence of the HR1 domain or HR2 domain or MPER domain, or any combination thereof, of HIV gp41 which is immunogenic (as can be determined using methods standard in the art without undue experimentation), and which contains all or a fraction of the region can be used as a native sequence into which one or more amino acid substitutions, preferably conservative, in the domain may be introduced to produce a synthetic peptide provided with the present invention. For purposes of illustration, such peptides derived from the native sequence, and from which a synthetic peptide may be produced, may include, but are not limited to, those illustrated in FIGS. 2, 7, 9, and 10 and provided in SEQ ID NO: 3-89.

It is apparent to those of ordinary skill in the art that some HR and MPER domain residues are less prone to substitution while others are more accepting of changes. For example, it is preferable not to mutate or to only conservatively mutate the amino acids at positions a and d of the heptad repeat (See FIGS. 3 and 5). In one embodiment, the heptad repeat domain has the formula a, b, c, d, e, f, g, wherein a and d are hydrophobic amino acids. In a further embodiment, the heptad repeat domain has two or more repeats of the formula a, b, c, d, e, f, g. For example, in one embodiment the HR domain will have the amino acid sequences illustrated in FIG. 3 or conservative substitutions thereof. Thus, the HR and HR-like domains have significant variability in amino acid sequence but will maintain an alpha helical structure and immunogenicity, particularly immunogenicity to produce a neutralizing antibody, preferably a BNAb.

The HR, HR-like, HR-analog, and MPER, MPER-like, and MPER analog domains are readily identifiable by those possessing ordinary skill in the art by sequence based homology, structural homology and/or functional homology. Such methods are well known in the art and include bioinformatics programs based on pairwise residue correlations (e.g., ch.embnet.org/software/COILS_form.html), which have the ability to recognize coiled coils from protein sequences and model their structures (See Lupas, A., et al. Science 1991. 252(5009); p. 1162-1164). Additional methods for identifying HR, HR-like and HR-analog domains are described in U.S. Pat. No. 6,824,783; U.S. Pat. No. 7,273,614; U.S. Pat. No. 5,464,933; and U.S. Pat. No. 7,122,190, all of which are herein incorporated by reference in their entirety.

Figure 1F:
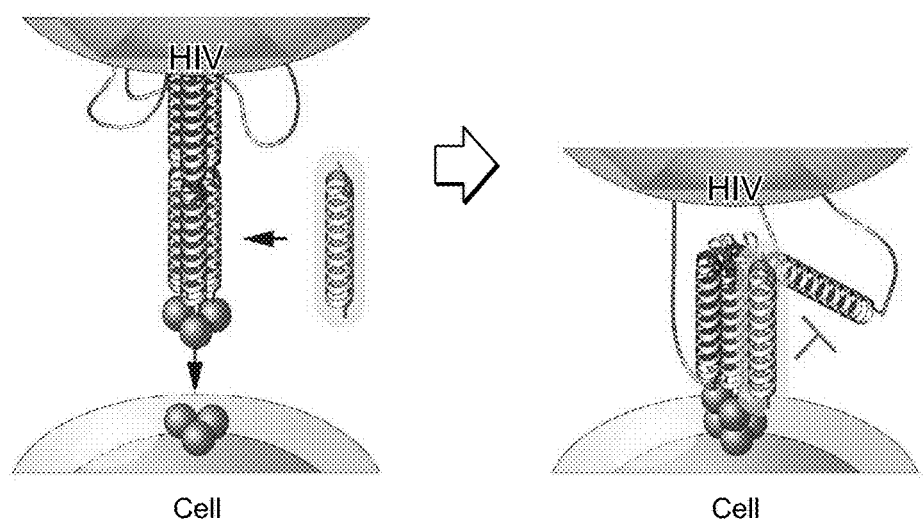

In one embodiment, the modified polypeptide of the invention is 70% or more similar at the interacting face to the amino acid sequence of SEQ ID NO:2-22, or as shown in FIGS. 1 through 3. The interacting face of MPER can be the membrane interacting face (e.g. host or viral). The "interacting face" of the alpha helix includes those amino acid residues which interact with other amino acid residues on other proteins and/or in other helices. For example, in the HIV gp41 HR-2 domain the interacting face includes the "a" and "d" position amino acids (See FIG. 3), while the interacting face of the HIV gp41 HR-1 domain includes amino acids at positions e, g that interact with HR-2 and a, d that engage in HR1-HR1 interactions (See FIG. 3). Methods for identifying heptad repeats and the interacting face residues are well known in the art and described herein.

An "HR-1 domain of HIV" or "heptad repeat one domain of HIV" is an N-terminal portion of the gp41 protein of HIV (the transmembrane subunit of HIV envelope) that forms an alpha-helix when properly folded. The HR-1 domain of HIV gp41 can include 5 to 55 amino acid residues, or any number of amino acids therebetween, and is based on the sequence of the native HR-1 domain of HIV gp41, or a combination or chimera thereof. The HR-1 domain of HIV can include the N36 domain which encompasses amino acid residues 546-581 HIV-1 Env (See e.g., Bewley et al., J. Biol. Chem. 277:14238-14245 (2002)). HR-1 domain polypeptides are known in the art and described herein. In one embodiment, the HR-1 domain has an amino acid sequence which is 30% or more identical to SEQ ID NO: 3-9.

An "HR-2 domain of HIV" or a heptad repeat two domain of HIV is located within the C-terminal portion of the gp41 protein of HIV (FIG. 1A) and forms an alpha-helix when properly folded. The HR-2 domain of HIV can include the C34 domain which encompasses amino acid residues 628-661 of HIV-1 Env (See FIG. 2). HR-2 domain polypeptides are known in the art and described herein. In one embodiment, the HR-2 domain has an amino acid sequence which is 40% or more identical to SEQ ID NO: 10, 26-40, 45-48, 58-63, and 71-74; and to the HR-2 portions of SEQ ID NO: 17-24, 49-57, 64-70, and 75-89.

As used herein, "HIV" is meant to include HIV-1 and HIV-2 and SIV. "HIV-1" means the human immunodeficiency virus type-1. HIV-1 includes but is not limited to extracellular virus particles and the forms of HIV-1 associated with HIV-1 infected cells. "HIV-2" means the human immunodeficiency virus type-2. HIV-2 includes but is not limited to extracellular virus particles and the forms of HIV-2 associated with HIV-2 infected cells. The term "SIV" refers to simian immunodeficiency virus which is an HIV-like virus that infects monkeys, chimpanzees, and other nonhuman primates. SIV includes but is not limited to extracellular virus particles and the forms of SIV associated with SIV infected cells.

As used herein, clinical "HIV infection" is understood as the demonstrated presence of HIV antibody, HIV antigen, and/or HIV nucleic acid in the human subject as demonstrated by the detection of the presence of virus using HIV tests known to those skilled in the art (e.g. HIV EIA, Western blot, PCR tests).

As used herein, "HIV exposure" is understood as contact of a subject not having an HIV infection or AIDS with a subject having HIV infection or AIDS, or contact with body fluids from such HIV-infected subject, in which such fluids from the infected subject contact a mucous membrane, a cut or abrasion in the tissue (e.g., needle stick, unprotected sexual intercourse), or other surface of the uninfected subject such that the virus could be transmitted from the uninfected subject or uninfected subject's body fluids to the infected subject.

As used herein, the term "hydrocarbon stapling", refers to a process for stably cross-linking a polypeptide having at least two modified amino acids that helps to conformationally bestow the native secondary structure of that polypeptide. Hydrocarbon stapling promotes or maintains a helical secondary structure in a peptide predisposed to have an helical secondary structure, e.g., alpha-helical secondary structure, to attain or maintain its native alpha-helical conformation. This secondary structure increases resistance of the polypeptide to proteolytic cleavage and heat, and also may increase hydrophobicity.

The hydrocarbon stapled polypeptides include one or more tethers (linkages) between two non-natural amino acids, which tether significantly enhances the helical secondary structure (e.g. α-helix, $3_{10}$-helix) of the polypeptide. Generally, to promote a helical structure, the tether extends across the length of one or two helical turns (i.e., about 3-3.6 or about 7 amino acids). Accordingly, amino acids positioned at i and i+3; and i+4; or i and i+7 are ideal candidates for chemical modification and cross-linking. Thus, for example, where a peptide has the sequence . . . X1, X2, X3, X4, X5, X6, X7, X8, X9 . . . , and the amino acid X is independently selected for each position, cross-links between X1 and X4, or between X1 and X5, or between X1 and X8 are useful as are cross-links between X2 and X5, or between X2 and X6, or between X2 and X9, etc. The use of multiple cross-links (e.g., 2, 3, 4 or more) is also contemplated. The use of multiple cross-links is effective at stabilizing and optimizing the peptide, especially with increasing peptide length, as is the case for some gp41 fusion peptides. Thus, the invention encompasses the incorporation of more than one crosslink within the polypeptide sequence. The use of multiple cross-links is effective at stabilizing and optimizing the peptide, especially with increasing peptide length, as is the case for some gp41 fusion peptides. Thus, the invention encompasses the incorporation of more than one crosslink within a polypeptide sequence.

As used herein, the terms "identity" or "percent identity", refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity. The identity between two sequences is a direct function of the number of matching or identical positions. Thus, if a portion of the reference sequence is deleted in a particular peptide, that deleted section is not counted for purposes of calculating sequence identity. Identity is often measured using sequence analysis software e.g., BLASTN or BLASTP (available at (www.ncbi.nih.gov/BLAST). The default parameters for comparing two sequences (e.g., "Blast"-ing two sequences against each other), by BLASTN (for nucleotide sequences) are reward for match=1, penalty for mismatch=−2, open gap=5, extension gap=2. When using BLASTP for protein sequences, the default parameters are reward for match=0, penalty for mismatch=0, open gap=11, and extension gap=1. Additional, computer programs for determining identity are known in the art.

As used herein, "immunogenic agent", for example an "immunogenic peptide" is understood as an agent or peptide that promotes an adaptive immune response, e.g., cellular (Th1) and/or humoral (Th2) immune response, in a subject to whom the agent is administered. The response can be a mucosal response or a systemic response, depending in route of delivery (e.g., by oral/mucosal administration or intramuscular, subcutaneous, or intraperitoneal injection). An adaptive immune response can be detected by the presence of antibodies (IgA, IgG, IgM, IgE) that specifically bind the immunogenic agent. In a preferred embodiment, the immunogenic agent stimulates a sufficient adaptive immune response to provide at least some protection of the immunized subject against pathogens that include an epitope of the immunogenic agent. Protection may not be conferred with a single dose of the immunogenic agent. Multiple rounds of administration relatively close together (interval of weeks to months) may be required for the generation of a sufficient immune response, with the possible need for "booster" doses at longer intervals (e.g., years to decades).

The term "inhibits" as used herein with reference to a viral infection refers to a decrease in viral transmission, decrease in virus binding to a cellular target or decrease in disease using structured peptides provided herein or antibodies made against or selected using the structured peptides provided herein. For example, the polypeptides of the present invention are used to inhibit viral transmission, syncytia formation, and disease associated with the virus (e.g. AIDS). A compound of the invention can be screened by many assays, known in the art and described herein, to determine whether the compound inhibits the virus (e.g., infectivity, transmission, etc.). For example, a compound of the invention can be assayed for its ability to inhibit viral infectivity by contacting a cell culture that is incubated with the virus with a test compound. The compound is found to inhibit viral infectivity when viral infectivity is 90%, 80%, 75%, 70%, 60%, 50%, 40%, 30%, 20%, 10%, 5% or less in the presence of the test compound as compared to a suitable control (population of cells not subjected to inhibitor).

The term "inhibit transmission", as used herein, refers to the agent's ability to inhibit viral infection of cells, via, for example, cell-cell fusion or free virus infection. Such infection may involve membrane fusion, as occurs in the case of enveloped viruses, or some other fusion event involving a viral structure and a cellular structure.

The term "inhibiting syncytia formation", as used herein, refers to an agent's ability to inhibit or reduce the level of membrane fusion events between two or more moieties relative to the level of membrane fusion which occurs between said moieties in the absence of the agent. The moieties may be, for example, cell membranes or viral structures, such as viral envelopes.

As used herein, "isolated" or "purified" when used in reference to a polypeptide means that a naturally polypeptide or protein has been removed from its normal physiological environment (e.g., protein isolated from plasma or tissue) or is synthesized in a non-natural environment (e.g., artificially synthesized in an in vitro translation system or using chemical synthesis). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition.

As used herein, "kits" are understood to contain at least one non-standard laboratory reagent for use in the methods of the invention. For example, a kit can include at least one of, preferably at least two of at least one peptide for modification, one or more aldehyde molecules for modification of peptides, and instructions for use, all in appropriate packaging. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

Figures 8A, 8B:
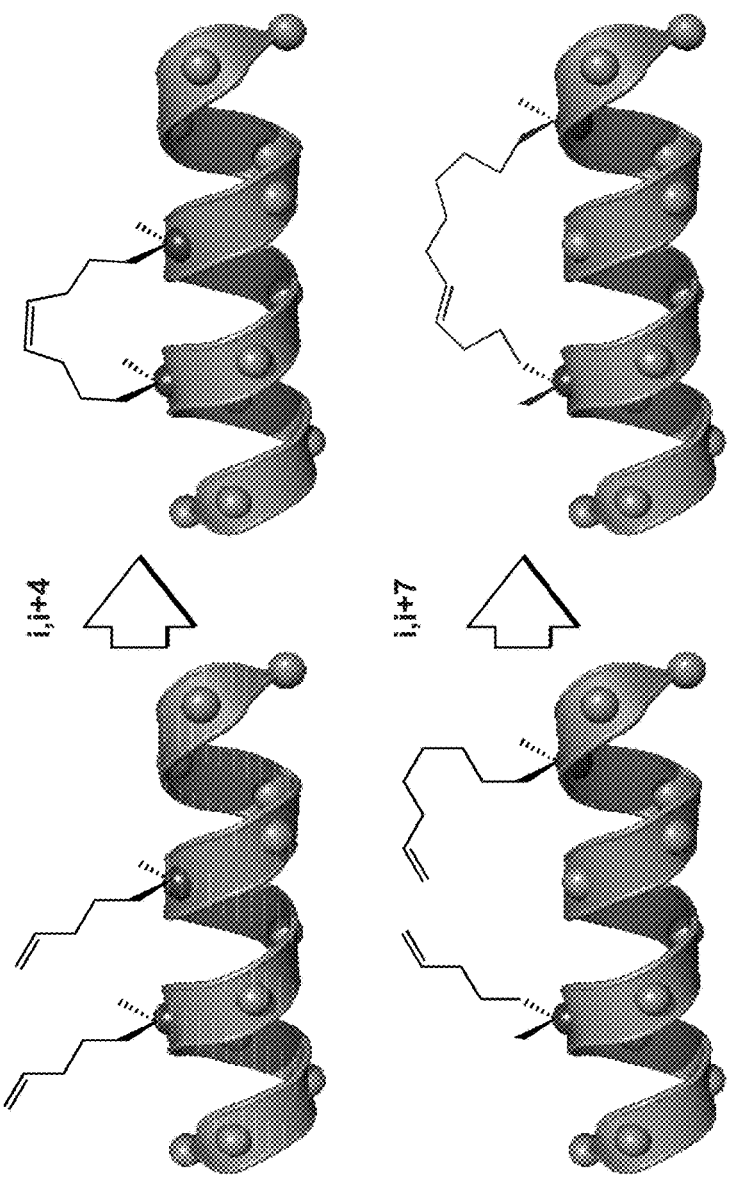
Figures 9A, 9B:
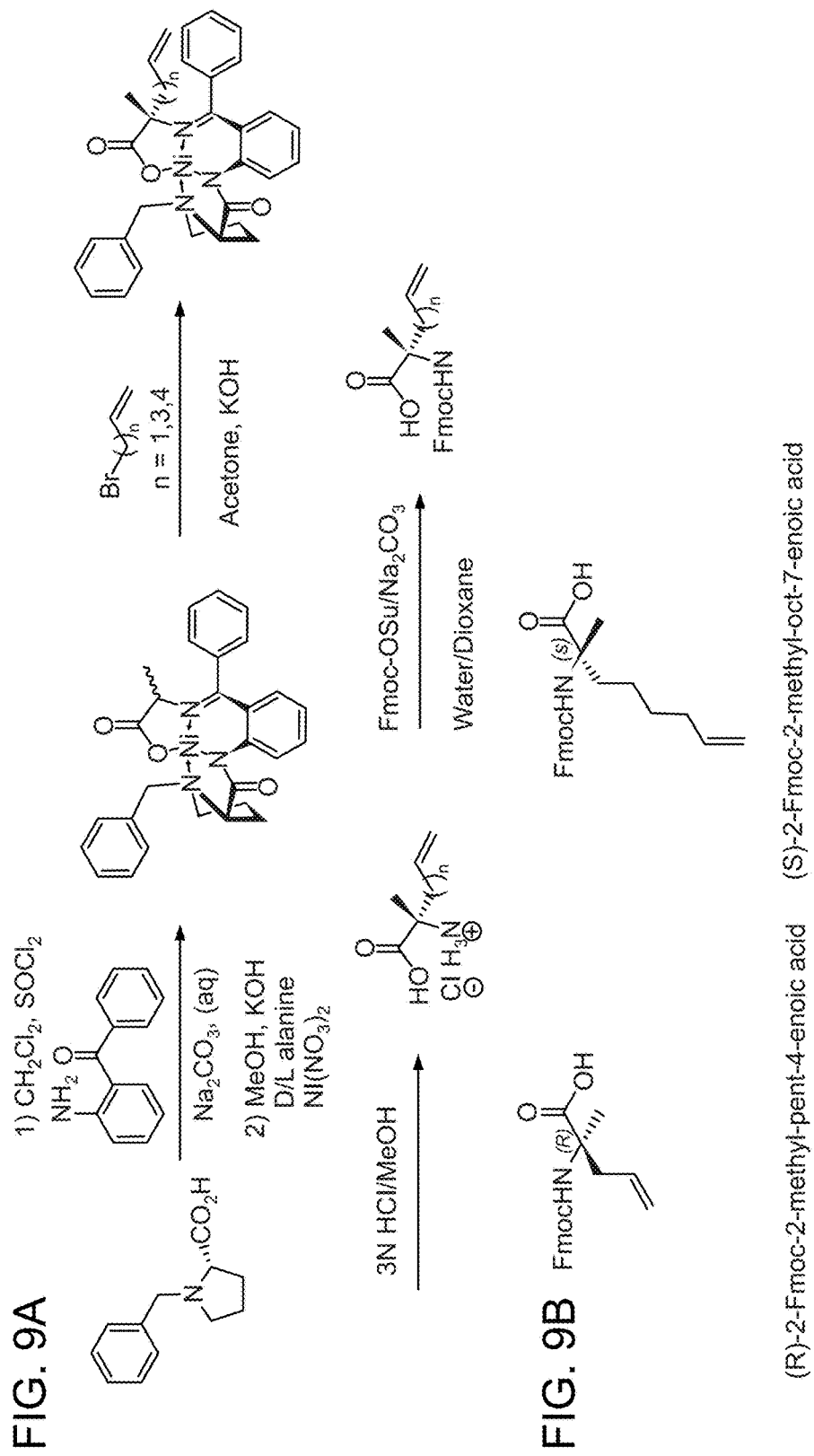
FIGS. 9A-B shows a reaction scheme for the generation of crosslinking novel non-natural amino acids optimized for facile production of i, i+3 stapled peptides.

As used herein, "membrane proximal external/ectodomain region" or "MPER" is understood as a sequence having a mixture of hydrophobic aromatic and hydrophilic residues. The general characteristics of the MPER are that it possesses a hydrophobic membrane-binding face containing 4 of the 5 Trp residues as well as the critical Phe 673 residue and a solvent exposed face comprised of 3 hydrophilic Asn. MPERs include specific structural features including, contiguously and in order, a short alpha-helix, an unstructured portion, and a $3_{10}$-helix (see, e.g., FIG. 8). MPER sequences are shown, for example, in FIGS. 2, 9, and 10, SEQ ID NOS: 41-43 and partially in 17-25, 49-57, 64-70, and 75-89. An MPER can include 1, 2, 3, 4, 5, 6, 7, or more amino acid modifications relative to the sequences provided in the listing or in the figures, e.g., to allow for the insertion of tethered amino acids, or for the inclusion of natural or non-natural amino acids to provide structure to the unstructured portion.

A "non-essential" amino acid residue is a residue that can be altered from the wild-type sequence of a polypeptide (e.g., an HR-1, HR-2, MPER domain) without abolishing or substantially altering its activity/secondary structure (alpha-helical structure).

"Obtaining" is understood herein as manufacturing, purchasing, or otherwise coming into possession of.

As used herein, "operably linked" is understood as joined, preferably by a covalent linkage, e.g., joining an amino-terminus of one peptide to a carboxy terminus of another peptide, in a manner that the two or more components that are operably linked either retain their original activity, or gain an activity upon joining such that the activity of the operably linked portions can be assayed and have detectable activity using at least one of the methods provided in the examples.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. For example, pharmaceutically acceptable carriers for administration of cells typically is a carrier acceptable for delivery by injection, and do not include agents such as detergents or other compounds that could damage the cells to be delivered. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intraperotineal, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

As used herein, "plurality" is understood to mean more than one. For example, a plurality refers to at least two, three, four, five, or more.

A "polypeptide" or "peptide" as used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments).

As used herein, "prevention" is understood as to limit, reduce the rate or degree of onset, or inhibit the development of at least one sign or symptom of a disease or condition. For example, a subject living in sub-Saharan Africa, an intravenous drug abuser, a homosexual male, and other individuals are more susceptible to HIV infection and AIDS than the general population. Prevention can include delaying the typical age of onset or the time after the initiation of risk increasing activities, of HIV infection or AIDS. Prevention can also include delaying the progression from HIV infection to AIDS. Prevention need not be elimination of HIV infection or the development of AIDS in all subjects after administration of a composition of the invention for the prevention of HIV infection or AIDS. Prevention can require the administration of more than one dose of an agent or therapeutic.

A "sample" as used herein refers to a biological material that is isolated from its environment (e.g., blood or tissue from an animal, cells, or conditioned media from tissue culture) and is suspected of containing, or known to contain an analyte, such as a virus, an antibody, or a product from a reporter construct. A sample can also be a partially purified fraction of a tissue or bodily fluid. A reference sample can be a "normal" sample, from a donor not having the disease or condition fluid, or from a normal tissue in a subject having the disease or condition (e.g., non-infected tissue vs. a infected tissue). A reference sample can also be from an untreated donor or cell culture not treated with an active agent (e.g., no treatment or administration of vehicle only). A reference sample can also be taken at a "zero time point" prior to contacting the cell or subject with the agent to be tested.

"Similarity" or "percent similarity" in the context of two or more polypeptide sequences, refer to two or more sequences or subsequences that are the same or have a specified percentage of amino acid residues, or conservative substitutions thereof, that are the same when compared and aligned for maximum correspondence, as measured using one of the following sequence comparison algorithms, or by visual inspection. By way of example, a first polypeptide can be considered similar to an HIV-1 HR-1 domain when the amino acid sequence of the first polypeptide is at least 20%, 50%, 60%, 70%, 75%, 80%, 90%, or even 95% or more identical, or conservatively substituted, to a region of the HIV-1 HR-1 domain when compared to any sequence of an equal number of amino acids as the number contained in the first polypeptide as aligned by a computer similarity program known in the art and described herein. Preferably, the polypeptide region of the first protein and the second protein includes one or more conserved amino acid residues.

The term "stable" or "stabilized", as used herein with reference to a polypeptide, refers to polypeptides which have been hydrocarbon-stapled to promote and/or maintain helical structure and/or improve protease resistance and/or improve acid stability and/or improve thermal stability and/or improve pharmacologic properties. Stabilized polypeptides are a type of structurally constrained polypeptides.

As used herein, "structurally constrained peptides" and the like are understood to include modified peptides having any (i.e., at least one) chemical modification, e.g., mutation of the original or native sequence with a natural or non-natural amino acid; chemical modification to incorporate a molecular tether; chemical modification to promote the formation of a disulfide bridge; etc. such that the structurally constrained peptide adopts a more limited number of structures than the unmodified peptide. A structurally constrained peptide can include 1, 2, 3, 4, 5, 6, 7, 8, 9, 10, 11, 12, or more mutations as compared to the native, wild-type sequence. For example, molecular tethers can include hydrocarbon staples to promote the formation of stable helical structures, especially alpha-helical and $3_{10}$ structures, or kinks depending on the positions of the ends of the tethers and the lengths of the tethers. Natural or non-natural amino acids can be employed to promote kinks (e.g. bends in the structure as defined by the variable angles between the two adjoining structures) or other preferred confirmations. For example, the natural amino acid proline can induce a kink in a peptide due to the structure of the amino acid R group and the lack of a hydrogen-bond donor. Non-natural amino acids, particularly those having large and/or charged R groups, or N-methylated amides, N-substituted glycines, cyclic alpha, alpha-disubstitution, cyclic N,N-disubstitution, and beta-amino acids can promote specific, desired confirmations. It is understood that a population of "structurally constrained" peptides in solution may not all have the desired confirmation all of the time. Instead, in a population of structurally constrained peptides in solution, the desired confirmation is present at least about 30%, 40%, 50%, 60%, 70%, 80%, 90%, 100%, or more of the time than the native or original peptide sequence in solution prior to chemical modification. The structure of a population of peptides in solution can be determined by various methods known to those of skill in the art including, but not limited to, circular dichroism and NMR spectroscopy. Xray crystallography can be applied to determine the structure of a constrained peptide when packed in the form of a crystal.

"Small molecule" as used herein is understood as a compound, typically an organic compound, having a molecular weight of no more than about 1500 Da, 1000 Da, 750 Da, or 500 Da. In an embodiment, a small molecule does not include a polypeptide or nucleic acid including only natural amino acids and/or nucleotides.

An agent, antibody, polypeptide, nucleic acid, or other compound "specifically binds" a target molecule, e.g., antigen, polypeptide, nucleic acid, or other compound, when the target molecule is bound with at least 100-fold, preferably at least 500-fold, preferably at least 1000-fold, preferably at least a 5000-fold, preferably at least a 10,000-fold preference as compared to a non-specific compounds, or a pool of non-specific compounds. Specifically binds can be used in relation to binding one of two or more related compounds that have physically related structures. Binding preferences and affinities, absolute or relative, can be determined, for example by determining the affinity for each pair separately or by the use of competition assays or other methods well known to those of skill in the art.

A "subject" as used herein refers to living organisms. In certain embodiments, the living organism is an animal. In certain preferred embodiments, the subject is a mammal. In certain embodiments, the subject is a domesticated mammal. Examples of subjects include humans, monkeys, dogs, cats, mice, rats, cows, horses, goats, and sheep. A human subject may also be referred to as a patient.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions such as HIV infection is within the ability of those in the art. Subjects suffering from, and suspected of suffering from, a specific disease, condition, or syndrome are not necessarily two distinct groups.

"Therapeutically effective amount," as used herein refers to an amount of an agent which is effective, upon single or multiple dose administration to the cell or subject, in prolonging the survivability of the patient with such a disorder, reducing one or more signs or symptoms of the disorder, preventing or delaying infection, preventing or delaying the progression of a disease or disorder (e.g., progression from HIV infection to AIDS), and the like beyond that expected in the absence of such treatment.

An agent can be administered to a subject, either alone or in combination with one or more therapeutic agents, as a pharmaceutical composition in mixture with conventional excipient, e.g., pharmaceutically acceptable carrier, or therapeutic treatments.

The pharmaceutical agents may be conveniently administered in unit dosage form and may be prepared by any of the methods well known in the pharmaceutical arts, e.g., as described in *Remington's Pharmaceutical Sciences* (Mack Pub. Co., Easton, Pa., 1985). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain agents.

It is understood that vaccines are typically administered with one or more agents, typically referred to as adjuvants, to increase the efficacy of the vaccine, or reduce the amount of antigen required to provide a therapeutically effective dose of the vaccine. Adjuvants include, but are not limited to mineral salts (e.g., aluminium hydroxide and aluminium or calcium phosphate gels); oil emulsions and surfactant based formulations, (e.g., MF59 (microfluidised detergent stabilised oil-in-water emulsion); QS21 (purified saponin), AS02 [SBAS2] (oil-in-water emulsion+MPL+QS-21), Montanide ISA-51 and ISA-720 (stabilised water-in-oil emulsion)) particulate adjuvants (e.g., virosomes (unilamellar liposomal vehicles incorporating influenza hemagglutinin), AS04 ([SBAS4] Al salt with MPL), ISCOMS (structured complex of saponins and lipids), polylactide co-glycolide (PLG)); microbial derivatives (natural and synthetic; e.g., monophosphoryl lipid A (MPL), Detox (MPL+ *M. Phlei* cell wall skeleton), AGP [RC-529] (synthetic acylated monosaccharide), DC_Chol (lipoidal immunostimulators able to self organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects)); endogenous human immunomodulators, (e.g., hGM-CSF or hIL-12 (cytokines that can be administered either as protein or plasmid encoded), Immudaptin (C3d tandem array). Adjuvants can also include non-chemical adjuvants such as the administration of desired wavelengths of light.

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the foregoing guidelines.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

The term "alkenyl" refers to a hydrocarbon chain that may be a straight chain or branched chain having one or more carbon-carbon double bonds. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive, i.e., 1, 2, 3, 4, 5, 6, 7, 8, 9, 10, 11, 12, 13, 14, 15, 16, 17, 18, 19, or 20) carbon atoms in it. The term "alkylene" refers to a divalent alkyl (i.e., —R—).

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

Ranges provided herein are understood to be shorthand for all of the values within the range. This includes all individual sequences when a range of SEQ ID NOs: is provided. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

The symbol

when used as part of a molecular structure refers to a single bond or a trans or cis double bond.

Any compositions or methods provided herein can be combined with one or more of any of the other compositions and methods provided herein.

Polypeptides

In an aspect, the invention is directed to a structurally constrained peptide having a stabilized viral alpha helix heptad repeat domain (e.g., HR-1, HR-2, HR-like or HR-analogs e.g., SEQ ID NO: 3-16, 26-40, 45-48, 58-63, and 71-74 and partial 17-25, 49-57, 64-70, 75-89) or active fragment thereof; or a membrane proximal external region (MPER, SEQ ID NO: partial 17-25, 41-43, 49-57, 64-70, and 75-89) having at least one of a stabilized alpha-helix, a stabilized kink portion, and a stabilized $3_{10}$-helix, or an active fragment thereof; or a peptide having a stabilized viral alpha helix heptad repeat 2 domain, or active fragment thereof, attached to an MPER, or at least an active fragment thereof. In an embodiment, the carboxy (C)-terminus of an HR-2 heptad repeat domain portion is attached to the amino (N)-terminus of an MPER portion, preferably from the same virus, but optionally from different viruses. In an embodiment, the heptad repeat domain alpha-helix that adjoins the MPER is terminated at the HR/MPER junction by insertion of a proline or other helix-breaking residue. The modified polypeptide may also comprise a chimera of an HR domain and/or an MPER domain. Suitable viral alpha helix heptad repeat domains and MPER domains can be derived from any virus with a helical domain that is directly or indirectly involved in cell attachment or entry.

Figure 7A:
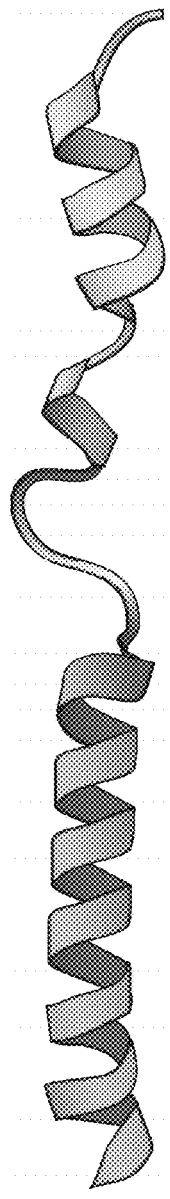
FIGS. 7A and B show exemplary structurally constrained peptide designs for the gp41 HR2 and MPER regions (aa 626 to 683 of SEQ ID NO: 1) based on the (A) schematically represented ribbon diagram structure with the HR2 and MPER domains, BNAb epitopes, and the amino acid sequence of the domains. As shown in (B), any of the HR2 staple containing peptide fragments a-j (SEQ ID NO: 31-40, respectively) can be joined with any of the three stapled MPER peptide fragments (SEQ ID NO: 41-43). * indicates position of hydrocarbon staples. SAS-gp41 peptides are constructed, for example, from one of three core staple reinforcements (A: i,i+3; B: i,i+4; C: i,i+7) designed to stabilize the C-terminal helical portion of the 4E10 epitope. The N-terminal portion of the MPER will have either no staple (enabling the 2F5 epitope to adopt an extended conformation) or one or more crosslinks in positions 1 (i,i+4), 2 (i,i+4), or 3 (i,i+7) to stabilize the N-terminal helical portion of the 4E10 epitope. To reinforce a kink surrounding F673, N671P, or D674P mutations are made to incorporate natural or non-natural amino acids. Mutations at position F673 can also be made, in conjunction with or independent of other mutations in the region, to incorporate any natural or non-natural amino acid, for example to a phenylalanine analog such as those shown in FIG. 11A. To examine the impact of lengthening the constructs to include the HR2 helix, a variety of single or multiply stapled HR2 domains are appended, such as the indicated doubly stapled HR2 peptides (a-j). For HR2-MPER constructs, an optional Q568P mutation is designed to terminate the HR2 helix just prior to the MPER. Deletion constructs of the HR2-MPER peptides that contain subsections of the indicated constructs are also envisioned (e.g. a C-terminal portion of HR2 in combination with MPER).
Figure 7B:
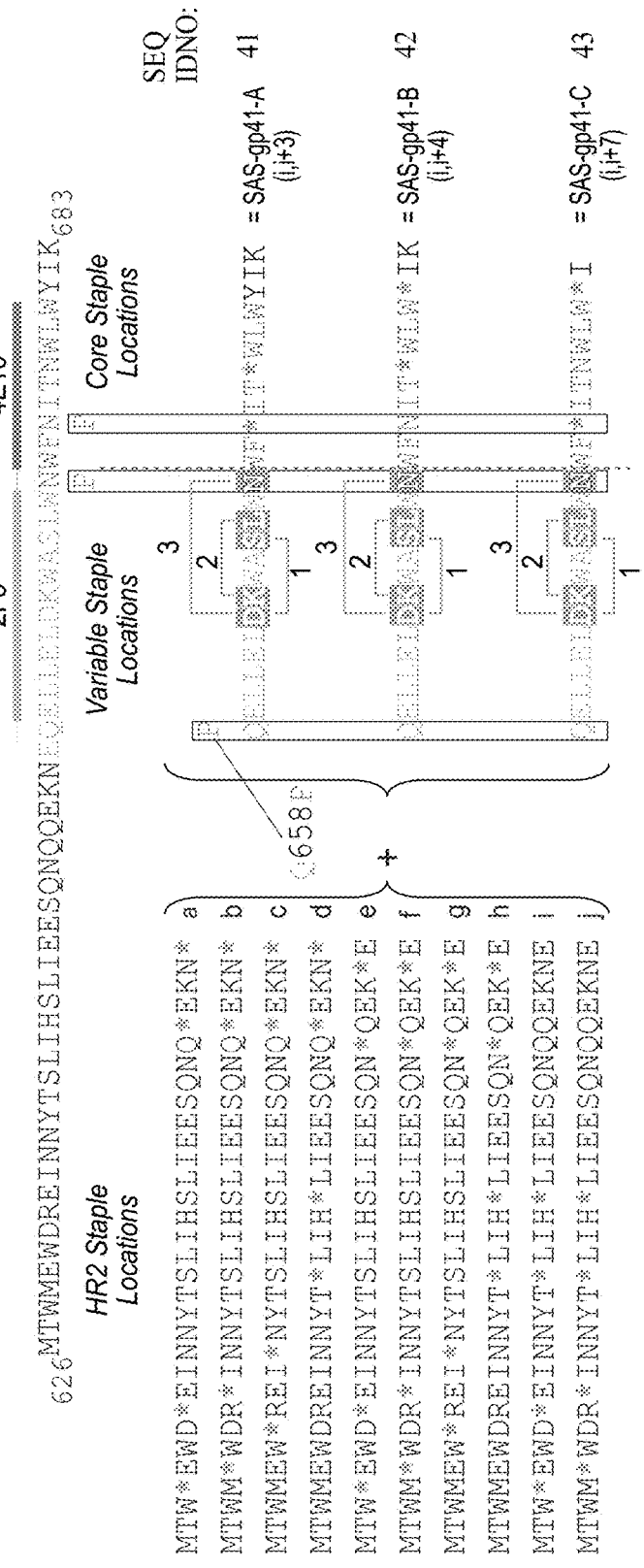

In an aspect, the invention is directed to a modified polypeptide having a stabilized HIV gp41 heptad repeat domain (e.g., heptad repeat domain 1 or 2 of HIV-1 or HIV-2), or an MPER domain of HIV-1, or a domain that traverses the HR2 domain and the MPER domain of HIV-1 (see, e.g., FIG. 7). The amino acid sequences of heptad repeat-1 and heptad repeat-2 domains are well known in the art and include those represented in FIGS. 2A and 2B. The amino acid sequences of MPER domains are well known in the art and include those represented in FIG. 2C. In one embodiment, the heptad repeat domain is 30% or more identical to an amino acid sequence of any of SEQ ID NO: 3-16, 26-40, 45-48, 58-63, 71-74 or to the HR portions of SEQ ID NO: 17-25, 49-57, 64-70, and 75-89, preferably SEQ ID NO: 3 or SEQ ID NO: 10, and forms an alpha helix. In one embodiment, the MPER is 30% or more identical to an amino acid sequence of any of SEQ ID NO: 17-25, 41-43, and 75-89, preferably the MPER portion of SEQ ID NO: 17, and forms, at least in part, an alpha helix or a $3_{10}$ helix. Alternatively, the heptad repeat domain or the MPER of the modified polypeptide may differ by more than 30% as long as the residues of the interacting face are identical to those of SEQ ID NO: 3, 10, or 17 or are conservative substitutions thereof. Methods for identifying the interacting face residues of the heptad repeat are well known in the art and described herein.

In another embodiment, the heptad repeat domain 2 is 30% or more identical to an amino acid sequence of SEQ ID NO: 10 to 16 and forms an alpha-helix. Alternatively, the heptad repeat 2 domain of the modified polypeptide may differ by more than 30% as long as the residues of the interacting face are identical to those of one of SEQ ID NO: 10 to 16, or have conservative substitutions thereof. Methods for identifying the interacting face residues of the heptad repeat are well known in the art and described herein.

In an embodiment, the modified polypeptide of the invention is has the same amino acid residues, or conservative substitutions thereof, of a face, for example the interacting face of the amino acid sequence of SEQ ID NO:3 to 89; or an active fragment thereof. For heptad repeat domains, the "interacting face" of the alpha helix are those amino acid residues which interact with other amino acid residues in the coiled coil structure, where the interacting helix is present on the same protein or in a different protein. For example, in the HIV gp41 HR-2 domain the interacting face includes the "a" and "d" position amino acids. (See FIG. 3), while the interacting face of the HIV gp41 HR-1 domain includes amino acids at positions e, g that interact with HR-2 and a, d that engage in HR1-HR1 interactions (See FIG. 3). Methods for identifying heptad repeats and the interacting face residues are well known in the art and described herein.

Preferably the alpha helix heptad repeat or MPER domain is stabilized with at least one hydrocarbon staple (e.g., FIGS. 4, 5, 6, 7, and 10). Hydrocarbon staples suitable for use with any of the modified polypeptides are described herein and in U.S. Publication No. 2005/0250680, which is incorporated by reference in its entirety. Hydrocarbon stapling allows a polypeptide, predisposed to have a helical secondary structure, to maintain its native helical conformation and increase its stability and efficacy. In one embodiment, the modified polypeptide has at least 10%, 20%, 30%, 35%, 40%, 45%, 50%, 60%, 70%, 80%, or 90% or more helicity in an aqueous solution as determined by circular dichroism. Assays for determining circular dichroism are known in the art and described herein.

The hydrocarbon stapled polypeptides include a tether (linkage) between two amino acids, which tether significantly enhances the helical secondary structure of the polypeptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, any of the amino acid residues of the modified polypeptides of the invention may be tethered (e.g., cross-linked) in conformity with the above. Suitable tethers are described herein and in U.S. Patent Publication No. 2005/0250680. It is understood that tethers such as hydrocarbon staples can be positioned at other intervals to promote helical variants (e.g. with different pitches, angles, or residues and fractions thereof per turn) or structures other than helices.

In a further embodiment, the hydrocarbon staple(s) is positioned so as to link a first amino acid (i) and a second amino acid (i+3) which is 3 amino acids downstream of the first amino acid. In another embodiment, the hydrocarbon staple links a first amino acid (i) and a second amino acid (i+4) which is 4 amino acids downstream of the first amino acid. In yet another embodiment, the hydrocarbon staple links a first amino acid (i) and a second amino acid (i+7) which is 7 amino acids downstream of the first amino acid.

In an embodiment, the modified, structurally constrained peptides include a heptad repeat domain with the sequence of SEQ ID NO 59-80, wherein X is any amino acid and further identifies the amino acid residues which are linked by a hydrocarbon staple, and B is methionine or norleucine. The modified polypeptides will generally have the structure of Formula (I), (II) or (III), as described herein.

The invention is also, inter alia, directed to modified, structurally constrained peptides from other viruses with alpha helical domains or MPER domains that are either directly or indirectly involved in the attachment and/or fusion of a virus to a cell, or are useful as a viral antigen for the stimulation of production of one or more BNAbs. For example, in one aspect the invention is directed to a modified polypeptide having a stabilized viral alpha helix (e.g., heptad repeat domain) or MPER domain that is derived from respiratory syncytial virus. The HR and MPER domains may include any alpha helical domain derived from RSV that is involved in viral infectivity. Suitable RSV alpha helix domains include those which are 30% or more identical to SEQ ID NO: 8, 15, and 90-93 and form an alpha-helix, and at least two of the residues of a selected face, such as the interacting face, are identical to those of SEQ ID NOs: 8, 15, and 90-93 or are conservative substitutions thereof. Methods for identifying a face of the heptad repeat or MPER domains are well known in the art and described herein.

In yet another aspect, the invention is directed to a modified polypeptide having a stabilized viral alpha helix heptad repeat domain or MPER domain that is derived from a parainfluenza virus. Suitable parainfluenza virus heptad repeat and MPER domains include those which are 30% or more identical to SEQ ID NO: 7, 14, and 94, and form an alpha-helix, and at least two residues of a selected face, such as the interacting face, are identical to those of SEQ ID NO: 7, 14, and 94 or are conservative substitutions thereof. Methods for identifying a face of the heptad repeat are well known in the art and described herein.

In another aspect, the invention is directed to a modified polypeptide having a stabilized viral alpha helix heptad repeat domain derived from a paramyxovirus, orthomyxovirus coronavirus, and a filovirus.

Coronavirus alpha helix heptad repeat and MPER domains are known in the art and include those which have an amino acid sequence which are 30% or more identical to SEQ ID NO: 9, 16, 25, and 95; and form an alpha-helix. Alternatively, the heptad repeat or MPER domain of the modified coronavirus polypeptide may differ by more than 30% as long as at least two residues of at least one face, for example, the interacting face are identical to those of SEQ ID NO: 9, 16, 25, and 95 or are conservative substitutions thereof. Methods for identifying a face of the heptad repeat are well known in the art and described herein.

Similarly, filovirus alpha helix heptad repeat and MPER domains are known in the art and include those that are 30% or more identical to SEQ ID NO: 4, 5, 11, 12, 97, and 98, and form an alpha-helix. Alternatively, the heptad repeat domain of the modified filovirus polypeptide may differ by more than 30% as long as the residues of a face, for example the interacting face, are identical to those of SEQ ID NO: 5 or 12 or are conservative substitutions thereof. Methods for identifying a face of the heptad repeat are well known in the art and described herein.

Retrovirus heptad repeat and MPER domains are also known in the art, e.g. parainfluenza virus sequences are provided in SEQ ID NOs: 7, 14, and 94. Further, a heptad repeat domain in Influenza A Virus (strain A/Aichi/2/68) occurs at residues 379-436, 387-453, and 380-456. Similarly, residues 383-471 were shown by Can and Kim to be an extended coiled coil when under acidic pH (Can and Kim, 1993, Cell 73: 823-832). Sequences for peptides for use in the methods of the invention include those that are 30% or more identical to SEQ ID NO: 7, 14, and 94, and form an alpha-helix. Alternatively, the heptad repeat domain of the modified filovirus polypeptide may differ by more than 30% as long as the residues of a face, for example the interacting face, are identical to those of SEQ ID NO: 7, 14, and 94 or are conservative substitutions thereof. Methods for identifying a face of the heptad repeat are well known in the art and described herein.

The modified polypeptides of the invention will generally include the structure of Formula (I), (II) or (III) provided below.

Any of the modified polypeptides described herein can be present in a composition (e.g., pharmaceutical composition) or kit. In some embodiments of the invention, the composition or kit comprises two or more modified polypeptides. For example, the composition may include two or more modified polypeptides having a stabilized HIV gp41 heptad repeat domain and/or a gp41MPER domain.

For clarity of discussion, the invention will be further described primarily for HR-1, HR-2, and MPER modified polypeptides of HIV. However, the principles may be analogously applied to other viruses, both enveloped and nonenveloped, and to other non-viral organisms. As used herein the term "heptad repeat" includes HR-2 and HR-1 peptides.

HR-2 and HR-2-Peptides

The modified polypeptides of the invention include the HR-2 peptides (amino acids 638 to 661 of SEQ ID NO:1) which corresponds to amino acid residues 638 to 673 and 626 and 662 respectively of gp160 from the HIV-1 (SEQ ID NO:1), and has the 36 and 37 amino acid sequences, respectively, of (reading from amino to carboxy terminus):

```
YTSLIHSLIEESQNQQEKNEQELLELDKWASLWNWF
and

MTWMEWDREINNYTSLIHSLIEESQNQQEKNEQELLE.
```

Other useful HR-2 polypeptides for use with the current invention are described in U.S. Pat. No. 7,273,614, which is incorporated herein by reference in its entirety.

In addition to the use of full-length HR-2 36 and 37-mers and the corresponding sequences and variants thereof found in the diversity of HIV-1 strains and mutants, the peptides of the invention may include truncations of the HR-2 peptide, gp41 polypeptide sequences that flank the HR-2 domain (ie. immediately upstream or downstream sequences), or chimeras which exhibit antifusogenic activity and antiviral activity. Truncations of HR-2 peptides include truncations from the C-terminus, or the N-terminus, or both and includes peptides of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37, contiguous amino acids, preferably at least 7 contiguous amino acid residues, or at least 2 residues, preferably 3, 4, 5, 6, 7, 8, or more residues of a face of a helix of SEQ ID NO: 10-16, 26-40, 45-48, 58-63, or 71-74, or partial sequences of SEQ ID NO: 17-25, 49-57, 64-70, and 75-89.

The modified peptides of the invention also include HR-2-like peptides. "HR-2-like" or "heptad repeat-like", as used herein, refers to full-length and truncated and chimeric HR-2 polypeptides which contain one or more amino acid substitutions, insertions and/or deletions as well as peptide sequences identified or recognized by homology searching. Representative HR-2 like polypeptides include those provided in SEQ ID NO: 10-16, 26-40, 45-48, 58-63, or 71-74. The modified HR-2-like peptides of the invention may exhibit antifusogenic or antiviral activity. In one embodiment, the heptad repeat domain 2 is 30% or more identical to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 contiguous amino acids, preferably at least 7 contiguous amino acids, or at least 2 residues, preferably 3, 4, 5, 6, 7, 8, or more residues of a face of a helix of SEQ ID NO: 10-16, 26-40, 45-48, 58-63, or 71-74 and form an alpha-helix. Alternatively, the heptad repeat domain 2 of the modified polypeptide may differ by more than 30% as long as at least two of the residues of a face, such as the interacting face, are identical to those of 10-16, 26-40, 45-48, 58-63, or 71-74 or are conservative substitutions thereof. Methods for identifying a face of the heptad repeat are well known in the art and described herein.

HIV-1 and HIV-2 enveloped proteins are structurally distinct, but there exists a striking amino acid conservation within the HR-2 regions of HIV-1 and HIV-2. The amino acid conservation is of a periodic nature, suggesting some conservation of structure and/or function. Therefore, one possible class of amino acid substitutions would include those amino acid changes which are predicted to stabilize the structure of the HR-2 peptides of the invention. Utilizing the HR-2 and HR-2 analog sequences described herein, the skilled artisan can readily compile HR-2 consensus sequences and ascertain from these, conserved amino acid residues which would represent preferred amino acid substitutions.

HR-1 and HR-1-Peptides

Further, the modified peptides of the invention include peptides having amino acid sequences corresponding to HR-1 analogs. HR-1 includes 38- and 51-amino acid peptides which exhibits potent antiviral activity, and corresponds to residues 553 to 590 and 542 to 592, respectively, of HIV-1 transmembrane (TM) gp41 protein of SEQ ID NO: 1.

In addition to the full-length HR-1 38-mer, the modified peptides of the invention include truncations of the HR-1 peptide which exhibit antifusogenic activity or antiviral activity. Truncations of HR-1 peptides can be made from either the C-terminus or N-terminus, or both. An HR-1 peptide can be 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38 amino acids in length.

The modified peptides of the invention also include HR-1-like peptides. "HR-1-like" or "heptad-repeat like", as used herein, refers to full-length and truncated HR-1 polypeptides which contain one or more amino acid substitutions, insertions and/or deletions and exhibiting antifusogenic or antiviral activity. In one embodiment, the heptad repeat domain 1 is 30% or more identical to an amino acid sequence of, or at least 2 residues, preferably 3, 4, 5, 6, 7, 8, or more residues of a face of a helix of one of SEQ ID NO: 3-9 and form an alpha-helix. Alternatively, the heptad repeat domain 1 of the modified polypeptide may differ by more than 30% as long as the residues of at least one face, such as the interacting face, are identical to those of SEQ ID NO: 3-9 or are conservative substitutions thereof. Methods for identifying the interacting face residues of the heptad repeat are well known in the art and described herein.

HIV-1 and HIV-2 enveloped proteins are structurally distinct, but there exists a striking amino acid conservation within the HR-1-corresponding regions of HIV-1 and HIV-2. The amino acid conservation is of a periodic nature, suggesting some conservation of structure and/or function. Therefore, one possible class of amino acid substitutions would include those amino acid changes which are predicted to stabilize the structure of the HR-1 peptides of the invention. Utilizing the HR-1 and HR-1 analog sequences described herein, the skilled artisan can readily compile HR-1 consensus sequences and ascertain from these, conserved amino acid residues which would represent preferred amino acid substitutions.

MPER and MPER-Peptides

MPER peptides are conserved through non-enveloped viruses. Multiple sequences of HR-2/MPER domains from various HIV strains are provided in FIG. 2C. A sequence alignment of an HIV and SARS MPER domains is also shown in FIG. 2C. MPERs are characterized as having an amino acid sequence capable of having a structure including an alpha-helix which is a continuation with the HR-2 helix, a kink, and a $3_{10}$-helix domain. However, the MPER domain is known to go through substantial structural changes during the infection process. Therefore, the structural changes that the peptide passes through during the infection process can reveal different epitopes that may be useful for the generation of neutralizing antibodies, e.g., broadly neutralizing antibodies.

Mutations, Truncations, and Extensions of HR and MPER Peptides

The amino acid substitutions may be of a conserved or non-conserved nature. Conserved amino acid substitutions consist of replacing one or more amino acids of the HR-1 peptide sequence with amino acids of similar charge, size, and/or hydrophobicity characteristics, such as, for example, a glutamic acid (E) to aspartic acid (D), aspartic acid (D) to asparagine (N), and glutamic acid (E) to glutamine (Q) amino acid substitution. Non-conserved substitutions consist of replacing one or more amino acids of the HR-1 peptide sequence with amino acids possessing dissimilar charge, size, and/or hydrophobicity characteristics, such as, for example, a glutamic acid (E) to valine (V) substitution. Substitutions can include the use of conserved or non-conserved non-natural amino acids.

Amino acid insertions may consist of single amino acid residues or stretches of residues. The insertions may be made at the carboxy or amino terminal end of the full-length or truncated HR-1, HR-2, or MPER peptides, as well as at a position internal to the peptide. Such insertions will generally range from 2 to 15 amino acids in length. It is contemplated that insertions made at either the carboxy or amino terminus of the peptide of interest may be of a broader size range, with about 2 to about 50 amino acids being preferred. One or more such insertions may be introduced into full-length or truncated HR-1, HR-2, or MPER peptides, as long as such insertions result in modified peptides which may still exhibit antifusogenic or antiviral activity.

Preferred amino or carboxy terminal insertions are peptides ranging from about 2 to about 50 amino acid residues in length, corresponding to gp41 protein regions either amino to or carboxy to the actual HR-1, HR-2, or MPER gp41 amino acid sequence, respectively. Thus, a preferred amino terminal or carboxy terminal amino acid insertion would contain gp41 amino acid sequences found immediately amino to or carboxy to the HR-1, HR-2, or MPER region of the gp41 protein, respectively.

Deletions of full-length or truncated HR-1, HR-2, or MPER peptides are also within the scope of the invention. Such deletions consist of the removal of one or more amino acids from the HR-1, HR-2, or MPER peptides; or HR-1, HR-2, or MPER-like peptide sequence, with the lower limit length of the resulting peptide sequence being 4, 5, or 6 amino acids. Such deletions may involve a single contiguous or greater than one discrete portion of the peptide sequences. One or more such deletions may be introduced into full-length or truncated HR-1, HR-2, or MPER peptides, as long as such deletions result in peptides which may still exhibit antifusogenic or antiviral activity HR-1, HR-2, and MPER Analogs Peptides corresponding to analogs of the full-length and truncated HR-1, HR-2, or MPER peptides, described, above, may be found in other enveloped and non-enveloped viruses. The term "HR-1, HR-2, or MPER-analogs", as used herein, refers to a peptide which is recognized or identified as having a heptad repeat-analog domain or MPER domain in a non-HIV virus. Methods for identifying heptad repeat-analog polypeptides are known in the art, for example, bioinformatics programs based on pairwise residue correlations (e.g., on the world wide web at: ch.embnet.org/software/COILS_form.html), which have the ability to recognize coiled coils from protein sequences and model their structures (See Lupas, A., et al. Science 1991. 252: 1162-1164, which is incorporated herein by reference). Further, such modified peptides exhibit antifusogenic or antiviral activity. Methods for identifying MPER domains are known in the art and can be performed using the criteria set forth herein.

Such HR-2 and HR-1 analogs may, for example, correspond to peptide sequences present in other enveloped and non-nonenveloped viruses. Such peptides may exhibit antifusogenic activity or antiviral activity and their amino acid sequences correspond to the amino acid sequences of peptide regions of, for example, other viruses that contain peptide regions homologous to the gp41 peptide region from which HR1 and HR2 peptides were derived (SEQ ID NO: 1, aa 553-590 and 542-592; and SEQ ID NO: 1, aa 626-661). A sequence corresponds to the HR-2 sequence when it forms an alpha helix, is at least 30% identical to HIV-1 HR-2, and is part of the viral fusion and infection apparatus. HR-2 analogs can be present in viruses including, but are not limited to, other HIV-1 isolates, HIV-2 isolates, SIV isolates, influenza, parainfluenza virus, coronavirus, RSV, etc. A sequence corresponds to the HR-1 sequence when it forms an alpha helix, is at least 30% identical to HIV-1 HR-2, and is part of the viral fusion and infection apparatus. HR-2 analogs can be present in viruses including, but are not limited to, other HIV-1 isolates, HIV-2 isolates, SIV isolates, influenza, parainfluenza virus, coronavirus, RSV, etc.

MPER analogs are peptides of HIV and non-HIV viruses whose amino acid sequences correspond to the amino acid sequences of peptide regions of, for example, other viruses that contain peptide regions corresponding to the gp41 peptide region from which MPER peptides were derived SEQ ID NO: 1, aa 662-683). A sequence corresponds to the MPER sequence when it can form in an exemplary membrane context, in order from N-terminus to C-terminus, a $3_{10}$ helix, a kink, and an alpha helix. However, the MPER domain is flexible and in the context of the full-length protein, portions of the MPER domain can be unfolded, as this region undergoes dynamic conformational changes. An MPER analog is at least 30% identical to HIV-1 MPER, and is part of the viral fusion and infection apparatus. MPER analogs can be present in viruses including, but are not limited to, other HIV-1 isolates, HIV-2 isolates, SIV isolates, influenza, parainfluenza virus, coronavirus, RSV, etc.

HR-1 and HR-2 analogs or other heptad repeat polypeptides include peptides whose amino acid sequences are comprised of the amino acid sequences of peptide regions of, for example, other viruses that contain peptide regions corresponding to the gp41 peptide region from which HR-1 (SEQ ID NO:3) and HR-2 (SEQ ID NO:7) peptides were derived. These polypeptides include: SEQ ID NO: 3-16, 26-40, 45-48, 58063, 71-74 and partially SEQ ID NO: 17-25, 49-57, 64-70, and 75-89.

RSV heptad repeat domains which are 30% or more identical to, and include at least 3 consecutive amino acids of, or share at least two amino acids on a face of the alpha helix formed by a peptide of the sequence of SEQ ID NO:8, 15, and 90-93 and form an alpha-helix.

Parainfluenza virus heptad repeat domains which are 30% or more identical to, and include at least 3 consecutive amino acids of, or share at least two amino acids on a face of the alpha helix formed by a peptide of the sequence of SEQ ID NO:7, 14, and 94 and form an alpha-helix.

Coronavirus alpha helix heptad repeat domains which are 30% or more identical to, and include at least 3 consecutive amino acids of, or share at least two amino acids on a face of the alpha helix formed by a peptide of the sequence of SEQ ID NO: 9, 16, 25, and 95 and form an alpha-helix.

Filovirus alpha helix heptad repeat domains which are 30% or more identical to, and include at least 3 consecutive amino acids of, or share at least two amino acids on a face of the alpha helix formed by a peptide of the sequence of SEQ ID NO: 4, 5, 11, 12, 97, and 98 and form an alpha-helix.

Retrovirus alpha helix heptad repeat domains which are 30% or more identical to, and include at least 3 consecutive amino acids of, or share at least two amino acids on a face of the alpha helix formed by a peptide of the sequence of SEQ ID NO: 6 and 13 and form an alpha-helix.

The modified polypeptides of the invention also contemplate the use of influenza virus heptad repeat domains.

Heptad repeats or heptad repeat-analogs are recognized or identified, for example, by utilizing computer-assisted search strategies known in the art. For example, bioinformatics programs based on pairwise residue correlations (e.g., on the world wide web at: ch.embnet.org/software/COILS_form.html), which have the ability to recognize coiled coils from protein sequences and model their structures (See Lupas, A., et al. Science 1991. 252(5009); p. 1162-1164, and U.S. Pat. No. 7,273,614 both of which are herein incorporated by reference in its entirety. The search strategy can identify additional peptide regions which are predicted to have structural and/or amino acid sequence features similar to those of HR-1 and/or HR-2 and/or MPER.

Stabilization of Heptad Repeat Polypeptides and MPER Peptides

The modified polypeptides of the present invention are structurally constrained (e.g., stabilized, stapled) helical and/or kink domains and/or include one or more amino acid sequence modifications as compared to the native (i.e., wild type or otherwise naturally occurring) sequence to incorporate natural and/or non-natural amino acids to limit the structural flexibility of the peptide as compared to the native sequence, which loses bioactive shape when taken out of physiologic context. Preferable the polypeptides include at least one molecular tether such as a hydrocarbon staple. Hydrocarbon stapling is described in U.S. Patent Publication No. 2005/0250680, which is incorporated herein by reference in its entirety.

The peptide α-helix participates in critically important protein interactions by presenting specific amino acid residues in an ordered and precise arrangement over a relatively large contact surface area (Chittenden, T., et al., *Embo Journal,* 1995. 14(22): p. 5589-5596; Kussie, P. H., et al. *Science,* 1996. 274(5289): p. 948-953; Ellenberger, T. E., et al., *Cell,* 1992. 71(7): p. 1223-1237). Alpha-helical domains and other protein structural features are frequently stabilized by scaffold sequences in the remainder of the protein, which facilitate the formation and/or maintenance of a helical structure, e.g., an α-helical structure. When taken out of context, α-helical peptide motifs can unfold, leading to loss of biological activity. Critical challenges is developing α-helical peptides include promoting and/or maintaining their natural α-helical structure and preparing peptides that can resist proteolytic, acid and thermal degradation, and thereby remain intact in vivo.

Hydrocarbon stapling, refers to a process for stably cross-linking a polypeptide via at least two substituted amino acids that helps to conformationally bestow the native secondary structure of that polypeptide. Hydrocarbon stapling promotes and maintains an alpha-helical secondary structure in peptides that thermodynamically favor an alpha-helical structure. This secondary structure increases resistance of the polypeptide to proteolytic cleavage and heat, and also may increase hydrophobicity. Accordingly, the hydrocarbon stapled (structurally constrained, e.g., crosslinked) polypeptides described herein have improved biological activity relative to a corresponding non-hydrocarbon stapled (not structurally constrained) polypeptide. For example the structurally constrained peptide can include an alpha-helical domain of an HIV polypeptide (e.g., HR-1, HR-2, or MPER domain), which can interfere with HIV attachment, fusion with, and infection of a cell, or promote an immune response to a viral structure that is essential for viral attachment, entry, or infection. In some instances, the structurally constrained peptide can be used to inhibit virus entry into a cell. The cross-linked polypeptides described herein can be used therapeutically, e.g., to treat HIV.

The hydrocarbon stapled polypeptides include a tether (linkage) between two amino acids, which tether significantly enhances the helical secondary structure of the polypeptide. Generally, the tether extends across the length of one or two helical turns (i.e., about 3-3.6 or about 7 amino acids). Accordingly, amino acids positioned at i and i+3; i and i+4; or i and i+7 are ideal candidates for chemical modification and cross-linking. Thus, for example, where a peptide has the sequence . . . X1, X2, X3, X4, X5, X6, X7, X8, X9 . . . , cross-links between X1 and X4, or between X1 and X5, or between X1 and X8 are useful as are cross-links between X2 and X5, or between X2 and X6, or between X2 and X9, etc. The use of multiple cross-links (e.g., 2, 3, 4 or more) has also been achieved, compounding the benefits of individual stapled adducts (e.g. improved helicity and activity; improved helicity and thermal stability; improved helicity and acid stability; improved helicity and pharmacologic properties). Thus, the invention encompasses the incorporation of more than one crosslink within the polypeptide sequence to either further stabilize the sequence or facilitate the structural stabilization, proteolytic resistance, thermal stability, acid stability, pharmacologic properties, and biological activity enhancement of longer polypeptide stretches.

In some embodiments of the invention, the tethers, e.g., hydrocarbon staples are used to stabilize structures other than helices. In such cases, the ends of the tethers can be placed at intervals other than at i, i+3, i+4, and i+7. For example, a molecular tether can be used to stabilize the kink region of the MPER domain to produce a curved surface rather than a flat continuous face as with a helix. The amino acid sequence and the placement of the ends of the tether will determine the number of amino acids spanned by the tether. Such considerations are well understood by those of skill in the art.

In one embodiment, the modified polypeptides of the invention have the formula (I), wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkyl, alkenyl, alkynyl; $[R_4—K—R_4]_n$; each of which is substituted with 0-6 $R_5$;

$R_4$ is alkyl, alkenyl, or alkynyl;

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

;

$R_6$ is H, alkyl, or a therapeutic agent;
n is an integer from 1-4;
x is an integer from 2-10;
each y is independently an integer from 0-100;
z is an integer from 1-10 (e.g., 1, 2, 3, 4, 5, 6, 7, 8, 9, 10); and
each Xaa is independently an amino acid. The modified polypeptides may includes an amino acid sequence which forms an alpha-helix and is 30% or more identical to, or contain at least 7 contiguous amino acids from an amino acid sequence of SEQ ID NO:2-23 or SEQ ID NO: 39-80; wherein X is any amino acid and further identifies the amino acid residues which are linked by a hydrocarbon staple, and B is methionine or norleucine.

The tether can include an alkyl, alkenyl, or alkynyl moiety (e.g., $C_5$, $C_8$ or $C_{11}$ alkyl or a $C_5$, $C_8$ or $C_{11}$ alkenyl, or $C_5$, $C_8$ or $C_{11}$ alkynyl). The tethered amino acid can be alpha disubstituted (e.g., $C_1$-$C_3$ or methyl).

In some instances, x is 2, 3, or 6.

In some instances, each y is independently an integer between 3 and 15.

In some instances each y is independently an integer between 1 and 15.

In some instances, $R_1$ and $R_2$ are each independently H or $C_1$-$C_6$ alkyl.

In some instances, $R_1$ and $R_2$ are each independently $C_1$-$C_3$ alkyl.

In some instances, at least one of $R_1$ and $R_2$ are methyl. For example $R_1$ and $R_2$ are both methyl.

In some instances $R_3$ is alkyl (e.g., $C_8$ alkyl) and x is 3.

In some instances, $R_3$ is $C_{11}$ alkyl and x is 6.

In some instances, $R_3$ is alkenyl (e.g., $C_8$ alkenyl) and x is 3.

In some instances x is 6 and $R_3$ is $C_{11}$ alkenyl.

In some instances, $R_3$ is a straight chain alkyl, alkenyl, or alkynyl.

In some instances $R_3$ is $—CH_2—CH_2—CH_2—CH{=}CH—CH_2—CH_2—CH_2—$.

In certain embodiments the two alpha, alpha disubstituted stereocenters are both in the R configuration or S configuration (e.g., i, i+4 cross-link), or one stereocenter is R and the other is S (e.g., i, i+7 cross-link). Thus, where formula I is depicted as

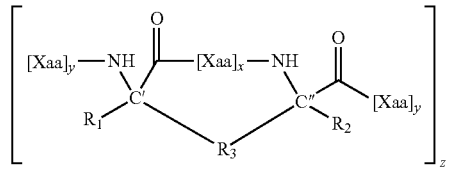

the C' and C" disubstituted stereocenters can both be in the R configuration or they can both be in the S configuration, for example when X is 3. When x is 6, the C' disubstituted stereocenter is in the R configuration and the C" disubstituted stereocenter is in the S configuration. The $R_3$ double bond may be in the E or Z stereochemical configuration.

In some instances $R_3$ is $[R_4—K—R_4]_n$; and $R_4$ is a straight chain alkyl, alkenyl, or alkynyl.

In some embodiments the modified polypeptide comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, or more contiguous amino acids of a heptad repeat or heptad repeat like domain, e.g., a HIV-1 HR-1 or HR-2 domain. Each [Xaa]y is a peptide that can independently comprise at least 5, 6, 7, 8, 9, 10, 11, 12, 13, 14, 15, 16, 17, 18, 19, 20, 25 or more contiguous amino acids of a heptad repeat or heptad repeat like domain, e.g., a HIV-1 HR-1 or HR-2 domain., e.g., a polypeptide depicted in any of FIGS. 5 and 6. $[Xaa]_x$ is a peptide that can comprise 3 or 6 contiguous amino acids of a heptad repeat or heptad repeat like domain, e.g., a HIV-1 HR-1 domain or HR-2, e.g., a polypeptide having the amino acid sequence of SEQ ID NO:1-14 or FIG. 5 or 6.

The modified polypeptide can comprise 3, 4, 5, 6, 7, 8, 9, 10, 11, 12, 13, 14, 15, 16, 17, 18, 19, 20, 25, 30, 35, 40, 45, 50 contiguous amino acids of a heptad repeat or heptad repeat like domain, e.g., a HIV-1 HR-1 domain or HR-2 domain; or MPER domain, e.g., a polypeptide having the amino acid sequence of SEQ ID NO:2 to 23 or 39 to 140, wherein two amino acids that are separated by two, three, or six amino acids are replaced by amino acid substitutes that are linked via $R_3$. Thus, at least two amino acids can be replaced by tethered amino acids or tethered amino acid substitutes. Thus, where formula (I) is depicted as 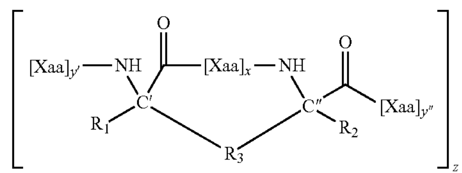 $[Xaa]_{y'}$ and $[Xaa]_{y''}$ can each comprise contiguous polypeptide sequences from the same or different heptad repeat or heptad repeat like domains.

The invention features cross-linked polypeptides comprising 10 (11, 12, 13, 14, 15, 16, 17, 18, 19, 20, 21, 22, 23, 24, 25, 30, 35, 40, 45, 50 or more) contiguous amino acids of a heptad repeat or heptad repeat like domain, e g, a HIV-1 HR-1 domain or HR-2 domain; or MPER domain, e.g., a polypeptide having the amino acid sequence of SEQ ID NO:10-16, 26-40, 45-48, 58-63, and 71-74, and partially 17-25, 49-57, 64-70, and 75-140, wherein the alpha carbons of two amino acids that are separated by two, three, or six amino acids are linked via $R_3$, one of the two alpha carbons is substituted by $R_1$ and the other is substituted by $R_2$ and each is linked via peptide bonds to additional amino acids.

In another embodiment, the modified polypeptides of the invention have the formula (II), 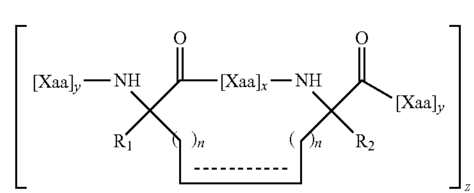 wherein
each $R_1$ and $R_2$ are independently H, alkyl, alkenyl, alkynyl, arylalkyl, cycloalkylalkyl; heteroarylalkyl; or heterocyclylalkyl;
each n is independently an integer from 1-15;
x is 2, 3, or 6
each y is independently an integer from 0-100;
z is an integer from 1-10 (e.g., 1, 2, 3, 4, 5, 6, 7, 8, 9, 10);
each Xaa is independently an amino acid.

The modified polypeptide forms an alpha-helix and can have an amino acid sequence which forms an alpha-helix and is 30% or more identical to, or contain at least 7 contiguous amino acids from an amino acid sequence of SEQ ID NO: SEQ ID NO:10-16, 26-40, 45-48, 58-63, and 71-74, and partially 17-25, 49-57, 64-70, and 75-140; wherein X is any amino acid and further identifies the amino acid residues which are linked by a hydrocarbon staple, and B is methionine or norleucine. The modified polypeptides may include an amino acid sequence that forms an alpha-helix and is 30% or more identical to, or contain at least 3, preferably at least 7 contiguous amino acids from an amino acid sequence, or at least two amino acids from a face of a helix formed by a peptide having the sequence of SEQ ID NO: SEQ ID NO:10-16, 26-40, 45-48, 58-63, and 71-74, and partially 17-25, 49-57, 64-70, and 75-140; wherein X is any amino acid and further identifies the amino acid residues which are linked by a hydrocarbon staple, and B is methionine or norleucine.

In still another embodiment, the modified polypeptides of the invention have the formula (III),

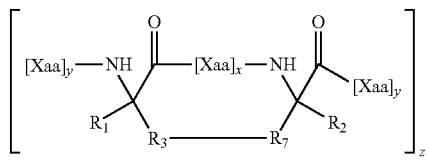

wherein;
each $R_1$ and $R_2$ are independently H, alkyl, alkenyl, alkynyl, arylalkyl, cycloalkylalkyl, heteroarylalkyl, or heterocyclylalkyl;
$R_3$ is alkyl, alkenyl, alkynyl; $[R_4—K—R_4]_n$ or a naturally occurring amino acid side chain; each of which is substituted with 0-6 $R_5$;
$R_4$ is alkyl, alkenyl, or alkynyl;
$R_5$ is halo, alkyl, $OR_6$, $N(R_6)_2$, $SR_6$, $SOR_E$, $SO_2R_6$, $CO_2R_6$, $R_6$, a fluorescent moiety, or a radioisotope;
K is O, S, SO, $SO_2$, CO, $CO_2$, $CONR_6$, or

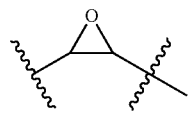 [SMILES: *C1OC1*]

$R_6$ is H, alkyl, or a therapeutic agent;
$R_7$ is alkyl, alkenyl, alkynyl; $[R_4—K—R_4]_n$ or an naturally occurring amino acid side chain; each of which is substituted with 0-6 $R_5$;
n is an integer from 1-4;
x is an integer from 2-10;
each y is independently an integer from 0-100;
z is an integer from 1-10 (e.g., 1, 2, 3, 4, 5, 6, 7, 8, 9, 10); and
each Xaa is independently an amino acid;

The modified polypeptides may include an amino acid sequence that forms an alpha-helix and is 30% or more identical to, or contain at least 7 contiguous amino acids from an amino acid sequence, or at least two amino acids from a face of a helix formed by a peptide having the sequence of SEQ ID NO: SEQ ID NO:10-16, 26-40, 45-48, 58-63, and 71-74, and partially 17-25, 49-57, 64-70, and 75-140; wherein X is any amino acid and further identifies the amino acid residues which are linked by a hydrocarbon staple, and B is methionine or norleucine.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary structure, whereas, in some instances, it is desirable to provide less constraint on the secondary structure, and thus a longer tether may be desired. It is further understood that the insertion of a tether at a site or in an amino acid sequence when the amino acid sequence has no tendency to form a helix will not result in helix formation.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids to promote and/or maintain the structures other than alpha helices.

As can be appreciated by the skilled artisan, methods of synthesizing the compounds of the described herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The specific method of synthesis of the peptides is not a limitation of the invention.

Synthesis of Peptides

The peptides of this invention can be made by chemical synthesis methods, which are well known to the skilled artisan and described herein. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the alpha-$NH_2$ protected by either t-Boc or F-moc chemistry using side chain protected amino acids on, for example, an Applied Biosystems Peptide Synthesizer Model 430A or 431 or the AAPPTEC multichannel synthesizer APEX 396.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides can also be made by conjoining individual synthetic peptides using native chemical ligation. Alternatively, longer synthetic peptides can be synthesized by well known recombinant DNA techniques. Such techniques are provided in well-known standard manuals with detailed protocols. To construct a coding sequence encoding a peptide of this invention, the amino acid sequence is reverse translated to obtain a nucleic acid sequence encoding the amino acid sequence, preferably with codons that are optimum for the organism in which the gene is to be expressed. Next, a coding sequence is made, typically by synthesizing oligonucleotides which encode the peptide and any regulatory elements, if necessary. The coding sequence is inserted in a suitable cloning vector and transfected into a host cell. Furthermore, the host cell is engineered so as to be able to incorporate the non-natural amino acids for the hydrocarbon staple. The peptide is then expressed under suitable conditions appropriate for the selected expression system and host. See Liu et al. *Proc. Nat. Acad. Sci. (USA)*, 94:10092-10097 (1997). The peptide is purified and characterized by standard methods.

The peptides can be made in a high-throughput, combinatorial fashion, e.g., using a high-throughput polychannel combinatorial synthesizer such as that available from Advanced Chemtech/APPTTEC.

Assaying Anti-Viral Activity

Described herein, are methods for evaluating the ability of a structurally constrained peptide of the instant invention, or an antibody generated against a structurally constrained peptides of the invention, to inhibit membrane fusion and/or exhibit anti-viral activity either in vitro, in vivo, or preferably both. Specifically, such assays are described below and in the Examples. Additional assays for evaluating anti-viral activity are well known to those with ordinary skill in the art. The method of determining anti-viral activity is not a limitation of the invention.

The antiviral activity exhibited by constrained peptides or antibodies generated against the peptides of the invention can be measured, for example, by easily performed in vitro assays, such as those described herein and known by those of ordinary skill in the art, which can test the peptides' ability to inhibit syncytia formation, or their ability to inhibit infection by cell-free virus (Madani, N., et al., *Journal of Virology*, 2007. 81(2): p. 532-538; Si, Z. H., M. Cayabyab, and J. Sodroski, *Journal of Virology*, 2001. 75(9): p. 4208-4218; Si, Z. H., et al., *PNAS USA*, 2004. 101(14): p. 5036-5041).

Using these assays, such parameters as the relative antiviral activity of the peptides, or antibodies derived thereof, exhibit against a given strain of virus and/or the strain specific inhibitory activity of the peptide or derived antipeptide antibody can be determined. Inhibitory activity of the peptides and antibodies of the instant invention can be compared to control peptides that are not structurally constrained (e.g., have a native sequence), or control antibodies (e.g., preimmune antibodies, non-specific immunoglobulins) respectively.

Assays to test a peptide's or antibody's antiviral capabilities are contemplated with the present invention. Taking HIV as an example, a reverse transcriptase (RT) assay may be utilized to test the peptide's or antibody's ability to inhibit infection of CD-4$^+$ cells by cell-free HIV. Such an assay may comprise culturing an appropriate concentration (i.e., Tissue Culture Infectious Dose 50 (ID$_{50}$)) of virus and CD-4$^+$ cells in the presence of the peptide or derived antibody to be tested. Culture conditions well known to those in the art are used. A range of peptide or antibody concentrations may be used, in addition to a control culture wherein no peptide or antibody has been added. After incubation for an appropriate period (e.g., 7 days) of culturing, a cell-free supernatant is prepared, using standard procedures, and tested for the present of RT activity as a measure of successful infection. The RT activity may be tested using standard techniques such as those described by, for example, Goff et al. (Goff, S. et al., 1981, *J. Virol.* 38:239-248) and/or Willey et al. (Willey, R. et al., 1988, *J. Virol.* 62:139-147). These references are incorporated herein by reference in their entirety.

Standard methods which are well-known to those of skill in the art may be utilized for assaying non-retroviral activity. See, for example, Pringle et al. (Pringle, C. R. et al., 1985, J. Medical Virology 17:377-386) for a discussion of respiratory syncytial virus and parainfluenza virus activity assay techniques. Further, see, for example, "Zinsser Microbiology", 1988, Joklik, W. K. et al., eds., Appleton & Lange, Norwalk, Conn., 19th ed., for a general review of such techniques. These references are incorporated by reference herein in their entirety.

Structurally constrained peptides of the invention, and likely antibodies targeted thereto, are able to inhibit infection and syncytial formation in enfuvirtide resistant HIV strains. One suitable method for assessing the ability of the modified polypeptides to treat these enfuvirtide resistant HIV strains is a five-helix bundle assay as described in Root, M. J., M. S. Kay, and P. S. Kim, *Science*, 2001. 291(5505): p. 884-888.

Briefly, the five-helix bundle assay would include helix bundle peptides that incorporate resistance mutations. FITC-labeled structurally constrained-gp41 compounds or antibodies raised thereto are screened against these mutant five-helix bundle proteins to determine if any structurally constrained-gp41 compounds retain activity despite HR domain mutations in the resistant viral strains. The FITC labeled mutants structurally constrained-gp41 peptides (e.g., mSAH-gp41 compounds in FIGS. 7, 9, and 10) compounds or targeted antibodies can be screened for binding affinity to mutant five-helix bundle proteins and for suppression of HIV infectivity using primary resistance strains.

In an aspect, the structurally constrained peptides of the invention and antibodies raised thereto can be used to monitor the evolution of resistance in HIV isolates. To explore the evolution of potential resistance to structurally constrained-gp41 compounds or antibodies targeted thereto, HIV strains can be incubated in the presence of increasing concentrations of structurally constrained-gp41 compounds or antibodies targeted thereto in a cell culture. Resistant strains can be genotyped to monitor the evolution of resistance. (See Dwyer et al. *Proc. Natl. Acad. Sci.,* 104:12772 (2007)). Because resistance to one modified polypeptide of the invention may not affect susceptibility to other variants, (Ray, N., et al., *Journal of Virology,* 2007. 81(7): p. 3240-3250) it is contemplated that treatment may include a combination of different structurally constrained-gp41 polypeptides or antibodies targeted thereto that are able to treat or prevent the development of resistant strains of HIV.

In vivo assays may also be utilized to test, for example, the antiviral activity of the peptides of the invention and the antibodies raised thereto. In vivo assays can also be used to determine the antigenicity of the structurally constrained peptides of the invention. To test for anti-HIV activity, for example, the in vivo model described in Barnett et al. (Barnett, S. W. et al., 1994, Science 266:642-646, incorporated herein by reference) may be used.

Additionally, anti-RSV activity can be assayed in vitro using the RSV plaque assay and in vivo via well known mouse models (Kong et al., *Virology J.* 2:3 (2005). For example, RSV can be administered intranasally to mice of various inbred strains. Virus replicates in lungs of all strains, but the highest titers are obtained in P/N, C57L/N and DBA/2N mice. Infection of BALB/c mice produces an asymptomatic bronchiolitis characterized by lymphocytic infiltrates and pulmonary virus titers of $10^4$ to $10^5$ pfu/g of lung tissue (Taylor, G. et al., 1984, *Infect. Immun.* 43:649-655). Cotton rat models of RSV are also well known. Virus replicates to high titer in the nose and lungs of the cotton rat but produces few if any signs of inflammation. Additional assays for evaluating the effectiveness of the modified viral polypeptides are well known to those of ordinary skill in the art, for example using assays to determine inhibition of syncytial formation and viral infection.

Pharmaceutical Compositions and Routes of Administration

One or more structurally constrained peptide of the instant invention can be used in a pharmaceutical composition for the prevention and/or treatment of HIV infection and AIDS. Combinations of pharmaceutical agents are frequently used for the treatment of complex or dangerous diseases, such as HIV infection and AIDS (e.g., protease inhibitor cocktail). Treatment and prevention method provided herein can be performed using a combination of the structurally constrained peptides, which can be selected and combined to prevent the development of resistance, or can be selected and combined depending on the particular strain or strain of viruses infecting the subject. Similarly, due to the high mutation frequency of viruses and the large number of strains, a combination of peptides is frequently used for the preparation of a vaccine. For example, a pharmaceutical composition of the instant invention can include 2, 3, 4, 5, 6, 7, 8, 9, 10, 11, 12, 13, 14, 15, or more structurally constrained peptides. The structurally constrained peptides can also be combined with other agents, e.g., anti-viral agents, vaccine adjuvants, DNA vaccines.

One or more antibodies (e.g. polyclonal, monoclonal) raised against one or more structurally constrained peptide of the instant invention can be used for the prevention and/or treatment of HIV infection or AIDS. Treatment and prevention methods provided herein can be performed with a combination of antibodies which can be selected and combined to prevent the development of resistance, or can be selected and combined depending on the particular strain or strain of viruses infecting the subject. For example, a pharmaceutical composition of the instant invention can include 2, 3, 4, 5, 6, 7, 8, 9, 10, 11, 12, 13, 14, 15, or more antibodies. The antibodies generated against structurally constrained peptides can also be combined with other agents, e.g., anti-viral agents, vaccines.

As used herein, the compounds of this invention are defined to include pharmaceutically acceptable derivatives thereof. A "pharmaceutically acceptable derivative" means any pharmaceutically acceptable salt, ester, salt of an ester, or other derivative of a compound of this invention which, upon administration to a recipient, is capable of providing (directly or indirectly) a compound of this invention. Particularly favored derivatives are those that increase the bioavailability of the compounds of this invention when such compounds are administered to a mammal (e.g., by allowing an orally administered compound to be more readily absorbed into the blood, to increase serum stability or decrease clearance rate of the compound) or which enhance delivery of the parent compound to a biological compartment (e.g., the brain or lymphatic system) relative to the parent species. Derivatives include derivatives where a group which enhances aqueous solubility or active transport through the gut membrane is appended to the structure of formulae described herein.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-$(alkyl)_{4+}$ salts. This invention also envisions the quaternization of any basic nitrogen-containing groups of the compounds disclosed herein. Water or oil-soluble or dispersible products may be obtained by such quaternization.

The compounds of the invention can, for example, be administered by injection, intravenously, intraarterially, subdermally, intraperitoneally, intramuscularly, or subcutaneously; or orally, buccally, nasally, transmucosally, intravaginally, cervically, topically, in an ophthalmic preparation, or by inhalation, with a dosage ranging from about 0.001 to about 100 mg/kg of body weight, or according to the requirements of the particular drug and more preferably from 0.5-10 mg/kg of body weight. The methods herein contemplate administration of an effective amount of compound or compound composition to achieve the desired or stated effect.

If the composition is to be used for vaccination/immunization it is preferred that the structured polypeptide compound, conjugated to carrier protein(s) and combined with adjuvant using vaccine compositions known in the art, be administered only rarely. In certain embodiments, the compound is to be delivered by injection, e.g., intramuscular, subcutaneous, or intraperitoneal injection, to produce a systemic response. Alternatively, or additionally, the structured peptide for immunization is delivered by mucosal route, e.g., orally, buccally, intravaginally, rectally, intranasally, by inhalation, In a preferred embodiment the composition is administered once in a lifetime, once about every 20 years, once about every 15 years, once about every 10 years, once about every 5 years, once about every 2 years, about once a year. In certain embodiments, the compound is administered multiple times, e.g., 2, 3, 4, 5, 6 or more times over a relatively short period of time (e.g., within a year, within 9 months, within 6 months, within 4 months, within 3 months, within 2 months, within one month), followed by a sustained period (e.g., 5 years, 10 years, 15 years, 20 years, or more) of immunity during which no further administration of the compound is required.

If the composition to be administered is an antibody generated against one or more of the structured peptides of the invention, including a monoclonal antibody generated by a hybridoma cell generated using a B cell of a subject immunized with one of the structured peptides of the invention, the frequency of administration would be more frequent than with an immunization. Further, over time the dose of antibody can change for the same subject depending on use as a therapeutic or a prophylactic, viral load, use as a chronic or acute therapy. For example, an antibody may be administered one or more times per day; one or more times per week; one or more times per month; one or more times per year. Dosing may be determined in conjunction with monitoring of infection, in response to viral flares, etc.

The amount of active ingredient that may be combined with the carrier materials to produce a single dosage form will vary depending upon the host treated and the particular mode of administration. A typical preparation will contain from about 1% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition or for prevention of infection, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms (e.g. increase in HIV viral load).

Pharmaceutical compositions of this invention comprise a compounds of the invention or a pharmaceutically acceptable salt thereof; an additional agent including for example, one or more therapeutic agents for the prevention and/or treatment of viral infection, particularly for the prevention and/or treatment of HIV infection, including, but not limited to any combination of one, two, or more of each of nucleoside analogue reverse transcriptase inhibitors (NARTIs or NRTIs), protease inhibitors, a non-nucleoside reverse transcriptase inhibitor (NNRTI), nucleoside analog reverse transcriptase inhibitors, and any pharmaceutically acceptable carrier, adjuvant or vehicle. Alternate compositions of this invention comprise a compound of the invention or a pharmaceutically acceptable salt thereof; and a pharmaceutically acceptable carrier, adjuvant or vehicle. The compositions delineated herein include the compounds of the invention delineated herein, as well as additional therapeutic agents (e.g. drugs, vaccines, antibodies) if present, in amounts effective for achieving a modulation of disease or disease symptoms, including HIV mediated disorders or symptoms thereof.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α.-tocopherol polyethyleneglycol 1000 succinate, surfactants used in pharmaceutical dosage forms such as Tween® or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, may also be advantageously used to enhance delivery of compounds of the formulae described herein.

The pharmaceutical compositions of this invention may be administered enterally for example by oral administration, parenterally, by inhalation spray, topically, rectally, nasally, buccally, vaginally or via an implanted reservoir, preferably by oral or vaginal administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases, or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional, and intracranial injection or infusion techniques.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween® 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of the invention may be administered topically or intravaginally. The pharmaceutical composition will be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. In still another embodiment, the pharmaceutical composition is formulated as a vaginal ring. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention. In one embodiment, the compound of the invention is administered vaginally as a prophylactic treatment for a sexually transmitted disease, e.g., HIV.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

With respect to HIV, peptides or antibodies targeted hereto of the invention may be used as therapeutics in the treatment of HIV infection and/or AIDS. In addition, the peptides or antibodies targeted hereto may be used as prophylactic measures in previously uninfected individuals after acute exposure to an HIV virus (e.g. post-exposure prophylaxis). Examples of such prophylactic use of the peptides or antibodies targeted hereto may include, but are not limited to, prevention of virus transmission from mother to infant and other settings where the likelihood of HIV transmission exists, such as, for example, sexual transmission or accidents in health care settings wherein workers are exposed to HIV-containing blood products.

Effective dosages of the peptides or antibodies targeted hereto of the invention to be administered may be determined through procedures well known to those in the art which address such parameters as biological half-life, bioavailability, and toxicity.

A therapeutically effective dose refers to that amount of the compound or antibody sufficient to result in amelioration of symptoms or a prolongation of survival in a patient. Toxicity and therapeutic efficacy of such compounds or antibodies can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds or antibodies which exhibit large therapeutic indices are preferred. The data obtained from these cell culture assays and animal studies can be used in formulating a range of dosage for use in humans. The dosage of such compounds or antibodies lies preferably within a range of circulating concentrations that include the ED50 with little or no toxicity. The dosage may vary within this range depending upon the dosage form employed and the route of administration utilized. For any compound or antibody used in the method of the invention, the therapeutically effective dose can be estimated initially from cell culture assays. A dose may be formulated in animal models to achieve a circulating plasma concentration range that includes the $IC_{50}$ (e.g., the concentration of the test compound which achieves a half-maximal inhibition of the fusogenic event, such as a half-maximal inhibition of viral infection relative to the amount of the event in the absence of the test compound) as determined in cell culture. Such information can be used to more accurately determine useful doses in humans. Levels in plasma may be measured, for example, by high performance liquid chromatography (HPLC) or mass spectrometry (MS).

Prophylactic Vaccine

The peptides of the invention can be used as a vaccine, both prior to HIV infection and potentially in a subject having an HIV infection with a sufficiently intact immune system (e.g., sufficiently high CD4+ cell count) due to the early stage of the infection or to successful treatment with antiviral agents, wherein the host raises antibodies against the peptides of the invention, which then serve to neutralize a virus (e.g., HIV, RSV, influenza, parainfluenza, coronavirus, ebolavirus) by, for example, inhibiting further infection, or clearing virally infected cells. Administration of the peptides of the invention as a prophylactic vaccine, therefore, would comprise administering to a host a concentration of one or more peptides effective in raising an immune response which is sufficient to neutralize the virus, by, for example, inhibiting virus ability to infect cells. The exact concentration depends upon the specific peptide to be administered, but may be determined by using standard techniques for assaying the development of an immune response which are well known to those of ordinary skill in the art. The peptides to be used as vaccines are usually administered intramuscularly. However, anti-viral vaccines can also be administered to mucosal surfaces, e.g., orally, vaginally, rectally, nasally, pulmonarily, etc. to produce a mucosal immune response at common sites of viral entry.

The peptides can be formulated with a carrier and/or suitable adjuvant in order to enhance the immunological response. Adjuvants may include, but are not limited to mineral gels such as aluminum hydroxide; surface active substances such as lysolecithin, pluronic polyols, polyanions; other peptides; oil emulsions; and potentially useful human adjuvants such as BCG and *Corynebacterium parvum*. Many methods may be used to introduce the vaccine formulations described here. These methods include but are not limited to oral, intradermal, intramuscular, intraperitoneal, intravenous, subcutaneous, and intranasal routes.

Alternatively, an effective concentration of polyclonal or monoclonal antibodies raised against the peptides of the invention can be administered to a host so that no uninfected cells become infected by the virus. The exact concentration of such antibodies will vary according to each specific antibody preparation, but may be determined using standard techniques well known to those of ordinary skill in the art. Administration of the antibodies can be accomplished using a variety of techniques, including, but not limited to those described herein.

In an aspect, the invention is directed to a method of generating an antibody to a structurally constrained peptide of the invention. The method includes administering a modified polypeptide(s) of the invention to a subject so as to generate an antibody to the structurally constrained polypeptide.

After immunization of subjects with the structurally constrained peptides of the instant invention, subjects can be tested to determine if a neutralizing antibody or a BNAb has been generated using well-known methods. For example, a blood sample can be obtained for a subject and tested to determine if antibodies present in the serum are able to inhibit viral infection or fusion in an in vitro assay. Such assays can be performed using more than one viral strain, or against a drug resistant viral strain, such as an enfuvirtide-resistant HIV strain. Upon identification of a subject (human or non-human subject) with an immune response that generated a neutralizing antibody or a BNAb, B cells can be collected from the subject and used for the generation of hybridoma cells for the production of monoclonal antibodies. The monoclonal antibodies can be tested for their activity as a neutralizing antibody or BNAb, and the a neutralizing antibody or BNAbs can be further characterized.

In an alternative embodiment, B cells can be collected from an immunized subject prior to determination that the subject has generated a neutralizing antibody or a BNAb and fused to generate a hybridoma cells. The monoclonal antibodies can then be tested to determine if they have a neutralizing antibody or BNAb activity using any of the methods provided herein.

If the neutralizing antibodies or BNAbs were raised in a non-human animal, the CDRs can be transferred from the non-human framework to a human framework to generate an antibody suitable for administration to a human. Methods to humanize antibodies and make antibodies acceptable for human administration are well known in the art. The framework can include a naturally occurring human antibody framework (e.g., IgG), or an artificial framework such as an scFv for use as a therapeutic or other desired purposes.

In yet another aspect, the invention is directed to an antibody that specifically binds a structurally constrained polypeptide, wherein the modified polypeptide has an amino acid sequence of any of the sequences comprising at least at least 3, preferably at least 7 contiguous amino acids the structurally constrained peptides provided herein with the sequence of any of SEQ ID NO: 39 to 80, wherein X is any amino acid and further identifies the amino acid residues which are linked by a hydrocarbon staple, and B is methionine or norleucine.

Kits

The present invention also encompasses a finished packaged and labeled pharmaceutical product or laboratory reagent. This article of manufacture includes the appropriate instructions for use in an appropriate vessel or container such as a glass vial or other container that is hermetically sealed. A pharmaceutical product may contain, for example, a compound of the invention in a unit dosage form in a first container, and in a second container, sterile water or adjuvant for injection. Alternatively, the unit dosage form may be a solid suitable for oral, transdermal, intranasal, intravaginal, cervical ring, or topical delivery.

In a specific embodiment, the unit dosage form is suitable for intravenous, intramuscular, intraperitoneal, intranasal, oral, intravaginal, cervical, topical or subcutaneous delivery. Thus, the invention encompasses solutions, solids, foams, gels, preferably sterile, suitable for each delivery route.

As with any pharmaceutical product, the packaging material and container are designed to protect the stability of the product during storage and shipment. Further, the products of the invention include instructions for use or other informational material that advise the physician, technician, or patient on how to appropriately prevent or treat the disease or disorder in question. In other words, the article of manufacture includes instructions indicating or suggesting a dosing regimen including, but not limited to, actual doses, monitoring procedures (e.g. detection and quantitation of infection), and other monitoring information.

Specifically, the invention provides an article of manufacture including packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises a compound of the invention, and wherein said packaging material includes instruction means which indicate that said compound can be used to prevent, manage, treat, and/or ameliorate one or more symptoms associated with a viral disease, or to stimulate an immune response to prevent a viral disease by administering specific doses and using specific dosing regimens as described herein.

The following examples are provided merely as illustrative of various aspects of the invention and shall not be construed to limit the invention in any way.

EXAMPLES

Example 1. Materials and Methods

Synthesis of Hydrocarbon Stapled Alpha Helical Polypeptides.

A combined strategy of structural analysis and chemical synthesis was applied to construct the modified, structurally constrained peptides. Asymmetric syntheses of α,α-disubstituted amino acids was performed as previously reported (Schafineister, C. E., J. Po, and G. L. Verdine, *Journal of the American Chemical Society*, 2000. 122(24): p. 5891-5892; Walensky, L. D., et al., *Science*, 2004. 305(5689): p. 1466-1470). The modified polypeptide compounds were generated by replacing at least two naturally occurring amino acids with the α,α-disubstituted non-natural amino acids at discrete locations flanking either 2, 3 or 6 amino acids, namely the "i, i+3," "i, i+4" or "i, i+7" positions, respectively.

Locations for the non-natural amino acids and subsequent hydrocarbon staple(s) were carefully chosen so as not to interfere with N36 interactions (Chan, D. C., et al., *Cell*, 1997. 89(2): p. 263-273). Residues in positions a and d interact directly with N36, whereas, residues e and g may contact the N36 core as a result of the pitch of the six-helix bundle. Residues b, f, and c localize to the opposite face of the α-helix and are thus ideally located for placement of the hydrocarbon staple(s). Similar selections were made for the positioning of hydrocarbon staples in the MPER domain.

The modified polypeptides were generated using solid phase Fmoc chemistry and ruthenium-catalyzed olefin metathesis, followed by peptide deprotection and cleavage, purification by reverse-phase high performance liquid chromatography, and chemical characterization using LC/MS mass spectrometry and amino acid analysis.

Alternatively an established fragment-based approach can be pursued ([Bray, B. L. *Nature Reviews Drug Discovery*, 2003. 2(7): p. 587-593; MYUNG-CHOL KANG, B. B., et al., *Methods and compositions for peptide synthesis*, U.S.P.a.T. Office, Editor. Jan. 18, 2000 USA). In this strategy, the peptide is divided into 3 fragments, such that an N-terminal, central, and C-terminal portion are synthesized independently. These polypeptide fragments should be generated using solid phase Fmoc chemistry and ruthenium-catalyzed olefin metathesis on super-acid cleavable resins, which yields fully protected peptides having an Fmoc at the N-terminus, and either a C-terminal amide (for the C-terminal fragment) or a free carboxylate (for the central and N-terminal fragments). These fully protected fragments are purified by reverse-phase high performance liquid chromatography, followed by sequential deprotection, coupling, and purification, to yield the full length, fully protected polypeptides. Global deprotection, followed by reverse-phase high performance liquid chromatography will yield the final products, which can be characterized using LC/MS mass spectrometry and amino acid analysis.

Stapled peptide synthesis. Peptides were produced on an Apex 396 (Aapptec) automated peptide synthesizer using Rink amide AM LL resin (EMD Biosciences, 0.2 mmol/g resin), at 50 mmol scale. The standard Fmoc protocol employed 2×10 min deprotections in 20% piperidine/NMP followed by a pair of consecutive methanol and dimethylformamide (DMF) washes. The incorporated non-natural amino acids were treated with 4×10 min incubations in 20% piperidine/NMP to achieve complete deprotection. Amino acid coupling was performed using 0.4 M stock solutions of Fmoc-protected amino acids, 0.67 M 2-(6-chloro-1H-benzotriazole-1-yl)-1,1,3,3-tetramethylaminium hexafluorophosphate (HCTU), and 2 M N,N-diisopropyl ethylamine (DIEA), yielding 1 mL of 0.2 M active ester (4 equivalents). Coupling frequency and incubation times were 2×30 min for standard residues, 2×45 min for the olefinic non-natural amino acids, and 3×45 min for the residue following a non-natural amino acid. The olefin metathesis step is carried out by first swelling the resin with 1,2-dichloroethane followed by exposure to a 10 mM solution of bis tricyclohexylphosphine)-benzylidene ruthenium(IV) dichloride (Grubbs' first generation catalyst) in 1,2-dichloroethane (0.20 mol % on the basis of resin substitution) for 2 h. The stapling reaction is carried out twice. The resin-bound peptide is then washed with 1,2-dichloroethane three times and dried under a stream of nitrogen. The completed peptide is cleaved from the resin and deprotected by exposure to trifluoroacetic acid (TFA)-based cleavage cocktails such as TFA/triisopropyl silane (TIS)/water (95%, 2.5%, 2.5%), and precipitated with methyl-tert-butyl ether followed by lyophilization. Lyophilized SAHB peptides are purified by reverse-phase HPLC by use of a C18 column. The compounds are characterized by LC/MS, with mass spectra obtained by electrospray in positive ion mode. Quantitation is achieved by amino acid analysis on a Beckman 6300 high-performance amino acid analyzer.

Determining the Secondary Structure and Proteolytic Stability of the Modified Polypeptides.

The α-helicity of stapled modified polypeptides was compared to their unmodified counterparts by circular dichroism. CD spectra were obtained on an Aviv spectropolarimeter at 20° C. using the following standard measurement parameters: wavelength, 190-260 nm; step resolution, 0.5 nm; speed, 20 nm/sec; accumulations, 10; response, 1 sec; bandwidth, 1 nm; path length, 0.1 cm. The α-helical content of each peptide was calculated by dividing the mean residue ellipticity $[\theta]222_{obs}$, by the reported $[\theta]222_{obs}$ for a model helical peptide (Forood, B., E. J. Feliciano, and K. P. Nambiar, *PNAS*, 1993. 90(3): p. 838-842; J. Martin Scholtz, Biopolymers, 1991. 31(13): p. 1463-1470; Lawless, M. K., et al., *Biochemistry*, 1996. 35(42): p. 13697-13708) or using, for example, the Aviv machine using CDNN software developed by Brohm in order to deduce five different secondary structure fractions (helix, parallel and antiparallel beta-sheet, beta-turn and random coil). Protein Engineering, 1992. 5(3); p. 191-195

Optimization of the Biophysical and Biochemical Properties of the Modified Polypeptides by Evaluating Diversified Modified Peptide Libraries Synthesized in High-Throughput Fashion.

High-throughput technologies were used to optimize the modified polypeptides activities for cellular and in vivo studies. For example, an Apex 396 multichannel synthesizer (AAPPTEC; Louisville, Ky.) was used to produce polypeptide libraries for biological evaluation. The polypeptide compounds were diversified by extension, truncation, or amino acid substitution across natural and select non-natural amino acids, and differential staple localization were made to maximize desirable biophysical and biochemical properties. The libraries were generated using high-throughput solid phase Fmoc chemistry and ruthenium-catalyzed olefin metathesis and peptide deprotection and cleavage. Peptide purification was achieved by reverse phase C18 HPLC, and products characterized by LC/MS mass spectrometry and amino acid analysis.

Evaluating the Ability of Structurally Constrained Peptides or Antibodies Targeted Thereto to Target and Inhibit HIV Fusion.

The binding activity and functional effects of the structurally constrained HIV-1 gp41 peptides were assessed in fluorescence polarization, syncytial fusion, and HIV infectivity assays. Equilibrium binding constants were determined by fluorescence polarization assays (FPA) using fluorescein isothiocyanate (FITC)-labeled modified polypeptides and titrated recombinant five-helix bundle protein. FPA experiments were performed using a BMG Labtech FLUOstar optima microplate reader or a SpectraMax microplate reader (Molecular Devices), and dissociation constants determined by nonlinear regression analysis using GraphPad software (Prism). The recombinant 5-helix bundle protein, first developed by Root et al., contains five of the six helices that comprise the core of the gp41 trimer-of-hairpins, which are connected by short peptide linkers (Root, M. J., M. S. Kay, and P. S. Kim, Science, 2001. 291(5505): p. 884-888). Because the 5-helix bundle lacks the third C-peptide helix and under experimental conditions is soluble, stable, and helical, incorporation of the sixth C-peptide in the form of FITC-modified polypeptide provided a direct measure of binding activity. In this manner, modified polypeptides, differing in peptide sequence, staple location, and staple number, can be screened for maximal binding activity as a surrogate for structural fidelity and thereby selected for stimulation of an immune response to produce a BNAb. Binding activity can also be determined indirectly by competition assays in which the 5-helix bundle is combined with a FITC-labeled unmodified HIV fusion inhibitor peptide and then unlabeled stapled gp41 peptides are added at increasing concentrations followed by measurement of fluorescence polarization and then calculation of Ki by nonlinear regression analysis, as indicated above.

An alternative binding assay can be employed based upon the "gp41-5" construct of Frey et al. Gp41-5 binds with high affinity to added peptides that contain all or part of the missing CHR. For example, using gp41-5 and fluorescein-labeled C38 (residues 117-154), Frey et al. successfully generated an FPA binding curve that revealed a $K_d$ of 3.6 nM (Frey, G., et al., *PNAS,* 2006. 103(38): p. 13938-13943).

Functional assays can be used to evaluate the activity of the antibodies produced. In culture, multinucleated giant cells or "syncytia" form as a result of direct cell-cell fusion between HIV-1-infected and uninfected CD4-positive cells. In the syncytia formation assay, an indicator cell line expressing the CD4 receptor, and a fusogenic cell line that lacks the CD4 receptor but contains HIV-1 proteins on the surface, fuse to generate 70-100 multinucleated giant cells in culture within 48 h. Syncytia are then counted using an inverted microscope. The ability of structured gp41 peptides or antibodies targeted thereto to inhibit syncytia formation in a dose-responsive fashion is used as a functional measure of fusion inhibition, for which $IC_{50}$s can be determined and compared with peptides T20 and T649, or established neutralization antibodies (Brenner, T. J., et al. *The Lancet,* 1991. 337(8748): p. 1001-1005; Madani, N., et al., *Journal of Virology,* 2007. 81(2): p. 532-538).

Also the direct inhibitory activity of modified polypeptides and the antibodies targeted thereto can be quantified based upon their capacity to directly block HIV infection of CD4-positive and CCR5-expressing canine thymus cells. Recombinant HIV-1 viruses (eg. HXBc2, YU2, and additional strains available through the NIH AIDS Research and Reference Reagent Program) expressing firefly luciferase and containing the indicated envelope glycoproteins can be used to infect Cf2Th-CD4-CCR5/CXCR4 cells in the presence of serially diluted modified HIV-1 gp41 polypeptides or antibodies targeted thereto After 48 hours, the cells are lysed and luciferase activity is quantified (Si, Z. H., M. Cayabyab, and J. Sodroski, *Journal of Virology,* 2001. 75(9): p. 4208-4218 Si, Z. H., et al., *PNAS,* 2004. 101(14): p. 5036-5041). The identical experiment is performed with the amphotropic murine leukemia virus (AMLV), to monitor for any nonspecific effects of the modified polypeptides or antibodies. Similar control assays may be performed with unmodified or non-HIV polypeptides of the invention or control antibodies and are known in the art.

Protease Resistance Assay

In vitro proteolytic degradation of HIV-1 gp41 structured peptides was measured by LC/MS (Agilent 1200) using the following parameters: 20 μL injection, 0.6 mL flow rate, 15 min run time consisting of a gradient of water (0.1% formic acid) to 20-80% acetonitrile (0.075% formic acid) over 10 min, 4 min wash to revert to starting gradient conditions, and 0.5 min post-time. The DAD signal was set to 280 nm with an 8 nm bandwidth and MSD set to scan mode with one channel at (M+2H)/2, +1 mass units and the other at (M+3H)/3, +1 mass units. Integration of each MSD signal yielded areas under the curve of $>10^8$ counts. Reaction samples were composed of 5 μL peptide in DMSO (1 mM stock) and 195 μL of buffer consisting of 50 mM phosphate buffer pH 7.4 containing 2 mM $CaCl_2$. Upon injection of the 0 hr time point sample, 2 μL of 50 ng/μL chymotrypsin (Sigma) was added and the amount of intact peptide quantitated by serial injection over time. An internal control of acetylated tryptophan carboxamide at a concentration of 100 μM was used to normalize each MSD data point. A plot of MSD area versus time yielded an exponential decay curve and half-lives were determined by nonlinear regression analysis using Prism software (GraphPad). The assay was also performed using trypsin and pepsin in their appropriate buffer conditions.

Plasma Stability and Pharmacokinetics

Peptides were incubated (5-10 μg) with mouse plasma at 37° C. or injected (10, mg/kg) by tail vein into male C57/BL6 mice. Ex vivo and in vivo samples (withdrawn by retro-orbital bleed) at various time intervals (e.g. 0.5, 1, 2, 4, 8, 12 hr; n=3 per time point) were processed for quantitation. For ex vivo serum stability studies, peptide half-lives were calculated by nonlinear regression analysis of exponential decay curves plotted using Prism software (Graphpad). In vivo plasma concentrations at the indicated time points were used to calculate plasma half-life, peak plasma levels, total plasma clearance, and apparent volume of distribution using noncompartmental analysis. The derived protease-resistance and PK profiles serve as a measure for selecting the most stable structured HIV-1 gp41 peptides for in vivo application. Peptide constructs that recapitulate proposed neutralization-competent structures, possess functional binding activity, and exhibit a degradation-resistant profile by stability testing are advanced to neutralizing immunogenicity testing.

Fluorescence Polarization Assay (FPA).

FPA was used to directly measure and compare the relative affinities of distinct structured HIV-1 gp41 peptide constructs for the neutralizing antibodies 4E10, 2F5, and Z13e1 (NIH AIDS Research and Reference Reagents Program). Antibody was serially diluted in binding buffer (50 mM Tris pH 7.4, 100 mM NaCl) in 96-well black Costar plates followed by addition of FITC-derivatized peptide (25 nM). The time to equilibrium was initially determined by monitoring the binding isotherms of triplicate samples over time until stabilization of binding activity. Fluorescence polarization (mP units) was measured on a BMG POLARstar Optima or SpectraMax platereader (Moleculer Devices) and Kd values calculated by nonlinear regression analysis of dose-response curves using Prism software (Graphpad). FPA of 4E10 antibody binding to control MPER peptide FITC-ELDKWASLWNWFNITNWLWYIK-NH$_2$ is demonstrated in FIG. 12.

Competitive 4E10 Antibody Binding by ELISA.

Half maximal inhibitory concentrations (IC$_{50}$s) were determined by competitive enzyme-linked assay (ELISA) using a constant concentration of biotinylated peptide and 4E10-IgG with a variable concentration of gp41 peptides. Microwells were coated overnight at 4° C. with 50 µl of PBS containing neutravidin (4 µg/ml). Wells were washed twice with PBS containing 0.05% Tween 20, and blocked with 4% non-fat dry milk (NFDM) in PBS for 45 min at 37° C. Meanwhile, a mixture of a biotinylated 4E10-peptide epitope, biotin-PEG2-ELDKWASLWNWFNITNWL-WYIK, (20 nM), IgG 4E10 (0.2 nM), and the competing peptide analogue (threefold dilution series starting at 10 µM) in 0.4% NFDM, 0.02% Tween and PBS was incubated in a separate 96-well plate at 37° C. for 2 h. After washing the blocked plate, the mixture of 4E10, biotinylated peptide and competing structured HIV-1 gp41 peptide was added to the wells. After 20 min at room temperature, the wells were washed five times, and a 1:500 dilution of Goat Anti-Human IgG F(ab')2, Peroxidase Conjugate was added. Following incubation at RT for 40 min, the wells were washed five times, and developed by adding 50 µl of tetramethylbenzidine (TMB) solution according to the manufacturer's instructions. After 20 min, wells containing TMB solution were stopped by adding 50 µl of H$_2$SO$_4$ (2 M), and the absorbance at 450 nm was read on a microplate reader (Molecular Devices). The concentration of competitor peptide corresponding to a half-maximal signal (IC50) was determined by interpolation of the resulting binding curve using GraphPad Prism. Each peptide competitor was tested in duplicate in at least two separate experiments.

HIV-1 Infectivity Assay

HIV-1 infectivity assays were performed using known methods (Madani et al., 2007 Inhibition of human immunodeficiency virus envelope glycoprotein-mediated single cell lysis by low-molecular-weight antagonists of viral entry. *J Virol*, 81: 532-538; and Si et al., 2001 Envelope glycoprotein determinants of neutralization resistance in a simian-human immunodeficiency virus (SHIV-HXBc2P 3.2) derived by passage in monkeys. *J Virol*, 75:4208-4218; both incorporated herein by reference). Briefly, HEK 293T cells were co-transfected with the pCMVΔP1ΔenvpA plasmid expressing the HIV-1 Gag-Pol packaging proteins, a plasmid expressing envelope glycoprotein (e.g. HXBc2, ADA, HXBc2P 3.2, YU2 HIV-1 isolates or the control A-MLV virus), and a vector containing the firefly luciferase reporter gene (DNA ratio 1:1:3 µg). Virus-containing supernatants were harvested 24-30 hr after transfection, filtered, aliquoted, and stored at −80° C. Target cells were seeded at a density of 6×10$^3$ cells/well in 96-well plates 24 hours prior to infection. Cf2Th-CD4-CCR5 cells were used for infections by viruses with the ADA, YU2, and A-MLV envelope glycoproteins, and Cf2Th-CD4-CXCR4 cells used for HXBc2, HXBc2P 3.2, and A-MLV. On the day of infection, the structured peptides (0-3 µM) were added to recombinant viruses (10,000 RT units) to a final volume of 50 µL and incubated at 37° C. for 30 min. Media was then removed and the target cells incubated with virus-peptide mixture for 48 hours at 37° C. The media was again removed and the cells lysed with 30 µL of passive lysis buffer (Promega) and three freeze-thaw cycles. D-luciferin (50 µL of 1 mM stock in 100 µL luciferin buffer) is then added to each well and luciferase activity measured using a luminometer (EG&G Berthold).

Immunogenicity

Structurally constrained-gp41 peptides are conjugated to protein carrier (e.g. KLH), followed by rabbit immunization, antisera collection, and ELISA-based immunogenicity testing. For a given structurally constrained-gp41 construct, the unmodified template peptide and three alternatively conjugated stapled analogs are compared in a neutralizing immunogenicity study. Once prebled (~5 mL serum), two NZW female rabbits (6-8 weeks old) per immunogen receive a primary intramuscular (IM) injection (250 ng with Freund's complete, CpG-ODN, or Ribi adjuvant) on day 1, followed by IM boosts (100 ng with corresponding adjuvant) on days 21, 42, 63, 84, and 105, and production bleeds on days 52, 73, 94, and 112. Direct ELISA assays is performed for each production bleed to monitor and compare specific antibody production titers. Briefly, 96-well microtiter plates are coated with individual gp41 immunogens (5 µg/mL) overnight at 4° C. The wells are washed twice with PBS containing 0.05% Tween 20 and blocked with 3% BSA for 45 min at 37° C. Serial dilutions of rabbit antisera are then added to the plate in triplicate and incubated at 37° C. for 2 hours. After washing three times, a 1:500 dilution of alkaline phosphatase-labeled goat anti-rabbit IgG in PBS/1% BSA is added, and the plate incubated for 40 min at room temperature. The wells are washed, exposed to alkaline phosphatase substrate for 30 minutes, and analyzed by microplate reader at 405 nm.

A gp120 DNA prime-protein boost immunization strategy has recently been shown to be more effective than protein-alone or DNA-alone vaccination to yield HIV-1 neutralization antibodies. This approach can be tested with lead structured HIV-1 gp41 conjugates by replacing the timed protein boosts with structured peptide boosts according to the published immunization protocols.

Neutralizing Antibody Response

To evaluate the neutralizing response of high-titer antibody elicited by structurally constrained gp41 peptides, antisera is evaluated by neutralization assay. For single round infection assays, stocks of Env-pseudotyped viruses (gp160 envelope with pSG3ΔEnv backbone) are prepared by transfection of 293T cells and titrated in TZM-b1 cells using known methods (Li et al. 2005. Human immunodeficiency virus type 1 env clones from acute and early subtype B infections for standardized assessments of vaccine-elicited neutralizing antibodies. *J Virol*, 79:10108-10125; Montefiori, 2005. Evaluating neutralizing antibodies against HIV, SIV, and SHIV in luciferase reporter gene assays. *Curr Protoc Immunol, Chapter* 12, Unit 12.11; both incorporated herein by reference). Virus (200 TCID50) is incubated with serial 3-fold dilutions of serum sample in triplicate in a total volume of 150 µL for 1 hour at 37° C. in 96-well flat-bottom culture plates. Freshly trypsinized cells (10,000 cells in 100 µL of growth medium containing 75 µg/mL DEAE dextran) are added to each well. Background control wells receive cells only, whereas positive control wells receive cells and virus without added serum. After 48 hour incubation, 100 µL cells are transferred to 96-well black Costar plates for luminescence measurement using the Britelite Luminescence Reporter Gene Assay System (Perkin Elmer). Neutralization is calculated as the percent reduction in luciferase activity in the presence of rabbit antisera compared to the luciferase activity induced by virus in the presence of preimmune sera. As a specificity control, antisera are incubated with 30 μg/mL peptide immunogen for 1 hour at 37° C. prior to the addition of virus, and the percent reduction in neutralization due to antisera quenching by peptide adsorption is calculated as described (Vaine et al. 2008. Improved induction of antibodies against key neutralizing epitopes by human immunodeficiency virus type 1 gp120 DNA prime-protein boost vaccination compared to gp120 protein-only vaccination. *J Virol*, 82: 7369-7378).

Peptide Derivatization for Carrier Conjugation

Figure 14A:
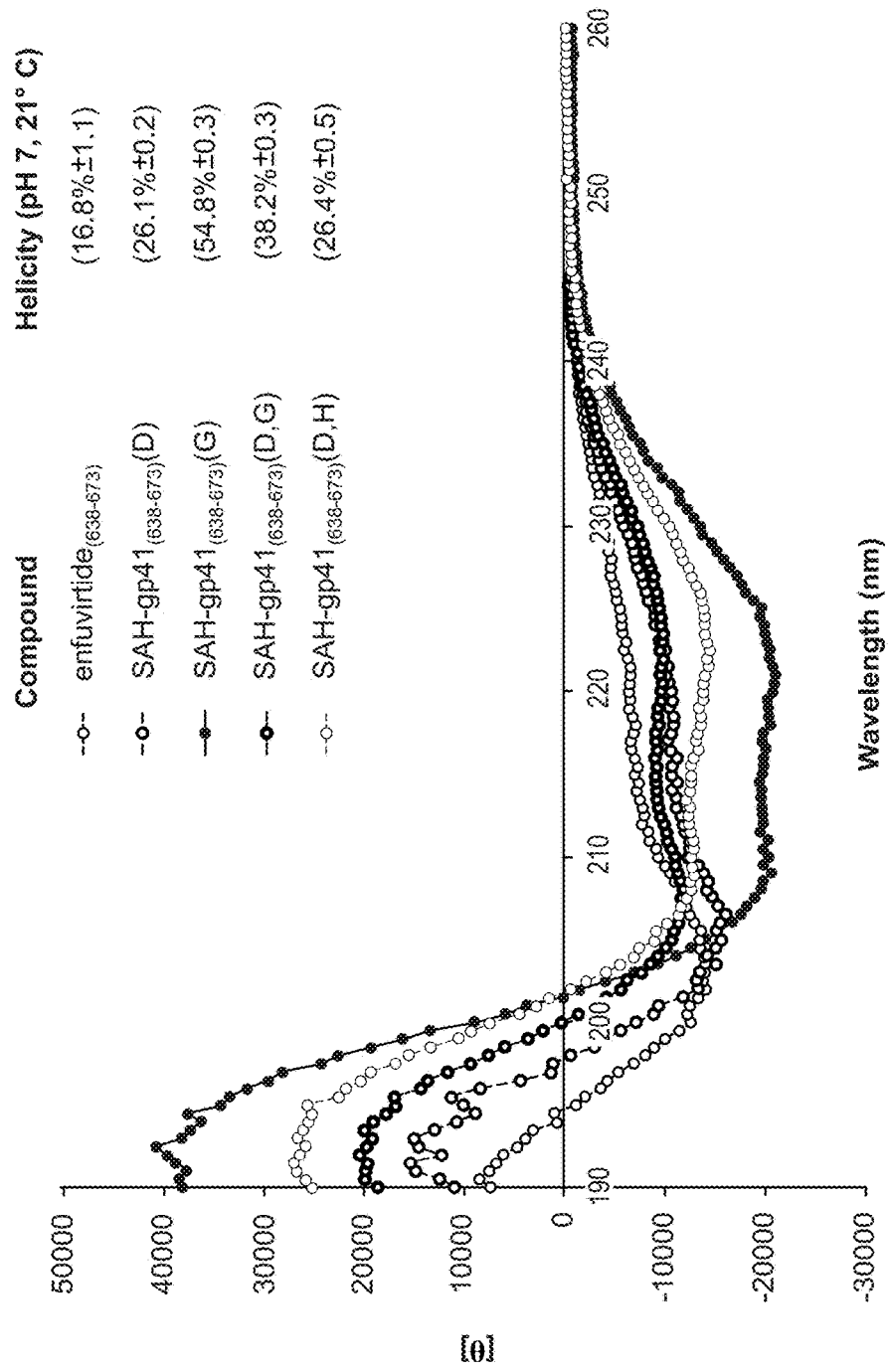
FIG. 14A-B shows that hydrocarbon-stapled gp41 HR2 peptides exhibit enhanced alpha-helical structure compared to the corresponding unmodified peptides by circular dichroism spectroscopy. (A) unstapled peptide enfuvirtide (SEQ ID NO: 49) and stapled peptides, in order, SEQ ID NO: 50, 52, 65, and 64. (B) unstapled peptide T649v (SEQ ID NO: 45) and stapled peptides, in order, SEQ ID NO: 47, 76, 58, and 59.
Figure 14B:
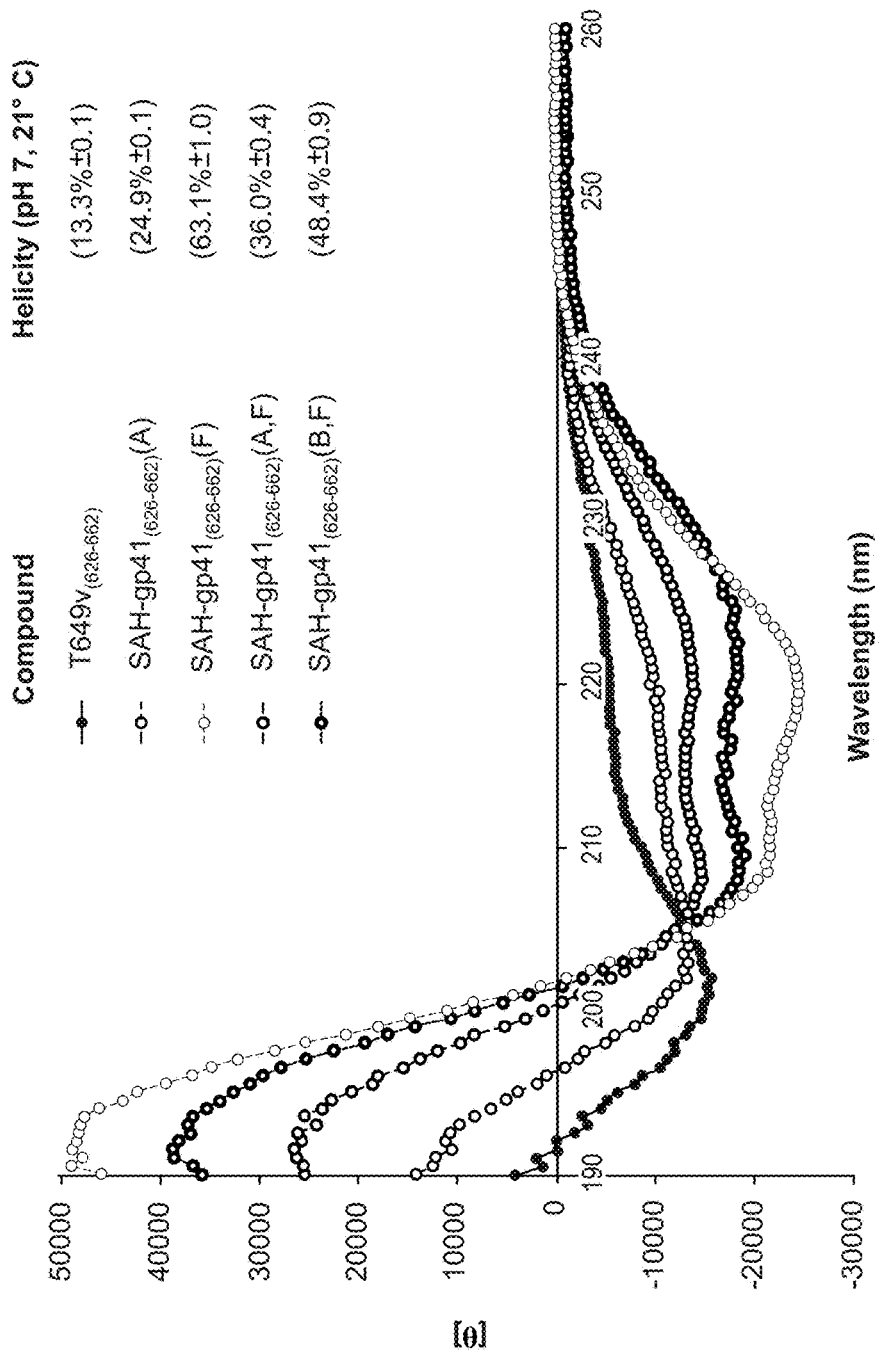
Figure 15A:
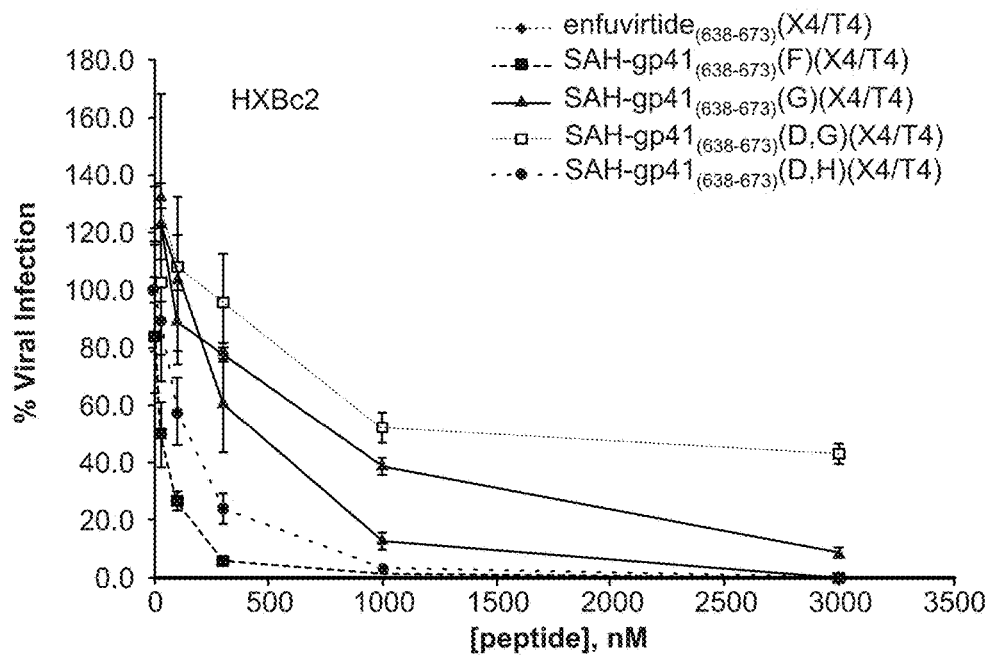
Figure 15B:
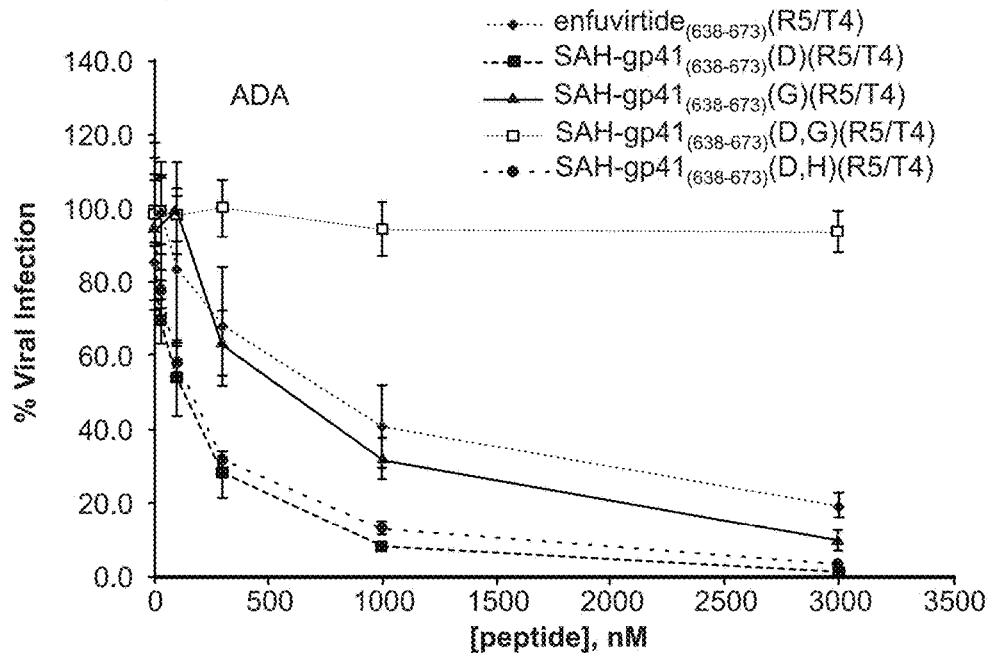
Figure 15C:
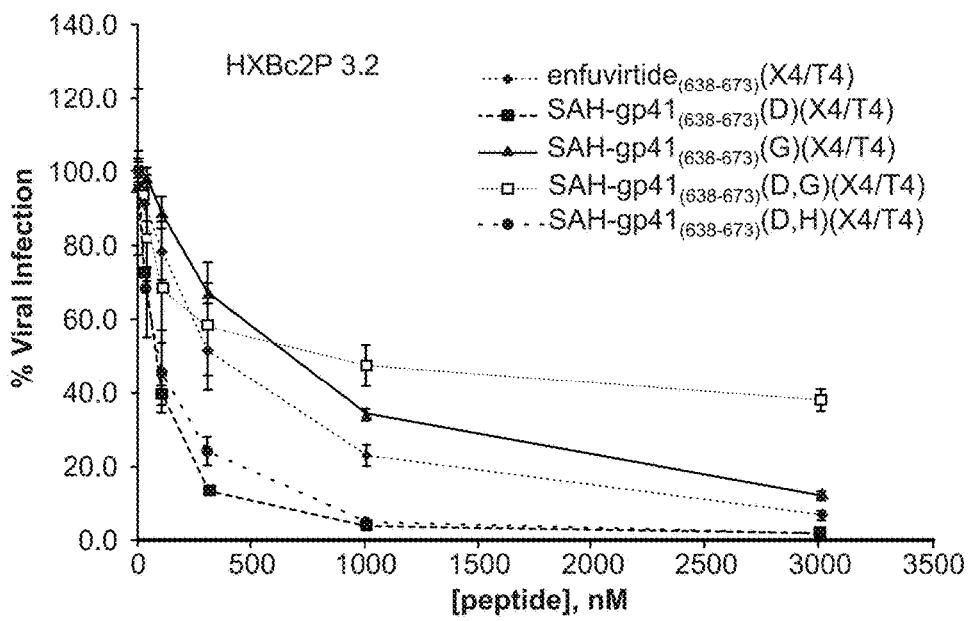
Figure 15D:
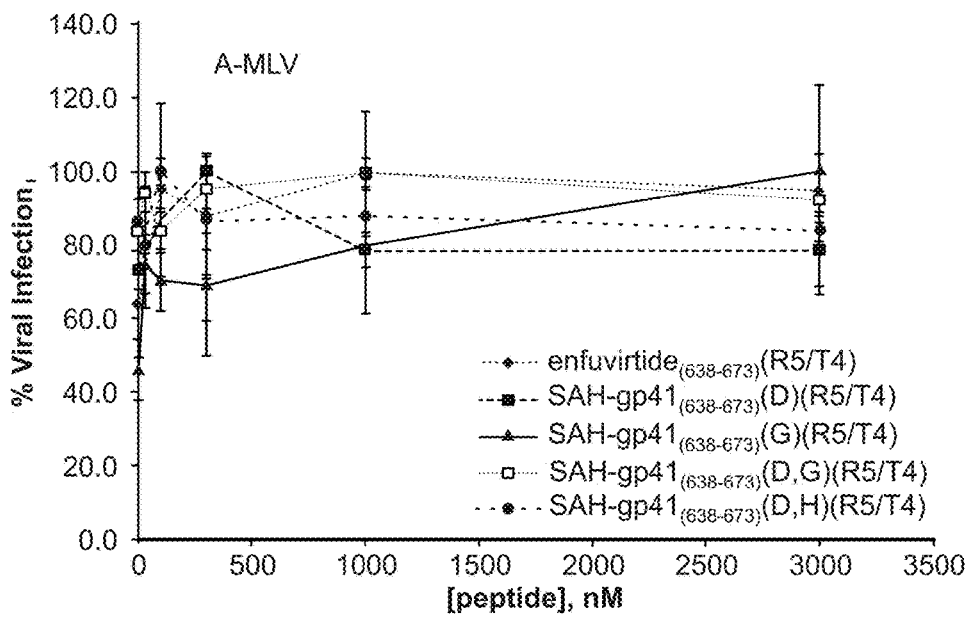

In addition to direct N-terminal conjugation of structured HIV-1 gp41 peptides (e.g. via thiol of installed cysteine), olefin derivatization of hydrocarbon staples is performed so the proposed "neutralizing face" of the constructs can be directed outward, maintaining the non-neutralizing face buried against the protein or lipid conjugate (e.g. KLH14, bovine serum albumin, cholera toxin, micelle) (FIG. 14). Catalytic osmium tetroxide was used to first dihydroxylate the olefin, followed by cyclization with thionyl chloride or carbonyl diimidazole. The electrophilic cyclic sulfite or carbonate was then reacted with sodium azide, which was reduced to an amine using phosphines. Reaction with the bifunctional reagent 3-thiopropionic acid installs a thiol, is then used to attach the carrier (e.g. maleimide-KLH). As an alternative approach, the peptides can be presented in the context of a lipid membrane, which may facilitate neutralizing antibody recognition For example, the peptides can be differentially conjugated to 1,3-dipalmitoyl-glycero-2-phosphoethanolamine, which is then combined with dodecylphosphocholine (DPC) to generate immunogen-tethered micelles.

The expanded CDR H3 region of 4E10 contains a lipid-recognition motif, which when mutated or deleted, can render the remaining MPER peptide binding activity insufficient to neutralize HIV-1. Thus, a lipid functionality can be incorporated into the MPER peptide to enhance neutralizing immunogenicity. Several chemical approaches to introduce a lipidic feature into our synthetic MPER antigen designs are performed, including (1) differential conjugation of MPER peptides to 1,3-dipalmitoyl-glycero-2-phosphoethanolamine, which is then combined with dodecylphosphocholine (DPC) to generate immunogen-tethered micelles, (2) incorporation of a myristoylated lysine and other lipopeptide conjugates at the C-terminus of the MPER peptide, (3) expanding the hydrocarbon staple itself as a hydrophobic and lipidic moiety [e.g. install and derivatize an 11-carbon chain (i, i+7) staple using (S)-2-(4'-pentenyl) alanine and (R)-2-(4'-octenyl)alanine], and (4) generating MPER-coated liposomes by incorporating a hexa-histidine motif at the C-terminus of SAH-MPER constructs for conjugation to lipid-NTA-Ni-containing liposomes (FIG. 18B-D). In each case, the SAH-MPER peptide is presented in the context of a lipid functionality, designed to elicit antibodies with features analogous to 4E10.

Fluorescence Polarization Assay. Fluoresceinylated peptides (25 nM) were incubated with 5-helix protein derived from HIV-1 gp41 HR1 and HR2 domains (or the corresponding sequence in RSV) at the indicated concentrations in room temperature binding buffer (50 mM sodium phosphate, 100 mM Nacl, pH 7.5).

Binding activity at 10 mM was measured by fluorescence polarization using a POLARstar OPTIMA microplate reader (BMG Labtech). The binding assays were run in triplicate and $K_D$s determined by nonlinear regression analysis of the binding isotherms using Prism software (GraphPad).

Synthesis of (R)-Fmoc-(2'-propenyl)alanine

A solution of (R)-proline and KOH in isopropanol was prepared to which benzyl chloride was added and stirred at room temperature for 3 hr. An acidic workup allowed for isolation of a precipitate in 89% yield. This product was dissolved in ice cold methylene chloride, to which thionyl chloride and 2-aminobenzophenone was added to the reaction mixture and allowed to warm to room temperature with stirring over 10 hours. A basic workup yielded (R)-2-[N—(N'-benzylprolyl)amino]benzophenone (BPB) in 81% yield. A solution of KOH in MeOH was poured into a stirred mixture of BPB, $Ni(NO_3)_2$-$6H_2O$, alanine in MeOH under inert gas at 40° C. The resulting mixture was stirred for 2 h and an acidic workup yielded Ala-Ni(II)-BPB-complex in 91% yield. (*Tetrahedron:Asymmetry* 9 (1998) 4249-4252)

The Ala-Ni(II)-BPB-complex was reacted with 3-bromo-1-propene in acetone under basic conditions to give a mixture of a Ni(II) complex of Schiff base of (R)-BPB-(R)-trans-(2'-propenyl)alanine [(R)-2] and Ni(II) complex of Schiff base of (S)-BPB-(S)-trans-(2'-propenyl)-alanine [(S)-2] with ratio 6:1.

After separation with silica gel column, diastereopure (R)-2 complexes were obtained at 44% yield. The (R)-2 complexes were decomposed with 3N HCl/MeOH to afford (R)-(2'-propenyl)alanine as well as a chiral ligand which was extracted with DCM. After work up, (R)-(2'-propenyl)alanine was protected with Fmoc-OSu to give the (R)-Fmoc-(2'-propenyl)alanine with 93% yield (two steps). (Tetrahedron 56 (2000) 2577-2582)

Example 2. Truncated C-Terminal Heptad Peptides Display Enhanced α-Helicity Upon Incorporation of an all-Hydrocarbon Staple In order to improve the biochemical properties of HIV gp41-HR-2 peptides the T649v peptide was truncated to yield a 20-mer consisting of residues 626-645 (FIG. 4). The truncated Stabilized Alpha Helix (SAH)-gp41 compound, SAH-gp41(626-645)(A), was successfully synthesized in high yield. Analysis of comparative CD spectra revealed marked enhancement of α-helical content for SAH-gp41 (626-645)(A) compared to its unstapled counterpart (48% vs. 20%). Evaluation of the compounds in an HIV syncytial formation assay revealed markedly enhanced inhibitory activity of SAH-gp41(626-645)(A) compared to its unstapled derivative. Thus, in spite of eliminating more than 40% of the residues of T649v, the hydrocarbon stapled peptide successfully transformed a 20-mer gp41 truncation with little α-helicity and only modest anti-syncytial activity, into an α-helical compound with significant structural stabilization and potent anti-syncytial activity (IC90, ~100 nM).

The activity of SAH-gp41(626-645)(A) peptide was compared to the clinically approved T20 peptide in an HIV infectivity assay using the HXBc2 strain. The SAH-gp41 (626-645)(A) displayed significant anti-HXBc2 activity, particularly given the markedly shortened construct.

Example 3. Structurally Constrained Gp41 Compounds Demonstrate Marked α-Helical Stabilization as Compared to Native Peptides To optimize the activity of SAH-gp41 peptides, an alternative strategy based upon inserting one or more hydrocarbon staples into the full-length gp41-HR-2 constructs was pursued (FIGS. 10A and 10B). Unmodified enfuvirtide and T649v were predominantly unstructured in pH 7 aqueous solution at 21° C., exhibiting less than 20% α-helicity. All stapled derivatives displayed comparatively increased α-helical content, with up to 4.7-fold structural stabilization. The insertion of either one or two hydrocarbon staples consistently transformed the circular dichroism spectra from a random coil pattern with a predominant single minimum at 204 nm to an α-helical contour with double minima at 208 and 222 nm. For select peptide templates, single C-terminal stapling conferred a greater degree of α-helical stabilization than single N-terminal stapling. Select doubly stapled SAH-gp41 compounds exhibited an enhancement in α-helical structure that was intermediate between N- and C-terminal singly stapled peptides. Enhancement of peptide α-helicity was likewise observed at pH2, and in most cases, SAH-gp41 compounds were even more helical at pH2 than at pH7 (see also FIG. 14).

| Compound | % helicity at pH 2 | % helicity at pH 7 |
|---|---|---|
| SAH-gp41(626-662) | 37 | 13 |
| SAH-gp41(626-662)(F) | 82 | 63 |
| SAH-gp41(626-662)(C, F) | 55 | 41 |
| SAH-gp41(638-673) | 49 | 19 |
| SAH-gp41(638-673)(D) | 79 | 23 |
| SAH-gp41(638-673)(F) | 57 | 30 |
| SAH-gp41(638-673)(G) | 61 | 48 |
| SAH-gp41(638-673)(H) | 66 | 26 |

The compounds of the invention were also measured for their affinity to gp41 in a five-helix binding assay as described herein. The modified compounds bound substantially better than enfuvirtide.

Example 4. Structurally Constrained Gp41 Compounds Demonstrate Marked Thermal Stability as Compared to Native Peptides To assess the resistance of SAH-gp41 peptides to thermal unfolding, we performed circular dichroism studies across a 1-91° C. temperature range. We observed that select single and double stapling of HIV-1 fusion inhibitor peptides conferred α-helical stabilization that was remarkably heat-resistant, sustaining an up to 2.3-fold enhancement in α-helicity even at 91° C.

Example 5. Structurally Constrained Gp41 Compounds Demonstrate Marked Proteolytic Stability as Compared to Native Peptides A major limitation of peptides as therapeutics is their susceptibility to rapid proteolytic degradation. Biologically active peptides such as enfuvirtide that are lengthy, unfolded, and replete with protease sites are particularly vulnerable. One of the potential benefits of a covalent crosslinking strategy to enforce peptide α-helicity is shielding of the vulnerable amide bonds from proteolysis. Because proteases require that peptides adopt an extended conformation to hydrolyze amide bonds, the structural constraint afforded by the hydrocarbon staple can render crosslinked peptides protease-resistant. To determine if hydrocarbon stapling, and especially double stapling, could protect the 36 to 37-mer HIV-1 fusion peptides from proteolysis, we subjected enfuvirtide, T649v, and SAH-gp41 peptides to direct protease exposure in vitro. To especially challenge the stapled peptides, we selected chymotrypsin, which can cleave gp41 HR2 peptides at numerous consensus cleavage sites, including 9-11 locations for SAH-gp41(638-673) and 7 locations for SAH-gp41(626-662).

In the presence of 0.5 ng/μL chymotrypsin, enfuvirtide and T649v (25 μM) exhibited rapid degradation, with half-lives of 12 and 14 minutes, respectively. In comparison, singly stapled SAH-gp41 compounds displayed longer half-lives that ranged from 21 to 200 minutes. The majority of doubly stapled compounds markedly surpassed their singly stapled counterparts, with select doubly stapled peptides achieving half-lives of up to 1275 minutes. In most cases, double stapling had a stronger influence on proteolytic stability than overall peptide α-helicity, as select doubly stapled peptides had lower α-helicity than select singly stapled peptides, but still exhibited superior protease resistance. Almost all stapled peptides had the identical number of chymotrypsin cleavage sites as the corresponding unmodified peptides, emphasizing that the observed protease resistance derived from peptide stapling itself, rather than elimination of cleavage sites (see also FIG. 17).

| Compound | Half-life (minutes) |
|---|---|
| SAH-gp41(626-662) | 14 |
| SAH-gp41(626-662)(F) | 102 |
| SAH-gp41(626-662)(A) | 79 |
| SAH-gp41(626-662)(A, F) | 301 |
| SAH-gp41(626-662)(B, F) | 1275 |
| SAH-gp41(626-662)(C, F) | 494 |
| SAH-gp41(626-662)(D, F) | 181 |
| SAH-gp41(638-673) | 15 |
| SAH-gp41(638-673)(D) | 32 |
| SAH-gp41(638-673)(F) | 21 |
| SAH-gp41(638-673)(G) | 128 |
| SAH-gp41(638-673)(H) | 201 |
| SAH-gp41(638-673)(D, H) | 510 |
| SAH-gp41(638-673)(D, G) | 1710 |
| SAH-gp41(638-673)(F, H) | 132 |
| SAH-gp41(638-673)(D, F) | 652 |
| SAH-gp41(638-673)(E, G) | 483 |

Peptides have poor oral bioavailability in part due to rapid acid hydrolysis in the proximal digestive tract. The compelling protease resistance of doubly stapled SAH-gp41 compounds at neutral pH prompted us to explore their stability under acidic conditions. In each case, acidification of the peptide solutions significantly enhanced their α-helical content as measured by CD. Upon exposure to pepsin at 0.5 ng/μL, enfuvirtide and T649v (25 μM) exhibited rapid degradation, with half-lives of 4 and 11 minutes, respectively. Select doubly stapled SAH-gp41 compounds displayed half-lives ranging from approximately 80-800-fold greater than the unmodified peptides, and consistently surpassed their singly stapled counterparts. Remarkably, select doubly-stapled SAH-gp41 peptides remained 80% intact after exposure to pepsin at pH 2 for more than 12 hours. As observed for chymotrypsin resistance, double stapling itself, rather than overall peptide α-helicity or number of cleavage sites, correlated with the superior resistance to pepsin hydrolysis. These studies highlighted the capacity of double stapling to generate HIV-1 fusion inhibitor peptides with unprecedented resistance to proteolytic hydrolysis at both neutral and acidic pH.

| Compound | Half-life (minutes) |
|---|---|
| SAH-gp41(626-662) | 11 |
| SAH-gp41(626-662)(F) | 129 |
| SAH-gp41(626-662)(A) | 118 |

| Compound | Half-life (minutes) |
|---|---|
| SAH-gp41(626-662)(A, F) | 2040 |
| SAH-gp41(626-662)(B, F) | 930 |
| SAH-gp41(638-673) | 4 |
| SAH-gp41(638-673)(D) | 3 |
| SAH-gp41(638-673)(G) | 227 |
| SAH-gp41(638-673)(D, G) | 3320 |
| SAH-gp41(638-673)(F, H) | 920 |

Example 6. Structurally Constrained Gp41 Peptide Demonstrates Striking Enhancement of In Vivo Stability and Bioavailability Compared to Native Peptide Male C57/BL6 mice were administered intravenously or by oral gavage 10 mg/kg of either the doubly stapled SAH-gp41$_{(626-662)}$(A,F) or the corresponding unmodified peptide. Blood samples withdrawn at 30 minutes by retro-orbital bleed were subjected to quantitation using LC/MS-based blood tests. The level of SAH-gp41$_{(626-662)}$(A,F) measured in the blood was more than 6-fold greater than the measured level of the corresponding unmodified peptide. Noncompartmental pharmacologic analysis based on serial blood draws, revealed a 10-fold enhancement in area under the curve of SAH-gp41 compared to enfuvirtide. Strikingly, 30 minutes after oral administration, intact SAH-gp41$_{(626-662)}$(A,F) was detected in the blood at measurable and dose-responsive levels, whereas the unmodified peptide was undetectable. Both AUC was increased and clearance decreased by about 10-fold.

These data emphasize that hydrocarbon stapling confers unique pharmacologic properties to gp41-based fusion peptide sequences, enhancing their in vivo stability and even conferring measurable oral bioavailability. This experiment further demonstrated that an equivalent oral dose of SAH-gp41 peptide could produce serum levels comparable that resulting from intravenous dosing of the unmodified peptide (i.e., enfuvirtide), suggesting that a therapeutically effective dose of SAH-gp41 peptide could be administered orally (see FIG. 17).

Example 7. Stapled MPER Peptides Containing an i, i+3 Staple, i, i+4 Staple, or Double (i, i+3) and (i, i+4) Staples Compete Effectively for Binding with Gp41 Peptides MPER peptides including an i, i+3 staple and/or an i, i+4 staple were tested for the ability to compete for binding to a gp41 peptide by ELISA assay. As shown in FIG. 21A, an i, i+3 stapled peptide was able to compete more effectively for binding than an i, i+4 stapled peptide stapled in a similar position (e.g., compare SEQ ID NO:136 to SEQ ID NO:135), whereas both stapled derivatives were superior to the wild-type MPER peptide. Further studies were performed using the peptides shown in FIGS. 21A and B which contain both an i, i+3 staple and an i, i+4 staple. These studies demonstrate effective competition using peptides including both an i, i+3 staple and/or an i, i+4 staple.

Figure 22:
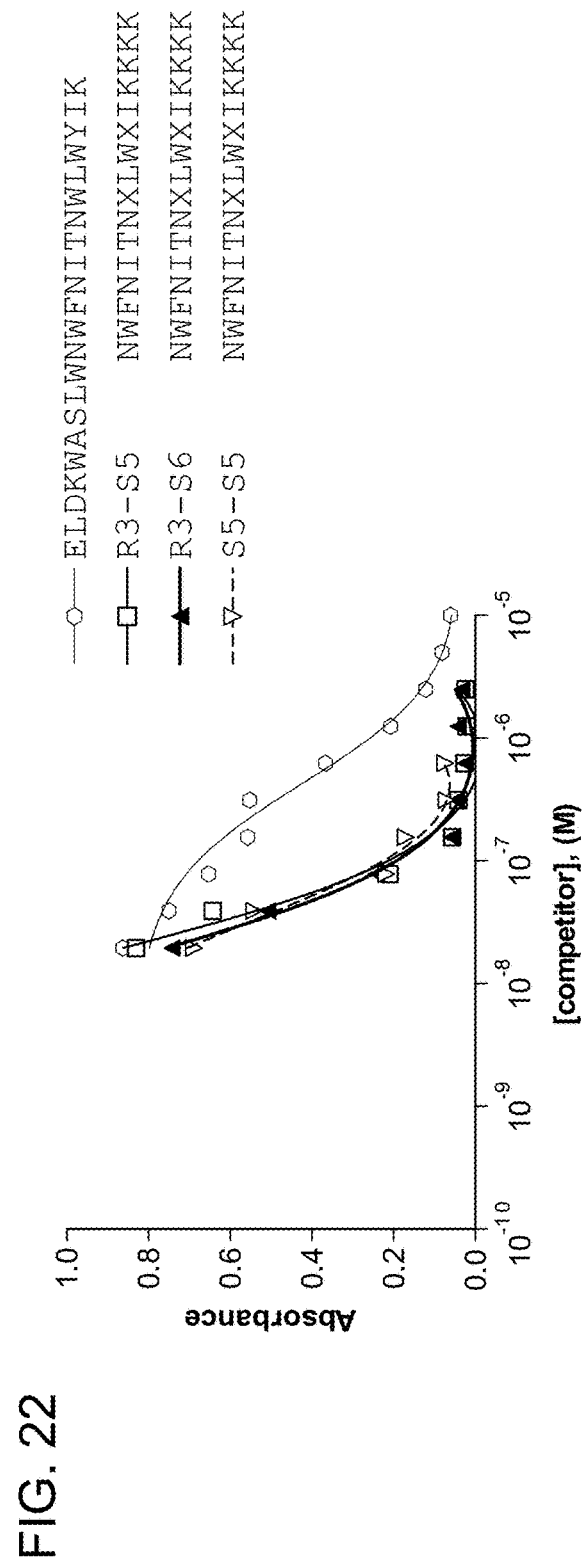
FIG. 22 shows the capacity of shortened SAH-MPER peptides containing R3-S5 and R3-S6 (i, i+3) crosslinks (SEQ ID NO: 137-140) to more effectively compete than the wild-type Ac-MPER peptide for 4E10 antibody binding.

FIG. 22 shows the capacity of shortened SAH-MPER peptides containing R3-S5 and R3-S6 (i, i+3) crosslinks to more effectively compete than the wild-type Ac-MPER peptide for 4E10 antibody binding. These data also highlight that i, i+3 staples of distinct compositions (ie. carbon chain length) also endow functionally superior structured peptides.

One of the potent 4E10-binding SAH-MPER peptides contained an (i, i+3) staple within the C-terminal region of the MPER domain, which is predicted to be a 310 helix based on structural studies. Although we successfully generated the (i, i+3) staple using our (S)-2-(4'-pentenyl) alanine ("S5") non-natural amino acids, the high temperature and prolonged reaction conditions impeded high yield production of doubly stapled (i, i+3), (i, i+4) peptides. Indeed, the 8-carbon chain staple may be too large for (i, i+3) crosslinking. Therefore, we generated 7- and 6-carbon chain staples by synthesizing alternate non-natural amino acid pairs, including R3-S6, R6-S3, R3-S5, and R5-S3 (FIG. 9A-B, FIG. 12D, FIG. 22). We generated the new non-natural amino acids according to the synthetic scheme demonstrated in FIG. 9A. We synthesized the (R)-2-(4'-allyl) ("R3") and (S)-2-(4'-hexenyl) ("S6") alanine derivatives and incorporated them to form an i, i+3 staple in SAH-MPER peptide SEQ ID 99, and performed the olefin metathesis reaction across a variety of conditions. We also installed an i, i+3 stapled into SAH-MPER SEQ ID 100 using the R3-S5 combination. The reactions proceeded to completion at room temperature after only a three hour incubation, nearly recapitulating the highly efficient room temperature/two hour metathesis reaction conditions employed for our prototype S5-S5 (i, i+4) crosslink.

Figure 16A:
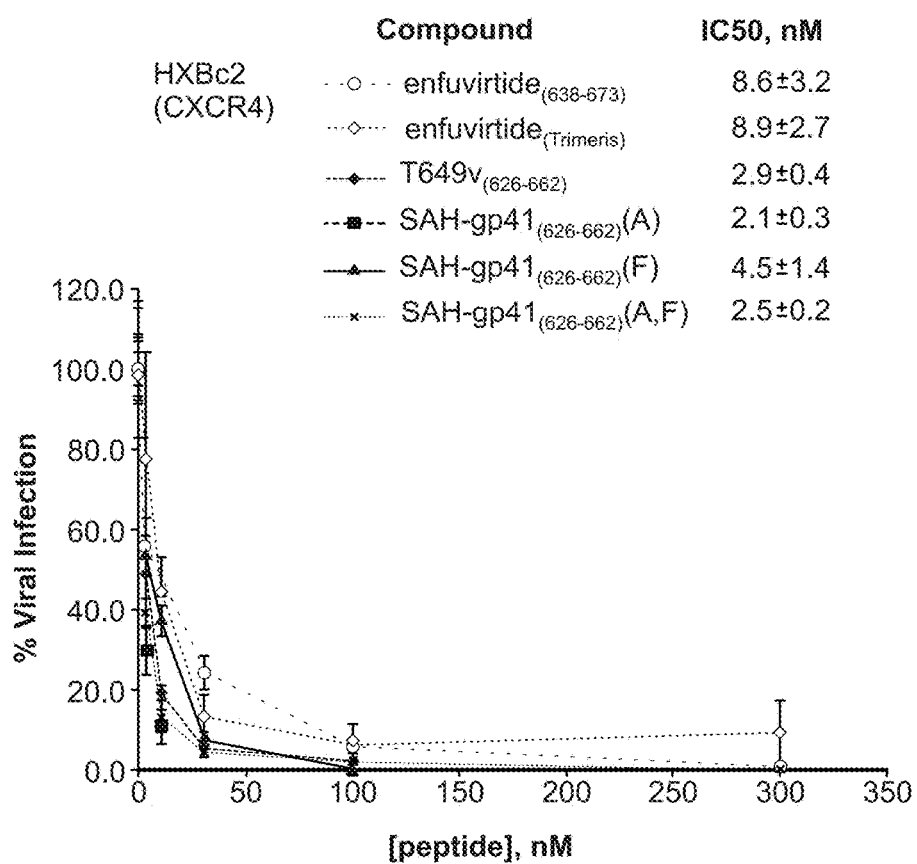
FIGS. 16A-I show the activity of the structurally constrained peptides of the instant invention to inhibit HIV-1 infectivity assay using (A) enfuvirtide-susceptible strain HXBc2 and (2) the enfuvirtide- and neutralization-resistant strain YU2 (B). The specificity of the constrained peptides for HIV-1 inhibition are exemplified by their inability to block the infectivity of the non-HIV-1 viral control strain A-MLV (C). Panels D-G demonstrate by native PAGE analysis that a doubly-stapled peptide can bind doubly-mutant HR1 domains that block enfuvirtide binding (C-E) and overcome enfuvirtide-resistant doubly mutant HXBc2 viral strains to block HIV-1 infectivity (F, G). Such mutations occur in HIV-1 infected humans and cause enfuvirtide resistance. Peptides used, SEQ ID NO: 49 (enfurvitide), 45 (T649v)), 47 (A), 46 (F), and 58 (a, F).
Figure 16B:
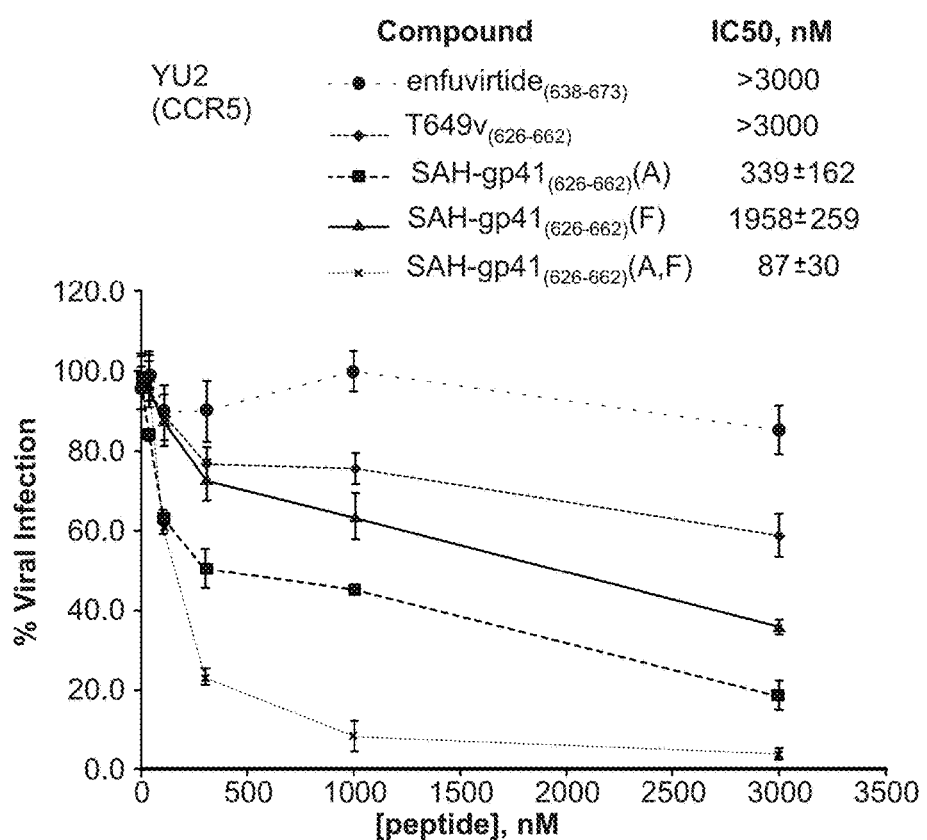

Example 8. Structurally Constrained Gp41 Peptides Demonstrate Markedly Enhanced Antiviral Potency Compared to the Unstructured Peptide Therapeutic Enfuvirtide To assess the functional impact of hydrocarbon stapling on gp41-based fusion inhibitor activity, SAH-gp41 peptides were tested and compared to their unmodified counterparts in a luciferase-based HIV-1 infectivity assay. Recombinant HIV-1 bearing the envelope glycoproteins from three distinct HIV-1 strains, HXBc2, ADA, and HXBc2P 3.2, and a negative control virus bearing the amphotropic murine leukemia virus (A-MLV) envelope glycoproteins, were evaluated. Compared to enfuvirtide, SAH-gp41$_{(638-673)}$(D) and SAH-gp41$_{(638-673)}$(D, H) exhibited a 3- to 15-fold enhancement of inhibitory activity across all three HIV-1 strains (FIG. 15). T649v, an HR2 peptide that encompasses a 37-amino acid fragment terminating 11 residues upstream of enfuvirtide's C-terminus (FIG. 10A), displays significantly greater anti-HIV-1 activity than enfuvirtide in these assays. In order to probe for differential anti-viral potencies among T649v-based stapled peptides, we screened the compounds against viruses with envelope glycoproteins derived from the resistant primary R5 isolate, YU2. Compared to T649v, SAH-gp41$_{(626-662)}$(A), SAH-gp41$_{(626-662)}$(F), and SAH-gp41$_{(626-662)}$(A, F) demonstrated enhanced anti-YU2 activity (FIG. 16B).

Figure 13A:
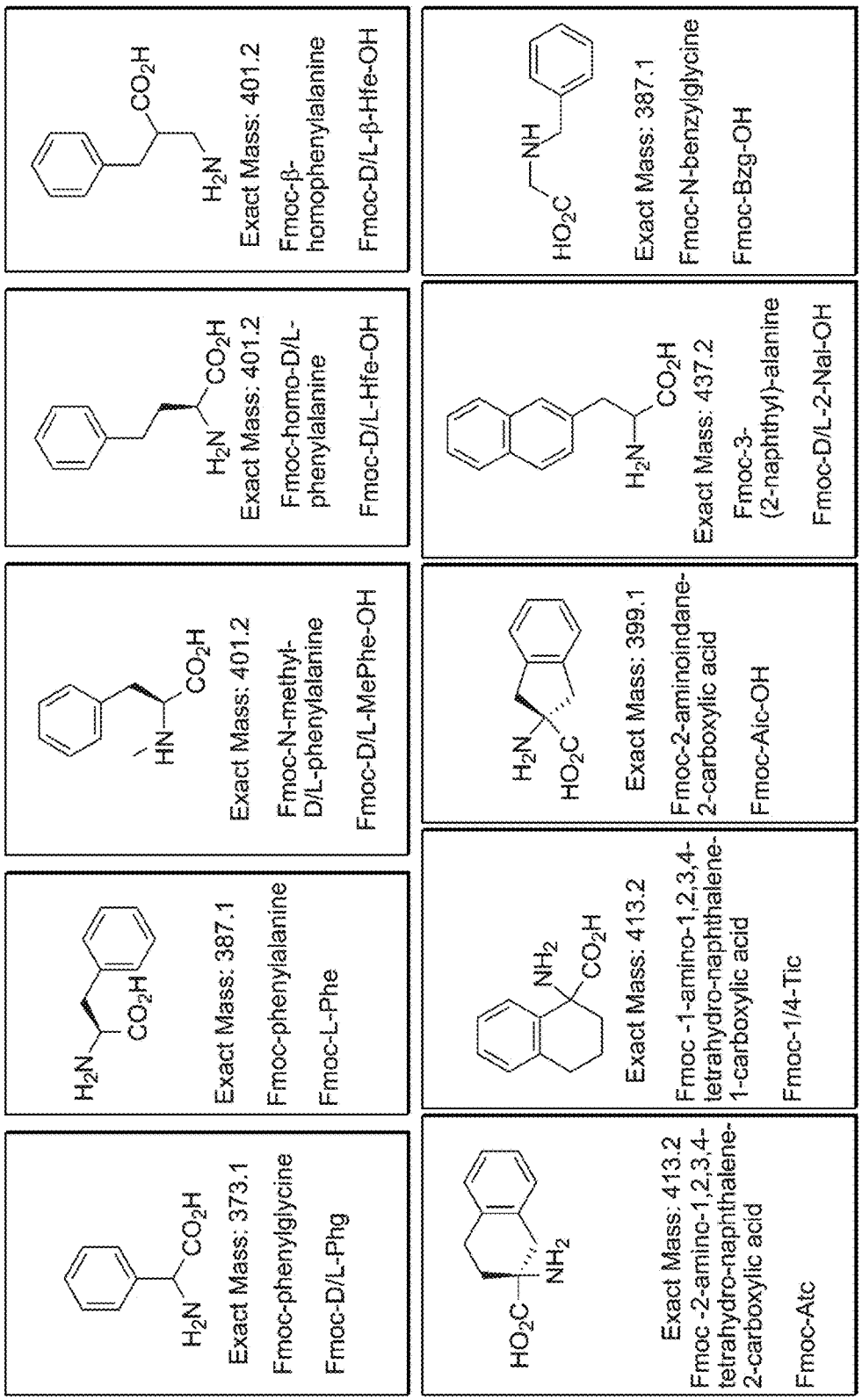
Figure 13A:
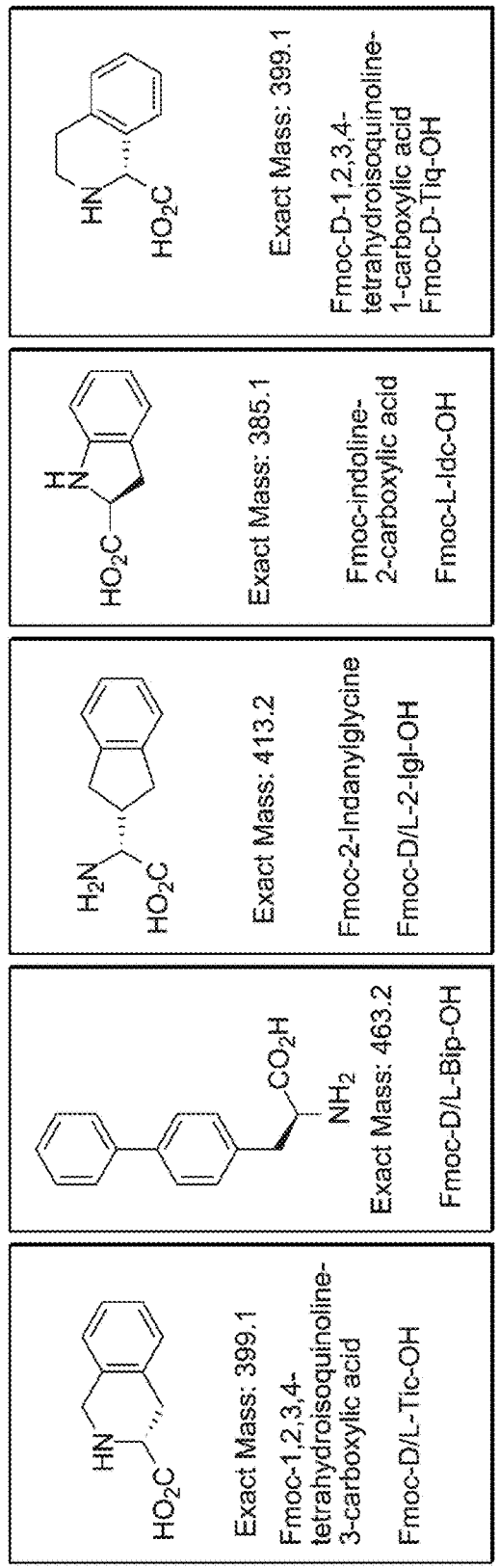
Figure 13B:
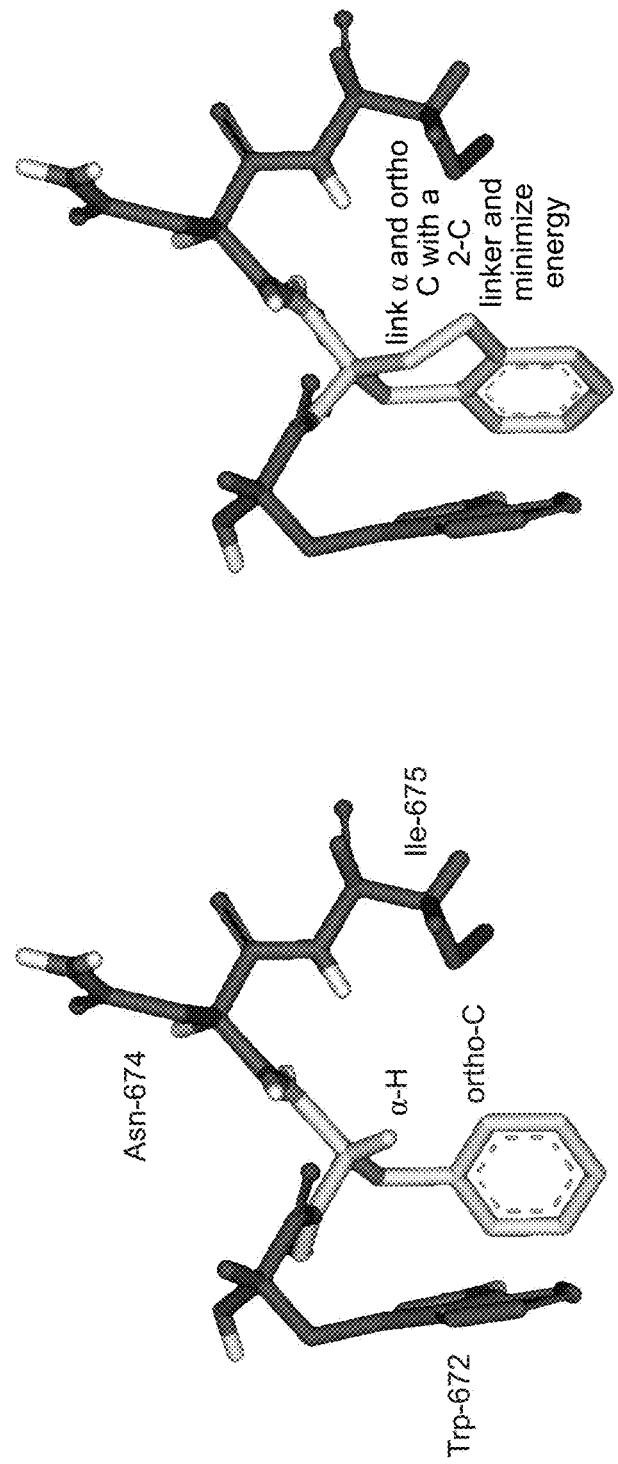

Taken together, these functional data revealed that single and double stapling can yield SAH-gp41 peptides with potent and broad anti-HIV-1 activity. Of note, none of the peptides tested demonstrated any activity against viruses with A-MLV envelope glycoproteins (FIGS. 12 and 13), highlighting the specificity of SAH-gp41 peptides. The importance of striking a balance between α-helical stabilization, proteolytic stability, and anti-viral activity was underscored by the functional penalty that results from over-stabilization, as evidenced by the relatively impaired anti-viral activity of the two doubly-stapled compounds with the most prominent α-helicity and proteolytic stability, SAH-gp41$_{(638-673)}$(D, G) and SAH-gp41$_{(626-662)}$(B, D). Indeed, the doubly-stapled SAH-gp41$_{(626-662)}$(A, D) peptide, which combined intermediate α-helical stabilization, the unique anti-proteolysis feature of double stapling, and potent anti-viral activity (FIG. 17), highlights the remarkable capacity of hydrocarbon stapling to optimize the structure, stability, and functional activity of HIV-1 fusion inhibitor peptides. Importantly, the structural and functional differences among SAH-gp41 peptides underscores the ability of hydrocarbon stapling to yield a diversity of peptides that differentially sample three dimensional space, arguably a key asset in screening for correctly structured immunogens for HIV-1 vaccination.

Figure 16C:
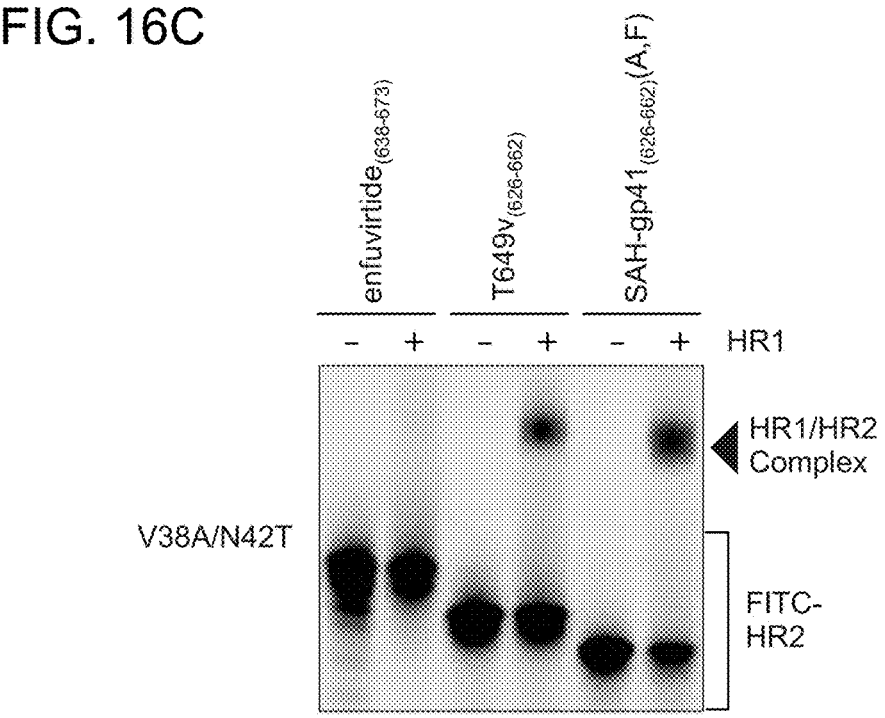
Figure 16D:
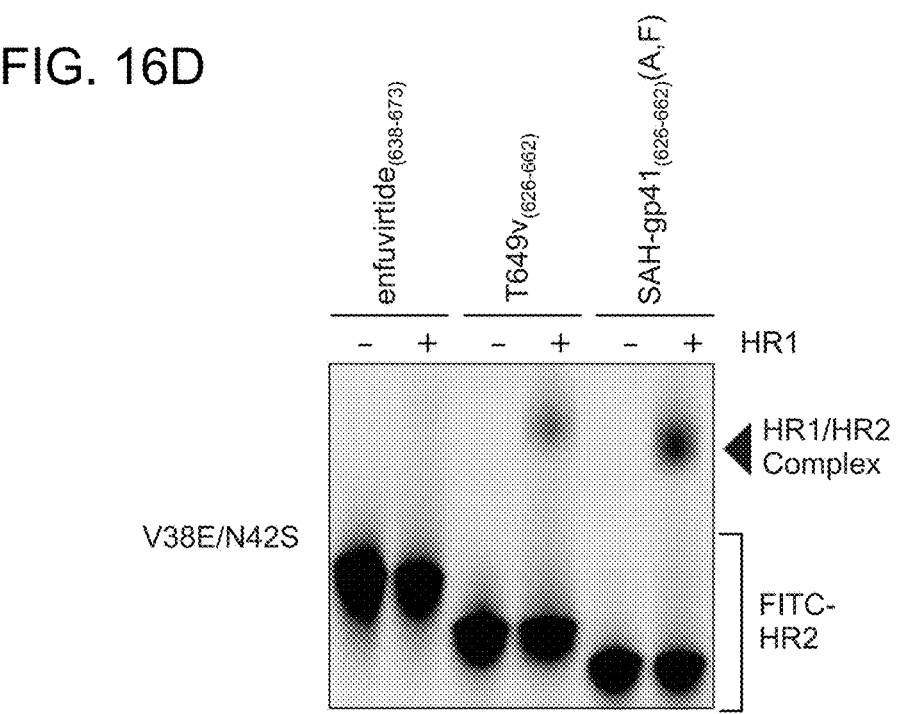
Figure 16E:
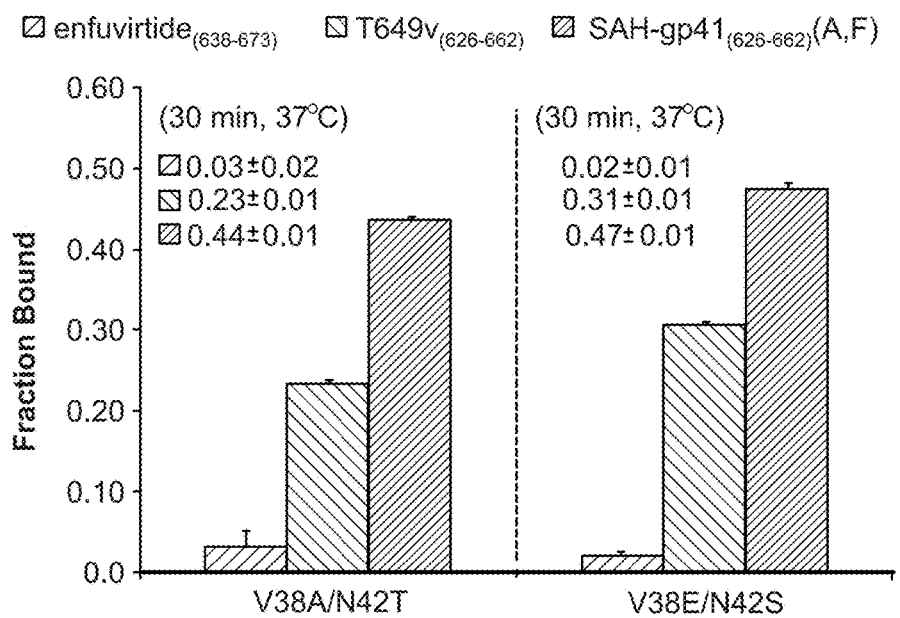
Figure 16F:
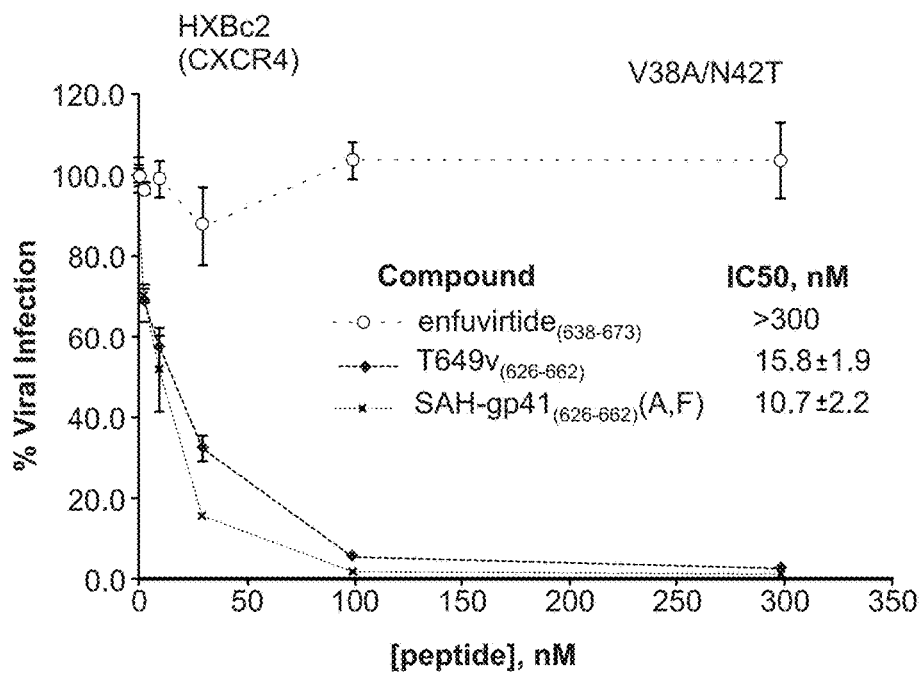
Figure 16G:
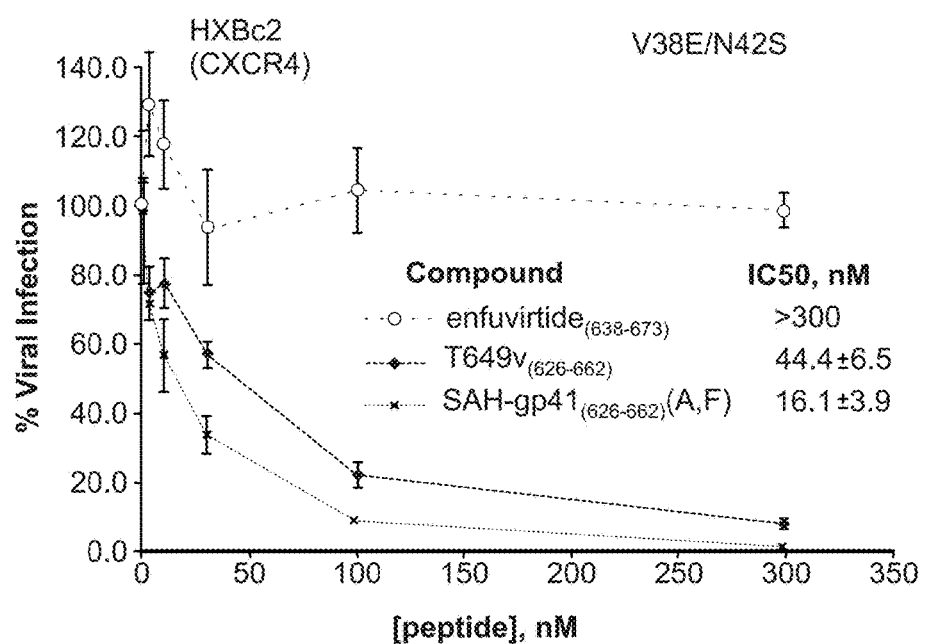

We next compared the functional activities of enfuvirtide, T649v, and SAH-gp41$_{(626-662)}$(A, F) in complex assembly and HIV-1 infectivity assays using peptides and recombinant HIV-1 HXBc2 virus bearing the HR1 double mutations V38A/N42T and V38E/N42S (He, Y., et al. *PNAS* (2008)). Both mutants support HIV-1 entry with differential efficiencies but remain comparable to the wild-type virus. The mechanistic basis for their resistance instead derives from blockade of enfuvirtide binding, which is required for the peptide's dominant-negative activity in preventing gp41 six-helix bundle assembly. We first performed a native PAGE-based assay designed to monitor the capacity of FITC-HR2 and mutant HR1 peptides to interact to form a stable higher-order complex (He, Y., et al. PNAS (2008)). Whereas FITC-labeled enfuvirtide showed no interactions with the doubly-mutant HR1 peptides, FITC-T649v and FITC-SAH-gp41$_{(626-662)}$(A, F) formed a higher-order complex with each of the mutant HR1 peptides (FIG. 16C-E). As evidenced by the fluorescence scans and the corresponding densitometric analyses, FITC-SAH-gp41(626-662)(A, B) bound effectively to the doubly-mutant HR1 peptides, even exhibiting up to 2-fold enhancement in binding activity compared to FITC-T649v. In infectivity assays that employed HIV-1 HXBc2 envelope constructs bearing the corresponding gp41 HR1 mutations, enfuvirtide again showed no functional activity, whereas T649v and SAH-gp41$_{(626-662)}$(A, F) dose-responsively suppressed HIV-1 infectivity (FIG. 16F-G). Consistent with the native PAGE binding analysis, SAH-gp41$_{(626-662)}$(A, F) effectively blocked viral infectivity, displaying a 1.5 to 2.8-fold improvement over T649v in overcoming mutations that uniformly abrogate enfuvirtide activity in humans.

Figure 16H:
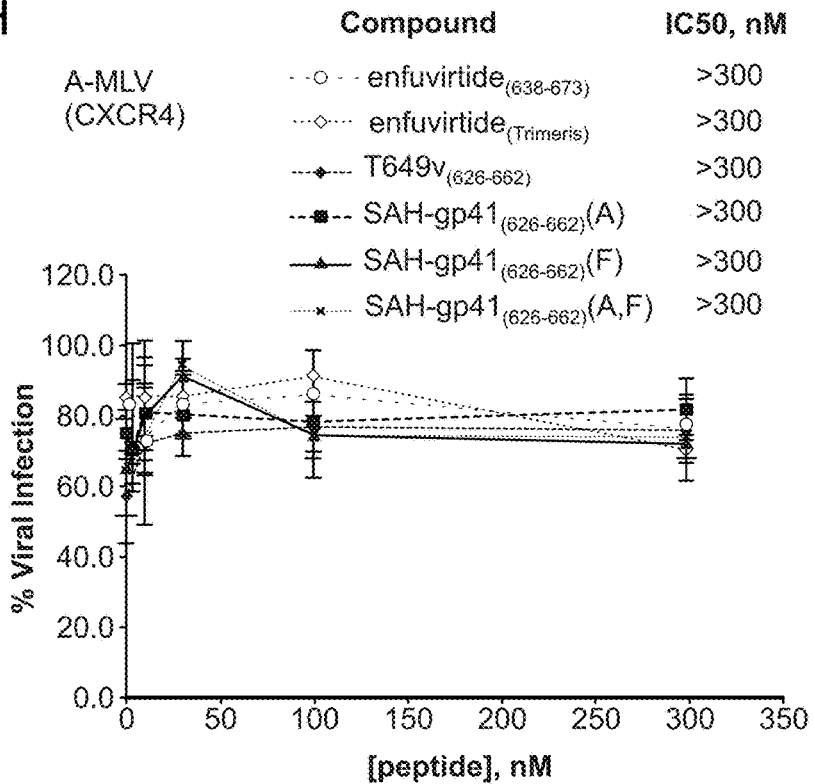
Figure 16I:
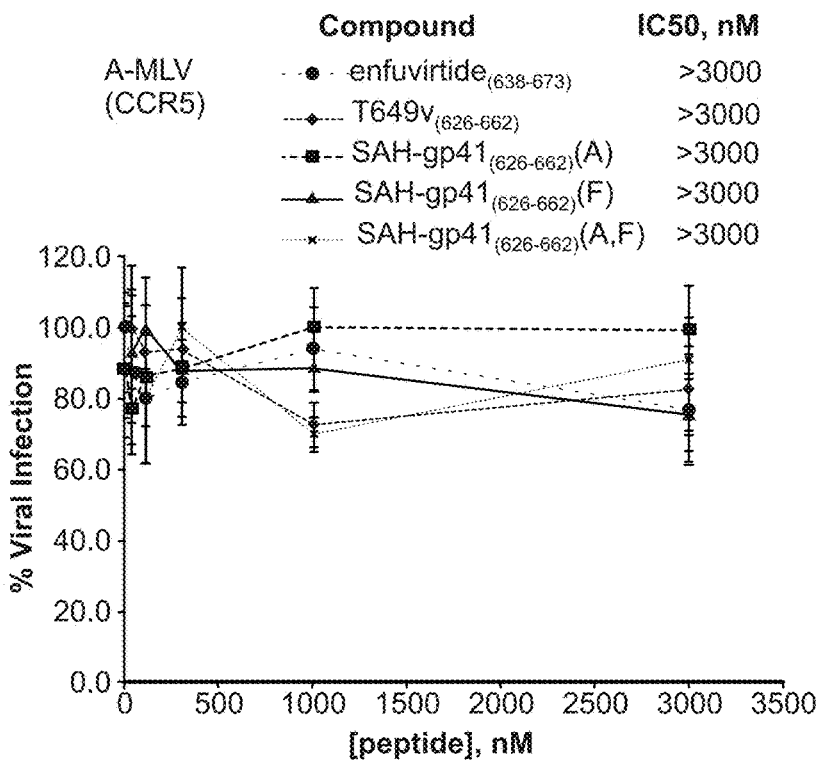
Figure 17B:
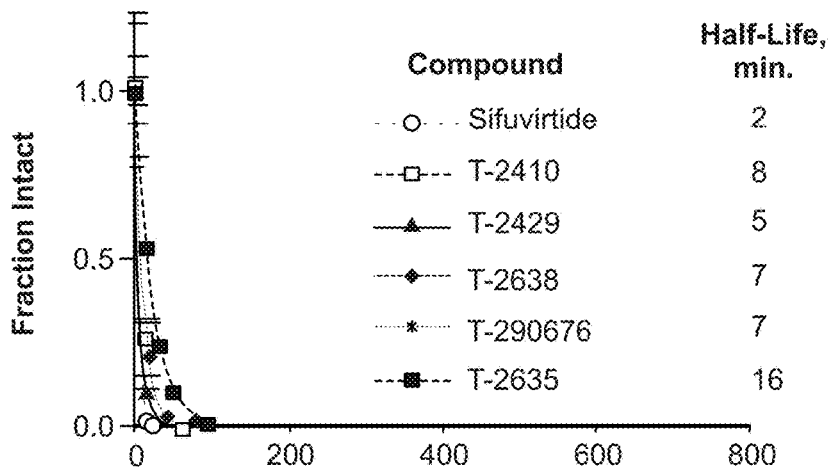
FIG. 17 shows (A-B) that a series of reported next-generation gp41 HR2 peptides (SEQ ID NOs: 49, 45, and 129-134) (Dwyer et al, *PNAS,* 2007; He et al *JBC,* 2008), which contain natural amino acid substitutions, helix-promoting alanine residues, and/or (i, i+4) salt bridges, exhibit rapid proteolytic degradation upon exposure to chymotrypsin; (C) the singly-stapled SAH-gp41$_{(626-662)}$ peptides (SEQ ID NOs: 45, 47, 46, and 58) exhibited 6-8 fold longer half-lives compared to the unmodified peptide, and double-stapling conferred a 24-fold enhancement in chymotrypsin resistance: (D) the singly-stapled SAH-gp41$_{(638-673)}$ derivatives (SEQ ID NOs: 49, 50, 52, and 65), like the SAH-gp41$_{(626-662)}$ peptides, had enhanced chymotrypsin resistance compared to the template peptide, and the doubly-stapled peptide was strikingly more resistant to proteolysis; (E) a pharmacokinetic analysis in which SAH-gp41$_{(626-662)}$(A,F) (SEQ ID NO: 58) and T649v (SEQ ID NO: 45) were injected intravenously into mice at 10 mg/kg and plasma concentrations of intact peptide measured at the indicated time points, revealing marked in vivo stability of SAH-gp41$_{(626-662)}$(A,F) compared to T649v; (F) circular dichroism analyses demonstrating that SAH-gp41$_{(626-662)}$(A,F) exhibits even greater α-helicity at pH 2 than at pH 7, surpassing T649v in both conditions; (G) striking acid protease resistance of SAH-gp41$_{(626-662)}$(A,F), as demonstrated by exposure of SAH-gp41$_{(626-662)}$(A,F) and T649v pepsin at pH 2; (H) acid protease resistance of SAH-gp41$_{(626-662)}$(A,F) translated into oral absorption, with orally administered SAH-gp41$_{(626-662)}$(A,F) achieving measurable and dose-responsive plasma concentrations but T649v was undetectable. Plasma concentration, mean±standard error; ND, nondetectable.
Figure 17C:
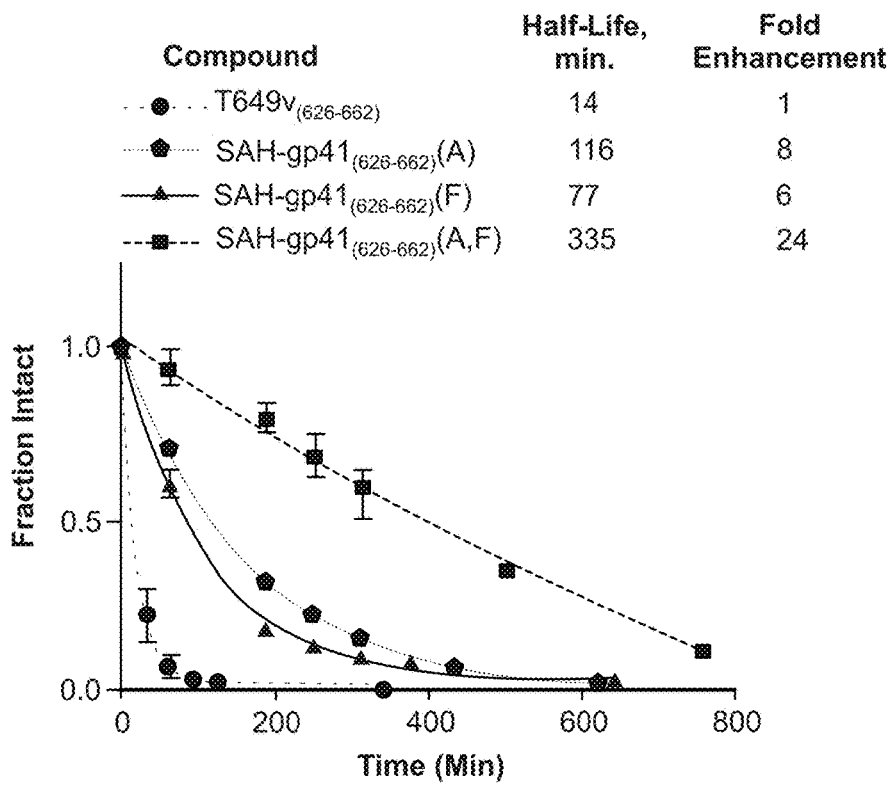
Figure 17D:
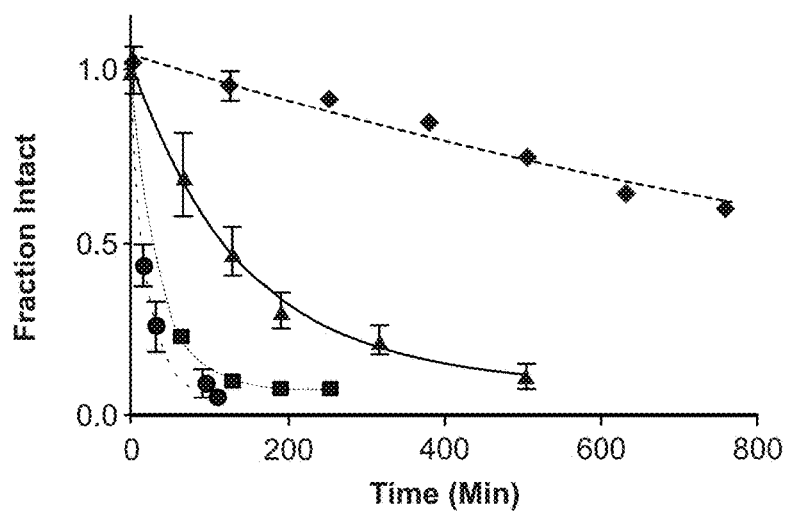
Figure 17E:
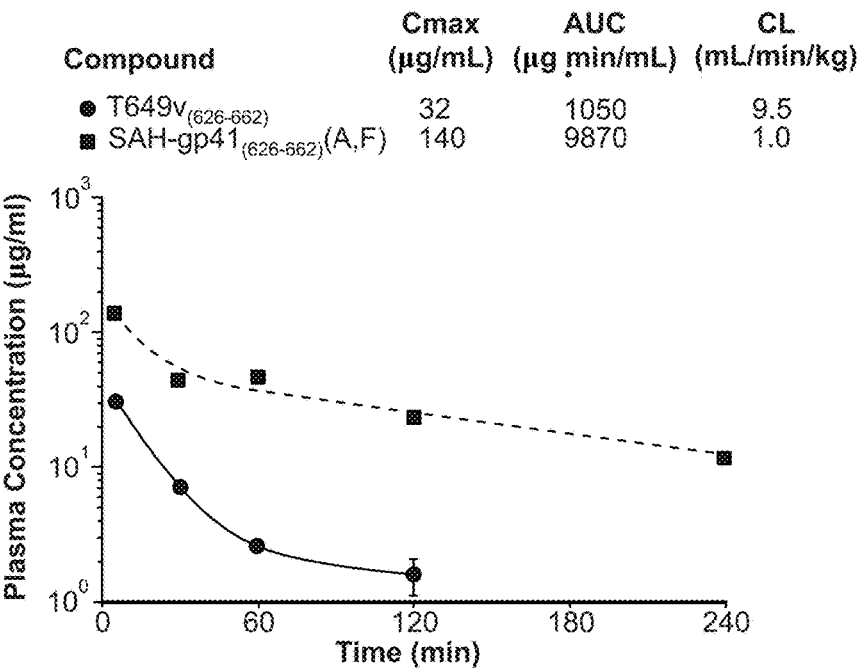
Figure 17F:
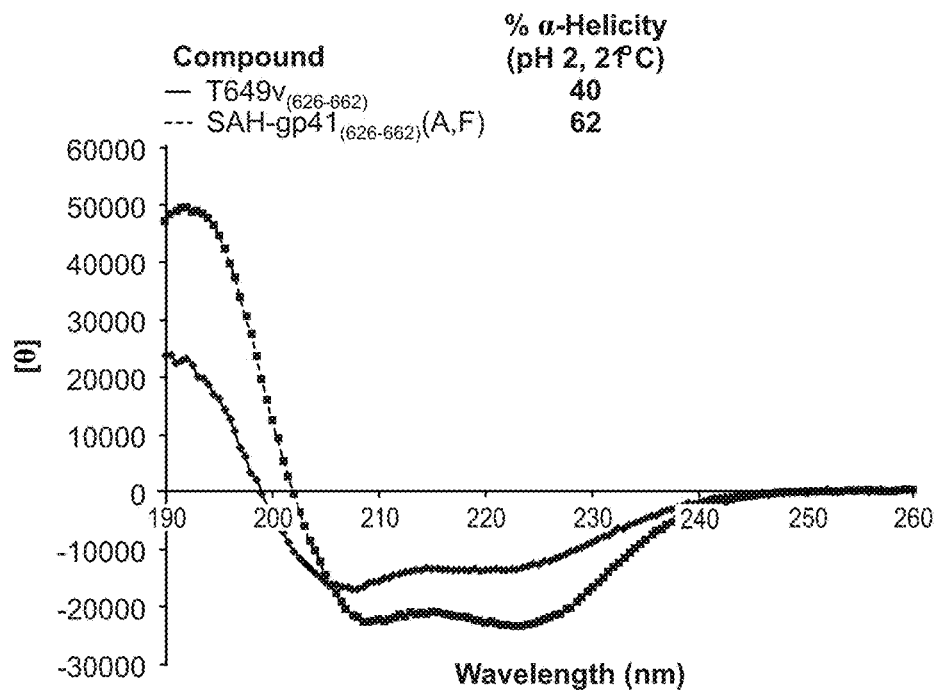
Figure 17G:
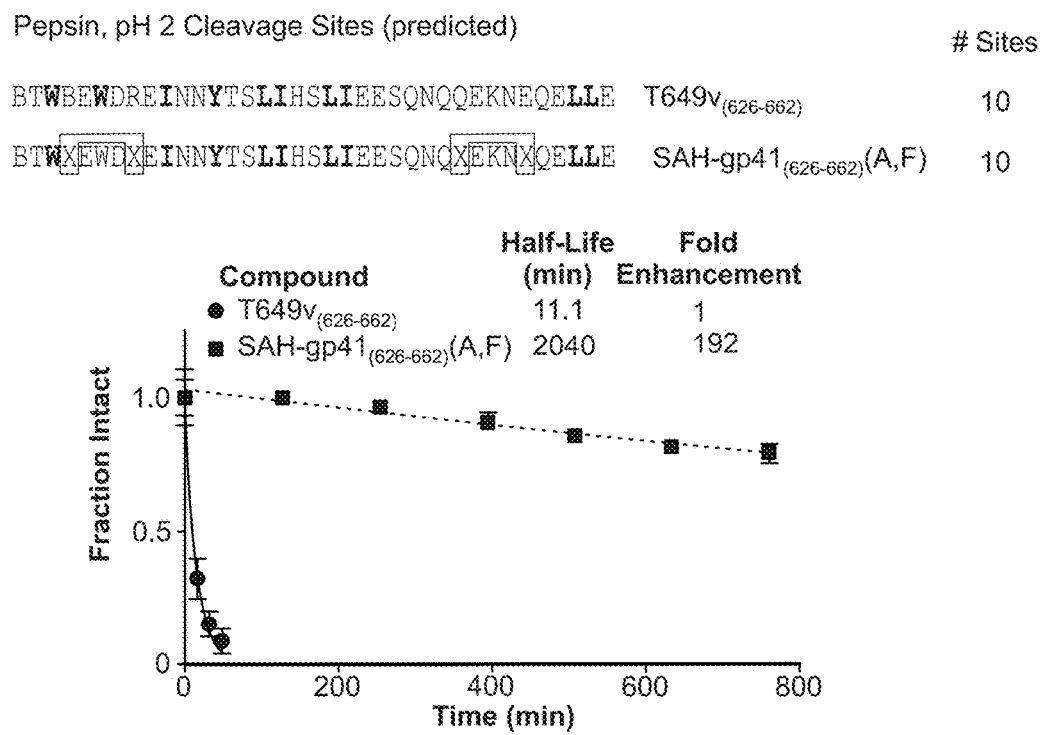
Figure 17H:
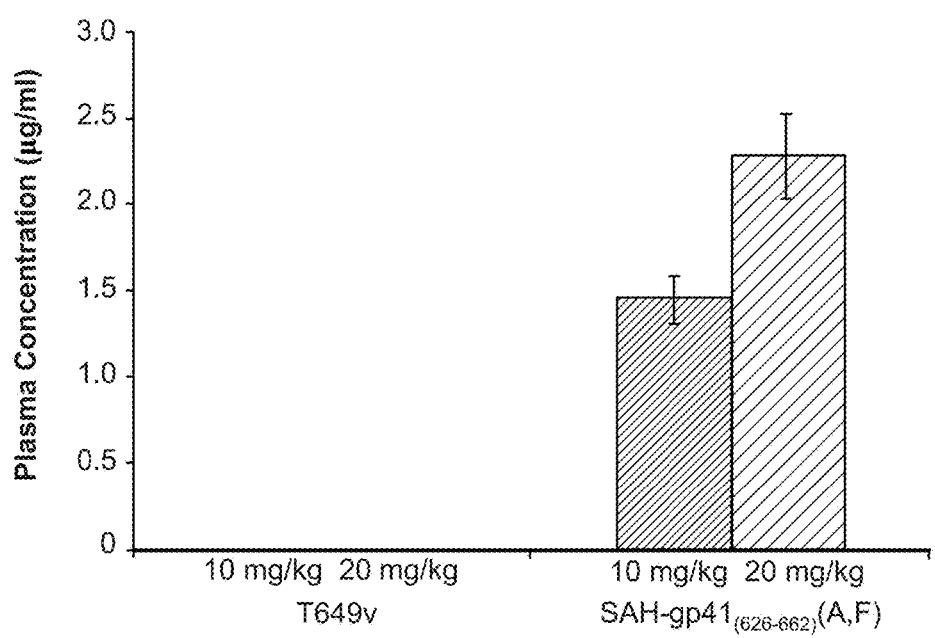

Taken together, these functional data revealed that single and double stapling can yield SAH-gp41 peptides with potent and broad anti-HIV-1 activity. Of note, none of the peptides tested demonstrated any activity against viruses with A-MLV envelope glycoproteins (FIGS. 15D and 16H-I), highlighting the specificity of SAH-gp41 peptides. The importance of striking a balance between α-helical stabilization, proteolytic stability, and anti-viral activity was underscored by the functional penalty that results from over-stabilization, as evidenced by the relatively impaired anti-viral activity of the two doubly-stapled compounds with the most prominent α-helicity and proteolytic stability, SAH-gp41$_{(638-673)}$(D, G) and SAH-gp41$_{(626-662)}$(B, F). Indeed, the doubly-stapled SAH-gp41$_{(626-662)}$(A, F) peptide, which combined intermediate α-helical stabilization, the unique anti-proteolysis feature of double stapling, and potent anti-viral activity (FIG. 17), highlights the remarkable capacity of hydrocarbon stapling to optimize the structure, stability, and functional activity of HIV-1 fusion inhibitor peptides. Importantly, the structural and functional differences among SAH-gp41 peptides underscores the ability of hydrocarbon stapling to yield a diversity of peptides that differentially sample three dimensional space, arguably a key asset in screening for correctly structured immunogens for HIV-1 vaccination.

Figure 20:
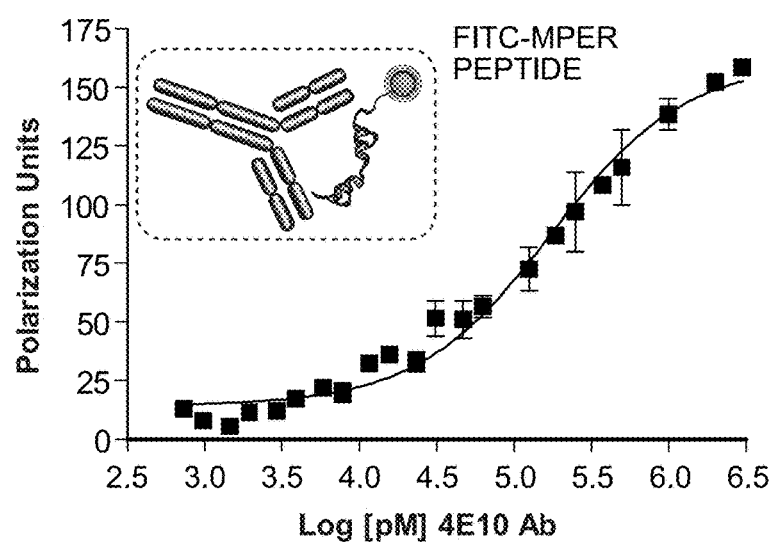
FIG. 20 shows the binding of the 4E10 antibody to a FITC-MPER wild-type peptide as measured by fluorescence polarization; this 4E10/FITC-MPER complex formed the basis for the 4E10 antibody competitive binding ELISA analysis used to test the comparative binding activities of SAH-MPER peptides.

Example 9. Fluorescence Polarization Assay (FPA) Demonstrates Specific Binding of the BNAb 4E10 to a Structurally Constrained MPER Peptide FPA is performed using the method above to directly measure and compare the relative affinities of distinct Stabilized Antigenic Structures of gp41 (SAS-gp41) constructs for the neutralizing antibodies 4E10, 2F5, and Z13e1 (NIH AIDS Research and Reference Reagents Program). Fluorescence polarization (mP units) is measured on a BMG POLARstar Optima or SpectraMax plate reader (Molecular Devices) and Kd values calculated by nonlinear regression analysis of dose-response curves using Prism software (Graphpad). The results from an FPA analysis of 4E10 antibody binding to control MPER peptide FITC-ELDK-WASLWNWFNITNWLWYIK-NH$_2$ is shown in FIG. 20.

Example 10. Biophysical and Biological Properties of MPER Domain-Containing Structurally Constrained Peptides Structurally constrained MPER domain containing peptides such as those shown in FIGS. 7, 10, and 12 were synthesized and analyzed using a variety of methods, as described above. The structurally constrained peptides have a greater tendency to have helical structures, either alpha helix or 3$_{10}$ helix, at the appropriate portions of the peptide as compared to the native peptides that show little to no helical structure. The structurally constrained MPER peptides also have a higher relative affinity for one or more BNAbs such as 2F5, Z13e1, and 4E10, as demonstrated by competitive antibody binding ELISA assays (FIGS. 21-22).

Example 11. Structural Determination of MPER Domain-Containing Structurally Constrained Peptides The application of hydrocarbon stapling to develop effective MPER-based immunogens is dependent on the synthetic recreation of neutralization-competent structure. As such, a variety of methodologies to characterize the structure(s) of SAS-gp41 peptides, including circular dichroism, x-ray crystallography, and NMR spectroscopy.

In order to evaluate secondary structure improvements of hydrocarbon-stapled peptides, we record and analyze circular dichroism (CD) spectra on an Aviv Biomedical spectrometer (model 410), as described above. The target peptide concentration for CD studies is 25-50 μM in 50 mM potassium phosphate (pH 7.5) or Milli-Q deionized water, and exact concentrations are confirmed by quantitative amino acid analysis of two CD sample dilutions. The CD spectra are initially plotted as wavelength versus millidegree. Once the precise peptide concentration is confirmed, the mean residue ellipticity [θ], in units of degree·cm$^2$·dmol$^{-1}$·residue$^{-1}$, is derived from the equation, [θ]=millidegree/molar concentration/number of amino acid residues. After conversion to mean residue ellipticity, percent α-helicity can be calculated using the equation, % helicity=100×[θ]$_{222}$/$^{max}$[θ]$_{222}$, where $^{max}$[θ]$_{222}$=−40,000×[1−(2.5/number of amino acid residues)]. We also employ the curve-fitting CDDN software that is bundled with our spectrometer to calculate the relative fractions of secondary structure including α-helix, parallel and antiparallel β-sheet, β-turn and random coil.

To define the explicit structure of SAS-gp41 peptides for comparison with Fab-bound and lipid-embedded MPER peptides, x-ray crystallography and NMR methods will be applied as described (Cardoso, R. M. et al. Immunity, 2005. 22L p. 163-173; Ofek et al. J Virol, 2004. 78: p 10724-10737; Sun, Z. Y. et al. Immunity, 2008. 28: p. 52-63; Cardoso, R. M., et al. J Mol Biol, 2007. 365: 1533-1544.) Crystallization conditions for SAS-gp41 peptides are screened using 96-well sitting drop plates (Crystal Quick, Hampton Research) set up using a Phoenix crystallization robot. Initial conditions include HT Index Screen (Hampton Research), JSCG+ Suite (Qiagen) and Pro-Complex Suite (Qiagen). Screening around the best hit, including varying pH and salt and detergent concentrations, are performed to identify the best condition for crystal growth. Once generated, the crystals are removed, washed in the crystallization buffer, and subjected to mass spectroscopy to verify the presence of peptide within the crystal. The crystal is then soaked in cryoprotectant, flash frozen, and stored in liquid nitrogen. Suitable crystals are examined at the Argonne National Laboratory synchrotron facility. Phases are obtained by molecular replacement followed by data analysis and refinement (Phaser, Phenix, and Coots software). Co-complexes of Fab/SAS-gp41 can also be examined using similar methodology, initiating screens based on published conditions (Cardoso, R. M. et al. Immunity, 2005. 22L p. 163-173; Ofek et al. J Virol, 2004. 78: p 10724-10737).

An alternative and complementary approach for structural analysis employs $^1$H-NMR analysis. Spectra of SAS-gp41 peptides in solution are acquired on a Bruker Avance DRX spectrometer at 600 MHz equipped with a z-shielded gradient and triple resonance cryoprobe. Two dimensional DQF-COSY, TOCSY, and NOESY spectra are measured in 100% $D_2O$ and 90% $H_2O$/10% $D_2O$. The TOCSY datasets are acquired with mixing times of 40 and 80 ms and NOESY spectra with mixing times of 75, 100, 125 and 200 ms. NMR data sets are processed with the NMRPipe spectral analysis package and assignment of proton resonances is performed with Cara. Structure calculations are carried out with the program CYANA using the standard protocol. The final structure family is comprised of the 20 structures with the lowest target function and the best overall values for chirality and stereochemistry measured with the programs WHATCHECK and PROCHECK_NMR. Structures are displayed and analyzed using the programs PYMOL and MOL-MOL.

The structural data are used to (1) select SAS-gp41 peptides for immunization that most closely reflect Fab-bound and lipid-embedded MPER structures and (2) correlate SAS-gp41 structure with functional activity as evaluated in the assays described herein.

Example 12. Immunogenicity Testing of Structurally Constrained gp41 Peptides

Structurally constrained gp41 peptides, particularly those identified as being most effective in binding assays, and/or in inhibition of viral fusion and infectivity studies, were used to make a pharmaceutical preparation for vaccination (e.g. conjugated to carrier protein and administered with adjuvant). The preparation for administration by injection, e.g., with an adjuvant, or for administration to a mucosal surface was prepared using routine methods. Animals are bled prior to vaccination and at appropriate intervals after initial vaccination and after booster vaccinations for immunogenicity testing. A flow chart for the methods is presented in FIGS. 6 and 19A. Serum were prepared and tested for the presence of antibodies that bind specifically to one or more of the structurally constrained peptides.

FIG. 19 shows the results of an immunogenicity study in which SAH-HR2(A,F) and its corresponding unmodified peptide were upscaled for conjugation to KLH and then deployed in a rabbit immunization protocol using timed boosts according to the schedule depicted in (A), followed by ELISA analysis of the derived antisera against the corresponding antigen (B) and cross-antigen analysis (C). Group 1 animals (n=3) received the SAH-HR2-KLH antigen and all were positive for SAH-HR2 binding by ELISA assay at week 2, only 2 weeks after the first inoculation (FIG. 19B). Titers increased to greater than 300,000 by week 10, 2 weeks after the third inoculation. Group 2 animals received the wild-type HR2-KLH antigen and all did not become positive for wild-type-HR2 binding until week 10, 2 weeks after the third inoculation. Only one animal injected with wild-type HR2-KLH showed any titer after week 2, with a second animal becoming positive at week 4. By week 14, titers increased to greater than 89,000 for all group 2 animals, but only one animal achieved titers of greater than 300,000. These data demonstrate that rabbits exposed to SAH-HR2-KLH achieved significantly more rapid and robust antibody responses. We next tested whether the antisera generated by one immunogen was capable of recognizing the other. This study led to the provocative finding that antisera derived from wild-type HR2-KLH immunized mice showed little to no recognition of the structured SAH-HR2 antigen (FIG. 19C). Maximum titers peaked below 15,000 and weren't even achieved until week 14, 2 weeks after the fourth inoculation. These data indicate that the morphology of SAH-HR2, which reflects the native α-helical conformation of gp41 HR2 domains, could not be detected after immunization with the relatively unstructured wild-type HR2 peptide. To rule out that SAH-HR2-KLH responses resulted from recognition of the hydrocarbon staples instead of the gp41 motif itself, we next tested whether SAH-HR2-KLH-derived antisera could recognize wild-type HR2 peptide by ELISA assay. Indeed, there was cross immunoreactivity of SAH-HR2-KLH derived antibodies with the wild-type HR2 peptide, proving that the response elicited by SAH-HR2-KLH was specific to the gp41 peptide sequence (FIG. 19C). Maximum titers ranging from 4580 to 547000 were achieved by week 14, 2 weeks after the fourth inoculation. For two of the SAH-HR2-KLH immunized animals, the titers achieved for wild-type HR2 recognition even surpassed the maximum titers derived from wild-type HR2-KLH immunized rabbits. Thus, the results of our rabbit immunization study indicate that structured antigens that lock the peptidic motif into its native three dimensional shape not only generate more robust antibody responses, but without this structural stabilization, the resultant antisera are essentially unable to recognize the natural gp41 structure.

B cells can be collected from animals producing BNAbs and hybridoma cell lines can be produced using known methods. Individual cell likes can be cloned and monoclonal antibodies having BNAb activity can be further characterized.

B cells can be collected from animals producing BNAbs and hybridoma cell lines can be produced using known methods. Individual cell likes can be cloned and monoclonal antibodies having BNAb activity can be further characterized.

Example 13. SAS-gp41 Vaccine Efficacy and Testing In Vivo Using Viral Challenge

Animal models of HIV-1 infection are used to evaluate the therapeutic efficacy of (1) SAS-gp41 peptide vaccines and (2) infusion of BNabs derived from SAS-gp41 immunization and antibody production, in preventing, suppressing, or eliminating infection. Such animal models and the design, execution, and analysis of efficacy studies are well known in the art and include the use of humanized Rag2$^{-/-}$ gamma c$^{-/-}$ (RAG-hu) mice infected with HIV-1 (Choudhary, S. K et al J Virol, 2009. Epub June 3; Berges et al. Retrovirol, 2006. 3: p 76) and rhesus monkeys infected with SIV (Keele, B. F. et al. J Exp Med, 2009, 206: p 1117-1134; Gardner, M. B. et al J Med Primatol, 1989. 18: p. 321-328; Gardner, M. B. Adv Exp Med Biol, 1989. 251: 279-293; Ruprecht, R. M. Methods Mol Biol, 2009. 525: 559-566). The close evolutionary similarity between rhesus monkeys and humans makes them especially suitable animal models to study the immunology of human immunodeficiency virus (HIV) infection using the rhesus monkey infectious homologue simian immunodeficiency virus (SIV) and other examples of prominent opportunistic infectious disease models with clinical applications. Specifically, both SIV and HIV are primate lentiviruses that use the CD4 protein as a primary receptor and chemokine receptors as coreceptors for cell entry. After infection with SIV, most rhesus monkeys develop a disease similar to HIV-1-induced AIDS; thus, SIV infection of the rhesus monkey is currently considered the best animal model for human HIV infection. Rhesus monkeys are considered the pre-clinical standard for HIV/AIDS vaccine development utilizing SIV challenge. Lead SAS-gp41 antigens for vaccination or the development of BNabs for passive immunotherapy will be advanced to human testing in accordance with federal standards and approved clinical research protocols (e.g. Harro, C. D. et al, AIDS Res Hum Retroviruses, 2009. 25: p. 103-114; Gudmundsdotter, L. et al. Vaccine, 2009. May 29 epub ahead of print).

Example 14. Structurally Constrained RSV Peptides Compete Effectively for Binding to RSV 5-Helix Bundle Protein FIG. 23A-B show (A) exemplary hydrocarbon-stapled RSV HR2 domain peptides containing i, i+4 crosslinks and (B) the results from fluorescence polarization binding analysis using FITC-SAH-RSV peptides and recombinant RSV 5-helix bundle. This confirms that adding a staple to specific locations at either end of the sequence does not interfere with the critical 6-helix bundle formation. In fact, stapling appeared to enhance the ability FITC-SAH-RSV and 5-helix bundle protein to combine into a fusogenic six-helix bundle.

REFERENCES

1. UNAIDS. (2008) Report on the global AIDS epidemic.
2. Zwick, M. B., Labrijn, A. F., Wang, M., Spenlehauer, C., Saphire, E. O., et al. (2001) Broadly neutralizing antibodies targeted to the membrane-proximal external region of human immunodeficiency virus type 1 glycoprotein gp41. J Virol, 75(22), 10892-10905.
3. Brunel, F. M., Zwick, M. B., Cardoso, R. M., Nelson, J. D., Wilson, I. A., et al. (2006) Structure-function analysis of the epitope for 4E10, a broadly neutralizing human immunodeficiency virus type 1 antibody. J Virol, 80(4), 1680-1687.
4. Cardoso, R. M., Zwick, M. B., Stanfield, R. L., Kunert, R., Binley, J. M., et al. (2005) Broadly neutralizing anti-HIV antibody 4E10 recognizes a helical conformation of a highly conserved fusion-associated motif in gp41 Immunity, 22(2), 163-173.
5. Coutant, J., Yu, H., Clement, M. J., Alfsen, A., Toma, F., et al. (2008) Both lipid environment and pH are critical for determining physiological solution structure of 3-D-conserved epitopes of the HIV-1 gp41-MPER peptide P1. Faseb J, September 15 epub ahead of print.
6. Huarte, N., Lorizate, M., Kunert, R., and Nieva, J. L. (2008) Lipid modulation of membrane-bound epitope recognition and blocking by HIV-1 neutralizing antibodies. FEBS Lett, October 16 epub ahead of print.
7. Montero, M., van Houten, N. E., Wang, X., and Scott, J. K. (2008) The membrane-proximal external region of the human immunodeficiency virus type 1 envelope: dominant site of antibody neutralization and target for vaccine design. Microbiol. Mol Biol Rev, 72(1), 54-84.
8. Ofek, G., Tang, M., Sambor, A., Katinger, H., Mascola, J. R., et al. (2004) Structure and mechanistic analysis of the anti-human immunodeficiency virus type 1 antibody 2F5 in complex with its gp41 epitope. J Virol, 78(19), 10724-10737.
9. Sun, Z. Y., Oh, K. J., Kim, M., Yu, J., Brusic, V., et al. (2008) HIV-1 broadly neutralizing antibody extracts its epitope from a kinked gp41 ectodomain region on the viral membrane. Immunity, 28(1), 52-63.
10. Walensky, L. D., Kung, A. L., Escher, I., Malia, T. J., Barbuto, S., et al. (2004) Activation of apoptosis in vivo by a hydrocarbon-stapled BH3 helix. Science, 305(5689), 1466-1470.
11. Nelson, J. D., Brunel, F. M., Jensen, R., Crooks, E. T., Cardoso, R. M., et al. (2007) An affinity-enhanced neutralizing antibody against the membrane-proximal external region of human immunodeficiency virus type 1 gp41 recognizes an epitope between those of 2F5 and 4E10. J Virol, 81(8), 4033-4043.
12. Penn-Nicholson, A., Han, D. P., Kim, S. J., Park, H., Ansari, R., et al. (2008) Assessment of antibody responses against gp41 in HIV-1-infected patients using soluble gp41 fusion proteins and peptides derived from M group consensus envelope. Virology, 372(2), 442-456.
13. Cardoso, R. M., Brunel, F. M., Ferguson, S., Zwick, M., Burton, D. R., et al. (2007) Structural basis of enhanced binding of extended and helically constrained peptide epitopes of the broadly neutralizing HIV-1 antibody 4E10. J Mol Biol, 365(5), 1533-1544.
14. Joyce, J. G., Hurni, W. M., Bogusky, M. J., Garsky, V. M., Liang, X., et al. (2002) Enhancement of alpha-helicity in the HIV-1 inhibitory peptide DP178 leads to an increased affinity for human monoclonal antibody 2F5 but does not elicit neutralizing responses in vitro. Implications for vaccine design. J Biol Chem, 277(48), 45811-45820.
15. McGaughey, G. B., Citron, M., Danzeisen, R. C., Freidinger, R. M., Garsky, V. M., et al. (2003) HIV-1 vaccine development: constrained peptide immunogens show improved binding to the anti-HIV-1 gp41 MAb. Biochemistry, 42(11), 3214-3223.
16. Bird, G. H., Bernal, F., Pitter, K., and Walensky, L. D. (2008) Synthesis and biophysical characterization of stabilized alpha-helices of BCL-2 domains. Methods Enzymol, 446, 369-386.
17. Gavathiotis, E., Suzuki, M., Davis, M. L., Pitter, K., Bird, G. H., et al. (2008) BAX activation is initiated at a novel interaction site. Nature, 455, 1076-1081.

18. Zhang, H., Zhao, Q., Bhattacharya, S., Waheed, A. A., Tong, X., et al. (2008) A cell-penetrating helical peptide as a potential HIV-1 inhibitor. J Mol Biol, 378(3), 565-580.
19. Madani, N., Hubicki, A. M., Perdigoto, A. L., Springer, M., and Sodroski, J. (2007) Inhibition of human immunodeficiency virus envelope glycoprotein-mediated single cell lysis by low-molecular-weight antagonists of viral entry. J Virol, 81(2), 532-538.
20. Si, Z., Cayabyab, M., and Sodroski, J. (2001) Envelope glycoprotein determinants of neutralization resistance in a simian-human immunodeficiency virus (SHIV-HXBc2P 3.2) derived by passage in monkeys. J Virol, 75(9), 4208-4218.
21. Weissenhorn, W., Dessen, A., Harrison, S. C., Skehel, J. J., and Wiley, D. C. (1997) Atomic structure of the ectodomain from HIV-1 gp41. Nature, 387(6631), 426-430.
22. Vaine, M., Wang, S., Crooks, E. T., Jiang, P., Montefiori, D. C., et al. (2008) Improved induction of antibodies against key neutralizing epitopes by human immunodeficiency virus type 1 gp120 DNA prime-protein boost vaccination compared to gp120 protein-only vaccination. J Virol, 82(15), 7369-7378.
23. Wang, S., Pal, R., Mascola, J. R., Chou, T. H., Mboudjeka, I., et al. (2006) Polyvalent HIV-1 Env vaccine formulations delivered by the DNA priming plus protein boosting approach are effective in generating neutralizing antibodies against primary human immunodeficiency virus type 1 isolates from subtypes A, B, C, D and E. Virology, 350(1), 34-47.
24. Li, M., Gao, F., Mascola, J. R., Stamatatos, L., Polonis, V. R., et al. (2005) Human immunodeficiency virus type 1 env clones from acute and early subtype B infections for standardized assessments of vaccine-elicited neutralizing antibodies. J Virol, 79(16), 10108-10125.
25. Montefiori, D. C. (2005) Evaluating neutralizing antibodies against HIV, SIV, and SHIV in luciferase reporter gene assays. Curr Protoc Immunol, Chapter 12, Unit 12.11.

All patents, patent applications, GenBank numbers, and published references cited herein are hereby incorporated by reference in their entirety as if they were incorporated individually. While this invention has been particularly shown and described with references to preferred embodiments thereof, it will be understood by those skilled in the art that various changes in form and details may be made therein without departing from the scope of the invention encompassed by the appended claims.

What is claimed is:

1. A cross-linked polypeptide comprising a stabilized HIV gp41 membrane proximal external region (MPER) domain, wherein said stabilized HIV gp41 MPER domain is stabilized with two hydrocarbon staples, wherein one of said hydrocarbon staples is positioned so as to link amino acid residues i and i+3 relative to amino acid positions of a first helix of the polypeptide, and wherein one of said hydrocarbon staples is positioned so as to link amino acid residues i and i+4 relative to amino acid positions of a second helix of the polypeptide.

2. The cross-linked polypeptide of claim 1, wherein the stabilized HIV gp41 MPER domain comprises an amino acid mutation or a non-natural amino acid incorporation relative to amino acids 662 to 683 of SEQ ID NO: 1.

3. The cross-linked polypeptide of claim 1, wherein the stabilized HIV gp41 MPER domain comprises at least two amino acids on a single face of a helix, at least two interacting face amino acids or a conservative substitution of an interacting face amino acid from SEQ ID NO: 1, wherein the interacting face amino acids are selected from positions corresponding to amino acids Trp-672, Phe-673, Asn-674, Ile-675, Thr-676, Leu-679, and W-680 when numbered in accordance with SEQ ID NO: 1.

4. The cross-linked polypeptide of claim 1, wherein a stacked column of amino acids is defined by positions corresponding to positions on a sequence provided by SEQ ID NO: 1, wherein the stacked column of amino acids comprises a group of amino acids selected from the groups consisting of Glu-662, Lys-665, Trp-666, Leu-669, and Trp-672; Leu-663, Trp-666, Ala-667, and Trp-670; Asp-664, Ala-667, Ser-668, and Asn-671; Lys-665, Ser-668, Leu-669, and Trp-672; Trp-666, Leu-669, and Trp-670; Ala-667, Trp-670, and Asn-671; Ser-668, Asn-671, and Trp-672; Ile-675, Trp-678, and Tyr-681; Asn-676, Leu-679, and Ile-682; Thr-677, Trp-680, and Lys-683; Ile-675, Trp-678, Trp-679, and Ile-682; Thr-676, Leu-679, Trp-680, and Lys-683; Asn-677, Trp-680, and Tyr-681; Trp-678, Tyr-681, and Ile-682; and Leu-679, Ile-682, and Lys-683 when numbered in accordance with SEQ ID NO: 1.

5. The cross-linked polypeptide of claim 3, wherein said cross-linked polypeptide comprises at least 3 interacting face amino acids or a conservative substitution of an interacting face amino acid from SEQ ID NO: 1, wherein the interacting face amino acids are selected from positions corresponding to amino acids Trp-672, Phe-673, Asn-674, Ile-675, Thr-676, Leu-679, and W-680 when numbered in accordance with SEQ ID NO: 1.

6. The cross-linked polypeptide of claim 1, wherein the peptide further comprises at least 3 contiguous amino acids of an HR-2 peptide, or at least two amino acids on a single face of a helix of an HR-2 peptide, or at least two interacting face amino acids of an HR-2 peptide or a conservative substitution of an interacting face amino acid from SEQ ID NO: 1.

7. The cross-linked polypeptide of claim 6, wherein the interacting face amino acids of the HR-2 peptide are selected from the group consisting of amino acids corresponding to positions Thr-627, Trp-628, Trp-631, Asp-632, Arg-633, Ile-635, Tyr-638, Ile-642, Leu-645, Ile-646, Ser-649, Gln-650, Gln-652, Gln-653, Glu-654, Lys-655, Asn-656, Glu-657, Glu-659, Leu-660, Glu-662, and Leu-663 on SEQ ID NO: 1.

8. The cross-linked polypeptide of claim 6, wherein the interacting face amino acids of the HR-2 peptide are selected from the group consisting of amino acids corresponding to positions Trp-628, Trp-631, Ile-635, Tyr-638, Ile-642, Leu-645, Ser-649, Gln-652, Asn-656, Glu-659, and Leu-663 on SEQ ID NO: 1.

9. The cross-linked polypeptide of claim 6, wherein said cross-linked polypeptide comprises at least two amino acids on a single face of a helix or at least two interacting face amino acids of an amino acid sequence selected from the group consisting of amino acids 37-57 of SEQ ID NO: 17-23; amino acids 19-36 of SEQ ID NO: 50-57 and 64-70; SEQ ID NO: 24, SEQ ID NO: 41-43, and SEQ ID NO: 75-89 operably linked either directly or indirectly to the carboxy-terminus to a peptide that comprises at least 3 contiguous amino acids, or at least two amino acids on a single face of a helix, or at least two interacting face amino acids of an amino acid sequence selected from the group consisting of SEQ ID NO: 10-23, SEQ ID NO: 26-40, SEQ ID NO: 45-48, SEQ ID NO: 58-63, SEQ ID NO: 71-74, and amino acids 1-25 of SEQ ID NO: 49-57, amino acids 1-25 of SEQ ID NO: 64-70; and the sequence of SEQ ID NO: 76-128 and 135-140.

10. The cross-linked peptide of claim 1 in a pharmaceutically acceptable carrier.

11. A kit comprising at least one cross-linked polypeptide of claim 1 and instructions for use.

12. The cross-linked polypeptide of claim 1, wherein one of the hydrocarbon staples comprises a pairing selected from the group consisting of an R3-S6 pairing, an R6-S3 pairing, an R3-S5 pairing, and an R5-S3 pairing.

13. The cross-linked polypeptide of claim 1, wherein the polypeptide comprises SEQ ID NO: 137 comprising a hydrocarbon staple between amino acid positions 17 and 20 and a hydrocarbon staple between amino acid positions 3 and 7.

14. The cross-linked peptide of claim 1, wherein the polypeptide comprises at least two interacting face amino acids of an amino acid sequence selected from the group consisting of amino acids 37-57 of SEQ ID NO: 17-23; amino acids 19-36 of SEQ ID NO: 50-57 and 64-70; SEQ ID NO: 24-25, SEQ ID NO: 41-43, and SEQ ID NO: 75-128 and 135-140.

15. The cross-linked polypeptide of claim 1, wherein the polypeptide comprises: amino acids 37-57 of SEQ ID NO: 17-23 or SEQ ID NO: 43.

16. The cross-linked polypeptide of claim 1, wherein the polypeptide comprises:
SEQ ID NO: 41 comprising a hydrocarbon staple between amino acid positions 17 and 20;
SEQ ID NO: 42 comprising a hydrocarbon staple between amino acid positions 20 and 24;
SEQ ID NO: 75 comprising a hydrocarbon staple between amino acid positions 6 and 10;
SEQ ID NO: 76 comprising a hydrocarbon staple between amino acid positions 5 and 9;
SEQ ID NO: 77 comprising a hydrocarbon staple between amino acid positions 4 and 8;
SEQ ID NO: 78 comprising a hydrocarbon staple between amino acid positions 3 and 7;
SEQ ID NO: 79 comprising a hydrocarbon staple between amino acid positions 2 and 6;
SEQ ID NO: 80 comprising a hydrocarbon staple between amino acid positions 1 and 5;
SEQ ID NO: 81 comprising a hydrocarbon staple between amino acid positions 13 and 17;
SEQ ID NO: 82 comprising a hydrocarbon staple between amino acid positions 9 and 13;
SEQ ID NO: 83 comprising a hydrocarbon staple between amino acid positions 19 and 22;
SEQ ID NO: 84 comprising a hydrocarbon staple between amino acid positions 18 and 21;
SEQ ID NO: 85 comprising a hydrocarbon staple between amino acid positions 17 and 20;
SEQ ID NO: 86 comprising a hydrocarbon staple between amino acid positions 16 and 19;
SEQ ID NO: 87 comprising a hydrocarbon staple between amino acid positions 15 and 18;
SEQ ID NO: 88 comprising a hydrocarbon staple between amino acid positions 14 and 17;
SEQ ID NO: 89 comprising a hydrocarbon staple between amino acid positions 13 and 16;
SEQ ID NO: 98 comprising a hydrocarbon staple between amino acid positions 8 and 11;
SEQ ID NO: 99 comprising a hydrocarbon staple between amino acid positions 8 and 11;
SEQ ID NO: 100 comprising a hydrocarbon staple between amino acid positions 8 and 11;
SEQ ID NO: 135 comprising a hydrocarbon staple between amino acid positions 17 and 21;
SEQ ID NO: 136 comprising a hydrocarbon staple between amino acid positions 17 and 20;
SEQ ID NO: 138 comprising a hydrocarbon staple between amino acid positions 8 and 11;
SEQ ID NO: 139 comprising a hydrocarbon staple between amino acid positions 8 and 11; or
SEQ ID NO: 140 comprising a hydrocarbon staple between amino acid positions 8 and 11.

17. The cross-linked polypeptide of claim 1, wherein the polypeptide comprises:
SEQ ID NO: 90 comprising a hydrocarbon staple between amino acid positions 1 and 5 and a hydrocarbon staple between amino acid positions 17 and 20;
SEQ ID NO: 91 comprising a hydrocarbon staple between amino acid positions 2 and 6 and a hydrocarbon staple between amino acid positions 17 and 20;
SEQ ID NO: 92 comprising a hydrocarbon staple between amino acid positions 3 and 7 and a hydrocarbon staple between amino acid positions 17 and 20;
SEQ ID NO: 93 comprising a hydrocarbon staple between amino acid positions 4 and 8 and a hydrocarbon staple between amino acid positions 17 and 20;
SEQ ID NO: 94 comprising a hydrocarbon staple between amino acid positions 1 and 5 and a hydrocarbon staple between amino acid positions 14 and 17;
SEQ ID NO: 95 comprising a hydrocarbon staple between amino acid positions 2 and 6 and a hydrocarbon staple between amino acid positions 14 and 17;
SEQ ID NO: 96 comprising a hydrocarbon staple between amino acid positions 3 and 7 and a hydrocarbon staple between amino acid positions 13 and 17;
SEQ ID NO: 97 comprising a hydrocarbon staple between amino acid positions 4 and 8 and a hydrocarbon staple between amino acid positions 14 and 17;
SEQ ID NO: 101 comprising a hydrocarbon staple between amino acid positions 1 and 5 and a hydrocarbon staple between amino acid positions 17 and 20;
SEQ ID NO: 102 comprising a hydrocarbon staple between amino acid positions 2 and 6 and a hydrocarbon staple between amino acid positions 17 and 20;
SEQ ID NO: 103 comprising a hydrocarbon staple between amino acid positions 3 and 7 and a hydrocarbon staple between amino acid positions 17 and 20;
SEQ ID NO: 104 comprising a hydrocarbon staple between amino acid positions 4 and 8 and a hydrocarbon staple between amino acid positions 17 and 20; or
SEQ ID NO: 105 comprising a hydrocarbon staple between amino acid positions 5 and 9 and a hydrocarbon staple between amino acid positions 17 and 20.

18. A cross-linked polypeptide comprising a stabilized alpha helix and a stabilized $3_{10}$ helix of HIV gp41 MPER domain, wherein said stabilized HIV gp41 MPER domain is stabilized with two hydrocarbon staples, wherein one of said hydrocarbon staples is positioned so as to link amino acid residues i and i+3 relative to amino acid positions of a first helix of the polypeptide, and wherein one of said hydrocarbon staples is positioned so as to link amino acid residues i and i+4 relative to amino acid positions of a second helix of the polypeptide.

* * * * *

SEQUENCE LISTING

```
<160> NUMBER OF SEQ ID NOS: 149

<210> SEQ ID NO 1
<211> LENGTH: 856
<212> TYPE: PRT
<213> ORGANISM: Human immunodeficiency virus type 1

<400> SEQUENCE: 1

Met Arg Val Lys Glu Lys Tyr Gln His Leu Trp Arg Trp Gly Trp Arg
 1               5                  10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
```

-continued

```
            195                 200                 205
Ser Phe Glu Pro Ile Pro Ile His Tyr Cys Ala Pro Ala Gly Phe Ala
210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                    245                 250                 255

Thr Gln Leu Leu Leu Asn Gly Ser Leu Ala Glu Glu Val Val Ile
                260                 265                 270

Arg Ser Val Asn Phe Thr Asp Asn Ala Lys Thr Ile Ile Val Gln Leu
                275                 280                 285

Asn Thr Ser Val Glu Ile Asn Cys Thr Arg Pro Asn Asn Asn Thr Arg
290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                    325                 330                 335

Lys Trp Asn Asn Thr Leu Lys Gln Ile Ala Ser Lys Leu Arg Glu Gln
                340                 345                 350

Phe Gly Asn Asn Lys Thr Ile Ile Phe Lys Gln Ser Ser Gly Gly Asp
                355                 360                 365

Pro Glu Ile Val Thr His Ser Phe Asn Cys Gly Gly Glu Phe Phe Tyr
370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                    405                 410                 415

Pro Cys Arg Ile Lys Gln Ile Ile Asn Met Trp Gln Lys Val Gly Lys
                420                 425                 430

Ala Met Tyr Ala Pro Pro Ile Ser Gly Gln Ile Arg Cys Ser Ser Asn
                435                 440                 445

Ile Thr Gly Leu Leu Leu Thr Arg Asp Gly Gly Asn Ser Asn Asn Glu
450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                    485                 490                 495

Ala Pro Thr Lys Ala Lys Arg Arg Val Val Gln Arg Glu Lys Arg Ala
                500                 505                 510

Val Gly Ile Gly Ala Leu Phe Leu Gly Phe Leu Gly Ala Ala Gly Ser
                515                 520                 525

Thr Met Gly Ala Ala Ser Met Thr Leu Thr Val Gln Ala Arg Gln Leu
                530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                    565                 570                 575

Gln Ala Arg Ile Leu Ala Val Glu Arg Tyr Leu Lys Asp Gln Gln Leu
                580                 585                 590

Leu Gly Ile Trp Gly Cys Ser Gly Lys Leu Ile Cys Thr Thr Ala Val
                595                 600                 605

Pro Trp Asn Ala Ser Trp Ser Asn Lys Ser Leu Glu Gln Ile Trp Asn
610                 615                 620
```

```
His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
            645                 650                 655

Glu Gln Glu Leu Leu Glu Leu Asp Lys Trp Ala Ser Leu Trp Asn Trp
                660                 665                 670

Phe Asn Ile Thr Asn Trp Leu Trp Tyr Ile Lys Leu Phe Ile Met Ile
            675                 680                 685

Val Gly Gly Leu Val Gly Leu Arg Ile Val Phe Ala Val Leu Ser Ile
690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855

<210> SEQ ID NO 2
<211> LENGTH: 843
<212> TYPE: PRT
<213> ORGANISM: Human immunodeficiency virus type 1

<400> SEQUENCE: 2

Met Arg Ala Thr Glu Ile Arg Lys Asn Tyr Gln His Leu Trp Lys Gly
1               5                   10                  15

Gly Thr Leu Leu Leu Gly Met Leu Met Ile Cys Ser Ala Ala Glu Gln
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Lys Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Ala Thr Asn Thr Thr Ser Ser Ser Trp
```

```
            130                 135                 140
Glu Thr Met Glu Lys Gly Ile Lys Asn Cys Ser Phe Asn Ile Thr
145                 150                 155                 160

Thr Ser Ile Arg Asp Lys Val Gln Lys Glu Tyr Ala Leu Phe Tyr Asn
                165                 170                 175

Leu Asp Val Val Pro Ile Asp Asn Ala Ser Tyr Arg Leu Ile Ser Cys
                180                 185                 190

Asn Thr Ser Val Ile Thr Gln Ala Cys Pro Lys Val Ser Phe Glu Pro
                195                 200                 205

Ile Pro Ile His Tyr Cys Ala Pro Ala Gly Phe Ala Ile Leu Lys Cys
                210                 215                 220

Asn Asp Lys Lys Phe Asn Gly Thr Gly Pro Cys Thr Asn Val Ser Thr
225                 230                 235                 240

Val Gln Cys Thr His Gly Ile Arg Pro Val Val Ser Thr Gln Leu Leu
                245                 250                 255

Leu Asn Gly Ser Leu Ala Glu Glu Ile Val Ile Arg Ser Glu Asn
                260                 265                 270

Phe Thr Asn Asn Ala Lys Thr Ile Ile Val Gln Leu Asn Glu Ser Val
                275                 280                 285

Val Ile Asn Cys Thr Arg Pro Asn Asn Asn Thr Arg Lys Ser Ile Asn
                290                 295                 300

Ile Gly Pro Gly Arg Ala Leu Tyr Thr Thr Gly Glu Ile Ile Gly Asp
305                 310                 315                 320

Ile Arg Gln Ala His Cys Asn Leu Ser Lys Thr Gln Trp Glu Asn Thr
                325                 330                 335

Leu Glu Gln Ile Ala Ile Lys Leu Lys Glu Gln Phe Gly Asn Asn Lys
                340                 345                 350

Thr Ile Ile Phe Asn Pro Ser Ser Gly Gly Asp Pro Glu Ile Val Thr
                355                 360                 365

His Ser Phe Asn Cys Gly Gly Glu Phe Phe Tyr Cys Asn Ser Thr Gln
                370                 375                 380

Leu Phe Thr Trp Asn Asp Thr Arg Lys Leu Asn Asn Thr Gly Arg Asn
385                 390                 395                 400

Ile Thr Leu Pro Cys Arg Ile Lys Gln Ile Ile Asn Met Trp Gln Glu
                405                 410                 415

Val Gly Lys Ala Met Tyr Ala Pro Pro Ile Arg Gly Gln Ile Arg Cys
                420                 425                 430

Ser Ser Asn Ile Thr Gly Leu Leu Leu Thr Arg Asp Gly Gly Lys Asp
                435                 440                 445

Thr Asn Gly Thr Glu Ile Phe Arg Pro Gly Gly Gly Asp Met Arg Asp
450                 455                 460

Asn Trp Arg Ser Glu Leu Tyr Lys Tyr Lys Val Lys Ile Glu Pro
465                 470                 475                 480

Leu Gly Val Ala Pro Thr Lys Ala Lys Arg Arg Val Val Gln Arg Glu
                485                 490                 495

Lys Arg Ala Val Gly Leu Gly Ala Leu Phe Leu Gly Phe Leu Gly Ala
                500                 505                 510

Ala Gly Ser Thr Met Gly Ala Ala Ser Ile Thr Leu Thr Val Gln Ala
                515                 520                 525

Arg Gln Leu Leu Ser Gly Ile Val Gln Gln Asn Asn Leu Leu Arg
                530                 535                 540

Ala Ile Glu Ala Gln Gln His Leu Leu Gln Leu Thr Val Trp Gly Ile
545                 550                 555                 560
```

```
Lys Gln Leu Gln Ala Arg Val Leu Ala Val Glu Arg Tyr Leu Arg Asp
                565                 570                 575

Gln Gln Leu Leu Gly Ile Trp Gly Cys Ser Gly Lys Leu Ile Cys Thr
            580                 585                 590

Thr Thr Val Pro Trp Asn Thr Ser Trp Ser Asn Lys Ser Leu Asn Glu
        595                 600                 605

Ile Trp Asp Asn Met Thr Trp Met Lys Trp Glu Arg Glu Ile Asp Asn
    610                 615                 620

Tyr Thr His Ile Ile Tyr Ser Leu Ile Glu Gln Ser Gln Asn Gln Gln
625                 630                 635                 640

Glu Lys Asn Glu Gln Glu Leu Leu Ala Leu Asp Lys Trp Ala Ser Leu
                645                 650                 655

Trp Asn Trp Phe Asp Ile Thr Lys Trp Leu Trp Tyr Ile Lys Ile Phe
            660                 665                 670

Ile Met Ile Val Gly Gly Leu Ile Gly Leu Arg Ile Val Phe Val Val
        675                 680                 685

Leu Ser Ile Val Asn Arg Val Arg Gln Gly Tyr Ser Pro Leu Ser Phe
690                 695                 700

Gln Thr His Leu Pro Ala Gln Arg Gly Pro Asp Arg Pro Asp Gly Ile
705                 710                 715                 720

Glu Glu Glu Gly Gly Glu Arg Asp Arg Asp Arg Ser Gly Pro Leu Val
                725                 730                 735

Asp Gly Phe Leu Ala Ile Ile Trp Val Asp Leu Arg Ser Leu Cys Leu
            740                 745                 750

Phe Ser Tyr His Arg Leu Arg Asp Leu Leu Leu Ile Val Thr Arg Ile
        755                 760                 765

Val Glu Leu Leu Gly Arg Arg Gly Trp Gly Val Leu Lys Tyr Trp Trp
    770                 775                 780

Asn Leu Leu Gln Tyr Trp Ile Gln Glu Leu Lys Asn Ser Ala Val Ser
785                 790                 795                 800

Leu Leu Asn Ala Thr Ala Ile Ala Val Ala Glu Gly Thr Asp Arg Val
                805                 810                 815

Ile Glu Ile Leu Gln Arg Ala Phe Arg Ala Val Leu His Ile Pro Val
            820                 825                 830

Arg Ile Arg Gln Gly Leu Glu Arg Ala Leu Leu
        835                 840

<210> SEQ ID NO 3
<211> LENGTH: 51
<212> TYPE: PRT
<213> ORGANISM: Human immunodeficiency virus type 1

<400> SEQUENCE: 3

Arg Gln Leu Leu Ser Gly Ile Val Gln Gln Gln Asn Asn Leu Leu Arg
1               5                   10                  15

Ala Ile Glu Ala Gln Gln His Leu Leu Gln Leu Thr Val Trp Gly Ile
            20                  25                  30

Lys Gln Leu Gln Ala Arg Ile Leu Ala Val Glu Arg Tyr Leu Gln Asp
        35                  40                  45

Gln Gln Leu
    50

<210> SEQ ID NO 4
<211> LENGTH: 44
<212> TYPE: PRT
```

<213> ORGANISM: Ebolavirus

<400> SEQUENCE: 4

Asp Gly Leu Ile Cys Gly Leu Arg Gln Leu Ala Asn Glu Thr Thr Gln
1               5                   10                  15

Ala Leu Gln Leu Phe Leu Arg Ala Thr Thr Glu Leu Arg Thr Phe Ser
            20                  25                  30

Ile Leu Asn Arg Lys Ala Ile Asp Phe Leu Ile Leu
        35                  40

<210> SEQ ID NO 5
<211> LENGTH: 42
<212> TYPE: PRT
<213> ORGANISM: Marburgvirus

<400> SEQUENCE: 5

Asn Asn Leu Val Cys Arg Leu Arg Arg Leu Ala Asn Gln Thr Ala Lys
1               5                   10                  15

Ser Leu Glu Leu Leu Leu Arg Val Thr Thr Glu Glu Arg Thr Phe Ser
            20                  25                  30

Leu Ile Asn Arg His Ala Ile Asp Phe Leu
        35                  40

<210> SEQ ID NO 6
<211> LENGTH: 50
<212> TYPE: PRT
<213> ORGANISM: Unknown
<220> FEATURE:
<223> OTHER INFORMATION: Description of Unknown: Leukemia virus
      polypeptide.

<400> SEQUENCE: 6

Met Ser Leu Ala Ser Gly Lys Ser Leu Leu His Glu Val Asp Lys Asp
1               5                   10                  15

Ile Ser Gln Leu Thr Gln Ala Ile Val Lys Asn His Lys Asn Leu Leu
            20                  25                  30

Lys Ile Ala Gln Tyr Ala Ala Gln Asn Arg Arg Gly Leu Asp Leu Leu
        35                  40                  45

Phe Trp
    50

<210> SEQ ID NO 7
<211> LENGTH: 65
<212> TYPE: PRT
<213> ORGANISM: Parainfluenza virus

<400> SEQUENCE: 7

Ala Leu Gly Val Ala Thr Ser Ala Gln Ile Thr Ala Ala Val Ala Leu
1               5                   10                  15

Val Glu Ala Lys Gln Ala Arg Ser Asp Ile Glu Lys Leu Lys Glu Ala
            20                  25                  30

Ile Arg Asp Thr Asn Lys Ala Val Gln Ser Val Gln Ser Ser Ile Gly
        35                  40                  45

Asn Leu Ile Val Ala Ile Lys Ser Val Gln Asp Tyr Val Asn Lys Glu
    50                  55                  60

Ile
65

<210> SEQ ID NO 8
<211> LENGTH: 57

```
<212> TYPE: PRT
<213> ORGANISM: Respiratory syncytial virus

<400> SEQUENCE: 8

Ser Gly Ile Ala Val Ser Lys Val Leu His Leu Glu Gly Glu Val Asn
1               5                   10                  15

Lys Ile Lys Asn Ala Leu Leu Ser Thr Asn Lys Ala Val Val Ser Leu
            20                  25                  30

Ser Asn Gly Val Ser Val Leu Thr Ser Lys Val Leu Asp Leu Lys Ser
        35                  40                  45

Tyr Ile Asn Asn Gln Leu Leu Pro Ile
    50                  55

<210> SEQ ID NO 9
<211> LENGTH: 79
<212> TYPE: PRT
<213> ORGANISM: SARS coronavirus

<400> SEQUENCE: 9

Asn Val Leu Tyr Glu Asn Gln Lys Gln Ile Ala Asn Gln Phe Asn Lys
1               5                   10                  15

Ala Ile Ser Gln Ile Gln Glu Ser Leu Ile Thr Thr Thr Ser Thr Ala
            20                  25                  30

Leu Gly Lys Leu Gln Asp Val Val Asn Gln Asn Ala Gln Ala Leu Asn
        35                  40                  45

Thr Leu Val Lys Gln Leu Ser Ser Asn Phe Gly Ala Ile Ser Ser Val
    50                  55                  60

Leu Asn Asp Ile Leu Ser Arg Leu Asp Ile Lys Val Glu Ala Glu
65                  70                  75

<210> SEQ ID NO 10
<211> LENGTH: 43
<212> TYPE: PRT
<213> ORGANISM: Human immunodeficiency virus type 1

<400> SEQUENCE: 10

Trp Asn Asn Met Thr Trp Met Glu Trp Glu Lys Glu Ile Asp Asn Tyr
1               5                   10                  15

Thr Ser Ile Ile Tyr Thr Leu Leu Glu Thr Ser Gln Asn Gln Gln Glu
            20                  25                  30

Lys Asn Glu Gln Glu Leu Leu Glu Leu Asp Lys
        35                  40

<210> SEQ ID NO 11
<211> LENGTH: 24
<212> TYPE: PRT
<213> ORGANISM: Ebolavirus

<400> SEQUENCE: 11

Asp Trp Thr Lys Asn Ile Thr Asp Lys Ile Asp Gln Ile Ile His Asp
1               5                   10                  15

Phe Val Asp Lys Thr Leu Pro Asp
            20

<210> SEQ ID NO 12
<211> LENGTH: 20
<212> TYPE: PRT
<213> ORGANISM: Marburgvirus

<400> SEQUENCE: 12
```

-continued

```
Ile Glu Asp Leu Ser Arg Asn Ile Ser Glu Gln Ile Asp Gln Ile Lys
1               5                   10                  15

Lys Asp Glu Gln
            20

<210> SEQ ID NO 13
<211> LENGTH: 30
<212> TYPE: PRT
<213> ORGANISM: Unknown
<220> FEATURE:
<223> OTHER INFORMATION: Description of Unknown: Leukemia virus
      polypeptide.

<400> SEQUENCE: 13

Cys Cys Phe Leu Asn Ile Thr Asn Ser His Val Ser Ile Leu Gln Glu
1               5                   10                  15

Arg Pro Pro Leu Glu Asn Arg Val Leu Thr Gly Trp Gly Leu
            20                  25                  30

<210> SEQ ID NO 14
<211> LENGTH: 56
<212> TYPE: PRT
<213> ORGANISM: Parainfluenza virus

<400> SEQUENCE: 14

Tyr Thr Pro Asn Asp Ile Thr Leu Asn Asn Ser Val Ala Leu Asp Pro
1               5                   10                  15

Ile Asp Ile Ser Ile Glu Leu Asn Lys Ala Lys Ser Asp Leu Glu Glu
            20                  25                  30

Ser Lys Glu Trp Ile Arg Arg Ser Asn Gln Lys Leu Asp Ser Ile Gly
        35                  40                  45

Asn Trp His Gln Ser Ser Thr Thr
    50                  55

<210> SEQ ID NO 15
<211> LENGTH: 54
<212> TYPE: PRT
<213> ORGANISM: Respiratory syncytial virus

<400> SEQUENCE: 15

Pro Ile Ile Asn Tyr Tyr Asp Pro Leu Val Phe Pro Ser Asp Glu Phe
1               5                   10                  15

Asp Ala Ser Ile Ser Gln Val Asn Glu Lys Ile Asn Gln Ser Leu Ala
            20                  25                  30

His Arg Arg Ser Asp Glu Leu Leu Phe Ile Asn Val Asn Thr Gly Lys
        35                  40                  45

Ser Thr Thr Asn Ile Met
    50

<210> SEQ ID NO 16
<211> LENGTH: 47
<212> TYPE: PRT
<213> ORGANISM: SARS coronavirus

<400> SEQUENCE: 16

Thr Ser Pro Asp Val Asp Phe Gly Asp Ile Ser Gly Ile Asn Ala Ser
1               5                   10                  15

Val Val Asn Ile Gln Lys Glu Ile Asp Arg Leu Asn Glu Val Ala Lys
            20                  25                  30

Asn Leu Asn Glu Ser Leu Ile Asp Leu Gln Glu Leu Gly Lys Tyr
        35                  40                  45
```

<210> SEQ ID NO 17
<211> LENGTH: 58
<212> TYPE: PRT
<213> ORGANISM: Human immunodeficiency virus type 1

<400> SEQUENCE: 17

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
                20                  25                  30

Gln Glu Leu Leu Glu Leu Asp Lys Trp Ala Asn Leu Trp Asn Trp Phe
            35                  40                  45

Asp Ile Ser Lys Trp Leu Trp Tyr Ile Lys
        50                  55

<210> SEQ ID NO 18
<211> LENGTH: 58
<212> TYPE: PRT
<213> ORGANISM: Human immunodeficiency virus type 1

<400> SEQUENCE: 18

Met Thr Trp Met Lys Trp Glu Arg Glu Ile Asp Asn Tyr Thr His Ile
1               5                   10                  15

Ile Tyr Ser Leu Ile Glu Gln Ser Gln Asn Gln Gln Glu Lys Asn Glu
                20                  25                  30

Gln Glu Leu Leu Ala Leu Asp Lys Trp Ala Ser Leu Trp Asn Trp Phe
            35                  40                  45

Asp Ile Thr Lys Trp Leu Trp Tyr Ile Lys
        50                  55

<210> SEQ ID NO 19
<211> LENGTH: 58
<212> TYPE: PRT
<213> ORGANISM: Simian immunodeficiency virus

<400> SEQUENCE: 19

Met Thr Trp Gln Glu Trp Glu Arg Gln Val Asp Phe Leu Glu Ala Asn
1               5                   10                  15

Ile Thr Gln Leu Leu Glu Glu Ala Gln Ile Gln Gln Glu Lys Asn Met
                20                  25                  30

Tyr Glu Leu Gln Lys Leu Asn Ser Trp Asp Ile Phe Gly Asn Trp Phe
            35                  40                  45

Asp Leu Thr Ser Trp Ile Arg Tyr Ile Gln
        50                  55

<210> SEQ ID NO 20
<211> LENGTH: 58
<212> TYPE: PRT
<213> ORGANISM: Human immunodeficiency virus type 1

<400> SEQUENCE: 20

Thr Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
                20                  25                  30

Gln Glu Leu Leu Glu Leu Asp Lys Trp Ala Ser Leu Trp Asn Trp Phe
            35                  40                  45

Asn Ile Thr Asn Trp Leu Trp Tyr Ile Lys

<210> SEQ ID NO 21
<211> LENGTH: 58
<212> TYPE: PRT
<213> ORGANISM: Human immunodeficiency virus type 1

<400> SEQUENCE: 21

Thr Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Trp Ala Ser Leu Trp Asn Trp Phe
        35                  40                  45

Asn Ile Thr Asn Trp Leu Trp Tyr Ile Lys
    50                  55

<210> SEQ ID NO 22
<211> LENGTH: 58
<212> TYPE: PRT
<213> ORGANISM: Human immunodeficiency virus type 1

<400> SEQUENCE: 22

Met Thr Trp Met Gln Trp Glu Lys Glu Ile Ser Asn Tyr Ser Tyr Glu
1               5                   10                  15

Ile Tyr Arg Leu Ile Glu Glu Ser Gln Asn Gln Gln Glu Lys Asn Glu
            20                  25                  30

Gln Glu Leu Leu Ala Leu Asp Lys Trp Thr Ser Leu Trp Ser Trp Phe
        35                  40                  45

Asp Ile Ser Asn Trp Leu Trp Tyr Ile Lys
    50                  55

<210> SEQ ID NO 23
<211> LENGTH: 58
<212> TYPE: PRT
<213> ORGANISM: Human immunodeficiency virus type 1

<400> SEQUENCE: 23

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Trp Ala Ser Leu Trp Asn Trp Phe
        35                  40                  45

Asn Ile Thr Asn Trp Leu Trp Tyr Ile Lys
    50                  55

<210> SEQ ID NO 24
<211> LENGTH: 40
<212> TYPE: PRT
<213> ORGANISM: Human immunodeficiency virus type 1

<400> SEQUENCE: 24

Glu Leu Leu Glu Leu Asp Lys Trp Ala Asn Leu Trp Asn Trp Phe Asp
1               5                   10                  15

Ile Ser Lys Trp Leu Trp Tyr Ile Lys Ile Phe Ile Met Ile Val Gly
            20                  25                  30

Gly Leu Val Gly Leu Arg Ile Ile
        35                  40

<210> SEQ ID NO 25
<211> LENGTH: 32
<212> TYPE: PRT
<213> ORGANISM: SARS coronavirus

<400> SEQUENCE: 25

Asp Leu Gln Glu Leu Gly Lys Tyr Glu Gln Tyr Ile Lys Trp Pro Trp
1               5                   10                  15

Tyr Val Trp Leu Gly Phe Ile Ala Gly Leu Ile Val Ile Val Met Val
            20                  25                  30

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle

<400> SEQUENCE: 26

Leu Thr Trp Leu Glu Trp Asp Arg Glu Ile Asn Asn Tyr Thr Ser Leu
1               5                   10                  15

Ile His Ser Leu
            20

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: (S)-2-(4'-pentenyl) alanine
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: (S)-2-(4'-pentenyl) alanine

<400> SEQUENCE: 27

Leu Thr Trp Ala Glu Trp Asp Ala Glu Ile Asn Asn Tyr Thr Ser Leu
1               5                   10                  15

Ile His Ser Leu
            20

<210> SEQ ID NO 28
<211> LENGTH: 38
<212> TYPE: PRT
<213> ORGANISM: Human immunodeficiency virus type 1

<400> SEQUENCE: 28

```
Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Leu Lys Asn Glu
            20                  25                  30

Gln Glu Leu Leu Glu Leu
        35

<210> SEQ ID NO 29
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (7)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(23)
<223> OTHER INFORMATION: Any amino acid
<220> FEATURE:
<221> NAME/KEY: MOD_RES
<222> LOCATION: (25)..(26)
<223> OTHER INFORMATION: Any amino acid
<220> FEATURE:
<221> NAME/KEY: MOD_RES
<222> LOCATION: (28)..(30)
<223> OTHER INFORMATION: Any amino acid
<220> FEATURE:
<221> NAME/KEY: MOD_RES
<222> LOCATION: (32)..(33)
<223> OTHER INFORMATION: Any amino acid
<220> FEATURE:
<221> NAME/KEY: MOD_RES
<222> LOCATION: (35)..(37)
<223> OTHER INFORMATION: Any amino acid

<400> SEQUENCE: 29

Xaa Xaa Trp Xaa Xaa Trp Xaa Xaa Xaa Ile Xaa Xaa Tyr Xaa Xaa Xaa
1               5                   10                  15

Ile Xaa Xaa Leu Xaa Xaa Xaa Ser Xaa Xaa Gln Xaa Xaa Xaa Asn Xaa
            20                  25                  30

Xaa Glu Xaa Xaa Xaa Leu
        35

<210> SEQ ID NO 30
<211> LENGTH: 38
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (22)..(24)
<223> OTHER INFORMATION: Any amino acid
<220> FEATURE:
<221> NAME/KEY: MOD_RES
<222> LOCATION: (26)..(27)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (33)..(34)
<223> OTHER INFORMATION: Any amino acid
<220> FEATURE:
<221> NAME/KEY: MOD_RES
<222> LOCATION: (36)..(36)
<223> OTHER INFORMATION: Any amino acid

<400> SEQUENCE: 30

Xaa Thr Trp Xaa Xaa Trp Asp Arg Xaa Ile Xaa Xaa Tyr Xaa Xaa Xaa
1               5                   10                  15

Ile Xaa Xaa Leu Ile Xaa Xaa Xaa Gln Xaa Xaa Gln Glu Lys Xaa Glu
            20                  25                  30

Xaa Xaa Leu Xaa Glu Leu
        35

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Non-natural amino acid used for cross-linking
<220> FEATURE:
<221> NAME/KEY: MOD_RES
<222> LOCATION: (8)..(8)
<223> OTHER INFORMATION: Non-natural amino acid used for cross-linking
<220> FEATURE:
<221> NAME/KEY: MOD_RES
<222> LOCATION: (28)..(28)
<223> OTHER INFORMATION: Non-natural amino acid used for cross-linking
```

```
<220> FEATURE:
<221> NAME/KEY: MOD_RES
<222> LOCATION: (32)..(32)
<223> OTHER INFORMATION: Non-natural amino acid used for cross-linking

<400> SEQUENCE: 31

Met Thr Trp Xaa Glu Trp Asp Xaa Glu Ile Asn Asn Tyr Thr Ser Leu
1               5                   10                  15

Ile His Ser Leu Ile Glu Glu Ser Gln Asn Gln Xaa Glu Lys Asn Xaa
                20                  25                  30

<210> SEQ ID NO 32
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Non-natural amino acid used for cross-linking
<220> FEATURE:
<221> NAME/KEY: MOD_RES
<222> LOCATION: (9)..(9)
<223> OTHER INFORMATION: Non-natural amino acid used for cross-linking
<220> FEATURE:
<221> NAME/KEY: MOD_RES
<222> LOCATION: (28)..(28)
<223> OTHER INFORMATION: Non-natural amino acid used for cross-linking
<220> FEATURE:
<221> NAME/KEY: MOD_RES
<222> LOCATION: (32)..(32)
<223> OTHER INFORMATION: Non-natural amino acid used for cross-linking

<400> SEQUENCE: 32

Met Thr Trp Met Xaa Trp Asp Arg Xaa Ile Asn Asn Tyr Thr Ser Leu
1               5                   10                  15

Ile His Ser Leu Ile Glu Glu Ser Gln Asn Gln Xaa Glu Lys Asn Xaa
                20                  25                  30

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Non-natural amino acid used for cross-linking
<220> FEATURE:
<221> NAME/KEY: MOD_RES
<222> LOCATION: (11)..(11)
<223> OTHER INFORMATION: Non-natural amino acid used for cross-linking
<220> FEATURE:
<221> NAME/KEY: MOD_RES
<222> LOCATION: (28)..(28)
<223> OTHER INFORMATION: Non-natural amino acid used for cross-linking
<220> FEATURE:
<221> NAME/KEY: MOD_RES
<222> LOCATION: (32)..(32)
<223> OTHER INFORMATION: Non-natural amino acid used for cross-linking

<400> SEQUENCE: 33

Met Thr Trp Met Glu Trp Xaa Arg Glu Ile Xaa Asn Tyr Thr Ser Leu
1               5                   10                  15

Ile His Ser Leu Ile Glu Glu Ser Gln Asn Gln Xaa Glu Lys Asn Xaa
                20                  25                  30
```

```
<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Non-natural amino acid used for cross-linking
<220> FEATURE:
<221> NAME/KEY: MOD_RES
<222> LOCATION: (19)..(19)
<223> OTHER INFORMATION: Non-natural amino acid used for cross-linking
<220> FEATURE:
<221> NAME/KEY: MOD_RES
<222> LOCATION: (28)..(28)
<223> OTHER INFORMATION: Non-natural amino acid used for cross-linking
<220> FEATURE:
<221> NAME/KEY: MOD_RES
<222> LOCATION: (32)..(32)
<223> OTHER INFORMATION: Non-natural amino acid used for cross-linking

<400> SEQUENCE: 34

Met Thr Trp Met Glu Trp Asp Arg Glu Ile Asn Asn Tyr Thr Xaa Leu
1               5                   10                  15

Ile His Xaa Leu Ile Glu Glu Ser Gln Asn Gln Xaa Glu Lys Asn Xaa
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Non-natural amino acid used for cross-linking
<220> FEATURE:
<221> NAME/KEY: MOD_RES
<222> LOCATION: (8)..(8)
<223> OTHER INFORMATION: Non-natural amino acid used for cross-linking
<220> FEATURE:
<221> NAME/KEY: MOD_RES
<222> LOCATION: (27)..(27)
<223> OTHER INFORMATION: Non-natural amino acid used for cross-linking
<220> FEATURE:
<221> NAME/KEY: MOD_RES
<222> LOCATION: (31)..(31)
<223> OTHER INFORMATION: Non-natural amino acid used for cross-linking

<400> SEQUENCE: 35

Met Thr Trp Xaa Glu Trp Asp Xaa Glu Ile Asn Asn Tyr Thr Ser Leu
1               5                   10                  15

Ile His Ser Leu Ile Glu Glu Ser Gln Asn Xaa Gln Glu Lys Xaa Glu
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Non-natural amino acid used for cross-linking
<220> FEATURE:
```

```
<221> NAME/KEY: MOD_RES
<222> LOCATION: (9)..(9)
<223> OTHER INFORMATION: Non-natural amino acid used for cross-linking
<220> FEATURE:
<221> NAME/KEY: MOD_RES
<222> LOCATION: (27)..(27)
<223> OTHER INFORMATION: Non-natural amino acid used for cross-linking
<220> FEATURE:
<221> NAME/KEY: MOD_RES
<222> LOCATION: (31)..(31)
<223> OTHER INFORMATION: Non-natural amino acid used for cross-linking

<400> SEQUENCE: 36

Met Thr Trp Met Xaa Trp Asp Arg Xaa Ile Asn Asn Tyr Thr Ser Leu
1               5                   10                  15

Ile His Ser Leu Ile Glu Glu Ser Gln Asn Xaa Gln Glu Lys Xaa Glu
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Non-natural amino acid used for cross-linking
<220> FEATURE:
<221> NAME/KEY: MOD_RES
<222> LOCATION: (11)..(11)
<223> OTHER INFORMATION: Non-natural amino acid used for cross-linking
<220> FEATURE:
<221> NAME/KEY: MOD_RES
<222> LOCATION: (27)..(27)
<223> OTHER INFORMATION: Non-natural amino acid used for cross-linking
<220> FEATURE:
<221> NAME/KEY: MOD_RES
<222> LOCATION: (31)..(31)
<223> OTHER INFORMATION: Non-natural amino acid used for cross-linking

<400> SEQUENCE: 37

Met Thr Trp Met Glu Trp Xaa Arg Glu Ile Xaa Asn Tyr Thr Ser Leu
1               5                   10                  15

Ile His Ser Leu Ile Glu Glu Ser Gln Asn Xaa Gln Glu Lys Xaa Glu
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Non-natural amino acid used for cross-linking
<220> FEATURE:
<221> NAME/KEY: MOD_RES
<222> LOCATION: (19)..(19)
<223> OTHER INFORMATION: Non-natural amino acid used for cross-linking
<220> FEATURE:
<221> NAME/KEY: MOD_RES
<222> LOCATION: (27)..(27)
<223> OTHER INFORMATION: Non-natural amino acid used for cross-linking
<220> FEATURE:
<221> NAME/KEY: MOD_RES
<222> LOCATION: (31)..(31)
<223> OTHER INFORMATION: Non-natural amino acid used for cross-linking

<400> SEQUENCE: 38
```

```
Met Thr Trp Met Glu Trp Asp Arg Glu Ile Asn Asn Tyr Thr Xaa Leu
1               5                   10                  15

Ile His Xaa Leu Ile Glu Glu Ser Gln Asn Xaa Gln Glu Lys Xaa Glu
            20                  25                  30
```

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Non-natural amino acid used for cross-linking
<220> FEATURE:
<221> NAME/KEY: MOD_RES
<222> LOCATION: (8)..(8)
<223> OTHER INFORMATION: Non-natural amino acid used for cross-linking
<220> FEATURE:
<221> NAME/KEY: MOD_RES
<222> LOCATION: (15)..(15)
<223> OTHER INFORMATION: Non-natural amino acid used for cross-linking
<220> FEATURE:
<221> NAME/KEY: MOD_RES
<222> LOCATION: (19)..(19)
<223> OTHER INFORMATION: Non-natural amino acid used for cross-linking

<400> SEQUENCE: 39

```
Met Thr Trp Xaa Glu Trp Asp Xaa Glu Ile Asn Asn Tyr Thr Xaa Leu
1               5                   10                  15

Ile His Xaa Leu Ile Glu Glu Ser Gln Asn Gln Gln Glu Lys Asn Glu
            20                  25                  30
```

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Non-natural amino acid used for cross-linking
<220> FEATURE:
<221> NAME/KEY: MOD_RES
<222> LOCATION: (9)..(9)
<223> OTHER INFORMATION: Non-natural amino acid used for cross-linking
<220> FEATURE:
<221> NAME/KEY: MOD_RES
<222> LOCATION: (15)..(15)
<223> OTHER INFORMATION: Non-natural amino acid used for cross-linking
<220> FEATURE:
<221> NAME/KEY: MOD_RES
<222> LOCATION: (19)..(19)
<223> OTHER INFORMATION: Non-natural amino acid used for cross-linking

<400> SEQUENCE: 40

```
Met Thr Trp Met Xaa Trp Asp Arg Xaa Ile Asn Asn Tyr Thr Xaa Leu
1               5                   10                  15

Ile His Xaa Leu Ile Glu Glu Ser Gln Asn Gln Gln Glu Lys Asn Glu
            20                  25                  30
```

<210> SEQ ID NO 41
<211> LENGTH: 26
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Non-natural amino acid used for cross-linking
<220> FEATURE:
<221> NAME/KEY: MOD_RES
<222> LOCATION: (20)..(20)
<223> OTHER INFORMATION: Non-natural amino acid used for cross-linking

<400> SEQUENCE: 41

Gln Glu Leu Leu Glu Leu Asp Lys Trp Ala Ser Leu Trp Asn Trp Phe
1               5                   10                  15

Xaa Ile Thr Xaa Trp Leu Trp Tyr Ile Lys
            20                  25

<210> SEQ ID NO 42
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Non-natural amino acid used for cross-linking
<220> FEATURE:
<221> NAME/KEY: MOD_RES
<222> LOCATION: (24)..(24)
<223> OTHER INFORMATION: Non-natural amino acid used for cross-linking

<400> SEQUENCE: 42

Gln Glu Leu Leu Glu Leu Asp Lys Trp Ala Ser Leu Trp Asn Trp Phe
1               5                   10                  15

Asn Ile Thr Xaa Trp Leu Trp Xaa Ile Lys
            20                  25

<210> SEQ ID NO 43
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Non-natural amino acid used for cross-linking
<220> FEATURE:
<221> NAME/KEY: MOD_RES
<222> LOCATION: (24)..(24)
<223> OTHER INFORMATION: Non-natural amino acid used for cross-linking

<400> SEQUENCE: 43

Gln Glu Leu Leu Glu Leu Asp Lys Trp Ala Ser Leu Trp Asn Trp Phe
1               5                   10                  15

Xaa Ile Thr Asn Trp Leu Trp Xaa Ile
            20                  25

<210> SEQ ID NO 44
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle

<400> SEQUENCE: 44

Leu Thr Trp Leu Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Trp Ala Ser Leu Trp Asn Trp Phe
        35                  40                  45

<210> SEQ ID NO 45
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle

<400> SEQUENCE: 45

Leu Thr Trp Leu Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu
        35

<210> SEQ ID NO 46
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (28)..(28)
<223> OTHER INFORMATION: (S)-2-(4'-pentenyl) alanine
<220> FEATURE:
<221> NAME/KEY: misc_feature
<222> LOCATION: (28)..(32)
<223> OTHER INFORMATION: Cross-link between residues
<220> FEATURE:
<221> NAME/KEY: MOD_RES
<222> LOCATION: (32)..(32)
<223> OTHER INFORMATION: (S)-2-(4'-pentenyl) alanine

<400> SEQUENCE: 46

Leu Thr Trp Leu Glu Trp Asp Arg Glu Ile Asn Asn Tyr Thr Ser Leu
1               5                   10                  15
```

Ile His Ser Leu Ile Glu Glu Ser Gln Asn Gln Ala Glu Lys Asn Ala
            20                  25                  30

Gln Glu Leu Leu Glu
        35

<210> SEQ ID NO 47
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: (S)-2-(4'-pentenyl) alanine
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: (S)-2-(4'-pentenyl) alanine

<400> SEQUENCE: 47

Leu Thr Trp Ala Glu Trp Asp Ala Glu Ile Asn Asn Tyr Thr Ser Leu
1               5                   10                  15

Ile His Ser Leu Ile Glu Glu Ser Gln Asn Gln Glu Lys Asn Glu
            20                  25                  30

Gln Glu Leu Leu Glu
        35

<210> SEQ ID NO 48
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (22)..(22)
<223> OTHER INFORMATION: (S)-2-(4'-pentenyl) alanine
<220> FEATURE:
<221> NAME/KEY: misc_feature
<222> LOCATION: (22)..(26)
<223> OTHER INFORMATION: Cross-link between residues
<220> FEATURE:
<221> NAME/KEY: MOD_RES
<222> LOCATION: (26)..(26)
<223> OTHER INFORMATION: (S)-2-(4'-pentenyl) alanine

<400> SEQUENCE: 48

Leu Thr Trp Leu Glu Trp Asp Arg Glu Ile Asn Asn Tyr Thr Ser Leu
1               5                   10                  15

Ile His Ser Leu Ile Ala Glu Ser Gln Ala Gln Gln Glu Lys Asn Glu
            20                  25                  30

```
Gln Glu Leu Leu Glu
        35

<210> SEQ ID NO 49
<211> LENGTH: 36
<212> TYPE: PRT
<213> ORGANISM: Human immunodeficiency virus type 1

<400> SEQUENCE: 49

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: (S)-2-(4'-pentenyl) alanine
<220> FEATURE:
<221> NAME/KEY: misc_feature
<222> LOCATION: (3)..(7)
<223> OTHER INFORMATION: Cross-link between residues
<220> FEATURE:
<221> NAME/KEY: MOD_RES
<222> LOCATION: (7)..(7)
<223> OTHER INFORMATION: (S)-2-(4'-pentenyl) alanine

<400> SEQUENCE: 50

Tyr Thr Ala Leu Ile His Ala Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 51
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: (S)-2-(4'-pentenyl) alanine
<220> FEATURE:
<221> NAME/KEY: misc_feature
<222> LOCATION: (16)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine

<400> SEQUENCE: 51

Tyr Thr Ser Leu Ile His Ser Leu Ile Glu Glu Ser Gln Asn Gln Ala
1               5                   10                  15
```

Glu Lys Asn Ala Gln Glu Leu Leu Glu Leu Asp Lys Trp Ala Ser Leu
            20                  25                  30

Trp Asn Trp Phe
        35

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: (S)-2-(4'-pentenyl) alanine
<220> FEATURE:
<221> NAME/KEY: misc_feature
<222> LOCATION: (27)..(31)
<223> OTHER INFORMATION: Cross-link between residues
<220> FEATURE:
<221> NAME/KEY: MOD_RES
<222> LOCATION: (31)..(31)
<223> OTHER INFORMATION: (S)-2-(4'-pentenyl) alanine

<400> SEQUENCE: 52

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Ala Lys Trp Ala Ala Leu
            20                  25                  30

Trp Asn Trp Phe
        35

<210> SEQ ID NO 53
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: (S)-2-(4'-pentenyl) alanine
<220> FEATURE:
<221> NAME/KEY: misc_feature
<222> LOCATION: (29)..(33)
<223> OTHER INFORMATION: Cross-link between residues
<220> FEATURE:
<221> NAME/KEY: MOD_RES
<222> LOCATION: (33)..(33)
<223> OTHER INFORMATION: (S)-2-(4'-pentenyl) alanine

<400> SEQUENCE: 53

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Ala Ala Ser Leu
            20                  25                  30

Ala Asn Trp Phe
        35

<210> SEQ ID NO 54
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

```
<221> NAME/KEY: MOD_RES
<222> LOCATION: (5)..(5)
<223> OTHER INFORMATION: (S)-2-(4'-pentenyl) alanine
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: (S)-2-(4'-pentenyl) alanine

<400> SEQUENCE: 54

Tyr Thr Ser Leu Ala His Ser Leu Ala Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 55
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: (S)-2-(4'-pentenyl) alanine
<220> FEATURE:
<221> NAME/KEY: misc_feature
<222> LOCATION: (10)..(14)
<223> OTHER INFORMATION: Cross-link between residues
<220> FEATURE:
<221> NAME/KEY: MOD_RES
<222> LOCATION: (14)..(14)
<223> OTHER INFORMATION: (S)-2-(4'-pentenyl) alanine

<400> SEQUENCE: 55

Tyr Thr Ser Leu Ile His Ser Leu Ile Ala Glu Ser Gln Ala Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 56
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: (S)-2-(4'-pentenyl) alanine
<220> FEATURE:
<221> NAME/KEY: misc_feature
<222> LOCATION: (17)..(21)
<223> OTHER INFORMATION: Cross-link between residues
<220> FEATURE:
<221> NAME/KEY: MOD_RES
<222> LOCATION: (21)..(21)
<223> OTHER INFORMATION: (S)-2-(4'-pentenyl) alanine

<400> SEQUENCE: 56

Tyr Thr Ser Leu Ile His Ser Leu Ile Glu Glu Ser Gln Asn Gln Gln
```

```
                1               5                  10                  15
Ala Lys Asn Glu Ala Glu Leu Leu Glu Leu Asp Lys Trp Ala Ser Leu
                    20                  25                  30

Trp Asn Trp Phe
        35

<210> SEQ ID NO 57
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: (S)-2-(4'-pentenyl) alanine
<220> FEATURE:
<221> NAME/KEY: misc_feature
<222> LOCATION: (21)..(25)
<223> OTHER INFORMATION: Cross-link between residues
<220> FEATURE:
<221> NAME/KEY: MOD_RES
<222> LOCATION: (25)..(25)
<223> OTHER INFORMATION: (S)-2-(4'-pentenyl) alanine

<400> SEQUENCE: 57

Tyr Thr Ser Leu Ile His Ser Leu Ile Glu Glu Ser Gln Asn Gln Gln
1               5                   10                  15

Glu Lys Asn Glu Ala Glu Leu Leu Ala Leu Asp Lys Trp Ala Ser Leu
                    20                  25                  30

Trp Asn Trp Phe
        35

<210> SEQ ID NO 58
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: (S)-2-(4'-pentenyl) alanine
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: (S)-2-(4'-pentenyl) alanine
<220> FEATURE:
<221> NAME/KEY: MOD_RES
<222> LOCATION: (28)..(28)
<223> OTHER INFORMATION: (S)-2-(4'-pentenyl) alanine
<220> FEATURE:
<221> NAME/KEY: misc_feature
<222> LOCATION: (28)..(32)
<223> OTHER INFORMATION: Cross-link between residues
<220> FEATURE:
<221> NAME/KEY: MOD_RES
<222> LOCATION: (32)..(32)
<223> OTHER INFORMATION: (S)-2-(4'-pentenyl) alanine

<400> SEQUENCE: 58
```

```
Leu Thr Trp Ala Glu Trp Asp Ala Glu Ile Asn Asn Tyr Thr Ser Leu
1               5                   10                  15

Ile His Ser Leu Ile Glu Glu Ser Gln Asn Gln Ala Glu Lys Asn Ala
            20                  25                  30

Gln Glu Leu Leu Glu
        35

<210> SEQ ID NO 59
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: (S)-2-(4'-pentenyl) alanine
<220> FEATURE:
<221> NAME/KEY: misc_feature
<222> LOCATION: (7)..(11)
<223> OTHER INFORMATION: Cross-link between residues
<220> FEATURE:
<221> NAME/KEY: MOD_RES
<222> LOCATION: (11)..(11)
<223> OTHER INFORMATION: (S)-2-(4'-pentenyl) alanine
<220> FEATURE:
<221> NAME/KEY: MOD_RES
<222> LOCATION: (28)..(28)
<223> OTHER INFORMATION: (S)-2-(4'-pentenyl) alanine
<220> FEATURE:
<221> NAME/KEY: misc_feature
<222> LOCATION: (28)..(32)
<223> OTHER INFORMATION: Cross-link between residues
<220> FEATURE:
<221> NAME/KEY: MOD_RES
<222> LOCATION: (32)..(32)
<223> OTHER INFORMATION: (S)-2-(4'-pentenyl) alanine

<400> SEQUENCE: 59

Leu Thr Trp Leu Glu Trp Ala Arg Glu Ile Ala Asn Tyr Thr Ser Leu
1               5                   10                  15

Ile His Ser Leu Ile Glu Glu Ser Gln Asn Gln Ala Glu Lys Asn Ala
            20                  25                  30

Gln Glu Leu Leu Glu
        35

<210> SEQ ID NO 60
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
```

```
<222> LOCATION: (11)..(11)
<223> OTHER INFORMATION: (S)-2-(4'-pentenyl) alanine
<220> FEATURE:
<221> NAME/KEY: misc_feature
<222> LOCATION: (11)..(15)
<223> OTHER INFORMATION: Cross-link between residues
<220> FEATURE:
<221> NAME/KEY: MOD_RES
<222> LOCATION: (15)..(15)
<223> OTHER INFORMATION: (S)-2-(4'-pentenyl) alanine
<220> FEATURE:
<221> NAME/KEY: MOD_RES
<222> LOCATION: (28)..(28)
<223> OTHER INFORMATION: (S)-2-(4'-pentenyl) alanine
<220> FEATURE:
<221> NAME/KEY: misc_feature
<222> LOCATION: (28)..(32)
<223> OTHER INFORMATION: Cross-link between residues
<220> FEATURE:
<221> NAME/KEY: MOD_RES
<222> LOCATION: (32)..(32)
<223> OTHER INFORMATION: (S)-2-(4'-pentenyl) alanine

<400> SEQUENCE: 60

Leu Thr Trp Leu Glu Trp Asp Arg Glu Ile Ala Asn Tyr Thr Ala Leu
1               5                   10                  15

Ile His Ser Leu Ile Glu Glu Ser Gln Asn Gln Ala Glu Lys Asn Ala
            20                  25                  30

Gln Glu Leu Leu Glu
        35

<210> SEQ ID NO 61
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (15)..(15)
<223> OTHER INFORMATION: (S)-2-(4'-pentenyl) alanine
<220> FEATURE:
<221> NAME/KEY: misc_feature
<222> LOCATION: (15)..(19)
<223> OTHER INFORMATION: Cross-link between residues
<220> FEATURE:
<221> NAME/KEY: MOD_RES
<222> LOCATION: (19)..(19)
<223> OTHER INFORMATION: (S)-2-(4'-pentenyl) alanine
<220> FEATURE:
<221> NAME/KEY: MOD_RES
<222> LOCATION: (28)..(28)
<223> OTHER INFORMATION: (S)-2-(4'-pentenyl) alanine
<220> FEATURE:
<221> NAME/KEY: misc_feature
<222> LOCATION: (28)..(32)
<223> OTHER INFORMATION: Cross-link between residues
<220> FEATURE:
<221> NAME/KEY: MOD_RES
<222> LOCATION: (32)..(32)
<223> OTHER INFORMATION: (S)-2-(4'-pentenyl) alanine

<400> SEQUENCE: 61

Leu Thr Trp Leu Glu Trp Asp Arg Glu Ile Asn Asn Tyr Thr Ala Leu
1               5                   10                  15
```

-continued

```
Ile His Ala Leu Ile Glu Glu Ser Gln Asn Gln Ala Glu Lys Asn Ala
            20                  25                  30

Gln Glu Leu Leu Glu
        35

<210> SEQ ID NO 62
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: (S)-2-(4'-pentenyl) alanine
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: (S)-2-(4'-pentenyl) alanine
<220> FEATURE:
<221> NAME/KEY: MOD_RES
<222> LOCATION: (22)..(22)
<223> OTHER INFORMATION: (S)-2-(4'-pentenyl) alanine
<220> FEATURE:
<221> NAME/KEY: misc_feature
<222> LOCATION: (22)..(26)
<223> OTHER INFORMATION: Cross-link between residues
<220> FEATURE:
<221> NAME/KEY: MOD_RES
<222> LOCATION: (26)..(26)
<223> OTHER INFORMATION: (S)-2-(4'-pentenyl) alanine

<400> SEQUENCE: 62

Leu Thr Trp Ala Glu Trp Asp Ala Glu Ile Asn Asn Tyr Thr Ser Leu
1               5                   10                  15

Ile His Ser Leu Ile Ala Glu Ser Gln Ala Gln Gln Glu Lys Asn Glu
            20                  25                  30

Gln Glu Leu Leu Glu
        35

<210> SEQ ID NO 63
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: (S)-2-(4'-pentenyl) alanine
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: (S)-2-(4'-pentenyl) alanine
```

```
-continued

<220> FEATURE:
<221> NAME/KEY: MOD_RES
<222> LOCATION: (15)..(15)
<223> OTHER INFORMATION: (S)-2-(4'-pentenyl) alanine
<220> FEATURE:
<221> NAME/KEY: misc_feature
<222> LOCATION: (15)..(19)
<223> OTHER INFORMATION: Cross-link between residues
<220> FEATURE:
<221> NAME/KEY: MOD_RES
<222> LOCATION: (19)..(19)
<223> OTHER INFORMATION: (S)-2-(4'-pentenyl) alanine
<220> FEATURE:
<221> NAME/KEY: MOD_RES
<222> LOCATION: (28)..(28)
<223> OTHER INFORMATION: (S)-2-(4'-pentenyl) alanine
<220> FEATURE:
<221> NAME/KEY: misc_feature
<222> LOCATION: (28)..(32)
<223> OTHER INFORMATION: Cross-link between residues
<220> FEATURE:
<221> NAME/KEY: MOD_RES
<222> LOCATION: (32)..(32)
<223> OTHER INFORMATION: (S)-2-(4'-pentenyl) alanine

<400> SEQUENCE: 63

Leu Thr Trp Ala Glu Trp Asp Ala Glu Ile Asn Asn Tyr Thr Ala Leu
1               5                   10                  15

Ile His Ala Leu Ile Glu Glu Ser Gln Asn Gln Ala Glu Lys Asn Ala
            20                  25                  30

Gln Glu Leu Leu Glu
            35

<210> SEQ ID NO 64
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: (S)-2-(4'-pentenyl) alanine
<220> FEATURE:
<221> NAME/KEY: misc_feature
<222> LOCATION: (3)..(7)
<223> OTHER INFORMATION: Cross-link between residues
<220> FEATURE:
<221> NAME/KEY: MOD_RES
<222> LOCATION: (7)..(7)
<223> OTHER INFORMATION: (S)-2-(4'-pentenyl) alanine
<220> FEATURE:
<221> NAME/KEY: MOD_RES
<222> LOCATION: (29)..(29)
<223> OTHER INFORMATION: (S)-2-(4'-pentenyl) alanine
<220> FEATURE:
<221> NAME/KEY: misc_feature
<222> LOCATION: (29)..(33)
<223> OTHER INFORMATION: Cross-link between residues
<220> FEATURE:
<221> NAME/KEY: MOD_RES
<222> LOCATION: (33)..(33)
<223> OTHER INFORMATION: (S)-2-(4'-pentenyl) alanine

<400> SEQUENCE: 64

Tyr Thr Ala Leu Ile His Ala Leu Ile Glu Glu Ser Gln Asn Gln Gln
1               5                   10                  15

Glu Lys Asn Glu Gln Glu Leu Leu Glu Leu Asp Lys Ala Ala Ser Leu
            20                  25                  30

Ala Asn Trp Phe
            35
```

```
<210> SEQ ID NO 65
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: (S)-2-(4'-pentenyl) alanine
<220> FEATURE:
<221> NAME/KEY: misc_feature
<222> LOCATION: (3)..(7)
<223> OTHER INFORMATION: Cross-link between residues
<220> FEATURE:
<221> NAME/KEY: MOD_RES
<222> LOCATION: (7)..(7)
<223> OTHER INFORMATION: (S)-2-(4'-pentenyl) alanine
<220> FEATURE:
<221> NAME/KEY: MOD_RES
<222> LOCATION: (27)..(27)
<223> OTHER INFORMATION: (S)-2-(4'-pentenyl) alanine
<220> FEATURE:
<221> NAME/KEY: misc_feature
<222> LOCATION: (27)..(31)
<223> OTHER INFORMATION: Cross-link between residues
<220> FEATURE:
<221> NAME/KEY: MOD_RES
<222> LOCATION: (31)..(31)
<223> OTHER INFORMATION: (S)-2-(4'-pentenyl) alanine

<400> SEQUENCE: 65

Tyr Thr Ala Leu Ile His Ala Leu Ile Glu Glu Ser Gln Asn Gln Gln
1               5                   10                  15

Glu Lys Asn Glu Gln Glu Leu Leu Glu Leu Ala Lys Trp Ala Ala Leu
            20                  25                  30

Trp Asn Trp Phe
        35

<210> SEQ ID NO 66
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: (S)-2-(4'-pentenyl) alanine
<220> FEATURE:
<221> NAME/KEY: misc_feature
<222> LOCATION: (16)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine
<220> FEATURE:
<221> NAME/KEY: MOD_RES
<222> LOCATION: (29)..(29)
<223> OTHER INFORMATION: (S)-2-(4'-pentenyl) alanine
<220> FEATURE:
<221> NAME/KEY: misc_feature
<222> LOCATION: (29)..(33)
<223> OTHER INFORMATION: Cross-link between residues
<220> FEATURE:
<221> NAME/KEY: MOD_RES
<222> LOCATION: (33)..(33)
<223> OTHER INFORMATION: (S)-2-(4'-pentenyl) alanine

<400> SEQUENCE: 66
```

```
Tyr Thr Ser Leu Ile His Ser Leu Ile Glu Glu Ser Gln Asn Gln Ala
1               5                   10                  15

Glu Lys Asn Ala Gln Glu Leu Leu Glu Leu Asp Lys Ala Ala Ser Leu
            20                  25                  30

Ala Asn Trp Phe
        35

<210> SEQ ID NO 67
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: (S)-2-(4'-pentenyl) alanine
<220> FEATURE:
<221> NAME/KEY: misc_feature
<222> LOCATION: (3)..(7)
<223> OTHER INFORMATION: Cross-link between residues
<220> FEATURE:
<221> NAME/KEY: MOD_RES
<222> LOCATION: (7)..(7)
<223> OTHER INFORMATION: (S)-2-(4'-pentenyl) alanine
<220> FEATURE:
<221> NAME/KEY: MOD_RES
<222> LOCATION: (16)..(16)
<223> OTHER INFORMATION: (S)-2-(4'-pentenyl) alanine
<220> FEATURE:
<221> NAME/KEY: misc_feature
<222> LOCATION: (16)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine

<400> SEQUENCE: 67

Tyr Thr Ala Leu Ile His Ala Leu Ile Glu Glu Ser Gln Asn Gln Ala
1               5                   10                  15

Glu Lys Asn Ala Gln Glu Leu Leu Glu Leu Asp Lys Trp Ala Ser Leu
            20                  25                  30

Trp Asn Trp Phe
        35

<210> SEQ ID NO 68
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: (S)-2-(4'-pentenyl) alanine
<220> FEATURE:
<221> NAME/KEY: misc_feature
<222> LOCATION: (10)..(14)
<223> OTHER INFORMATION: Cross-link between residues
<220> FEATURE:
<221> NAME/KEY: MOD_RES
<222> LOCATION: (14)..(14)
<223> OTHER INFORMATION: (S)-2-(4'-pentenyl) alanine
<220> FEATURE:
<221> NAME/KEY: MOD_RES
<222> LOCATION: (27)..(27)
<223> OTHER INFORMATION: (S)-2-(4'-pentenyl) alanine
<220> FEATURE:
```

```
<221> NAME/KEY: misc_feature
<222> LOCATION: (27)..(31)
<223> OTHER INFORMATION: Cross-link between residues
<220> FEATURE:
<221> NAME/KEY: MOD_RES
<222> LOCATION: (31)..(31)
<223> OTHER INFORMATION: (S)-2-(4'-pentenyl) alanine

<400> SEQUENCE: 68

Tyr Thr Ser Leu Ile His Ser Leu Ile Ala Glu Ser Gln Ala Gln Gln
1               5                   10                  15

Glu Lys Asn Glu Gln Glu Leu Leu Glu Leu Ala Lys Trp Ala Ala Leu
            20                  25                  30

Trp Asn Trp Phe
        35

<210> SEQ ID NO 69
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: (S)-2-(4'-pentenyl) alanine
<220> FEATURE:
<221> NAME/KEY: misc_feature
<222> LOCATION: (10)..(14)
<223> OTHER INFORMATION: Cross-link between residues
<220> FEATURE:
<221> NAME/KEY: MOD_RES
<222> LOCATION: (14)..(14)
<223> OTHER INFORMATION: (S)-2-(4'-pentenyl) alanine
<220> FEATURE:
<221> NAME/KEY: MOD_RES
<222> LOCATION: (21)..(21)
<223> OTHER INFORMATION: (S)-2-(4'-pentenyl) alanine
<220> FEATURE:
<221> NAME/KEY: misc_feature
<222> LOCATION: (21)..(25)
<223> OTHER INFORMATION: Cross-link between residues
<220> FEATURE:
<221> NAME/KEY: MOD_RES
<222> LOCATION: (25)..(25)
<223> OTHER INFORMATION: (S)-2-(4'-pentenyl) alanine

<400> SEQUENCE: 69

Tyr Thr Ser Leu Ile His Ser Leu Ile Ala Glu Ser Gln Ala Gln Gln
1               5                   10                  15

Glu Lys Asn Glu Ala Glu Leu Leu Ala Leu Asp Lys Trp Ala Ser Leu
            20                  25                  30

Trp Asn Trp Phe
        35

<210> SEQ ID NO 70
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: (S)-2-(4'-pentenyl) alanine
<220> FEATURE:
<221> NAME/KEY: misc_feature
<222> LOCATION: (3)..(7)
<223> OTHER INFORMATION: Cross-link between residues
```

```
<220> FEATURE:
<221> NAME/KEY: MOD_RES
<222> LOCATION: (7)..(7)
<223> OTHER INFORMATION: (S)-2-(4'-pentenyl) alanine
<220> FEATURE:
<221> NAME/KEY: MOD_RES
<222> LOCATION: (16)..(16)
<223> OTHER INFORMATION: (S)-2-(4'-pentenyl) alanine
<220> FEATURE:
<221> NAME/KEY: misc_feature
<222> LOCATION: (16)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine
<220> FEATURE:
<221> NAME/KEY: MOD_RES
<222> LOCATION: (27)..(27)
<223> OTHER INFORMATION: (S)-2-(4'-pentenyl) alanine
<220> FEATURE:
<221> NAME/KEY: misc_feature
<222> LOCATION: (27)..(31)
<223> OTHER INFORMATION: Cross-link between residues
<220> FEATURE:
<221> NAME/KEY: MOD_RES
<222> LOCATION: (31)..(31)
<223> OTHER INFORMATION: (S)-2-(4'-pentenyl) alanine

<400> SEQUENCE: 70

Tyr Thr Ala Leu Ile His Ala Leu Ile Glu Glu Ser Gln Asn Gln Ala
1               5                   10                  15

Glu Lys Asn Ala Gln Glu Leu Leu Glu Leu Ala Lys Trp Ala Ala Leu
            20                  25                  30

Trp Asn Trp Phe
        35

<210> SEQ ID NO 71
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(5)
<223> OTHER INFORMATION: (S)-2-(4'-pentenyl) alanine
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: (S)-2-(4'-pentenyl) alanine

<400> SEQUENCE: 71

Leu Thr Trp Leu Ala Trp Asp Arg Ala Ile Asn Asn Tyr Thr Ser Leu
1               5                   10                  15

Ile His Ser Leu Ile Glu Glu Ser Gln Asn Gln Glu Lys Asn Glu
            20                  25                  30

Gln Glu Leu Leu Glu
        35
```

<210> SEQ ID NO 72
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (27)..(27)
<223> OTHER INFORMATION: (S)-2-(4'-pentenyl) alanine
<220> FEATURE:
<221> NAME/KEY: misc_feature
<222> LOCATION: (27)..(31)
<223> OTHER INFORMATION: Cross-link between residues
<220> FEATURE:
<221> NAME/KEY: MOD_RES
<222> LOCATION: (31)..(31)
<223> OTHER INFORMATION: (S)-2-(4'-pentenyl) alanine

<400> SEQUENCE: 72

Leu Thr Trp Leu Glu Trp Asp Arg Glu Ile Asn Asn Tyr Thr Ser Leu
1               5                   10                  15

Ile His Ser Leu Ile Glu Glu Ser Gln Asn Ala Gln Glu Lys Ala Glu
            20                  25                  30

Gln Glu Leu Leu Glu
        35

<210> SEQ ID NO 73
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(5)
<223> OTHER INFORMATION: (S)-2-(4'-pentenyl) alanine
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: (S)-2-(4'-pentenyl) alanine
<220> FEATURE:
<221> NAME/KEY: MOD_RES
<222> LOCATION: (28)..(28)
<223> OTHER INFORMATION: (S)-2-(4'-pentenyl) alanine
<220> FEATURE:
<221> NAME/KEY: misc_feature
<222> LOCATION: (28)..(32)
<223> OTHER INFORMATION: Cross-link between residues
<220> FEATURE:
<221> NAME/KEY: MOD_RES

```
<222> LOCATION: (32)..(32)
<223> OTHER INFORMATION: (S)-2-(4'-pentenyl) alanine

<400> SEQUENCE: 73

Leu Thr Trp Leu Ala Trp Asp Arg Ala Ile Asn Asn Tyr Thr Ser Leu
1               5                   10                  15

Ile His Ser Leu Ile Glu Glu Ser Gln Asn Gln Ala Glu Lys Asn Ala
            20                  25                  30

Gln Glu Leu Leu Glu
        35

<210> SEQ ID NO 74
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(5)
<223> OTHER INFORMATION: (S)-2-(4'-pentenyl) alanine
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: (S)-2-(4'-pentenyl) alanine
<220> FEATURE:
<221> NAME/KEY: MOD_RES
<222> LOCATION: (27)..(27)
<223> OTHER INFORMATION: (S)-2-(4'-pentenyl) alanine
<220> FEATURE:
<221> NAME/KEY: misc_feature
<222> LOCATION: (27)..(31)
<223> OTHER INFORMATION: Cross-link between residues
<220> FEATURE:
<221> NAME/KEY: MOD_RES
<222> LOCATION: (31)..(31)
<223> OTHER INFORMATION: (S)-2-(4'-pentenyl) alanine

<400> SEQUENCE: 74

Leu Thr Trp Leu Ala Trp Asp Arg Ala Ile Asn Asn Tyr Thr Ser Leu
1               5                   10                  15

Ile His Ser Leu Ile Glu Glu Ser Gln Asn Ala Gln Glu Lys Ala Glu
            20                  25                  30

Gln Glu Leu Leu Glu
        35

<210> SEQ ID NO 75
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: (S)-2-(4'-pentenyl) alanine
<220> FEATURE:
```

```
<221> NAME/KEY: misc_feature
<222> LOCATION: (6)..(10)
<223> OTHER INFORMATION: Cross-link between residues
<220> FEATURE:
<221> NAME/KEY: MOD_RES
<222> LOCATION: (10)..(10)
<223> OTHER INFORMATION: (S)-2-(4'-pentenyl) alanine

<400> SEQUENCE: 75

Glu Leu Asp Lys Trp Ala Ser Leu Trp Ala Trp Phe Asn Ile Thr Asn
1               5                   10                  15

Trp Leu Trp Tyr Ile Lys
            20

<210> SEQ ID NO 76
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (S)-2-(4'-pentenyl) alanine
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: (S)-2-(4'-pentenyl) alanine

<400> SEQUENCE: 76

Glu Leu Asp Lys Ala Ala Ser Leu Ala Asn Trp Phe Asn Ile Thr Asn
1               5                   10                  15

Trp Leu Trp Tyr Ile Lys
            20

<210> SEQ ID NO 77
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: (S)-2-(4'-pentenyl) alanine
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: (S)-2-(4'-pentenyl) alanine

<400> SEQUENCE: 77

Glu Leu Asp Ala Trp Ala Ser Ala Trp Asn Trp Phe Asn Ile Thr Asn
1               5                   10                  15

Trp Leu Trp Tyr Ile Lys
            20

<210> SEQ ID NO 78
<211> LENGTH: 22
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: (S)-2-(4'-pentenyl) alanine
<220> FEATURE:
<221> NAME/KEY: misc_feature
<222> LOCATION: (3)..(7)
<223> OTHER INFORMATION: Cross-link between residues
<220> FEATURE:
<221> NAME/KEY: MOD_RES
<222> LOCATION: (7)..(7)
<223> OTHER INFORMATION: (S)-2-(4'-pentenyl) alanine

<400> SEQUENCE: 78

Glu Leu Ala Lys Trp Ala Ala Leu Trp Asn Trp Phe Asn Ile Thr Asn
1               5                   10                  15

Trp Leu Trp Tyr Ile Lys
            20

<210> SEQ ID NO 79
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (S)-2-(4'-pentenyl) alanine
<220> FEATURE:
<221> NAME/KEY: misc_feature
<222> LOCATION: (2)..(6)
<223> OTHER INFORMATION: Cross-link between residues
<220> FEATURE:
<221> NAME/KEY: MOD_RES
<222> LOCATION: (6)..(6)
<223> OTHER INFORMATION: (S)-2-(4'-pentenyl) alanine

<400> SEQUENCE: 79

Glu Ala Asp Lys Trp Ala Ser Leu Trp Asn Trp Phe Asn Ile Thr Asn
1               5                   10                  15

Trp Leu Trp Tyr Ile Lys
            20

<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-(4'-pentenyl) alanine
<220> FEATURE:
<221> NAME/KEY: misc_feature
<222> LOCATION: (1)..(5)
<223> OTHER INFORMATION: Cross-link between residues
<220> FEATURE:
<221> NAME/KEY: MOD_RES
<222> LOCATION: (5)..(5)
<223> OTHER INFORMATION: (S)-2-(4'-pentenyl) alanine

<400> SEQUENCE: 80

Ala Leu Asp Lys Ala Ala Ser Leu Trp Asn Trp Phe Asn Ile Thr Asn
1               5                   10                  15
```

```
Trp Leu Trp Tyr Ile Lys
            20

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: (S)-2-(4'-pentenyl) alanine
<220> FEATURE:
<221> NAME/KEY: misc_feature
<222> LOCATION: (13)..(17)
<223> OTHER INFORMATION: Cross-link between residues
<220> FEATURE:
<221> NAME/KEY: MOD_RES
<222> LOCATION: (17)..(17)
<223> OTHER INFORMATION: (S)-2-(4'-pentenyl) alanine

<400> SEQUENCE: 81

Glu Leu Asp Lys Trp Ala Ser Leu Trp Asn Trp Phe Ala Ile Thr Asn
1               5                   10                  15

Ala Leu Trp Tyr
            20

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: (S)-2-(4'-pentenyl) alanine
<220> FEATURE:
<221> NAME/KEY: misc_feature
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: (S)-2-(4'-pentenyl) alanine

<400> SEQUENCE: 82

Glu Leu Asp Lys Trp Ala Ser Leu Ala Asn Trp Phe Ala Ile Thr Asn
1               5                   10                  15

Trp Leu Trp Tyr
            20

<210> SEQ ID NO 83
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: (S)-2-(4'-pentenyl) alanine
<220> FEATURE:
<221> NAME/KEY: misc_feature
<222> LOCATION: (19)..(22)
<223> OTHER INFORMATION: Cross-link between residues
<220> FEATURE:
<221> NAME/KEY: MOD_RES
```

```
<222> LOCATION: (22)..(22)
<223> OTHER INFORMATION: (S)-2-(4'-pentenyl) alanine

<400> SEQUENCE: 83

Glu Leu Asp Lys Trp Ala Ser Leu Trp Asn Trp Phe Asn Ile Thr Asn
1               5                   10                  15

Trp Leu Ala Tyr Ile Ala
            20

<210> SEQ ID NO 84
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: (S)-2-(4'-pentenyl) alanine
<220> FEATURE:
<221> NAME/KEY: misc_feature
<222> LOCATION: (18)..(21)
<223> OTHER INFORMATION: Cross-link between residues
<220> FEATURE:
<221> NAME/KEY: MOD_RES
<222> LOCATION: (21)..(21)
<223> OTHER INFORMATION: (S)-2-(4'-pentenyl) alanine

<400> SEQUENCE: 84

Glu Leu Asp Lys Trp Ala Ser Leu Trp Asn Trp Phe Asn Ile Thr Asn
1               5                   10                  15

Trp Ala Trp Tyr Ala Lys
            20

<210> SEQ ID NO 85
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: (S)-2-(4'-pentenyl) alanine
<220> FEATURE:
<221> NAME/KEY: misc_feature
<222> LOCATION: (17)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine

<400> SEQUENCE: 85

Glu Leu Asp Lys Trp Ala Ser Leu Trp Asn Trp Phe Asn Ile Thr Asn
1               5                   10                  15

Ala Leu Trp Ala Ile Lys
            20

<210> SEQ ID NO 86
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (16)..(16)
<223> OTHER INFORMATION: (S)-2-(4'-pentenyl) alanine
<220> FEATURE:
<221> NAME/KEY: misc_feature
<222> LOCATION: (16)..(19)
<223> OTHER INFORMATION: Cross-link between residues
<220> FEATURE:
<221> NAME/KEY: MOD_RES
<222> LOCATION: (19)..(19)
<223> OTHER INFORMATION: (S)-2-(4'-pentenyl) alanine

<400> SEQUENCE: 86

Glu Leu Asp Lys Trp Ala Ser Leu Trp Asn Trp Phe Asn Ile Thr Ala
 1               5                  10                  15

Trp Leu Ala Tyr Ile Lys
            20

<210> SEQ ID NO 87
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: (S)-2-(4'-pentenyl) alanine
<220> FEATURE:
<221> NAME/KEY: misc_feature
<222> LOCATION: (15)..(18)
<223> OTHER INFORMATION: Cross-link between residues
<220> FEATURE:
<221> NAME/KEY: MOD_RES
<222> LOCATION: (18)..(18)
<223> OTHER INFORMATION: (S)-2-(4'-pentenyl) alanine

<400> SEQUENCE: 87

Glu Leu Asp Lys Trp Ala Ser Leu Trp Asn Trp Phe Asn Ile Ala Asn
 1               5                  10                  15

Trp Ala Trp Tyr Ile Lys
            20

<210> SEQ ID NO 88
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: (S)-2-(4'-pentenyl) alanine
<220> FEATURE:
<221> NAME/KEY: misc_feature
<222> LOCATION: (14)..(17)
<223> OTHER INFORMATION: Cross-link between residues
<220> FEATURE:
<221> NAME/KEY: MOD_RES
<222> LOCATION: (17)..(17)
<223> OTHER INFORMATION: (S)-2-(4'-pentenyl) alanine

<400> SEQUENCE: 88

Glu Leu Asp Lys Trp Ala Ser Leu Trp Asn Trp Phe Asn Ala Thr Asn
 1               5                  10                  15

Ala Leu Trp Tyr Ile Lys
            20

<210> SEQ ID NO 89
```

```
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: (S)-2-(4'-pentenyl) alanine
<220> FEATURE:
<221> NAME/KEY: misc_feature
<222> LOCATION: (13)..(16)
<223> OTHER INFORMATION: Cross-link between residues
<220> FEATURE:
<221> NAME/KEY: MOD_RES
<222> LOCATION: (16)..(16)
<223> OTHER INFORMATION: (S)-2-(4'-pentenyl) alanine

<400> SEQUENCE: 89

Glu Leu Asp Lys Trp Ala Ser Leu Trp Asn Trp Phe Ala Ile Thr Ala
1               5                   10                  15

Trp Leu Trp Tyr Ile Lys
            20

<210> SEQ ID NO 90
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-(4'-pentenyl) alanine
<220> FEATURE:
<221> NAME/KEY: misc_feature
<222> LOCATION: (1)..(5)
<223> OTHER INFORMATION: Cross-link between residues
<220> FEATURE:
<221> NAME/KEY: MOD_RES
<222> LOCATION: (5)..(5)
<223> OTHER INFORMATION: (S)-2-(4'-pentenyl) alanine
<220> FEATURE:
<221> NAME/KEY: MOD_RES
<222> LOCATION: (17)..(17)
<223> OTHER INFORMATION: (S)-2-(4'-pentenyl) alanine
<220> FEATURE:
<221> NAME/KEY: misc_feature
<222> LOCATION: (17)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine

<400> SEQUENCE: 90

Ala Leu Asp Lys Ala Ala Ser Leu Trp Asn Trp Phe Asn Ile Thr Asn
1               5                   10                  15

Ala Leu Trp Ala Ile Lys
            20

<210> SEQ ID NO 91
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

-continued

```
<223> OTHER INFORMATION: (S)-2-(4'-pentenyl) alanine
<220> FEATURE:
<221> NAME/KEY: misc_feature
<222> LOCATION: (2)..(6)
<223> OTHER INFORMATION: Cross-link between residues
<220> FEATURE:
<221> NAME/KEY: MOD_RES
<222> LOCATION: (6)..(6)
<223> OTHER INFORMATION: (S)-2-(4'-pentenyl) alanine
<220> FEATURE:
<221> NAME/KEY: MOD_RES
<222> LOCATION: (17)..(17)
<223> OTHER INFORMATION: (S)-2-(4'-pentenyl) alanine
<220> FEATURE:
<221> NAME/KEY: misc_feature
<222> LOCATION: (17)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine

<400> SEQUENCE: 91

Glu Ala Asp Lys Trp Ala Ser Leu Trp Asn Trp Phe Asn Ile Thr Asn
1               5                   10                  15

Ala Leu Trp Ala Ile Lys
            20

<210> SEQ ID NO 92
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: (S)-2-(4'-pentenyl) alanine
<220> FEATURE:
<221> NAME/KEY: misc_feature
<222> LOCATION: (3)..(7)
<223> OTHER INFORMATION: Cross-link between residues
<220> FEATURE:
<221> NAME/KEY: MOD_RES
<222> LOCATION: (7)..(7)
<223> OTHER INFORMATION: (S)-2-(4'-pentenyl) alanine
<220> FEATURE:
<221> NAME/KEY: MOD_RES
<222> LOCATION: (17)..(17)
<223> OTHER INFORMATION: (S)-2-(4'-pentenyl) alanine
<220> FEATURE:
<221> NAME/KEY: misc_feature
<222> LOCATION: (17)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine

<400> SEQUENCE: 92

Glu Leu Ala Lys Trp Ala Ala Leu Trp Asn Trp Phe Asn Ile Thr Asn
1               5                   10                  15

Ala Leu Trp Ala Ile Lys
            20

<210> SEQ ID NO 93
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)..(4)
<223> OTHER INFORMATION: (S)-2-(4'-pentenyl) alanine
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: (S)-2-(4'-pentenyl) alanine
<220> FEATURE:
<221> NAME/KEY: MOD_RES
<222> LOCATION: (17)..(17)
<223> OTHER INFORMATION: (S)-2-(4'-pentenyl) alanine
<220> FEATURE:
<221> NAME/KEY: misc_feature
<222> LOCATION: (17)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine

<400> SEQUENCE: 93

Glu Leu Asp Ala Trp Ala Ser Ala Trp Asn Trp Phe Asn Ile Thr Asn
1               5                   10                  15

Ala Leu Trp Ala Ile Lys
            20

<210> SEQ ID NO 94
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-(4'-pentenyl) alanine
<220> FEATURE:
<221> NAME/KEY: misc_feature
<222> LOCATION: (1)..(5)
<223> OTHER INFORMATION: Cross-link between residues
<220> FEATURE:
<221> NAME/KEY: MOD_RES
<222> LOCATION: (5)..(5)
<223> OTHER INFORMATION: (S)-2-(4'-pentenyl) alanine
<220> FEATURE:
<221> NAME/KEY: MOD_RES
<222> LOCATION: (14)..(14)
<223> OTHER INFORMATION: (S)-2-(4'-pentenyl) alanine
<220> FEATURE:
<221> NAME/KEY: misc_feature
<222> LOCATION: (14)..(17)
<223> OTHER INFORMATION: Cross-link between residues
<220> FEATURE:
<221> NAME/KEY: MOD_RES
<222> LOCATION: (17)..(17)
<223> OTHER INFORMATION: (S)-2-(4'-pentenyl) alanine

<400> SEQUENCE: 94

Ala Leu Asp Lys Ala Ala Ser Leu Trp Asn Trp Phe Asn Ala Thr Asn
1               5                   10                  15

Ala Leu Trp Tyr Ile Lys
            20

<210> SEQ ID NO 95
<211> LENGTH: 22
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (S)-2-(4'-pentenyl) alanine
<220> FEATURE:
<221> NAME/KEY: misc_feature
<222> LOCATION: (2)..(6)
<223> OTHER INFORMATION: Cross-link between residues
<220> FEATURE:
<221> NAME/KEY: MOD_RES
<222> LOCATION: (6)..(6)
<223> OTHER INFORMATION: (S)-2-(4'-pentenyl) alanine
<220> FEATURE:
<221> NAME/KEY: MOD_RES
<222> LOCATION: (14)..(14)
<223> OTHER INFORMATION: (S)-2-(4'-pentenyl) alanine
<220> FEATURE:
<221> NAME/KEY: misc_feature
<222> LOCATION: (14)..(17)
<223> OTHER INFORMATION: Cross-link between residues
<220> FEATURE:
<221> NAME/KEY: MOD_RES
<222> LOCATION: (17)..(17)
<223> OTHER INFORMATION: (S)-2-(4'-pentenyl) alanine

<400> SEQUENCE: 95

Glu Ala Asp Lys Trp Ala Ser Leu Trp Asn Trp Phe Asn Ala Thr Asn
1               5                   10                  15

Ala Leu Trp Tyr Ile Lys
            20

<210> SEQ ID NO 96
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: (S)-2-(4'-pentenyl) alanine
<220> FEATURE:
<221> NAME/KEY: misc_feature
<222> LOCATION: (3)..(7)
<223> OTHER INFORMATION: Cross-link between residues
<220> FEATURE:
<221> NAME/KEY: MOD_RES
<222> LOCATION: (7)..(7)
<223> OTHER INFORMATION: (S)-2-(4'-pentenyl) alanine
<220> FEATURE:
<221> NAME/KEY: MOD_RES
<222> LOCATION: (14)..(14)
<223> OTHER INFORMATION: (S)-2-(4'-pentenyl) alanine
<220> FEATURE:
<221> NAME/KEY: misc_feature
<222> LOCATION: (14)..(17)
<223> OTHER INFORMATION: Cross-link between residues
<220> FEATURE:
<221> NAME/KEY: MOD_RES
<222> LOCATION: (17)..(17)
<223> OTHER INFORMATION: (S)-2-(4'-pentenyl) alanine

<400> SEQUENCE: 96

Glu Leu Ala Lys Trp Ala Ala Leu Trp Asn Trp Phe Asn Ala Thr Asn
1               5                   10                  15

Ala Leu Trp Tyr Ile Lys
            20

<210> SEQ ID NO 97
```

```
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: (S)-2-(4'-pentenyl) alanine
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: (S)-2-(4'-pentenyl) alanine
<220> FEATURE:
<221> NAME/KEY: MOD_RES
<222> LOCATION: (14)..(14)
<223> OTHER INFORMATION: (S)-2-(4'-pentenyl) alanine
<220> FEATURE:
<221> NAME/KEY: misc_feature
<222> LOCATION: (14)..(17)
<223> OTHER INFORMATION: Cross-link between residues
<220> FEATURE:
<221> NAME/KEY: MOD_RES
<222> LOCATION: (17)..(17)
<223> OTHER INFORMATION: (S)-2-(4'-pentenyl) alanine

<400> SEQUENCE: 97

Glu Leu Asp Ala Trp Ala Ser Ala Trp Asn Trp Phe Asn Ala Thr Asn
1               5                   10                  15

Ala Leu Trp Tyr Ile Lys
            20

<210> SEQ ID NO 98
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: (R)-2-(4'-allyl) alanine
<220> FEATURE:
<221> NAME/KEY: misc_feature
<222> LOCATION: (8)..(11)
<223> OTHER INFORMATION: Cross-link between residues
<220> FEATURE:
<221> NAME/KEY: MOD_RES
<222> LOCATION: (11)..(11)
<223> OTHER INFORMATION: (S)-2-(4'-pentenyl) alanine

<400> SEQUENCE: 98

Asn Trp Phe Asn Ile Thr Asn Ala Leu Trp Ala Ile Lys Lys Lys Lys
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: (R)-2-(4'-allyl) alanine
<220> FEATURE:
<221> NAME/KEY: misc_feature
```

```
<222> LOCATION: (8)..(11)
<223> OTHER INFORMATION: Cross-link between residues
<220> FEATURE:
<221> NAME/KEY: MOD_RES
<222> LOCATION: (11)..(11)
<223> OTHER INFORMATION: (S)-2-(4'-hexenyl) alanine

<400> SEQUENCE: 99

Asn Trp Phe Asn Ile Thr Asn Ala Leu Trp Ala Ile Lys Lys Lys Lys
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: (S)-2-(4'-pentenyl) alanine
<220> FEATURE:
<221> NAME/KEY: misc_feature
<222> LOCATION: (8)..(11)
<223> OTHER INFORMATION: Cross-link between residues
<220> FEATURE:
<221> NAME/KEY: MOD_RES
<222> LOCATION: (11)..(11)
<223> OTHER INFORMATION: (S)-2-(4'-pentenyl) alanine

<400> SEQUENCE: 100

Asn Trp Phe Asn Ile Thr Asn Ala Leu Trp Ala Ile Lys Lys Lys Lys
1               5                   10                  15

<210> SEQ ID NO 101
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (S)-2-(4'-pentenyl) alanine
<220> FEATURE:
<221> NAME/KEY: misc_feature
<222> LOCATION: (1)..(5)
<223> OTHER INFORMATION: Cross-link between residues
<220> FEATURE:
<221> NAME/KEY: MOD_RES
<222> LOCATION: (5)..(5)
<223> OTHER INFORMATION: (S)-2-(4'-pentenyl) alanine
<220> FEATURE:
<221> NAME/KEY: MOD_RES
<222> LOCATION: (17)..(17)
<223> OTHER INFORMATION: (R)-2-(4'-allyl) alanine
<220> FEATURE:
<221> NAME/KEY: misc_feature
<222> LOCATION: (17)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine

<400> SEQUENCE: 101

Ala Leu Asp Lys Ala Ala Ser Leu Trp Asn Trp Phe Asn Ile Thr Asn
1               5                   10                  15

Ala Leu Trp Ala Ile Lys Lys Lys Lys
                20                  25
```

```
<210> SEQ ID NO 102
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: (S)-2-(4'-pentenyl) alanine
<220> FEATURE:
<221> NAME/KEY: misc_feature
<222> LOCATION: (2)..(6)
<223> OTHER INFORMATION: Cross-link between residues
<220> FEATURE:
<221> NAME/KEY: MOD_RES
<222> LOCATION: (6)..(6)
<223> OTHER INFORMATION: (S)-2-(4'-pentenyl) alanine
<220> FEATURE:
<221> NAME/KEY: MOD_RES
<222> LOCATION: (17)..(17)
<223> OTHER INFORMATION: (R)-2-(4'-allyl) alanine
<220> FEATURE:
<221> NAME/KEY: misc_feature
<222> LOCATION: (17)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine

<400> SEQUENCE: 102

Glu Ala Asp Lys Trp Ala Ser Leu Trp Asn Trp Phe Asn Ile Thr Asn
1               5                   10                  15

Ala Leu Trp Ala Ile Lys Lys Lys Lys
            20                  25

<210> SEQ ID NO 103
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: (S)-2-(4'-pentenyl) alanine
<220> FEATURE:
<221> NAME/KEY: misc_feature
<222> LOCATION: (3)..(7)
<223> OTHER INFORMATION: Cross-link between residues
<220> FEATURE:
<221> NAME/KEY: MOD_RES
<222> LOCATION: (7)..(7)
<223> OTHER INFORMATION: (S)-2-(4'-pentenyl) alanine
<220> FEATURE:
<221> NAME/KEY: MOD_RES
<222> LOCATION: (17)..(17)
<223> OTHER INFORMATION: (R)-2-(4'-allyl) alanine
<220> FEATURE:
<221> NAME/KEY: misc_feature
<222> LOCATION: (17)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine

<400> SEQUENCE: 103

Glu Leu Ala Lys Trp Ala Ala Leu Trp Asn Trp Phe Asn Ile Thr Asn
1               5                   10                  15
```

Ala Leu Trp Ala Ile Lys Lys Lys Lys
            20                  25

<210> SEQ ID NO 104
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: (S)-2-(4'-pentenyl) alanine
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: (S)-2-(4'-pentenyl) alanine
<220> FEATURE:
<221> NAME/KEY: MOD_RES
<222> LOCATION: (17)..(17)
<223> OTHER INFORMATION: (R)-2-(4'-allyl) alanine
<220> FEATURE:
<221> NAME/KEY: misc_feature
<222> LOCATION: (17)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine

<400> SEQUENCE: 104

Glu Leu Asp Ala Trp Ala Ser Ala Trp Asn Trp Phe Asn Ile Thr Asn
1               5                   10                  15

Ala Leu Trp Ala Ile Lys Lys Lys Lys
            20                  25

<210> SEQ ID NO 105
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (S)-2-(4'-pentenyl) alanine
<220> FEATURE:
<221> NAME/KEY: misc_feature
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: (S)-2-(4'-pentenyl) alanine
<220> FEATURE:
<221> NAME/KEY: MOD_RES
<222> LOCATION: (17)..(17)
<223> OTHER INFORMATION: (R)-2-(4'-allyl) alanine
<220> FEATURE:
<221> NAME/KEY: misc_feature
<222> LOCATION: (17)..(20)
<223> OTHER INFORMATION: Cross-link between residues
<220> FEATURE:
<221> NAME/KEY: MOD_RES
<222> LOCATION: (20)..(20)
<223> OTHER INFORMATION: (S)-2-(4'-pentenyl) alanine

<400> SEQUENCE: 105

```
Glu Leu Asp Lys Ala Ala Ser Leu Ala Asn Trp Phe Asn Ile Thr Asn
1               5                   10                  15

Ala Leu Trp Ala Ile Lys Lys Lys Lys
            20                  25

<210> SEQ ID NO 106
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: L-Methyl-Phe

<400> SEQUENCE: 106

Glu Leu Asp Lys Trp Ala Ser Leu Trp Asn Trp Phe Asn Ile Thr Asn
1               5                   10                  15

Trp Leu Trp Tyr Ile Lys
            20

<210> SEQ ID NO 107
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: D-Methyl-Phe

<400> SEQUENCE: 107

Glu Leu Asp Lys Trp Ala Ser Leu Trp Asn Trp Phe Asn Ile Thr Asn
1               5                   10                  15

Trp Leu Trp Tyr Ile Lys
            20

<210> SEQ ID NO 108
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: L-Beta-Phe

<400> SEQUENCE: 108

Glu Leu Asp Lys Trp Ala Ser Leu Trp Asn Trp Phe Asn Ile Thr Asn
1               5                   10                  15

Trp Leu Trp Tyr Ile Lys
            20

<210> SEQ ID NO 109
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (12)..(12)
<223> OTHER INFORMATION: D-Beta-Phe

<400> SEQUENCE: 109

Glu Leu Asp Lys Trp Ala Ser Leu Trp Asn Trp Phe Asn Ile Thr Asn
1               5                   10                  15

Trp Leu Trp Tyr Ile Lys
            20

<210> SEQ ID NO 110
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: L-Homo-Phe

<400> SEQUENCE: 110

Glu Leu Asp Lys Trp Ala Ser Leu Trp Asn Trp Phe Asn Ile Thr Asn
1               5                   10                  15

Trp Leu Trp Tyr Ile Lys
            20

<210> SEQ ID NO 111
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: D-Homo-Phe

<400> SEQUENCE: 111

Glu Leu Asp Lys Trp Ala Ser Leu Trp Asn Trp Phe Asn Ile Thr Asn
1               5                   10                  15

Trp Leu Trp Tyr Ile Lys
            20

<210> SEQ ID NO 112
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: L-indoline-2-carboxylic acid

<400> SEQUENCE: 112

Glu Leu Asp Lys Trp Ala Ser Leu Trp Asn Trp Xaa Asn Ile Thr Asn
1               5                   10                  15

Trp Leu Trp Tyr Ile Lys
            20

<210> SEQ ID NO 113
<211> LENGTH: 22
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: L-Nal

<400> SEQUENCE: 113

Glu Leu Asp Lys Trp Ala Ser Leu Trp Asn Trp Ala Asn Ile Thr Asn
1               5                   10                  15

Trp Leu Trp Tyr Ile Lys
            20

<210> SEQ ID NO 114
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: D-Nal

<400> SEQUENCE: 114

Glu Leu Asp Lys Trp Ala Ser Leu Trp Asn Trp Ala Asn Ile Thr Asn
1               5                   10                  15

Trp Leu Trp Tyr Ile Lys
            20

<210> SEQ ID NO 115
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: L-Phenyl-Gly

<400> SEQUENCE: 115

Glu Leu Asp Lys Trp Ala Ser Leu Trp Asn Trp Gly Asn Ile Thr Asn
1               5                   10                  15

Trp Leu Trp Tyr Ile Lys
            20

<210> SEQ ID NO 116
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: D-Phenyl-Gly

<400> SEQUENCE: 116

Glu Leu Asp Lys Trp Ala Ser Leu Trp Asn Trp Gly Asn Ile Thr Asn
1               5                   10                  15

Trp Leu Trp Tyr Ile Lys
            20
```

```
<210> SEQ ID NO 117
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: L-Tic

<400> SEQUENCE: 117

Glu Leu Asp Lys Trp Ala Ser Leu Trp Asn Trp Xaa Asn Ile Thr Asn
1               5                   10                  15

Trp Leu Trp Tyr Ile Lys
            20

<210> SEQ ID NO 118
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: D-Tic

<400> SEQUENCE: 118

Glu Leu Asp Lys Trp Ala Ser Leu Trp Asn Trp Xaa Asn Ile Thr Asn
1               5                   10                  15

Trp Leu Trp Tyr Ile Lys
            20

<210> SEQ ID NO 119
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: D-Tiq

<400> SEQUENCE: 119

Glu Leu Asp Lys Trp Ala Ser Leu Trp Asn Trp Xaa Asn Ile Thr Asn
1               5                   10                  15

Trp Leu Trp Tyr Ile Lys
            20

<210> SEQ ID NO 120
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Glu Leu Asp Lys Trp Ala Ser Leu Trp Asn Trp Phe Asn Ile Thr Asn
1               5                   10                  15

Trp Leu Trp Tyr Ile Lys
            20
```

<210> SEQ ID NO 121
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: D-Phe

<400> SEQUENCE: 121

Glu Leu Asp Lys Trp Ala Ser Leu Trp Asn Trp Phe Asn Ile Thr Asn
1               5                   10                  15

Trp Leu Trp Tyr Ile Lys
            20

<210> SEQ ID NO 122
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Atc

<400> SEQUENCE: 122

Glu Leu Asp Lys Trp Ala Ser Leu Trp Asn Trp Xaa Asn Ile Thr Asn
1               5                   10                  15

Trp Leu Trp Tyr Ile Lys
            20

<210> SEQ ID NO 123
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aic

<400> SEQUENCE: 123

Glu Leu Asp Lys Trp Ala Ser Leu Trp Asn Trp Xaa Asn Ile Thr Asn
1               5                   10                  15

Trp Leu Trp Tyr Ile Lys
            20

<210> SEQ ID NO 124
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: L-2-Indanyl-Gly

<400> SEQUENCE: 124

```
Glu Leu Asp Lys Trp Ala Ser Leu Trp Asn Trp Gly Asn Ile Thr Asn
1               5                   10                  15

Trp Leu Trp Tyr Ile Lys
            20

<210> SEQ ID NO 125
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: D-2-Indanyl-Gly

<400> SEQUENCE: 125

Glu Leu Asp Lys Trp Ala Ser Leu Trp Asn Trp Gly Asn Ile Thr Asn
1               5                   10                  15

Trp Leu Trp Tyr Ile Lys
            20

<210> SEQ ID NO 126
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: L-Bip

<400> SEQUENCE: 126

Glu Leu Asp Lys Trp Ala Ser Leu Trp Asn Trp Xaa Asn Ile Thr Asn
1               5                   10                  15

Trp Leu Trp Tyr Ile Lys
            20

<210> SEQ ID NO 127
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: D-Bip

<400> SEQUENCE: 127

Glu Leu Asp Lys Trp Ala Ser Leu Trp Asn Trp Xaa Asn Ile Thr Asn
1               5                   10                  15

Trp Leu Trp Tyr Ile Lys
            20

<210> SEQ ID NO 128
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (12)..(12)
<223> OTHER INFORMATION: Benzyl-Gly

<400> SEQUENCE: 128

Glu Leu Asp Lys Trp Ala Ser Leu Trp Asn Trp Gly Asn Ile Thr Asn
1               5                   10                  15

Trp Leu Trp Tyr Ile Lys
            20

<210> SEQ ID NO 129
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ser Trp Glu Thr Trp Glu Arg Glu Ile Glu Asn Tyr Thr Arg Gln Ile
1               5                   10                  15

Tyr Arg Ile Leu Glu Glu Ser Gln Glu Gln Gln Asp Arg Asn
            20                  25                  30

<210> SEQ ID NO 130
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys
            20                  25                  30

<210> SEQ ID NO 131
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Thr Thr Trp Glu Glu Trp Asp Arg Glu Ile Asn Glu Tyr Thr Ser Arg
1               5                   10                  15

Ile Glu Ser Leu Ile Arg Glu Ser Gln Glu Gln Gln Glu Lys
            20                  25                  30

<210> SEQ ID NO 132
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Thr Trp Met Ala Trp Asp Arg Ala Ile Ala Asn Tyr Ala Ala Leu
1               5                   10                  15

Ile His Ala Leu Ile Glu Ala Ala Gln Asn Gln Gln Glu Lys
            20                  25                  30
```

```
<210> SEQ ID NO 133
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Thr Thr Trp Glu Ala Trp Asp Arg Ala Ile Ala Glu Tyr Ala Ala Arg
1               5                   10                  15

Ile Glu Ala Leu Ile Arg Ala Ser Gln Glu Gln Gln Glu Lys
            20                  25                  30

<210> SEQ ID NO 134
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Thr Thr Trp Glu Ala Trp Asp Arg Ala Ile Ala Glu Tyr Ala Ala Arg
1               5                   10                  15

Ile Glu Ala Leu Ile Arg Ala Ala Gln Glu Gln Gln Glu Lys
            20                  25                  30

<210> SEQ ID NO 135
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: (S)-2-(4'-pentenyl) alanine
<220> FEATURE:
<221> NAME/KEY: misc_feature
<222> LOCATION: (17)..(21)
<223> OTHER INFORMATION: Cross-link between residues
<220> FEATURE:
<221> NAME/KEY: MOD_RES
<222> LOCATION: (21)..(21)
<223> OTHER INFORMATION: (S)-2-(4'-pentenyl) alanine

<400> SEQUENCE: 135

Glu Leu Asp Lys Trp Ala Ser Leu Trp Asn Trp Phe Asn Ile Thr Asn
1               5                   10                  15

Ala Leu Trp Tyr Ala Lys
            20

<210> SEQ ID NO 136
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: (S)-2-(4'-pentenyl) alanine
<220> FEATURE:
<221> NAME/KEY: misc_feature
<222> LOCATION: (17)..(20)
<223> OTHER INFORMATION: Cross-link between residues
```

```
<220> FEATURE:
<221> NAME/KEY: MOD_RES
<222> LOCATION: (20)..(20)
<223> OTHER INFORMATION: (S)-2-(4'-pentenyl) alanine

<400> SEQUENCE: 136

Glu Leu Asp Lys Trp Ala Ser Leu Trp Asn Trp Phe Asn Ile Thr Asn
1               5                   10                  15

Ala Leu Trp Ala Ile Lys
            20

<210> SEQ ID NO 137
<211> LENGTH: 22
<212> TYPE: PRT
<213> ORGANISM: Human immunodeficiency virus type 1

<400> SEQUENCE: 137

Glu Leu Asp Lys Trp Ala Ser Leu Trp Asn Trp Phe Asn Ile Thr Asn
1               5                   10                  15

Trp Leu Trp Tyr Ile Lys
            20

<210> SEQ ID NO 138
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: (R)-2-(4'-allyl) alanine
<220> FEATURE:
<221> NAME/KEY: misc_feature
<222> LOCATION: (8)..(11)
<223> OTHER INFORMATION: Cross-link between residues
<220> FEATURE:
<221> NAME/KEY: MOD_RES
<222> LOCATION: (11)..(11)
<223> OTHER INFORMATION: (S)-2-(4'-pentenyl) alanine

<400> SEQUENCE: 138

Asn Trp Phe Asn Ile Thr Asn Ala Leu Trp Ala Ile Lys Lys Lys Lys
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: (R)-2-(4'-allyl) alanine
<220> FEATURE:
<221> NAME/KEY: misc_feature
<222> LOCATION: (8)..(11)
<223> OTHER INFORMATION: Cross-link between residues
<220> FEATURE:
<221> NAME/KEY: MOD_RES
<222> LOCATION: (11)..(11)
<223> OTHER INFORMATION: (S)-2-(4'-hexenyl) alanine

<400> SEQUENCE: 139

Asn Trp Phe Asn Ile Thr Asn Ala Leu Trp Ala Ile Lys Lys Lys Lys
1               5                   10                  15
```

```
<210> SEQ ID NO 140
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: (S)-2-(4'-pentenyl) alanine
<220> FEATURE:
<221> NAME/KEY: misc_feature
<222> LOCATION: (8)..(11)
<223> OTHER INFORMATION: Cross-link between residues
<220> FEATURE:
<221> NAME/KEY: MOD_RES
<222> LOCATION: (11)..(11)
<223> OTHER INFORMATION: (S)-2-(4'-pentenyl) alanine

<400> SEQUENCE: 140

Asn Trp Phe Asn Ile Thr Asn Ala Leu Trp Ala Ile Lys Lys Lys Lys
1               5                   10                  15

<210> SEQ ID NO 141
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: (S)-2-(4'-pentenyl) alanine
<220> FEATURE:
<221> NAME/KEY: misc_feature
<222> LOCATION: (2)..(6)
<223> OTHER INFORMATION: Cross-link between residues
<220> FEATURE:
<221> NAME/KEY: MOD_RES
<222> LOCATION: (6)..(6)
<223> OTHER INFORMATION: (S)-2-(4'-pentenyl) alanine

<400> SEQUENCE: 141

Phe Ala Ala Ser Ile Ala Gln Val Asn Glu Lys Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35

<210> SEQ ID NO 142
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: (S)-2-(4'-pentenyl) alanine
<220> FEATURE:
<221> NAME/KEY: misc_feature
<222> LOCATION: (3)..(7)
<223> OTHER INFORMATION: Cross-link between residues
<220> FEATURE:
<221> NAME/KEY: MOD_RES
<222> LOCATION: (7)..(7)
<223> OTHER INFORMATION: (S)-2-(4'-pentenyl) alanine
```

-continued

```
<400> SEQUENCE: 142

Phe Asp Ala Ser Ile Ser Ala Val Asn Glu Lys Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35

<210> SEQ ID NO 143
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: (S)-2-(4'-pentenyl) alanine
<220> FEATURE:
<221> NAME/KEY: misc_feature
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: (S)-2-(4'-pentenyl) alanine

<400> SEQUENCE: 143

Phe Asp Ala Ala Ile Ser Gln Ala Asn Glu Lys Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35

<210> SEQ ID NO 144
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: (S)-2-(4'-pentenyl) alanine
<220> FEATURE:
<221> NAME/KEY: misc_feature
<222> LOCATION: (23)..(27)
<223> OTHER INFORMATION: Cross-link between residues
<220> FEATURE:
<221> NAME/KEY: MOD_RES
<222> LOCATION: (27)..(27)
<223> OTHER INFORMATION: (S)-2-(4'-pentenyl) alanine

<400> SEQUENCE: 144

Phe Asp Ala Ser Ile Ser Gln Val Asn Glu Lys Ile Asn Gln Ser Leu
1               5                   10                  15

Ala Phe Ile Arg Lys Ser Ala Glu Leu Leu Ala Asn Val Asn Ala Gly
            20                  25                  30

Lys Ser Thr
        35

<210> SEQ ID NO 145
<211> LENGTH: 35
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: (S)-2-(4'-pentenyl) alanine
<220> FEATURE:
<221> NAME/KEY: misc_feature
<222> LOCATION: (24)..(28)
<223> OTHER INFORMATION: Cross-link between residues
<220> FEATURE:
<221> NAME/KEY: MOD_RES
<222> LOCATION: (28)..(28)
<223> OTHER INFORMATION: (S)-2-(4'-pentenyl) alanine

<400> SEQUENCE: 145

Phe Asp Ala Ser Ile Ser Gln Val Asn Glu Lys Ile Asn Gln Ser Leu
1               5                   10                  15

Ala Phe Ile Arg Lys Ser Asp Ala Leu Leu His Ala Val Asn Ala Gly
            20                  25                  30

Lys Ser Thr
        35

<210> SEQ ID NO 146
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: (S)-2-(4'-pentenyl) alanine
<220> FEATURE:
<221> NAME/KEY: misc_feature
<222> LOCATION: (25)..(29)
<223> OTHER INFORMATION: Cross-link between residues
<220> FEATURE:
<221> NAME/KEY: MOD_RES
<222> LOCATION: (29)..(29)
<223> OTHER INFORMATION: (S)-2-(4'-pentenyl) alanine

<400> SEQUENCE: 146

Phe Asp Ala Ser Ile Ser Gln Val Asn Glu Lys Ile Asn Gln Ser Leu
1               5                   10                  15

Ala Phe Ile Arg Lys Ser Asp Glu Ala Leu His Asn Ala Asn Ala Gly
            20                  25                  30

Lys Ser Thr
        35

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 147

His His His His His His
1               5

<210> SEQ ID NO 148
<211> LENGTH: 37
<212> TYPE: PRT
<213> ORGANISM: Human immunodeficiency virus type 1
```

```
<400> SEQUENCE: 148

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
                20                  25                  30

Gln Glu Leu Leu Glu
        35

<210> SEQ ID NO 149
<211> LENGTH: 48
<212> TYPE: PRT
<213> ORGANISM: Human immunodeficiency virus type 1

<400> SEQUENCE: 149

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
                20                  25                  30

Gln Glu Leu Leu Glu Leu Asp Lys Trp Ala Ser Leu Trp Asn Trp Phe
        35                  40                  45
```